US012729239B2

(12) United States Patent
Anderl et al.

(10) Patent No.: US 12,729,239 B2
(45) Date of Patent: Sep. 8, 2026

(54) ANTI-CEACAM5 ANTIBODIES AND CONJUGATES AND USES THEREOF

(71) Applicant: Merck Patent GmbH, Darmstadt (DE)

(72) Inventors: Jan Anderl, Darmstadt (DE); Sabine Raab-Westphal, Darmstadt (DE); Stefan Hecht, Darmstadt (DE); Carl Deutsch, Darmstadt (DE); Min Shan, Darmstadt (DE); Doreen Könning, Darmstadt (DE); Willem N. Sloot, Darmstadt (DE); Felix Hart, Darmstadt (DE); Christian Schröter, Darmstadt (DE); Lars Toleikis, Darmstadt (DE); Nir Berger, Yavne (IL)

(73) Assignee: MERCK PATENT GMBH, Darmstadt (DE)

( * ) Notice: Subject to any disclaimer, the term of this patent is extended or adjusted under 35 U.S.C. 154(b) by 721 days.

(21) Appl. No.: 18/043,715

(22) PCT Filed: Aug. 13, 2021

(86) PCT No.: PCT/EP2021/072595

§ 371 (c)(1),
(2) Date: Mar. 1, 2023

(87) PCT Pub. No.: WO2022/048883

PCT Pub. Date: Mar. 10, 2022

(65) Prior Publication Data

US 2024/0010749 A1 Jan. 11, 2024
US 2025/0122282 A2 Apr. 17, 2025

(30) Foreign Application Priority Data

Sep. 4, 2020 (EP) .................................... 20194711
Sep. 10, 2020 (EP) .................................... 20195559

(51) Int. Cl.

| | |
|---|---|
| ***A61P 35/00*** | (2006.01) |
| ***A61K 47/68*** | (2017.01) |
| ***C07K 16/28*** | (2006.01) |
| ***C07K 16/30*** | (2006.01) |

(52) U.S. Cl.

CPC .... *C07K 16/2803* (2013.01); *A61K 47/68033* (2023.08); *A61K 47/68037* (2023.08); *A61K 47/6853* (2017.08); *A61P 35/00* (2018.01); *C07K 16/3007* (2013.01)

(58) Field of Classification Search

CPC ............ C07K 16/2803; C07K 16/3007; C07K 2317/515; C07K 2317/565; A61K 47/68033; A61K 47/68037; A61K 47/6853; A61K 47/6889; A61K 2039/505; A61K 47/6803; A61P 35/00

USPC ...................................................... 424/134.1

See application file for complete search history.

(56) References Cited

U.S. PATENT DOCUMENTS

| | | | |
|---|---|---|---|
| 5,208,020 A | 5/1993 | Chari et al. | |
| 8,287,865 B2 * | 10/2012 | Hansen .............. | A61K 47/6813 530/387.3 |
| 10,081,679 B2 | 9/2018 | Ben-Moshe et al. | |
| 11,123,439 B2 | 9/2021 | Lerchen et al. | |
| 2007/0071675 A1 | 3/2007 | Wu et al. | |
| 2015/0125386 A1 | 5/2015 | Hansen et al. | |
| 2015/0343083 A1 | 12/2015 | Chu | |
| 2016/0310612 A1 | 10/2016 | Lyon et al. | |
| 2017/0182179 A1 | 6/2017 | Ackler et al. | |
| 2017/0266308 A1 | 9/2017 | Liu et al. | |
| 2019/0077752 A1 | 3/2019 | Lerchen et al. | |
| 2019/0351066 A1 | 11/2019 | Lerchen et al. | |
| 2020/0109196 A1 | 4/2020 | Eun et al. | |
| 2020/0247845 A1 | 8/2020 | Ban et al. | |

FOREIGN PATENT DOCUMENTS

| | | |
|---|---|---|
| CA | 3114137 | 4/2020 |
| EP | 3 101 032 | 12/2016 |
| EP | 3 130 608 | 2/2017 |
| KR | 20180108183 A | 10/2018 |
| RU | 2697522 C1 | 8/2019 |
| WO | 96/08514 | 3/1996 |
| WO | 01/77342 A1 | 10/2001 |
| WO | 2004/091668 | 10/2004 |
| WO | 2007/011968 | 1/2007 |
| WO | 2008/010101 | 1/2008 |
| WO | 2009/099741 | 8/2009 |
| WO | 2011/034660 | 3/2011 |
| WO | 2014/079886 | 5/2014 |
| WO | 2014/100762 | 6/2014 |

(Continued)

OTHER PUBLICATIONS

Badri, et al., "Optimization of radiation dosing schedules for proneural glioblastoma", J. Mathematical Biology, vol. 72, N. 5, 2016, 36 pages.

(Continued)

*Primary Examiner* — Yan Xiao

(74) *Attorney, Agent, or Firm* — Fox Rothschild LLP

(57) ABSTRACT

Antibodies which bind human CEACAM5 protein, as well as isolated nucleic acids and host cells containing a sequence encoding said antibodies are disclosed. Immunoconjugates containing said antibodies linked to a growth-inhibitory agent, and pharmaceutical compositions containing antibodies or said immunoconjugates are also disclosed. A use of the antibodies, immunoconjugates, and pharmaceutical compositions disclosed herein is provided for the treatment of cancer or for diagnostic purposes.

16 Claims, 29 Drawing Sheets

Specification includes a Sequence Listing.

(56) References Cited

FOREIGN PATENT DOCUMENTS

| | | |
|---|---|---|
| WO | 2015/012904 | 1/2015 |
| WO | 2015/095755 | 6/2015 |
| WO | 2015/146132 | 10/2015 |
| WO | 2015/162291 | 10/2015 |
| WO | 2015/162293 | 10/2015 |
| WO | 2015/195904 | 12/2015 |
| WO | 2015/196089 | 12/2015 |
| WO | 2015/196167 | 12/2015 |
| WO | 2016/094517 | 6/2016 |
| WO | 2016/127081 | 8/2016 |
| WO | 2016/173682 | 11/2016 |
| WO | 2016/207089 | 12/2016 |
| WO | 2016/210108 | 12/2016 |
| WO | 2017/059158 | 4/2017 |
| WO | 2017/059160 | 4/2017 |
| WO | 2017/072662 | 5/2017 |
| WO | 2017/112624 | 6/2017 |
| WO | 2017/162663 | 9/2017 |
| WO | 2017/214456 | 12/2017 |
| WO | 2018/075842 | 4/2018 |
| WO | 2018/112253 | 6/2018 |
| WO | 2018/114798 | 6/2018 |
| WO | 2018/198091 | 11/2018 |
| WO | 2019/195665 | 10/2019 |
| WO | 2019/231879 | 12/2019 |
| WO | 2019/236954 | 12/2019 |
| WO | 2020/089811 | 5/2020 |
| WO | 2020/112588 | 6/2020 |
| WO | 2020/219287 | 10/2020 |

OTHER PUBLICATIONS

Baylot et al., "TCTP Has a Crucial Role in the Different Stages of Prostate Cancer Malignant Progression", Results Probl Cell Differ, vol. 64, 2017, pp. 255-261.

Mariuzza R.A., "The structural basis of antigen-antibody recognition", Ann. Rev. Biophys, Biophys, Chem., vol. 16, 1987, pp. 139-159.

Abe et al., "Targeted Sonodynamic Therapy of Cancer Using a Photosensitizer Conjugated with Antibody against Carcinoembryonic Antigen", Anticancer Research, vol. 22, 2002, pp. 1575-1580.

Abou-Alfa et al., "A Phase II Study of Intravenous Exatecan Administered Daily for 5 Days, Every 3 Weeks to Patients with Biliary Tract Cancers", American Journal of Clinical Oncology, vol. 28, No. 4, Aug. 2005, pp. 334-339.

Abou-Alfa et al., "Randomized Phase III Study of Exatecan and Gemcitabine Compared with Gemcitabine Alone in Untreated Advanced Pancreatic Cancer", Journal of Clinical Oncology, vol. 24, No. 27, Sep. 20, 2006, pp. 4441-4447.

Ajani et al., "A phase II clinical and pharmacokinetic study of intravenous exatecan mesylate (DX-8951f) in patients with untreated metastatic gastric cancer", Investigational New Drugs, vol. 23, 2005, pp. 479-484.

Almagro et al., "Humanization of antibodies", Frontiers in Bioscience, vol. 13, Jan. 1, 2008, pp. 1619-1633.

Anselmi et al., "Linker Hydrophilicity Modulates the Anticancer Activity of RGD-Cryptophycin Conjugates", Chemistry—A European Journal, vol. 27, 2021, pp. 1015-1022.

Atsumi et al., "Urinary Metabolites of DX-8951, a Novel Camptothecin Analog, in Rats and Humans". Arzneim.-Forsch./Drug Res. vol. 51 ,(I) 2001, pp. 253-257.

Bajenova et al., "Carcinoembryonic antigen promotes colorectal cancer progression by targeting adherens junction complexes", Experimental Cell Research, vol. 324, 2014, pp. 115-123.

Bajjuri et al., "The Legumain Protease-Activated Auristatin Prodrugs Suppress Tumor Growth and Metastasis without Toxicity", ChemMedChem, vol. 6, 2011, pp. 54-59.

Bargh et al., "Cleavable linkers in antibody-drug conjugates", Chemical Society Reviews, vol. 48, 2019, pp. 4361-4374.

Beauchemin et al., "Carcinoembryonic antigen-related cell adhesion molecules (CEACAMs) in cancer progression and metastasis", Cancer Metastatsis Rev. vol. 32, 2013, pp. 643-671.

Bechmann et al., "Heterogeneity of CEACAM5 in breast cancer", Oncotarget, vol. 11, No. 43, 2020, pp. 3886-3899.

Beck et al., "Strategies and challenges for the next generation of antibody-drug conjugates", Nature Reviews, Drug Discovery, vol. 16, May 2017, pp. 315-337.

Behr et al., "Cure of Metastatic Human Colonic Cancer in Mice with Radiolabeled Monoclonal Antibody Fragments", Clinical Cancer Research, vol. 6, Dec. 2000, pp. 4900-4907.

Behr et al., "Radioimmunotherapy of Small Volume Disease of Colorectal Cancer Metastatic to the Liver: Preclinical Evaluation in Comparison to Standard Chemotherapy and Initial Results of a Phase I Clinical Study", Clinical Cancer Research, vol. 5, Oct. 1999, pp. 3232s-3242s.

Behr et al., "Radioimmunotherapy of Small-Volume Disease of Metastatic Colorectal Cancer", American Cancer, vol. 94, No. 4, Feb. 15, 2002, pp. 1373-1381.

Behr et al., "Therapeutic Efficacy and Dose-Limiting Toxicity of Auger-Electron vs. Beta Emitters in Radioimmunotherapy with Internalizing Antibodies: Evaluation of $^{125}$I-vs. $^{131}$I-labeled CO17-1A in a Human Colorectal Cancer Model", Int. Journal of Cancer, vol. 76, 1998, pp. 738-748.

Birrer et al., "Antibody-Drug Conjugate-Based Therapeutics: State of the Science", JNCI J Natl. Cancer Institute, vol. 111, No. 6, 2019, pp. 538-549.

Blumenthal et al., "Carcinoembryonic antigen antibody inhibits lung metastasis and augments chemotherapy in a human colonic carcinoma xenograft", Cancer Immunol Immunother, vol. 54, 2005, pp. 315-327.

Blumenthal et al., "Comparison of Equitoxic Radioimmunotherapy and Chemotherapy in the Treatment of Human Colonic Cancer Xenografts", Cancer Research, vol. 54, Jan. 1, 1994, pp. 142-151.

Blumenthal et al., "Inhibition of Adhesion, Invasion, and Metastasis by Antibodies Targeting CEACAM6 (NCA-90) and CEACAM5 (Carcinoembryonic Antigen)", Cancer Research, vol. 65, No. 19, Oct. 1, 2005, pp. 8809-8817.

Boige et al., "Phase I and Pharmacokinetic Study of the Camptothecin Analog DX-8951f Administered as a 30-Minute Infusion Every 3 Weeks in Patients with Advanced Cancer", Journal of Clinical Oncology, vol. 18, No. 23, Dec. 1, 2000, pp. 3986-3992.

Boven et al., "New Analogues of Camptothecins Activity and Resistance", Annals New York Academy of Sciences, 2000, pp. 175-177.

Braybrooke et al., "Phase I and Pharmacokinetic Study of the Topoisomerase I Inhibitor, Exatecan Mesylate (DX-8951f), Using a Weekly 30-Minute Intravenous Infusion, in Patients with Advanced Solid Malignancies", Annals of Oncology, vol. 14, 2003, pp. 913-921.

Braybrooke et al., "Phase II study of exatecan mesylate (DX-8951f) as first line therapy for advanced non-small cell lung cancer", Lung Cancer, vol. 41, 2003, pp. 215-219.

Buchegger et al., "Radioimmunotherapy of Colorectal Cancer Liver Metastases: Combination with Radiotherapy", Annals New York Academy of Sciences 2006, pp. 263-270.

Burke et al. "Optimization of a PEGylated Glucuronide-Monomethylauristatin E Linker for Antibody-Drug Conjugates", Molecular Cancer Therapeutics vol. 16, No. 1, Jan. 2017, pp. 116-123.

Burke et al., "Design, Synthesis, and Biological Evaluation of Antibody-Drug Conjugates Comprised of Potent Camptothecin Analogues", Bioconjugate Chemistry 2009, vol. 20, No. 6, pp. 1242-1250.

Chari et al., "Antibody-Drug Conjugates: An Emerging Concept in Cancer Therapy", Angewandte Chemie International Edition, vol. 53, 2014, pp. 3796-3827.

Chau et al., "Antibody—drug conjugates for cancer", The Lancet, Aug. 31, 2019, vol. 394, pp. 793-804.

Chen et al., "Construction of humanized carcinoembryonic antigen specific single chain variable fragment and mitomycin conjugate", World Journal of Gastroenterol, vol. 13, No. 43, Nov. 21, 2007, pp. 5765-5770.

(56) References Cited

OTHER PUBLICATIONS

Chen et al., "Cloning, Isolation, and Characterization of Mammalian Legumain, an Asparaginyl Endopeptidase", The Journal of Biological Chemistry, vol. 272, No. 12, Mar. 21, 1997, pp. 8090-8098.
Chester et al., "Recombinant anti-carcinoembryonic antigen antibodies for targeting cancer", Cancer Chemother. Pharmacol., vol. 46, 2000, pp. S8-S12.
Chuprakov et al., "Tandem-Cleavage Linkers Improve the In Vivo Stability and Tolerability of Anti-Drug Conjugates", Bioconjugate Chemistry, vol. 32, 2021, pp. 746-754.
Clamp et al., "A Phase IIA Study of the Topoisomerase I Inhibitor, Exatecan Mesylate (DX-8951f), Administered at two different dose schedules in Patients with Platinum- and Taxane-Resistant/Refractory Ovarian Cancer", Gynecologic Oncology, vol. 95, 2004, pp. 114-119.
Compain et al., "A β-glucuronidase-responsive albumin-binding prodrug for potential selective kinase inhibitor-based cancer chemotherapy", European Journal of Medicinal Chemistry, vol. 158, 2018, pp. 1-6.
Cortés et al., "Trastuzumab Deruxtecan versus Trastuzumab Emtansine for Breast Cancer", The New England Journal of Medicine, vol. 386, No. 12, Mar. 24, 2022, pp. 1143-1154.
Criscitiello et al., "Antibody-drug conjugates in solid tumors: a look into novel targets", Journal of Hematology & Oncology, vol. 14, No. 20, pp. 1-18.
Dall et al., "Structure and function of legumain in health and disease", Biochimie, vol. 122, 2016, pp. 126-150.
David M. Goldenberg, "Carcinoembryonic Antigen as a Target Cancer Antigen for Radiolabeled Antibodies: Prospects for Cancer Imaging and Therapy", Tumor Biol., vol. 16, 1995, pp. 62-73.
Decary et al., "Abstract 1688: A novel anti-CEACAM5 maytansinoid-antibody-drug conjugate for the treatment of colorectal, lung and gastric tumors", Experimental and Molecular Therapeutics, Cancer Research, vol. 75, Issue 15, Aug. 2015, 4 pages.
Decary et al., "Preclinical Activity of SAR408701: A Novel Anti-CEACAM5- maytansinoid Antibody-drug Conjugate for the Treatment of CEACAM5-positive Epithelial Tumors", Clinical Cancer Research, vol. 26, No. 24, Dec. 15, 2020, pp. 6589-6599.
Delucia et al., "Regulation of CEACAM5 and Therapeutic Efficacy of an Anti- CEACAM5-SN38 Antibody-drug Conjugate in Neuroendocrine Prostate Cancer", Clinical Cancer Research, vol. 27, No. 3, Feb. 1, 2021, pp. 759-774.
Doi et al., "Safety, pharmacokinetics, and antitumour activity of trastuzumab deruxtecan (DS-8201), a HER2-targeting antibody-drug conjugate, in patients with advanced breast and gastric or gastro-oesophageal tumours: a phase 1 dose- escalation study", The Lancet Oncology, vol. 18, Nov. 2017, pp. 1512-1522.
Dong et al., "Antibody-drug conjugates of 7-ethyl-10-hydroxycamptothecin: Sacituzumab govitecan and labetuzumab govitecan", European Journal of Medicinal Chemistry, vol. 167, 2019, pp. 583-593.
Dotan et al., "Phase I/II Trial of Labetuzumab Govitecan (Anti-CEACAM5/SN-38 Antibody-Drug Conjugate) in Patients With Refractory or Relapsing Metastatic Colorectal Cancer", Journal of Clinical Oncology, vol. 35, No. 29, Oct. 10, 2017, pp. 3338-3346.
Drago et al. "Unlocking the potential of antibody-drug conjugates for cancer therapy", Nature Reviews, Clinical Oncology, 2021, 18 pages.
Dubowchik et al., "Cathepsin B-Sensitive Dipeptide Prodrugs. 1.A Model Study of Structural Requirements for Efficient Release of Doxorubicin", Bioorganic & Medicinal Chemistry Letter, vol. 8, 1998, pp. 3341-3346.
Ebrahimnejad et al., "Cell Adhesion Molecule CEACAM1 Associates with Paxillin in Granulocytes and Epithelial and Endothelial Cells", Rapid Communication, Experimental Cell Research, vol. 260, 2000, pp. 365-373.
Edupuganti et al., "Self-immolative Linkers in Prodrugs and Antibody Drug Conjugates in Cancer Treatment", Recent Patents on Anti-Cancer Drugs Discovery, vol. 16, No. 4, 2021, pp. 479-497.
Elie Dolgin, "Specter of eye toxicity looms over BCMA-targeted therapy", Nature Biotechnology, vol. 38, Dec. 2020, pp. 1363-1370.
Esteva et al., "A Phase II Study of Intravenous Exatecan Mesylate (DX-8951f) Administered Daily for 5 Days Every 3 Weeks to Patients with Metastatic Breast Carcinoma", Cancer, vol. 98, No. 5, Sep. 1, 2003, pp. 900-907.
Ford et al., "Localisation and toxicity study of a vindesine-anti-CEA conjugate in patients with advanced cancer", British Journal of Cancer, vol. 47, 1983, pp. 035-042.
Francis et al., A phase I trial of antibody directed enzyme prodrug therapy (ADEPT) in patients with advanced colorectal carcinoma or the other CEA producing tumours, British Journal of Cancer, vol. 87, 2002, pp. 600-607.
Fu et al., "DNA damaging agent-based antibody-drug conjugates for cancer therapy", Antibody Therapeutics, vol. 1, No. 2, 2018, pp. 43-53.
Garrison et al., "A Phase I and Pharmocokinetic Study of Exatecan Mesylate Administered as a Protracted 21-Day Infusion in Patients with Advanced Solid Malignancies", Clinical Cancer Research, vol. 9, Jul. 2003, pp. 2527-2537.
Gazzah et al., "Safety, pharmacokinetics, and antitumor activity of the anti-CEACAM5-DM4 antibody-drug conjugate tusamitamab ravtansine (SAR408701) in patients with advanced solid tumors: first-in-human dose-escalation study", Annals of Oncology, vol. 33, Issue 4, 2022, pp. 416-425.
Giles et al., "Phase I and Pharmacokinetic Study of DX-8951f (Exatecan Mesylate), a Hexacyclic Camptothecin, on a Daily-Times-Five Schedule in Patients with Advanced Leukemia" Clinical Cancer Research, vol. 8, Jul. 2002 pp. 2134-2141.
De Goeij et al., "New developments for antibody-drug conjugate-based therapeutic approaches", Current Opinion in Immunology, vol. 40, pp. 14-23.
Gold et al., "Demonstration of Tumor-Specific Antigens in Human Colonic Carcinomata by Immunological Tolerance and Absorption Techniques", The Journal of Experimental Medicine, vol. 121, Nov. 16, 1964, 33 pages.
De Gooyer et al., "Mutimodal CEA-Targeted Image-Guided Colorectal Cancer Surgery using In-Labeled SGM-101", Clinical Cancer Research, vol. 26, No. 22 Nov. 15, 2020, pp. 5934-5942.
De Gooyer et al., "Multimodal CEA-targeted fluorescence and radioguided cytoreductive surgery for peritoneal metastases of colorectal origin", Nature Communications, vol. 13, No. 2621, 2022, pp. 1-10.
Govindan et al., "Improving the Therapeutic Index in Cancer Therapy by Using Antibody-Drug Conjugates Designed with a Moderately Cytotoxic Drug", American Chemical Society, Molecular Pharmaceutics, vol. 12, 2015, pp. 1836-1847.
Govindan et al., "CEACAM5-Targeted Therapy of Human Colonic and Pancreatic Cancer Xenografts with Potent Labetuzumab-SN-38 Immunoconjugates", Clinical Cancer Research, vol. 15, No. 19, Oct. 1, 2009, pp. 6052-6061.
Gregson et al., "Synthesis and evaluation of pyrrolobenzodiazepine dimer antibody-drug conjugates with dual β-glucuronide and dipeptide triggers", European Journal of Medicinal Chemistry, vol. 179, 2019, pp. 591-607.
Haikala et al., "EGFR Inhibition Enhances the Cellular Uptake and Antitumor-Activity of the HER3 Antibody-Drug Conjugate HER3-DXd", Cancer Research, vol. 82, No. 1, Jan. 1, 2022, pp. 130-141.
Hajjar et al., "Phase I Radioimmunotherapy Trial with Iodine-131-Labeled Humanized MN-14 Anti-Carcinoembryonic Antigen Monoclonal Antibody in Patients with Metastatic Gastrointestinal and Colorectal Cancer", Clinical Colorectal Cancer, vol. 2, No. 1, May 2002, pp. 31-42.
Hamblett et al., "SLC46A3 is Required to Transport Catabolites of Noncleavable Antibody Maytansine Conjugates from the Lysosome to the Cytoplasm", American Association for Cancer Research, vol. 75, No. 24, Dec. 15, 2015, pp. 5329-5340.
Hamilton et al., 204TiP "A phase II study of HER3-DXD in patients (pts) with metastatic breast cancer (MBC)", Annals of Oncology, vol. 33, Issue S3, 2022, p. S220.
Hamilton et al., "Improving Antibody-Tubulysin Conjugates through Linker Chemistry and Site-Specific Conjugation", ChemMedChem, vol. 16, 2021, pp. 1077-1081.

(56) References Cited

OTHER PUBLICATIONS

Han et al., "The old CEACAMs find their new role in tumor immunotherapy", Investigational New Drug, vol. 38, 2020, pp. 1888-1898.
Hansen et al., "Characterization of Second-Generation Monoclonal Antibodies Against Carcinoembryonic Antigen", Cancer, vol. 71, No. 11, Jun. 1, 1993, pp. 3478-3485.
Van Hattum et al., "Induction of Breast Cancer Resistance Protein by the Camptothecin Derivative DX-8951f Is Associated with Minor Reduction of Antitumour Activity", British Journal of Cancer, vol. 87, 2002, pp. 665-672.
Van Hattum et al., "The Activity Profile of the Hexacyclic Camptothecin Derivative DX-8951f in Experimental Human Colon Cancer and Ovarian Cancer", Biochemical Pharmacology, vol. 64, 2002, pp. 1267-1277.
Haugen et al., "High expression of the cysteine proteinase legumain in colorectal cancer Implications for therapeutic targeting", European Journal of Cancer, vol. 51, 2015, pp. 9-17.
He et al., "Inflammatory Monocytes Loading Protease-Sensitive Nanoparticles Enable Lung Metastasis Targeting and Intelligent Drug Release for Anti-Metastasis Therapy", American Chemical Society, NANO Letters, vol. 17, 2017, pp. 5546-5554.
Heather Donaghy, "Effects of antibody, drug and linker on the preclinical and clinical toxicities of antibody-drug conjugates", vol. 8, No. 4, 2016, pp. 659-671.
Hezareh et al., "Effector Function Activities of a Panel of Mutants of a Broadly Neutralizing Antibody against Human Immunodeficiency Virus Type 1", Journal of Virology, vol. 75, No. 24, Dec. 2001, pp. 12161-12168.
Hollandsworth et al., "A review of tumor-specific fluorescence-guided surgery for colorectal cancer", Surgical Oncology, vol. 36, 2021, pp. 84-90.
Hyunbo Shim, "Bispecific Antibodies and Antibody-Drug Conjugates for Cancer Therapy: Technological Considerations", Biomolecules, vol. 10, No. 360, 2020, pp. 1-31.
Imakiire et al., "Generation, Immunologic Characterization and Antitumor Effects of Human Monoclonal Antibodies for Carcinoembryonic Antigen", Int. Journal of Cancer, vol. 108, 2004, pp. 564-570.
Kazuhiro Inoue et al., "CM-Dextran-Polyalcohol-Camptothecin Conjugate", Polymer Drugs in the Clinical Stage, edited by Maeda et al., 2003, pp. 145-153.
International Search Report issued Nov. 16, 2021, in PCT/EP2021/072595, 8 pages.
Mineko Ishii et al., "Growth Inhibitory Effect of a New Camptothecin Analog, DX-8951f, on Various Drug-Resistant Sublines Including BCRP-Mediated Camptothecin Derivative-Resistant Variants Derived from the Human Lung Cancer Cell Line PC-6", Anti-Cancer Drugs, vol. 11, 2000, pp. 353-362.
Junko Iwano et al., "Impact of Different Selectivity between Soluble and Membrane-bound Forms of Carcinoembryonic Antigen (CEA) on the Target-mediated Disposition of Anti-CEA Monoclonal Antibodies", Drug Metabolism and Disposition, vol. 47, Nov. 2019, pp. 1240-1246.
Tomomi Nakayama Iwata et al., "A HER2-Targeting Antibody-Drug Conjugate, Trastuzumab Deruxtecan (DS-8201a), Enhances Antitumor Immunity in a Mouse Model", Molecular Cancer Therapeutics, vol. 17, No. 7, Jul. 2018, pp. 1494-1503.
De Jager et al., "DX-8951f: Summary of Phase I Clinical Trials", Annals New York Academy of Sciences 922, 2000, pp. 260-273.
Jänne et al., "Efficacy and Safety of Patritumab Deruxtecan (HER3-DXd) in EGFR Inhibitor-Resistant, EGFR-Mutated Non-Small Cell Lung Cancer", American Association of Cancer Research, Cancer Discovery, Jan. 2022, pp. 74-89.
Jänne et al., "P01.03 Phase 1 Study of Patritumab Deruxtecan (HER3-DXd; U3-1402) in Combination with Osimertinib in Patients with Locally Advanced or Metastatic EGFR-mutated NSCLC", Journal of Thoracic Oncology 2021, vol. 16, Nr. 3, pp. S237.
Jeffrey et al., "Development and Properties of β-Glucuronide Linkers for Monoclonal Antibody-Drug Conjugates", Bioconjugate Chemistry, vol. 17, 2006, pp. 831-840.
Jeffrey et al., "Expanded Utility of the β-Glucuronide Linker: ADCs That Deliver Phenolic Cytotoxic Agents", ACS Medicinal Chemistry Letters, American Chemical Society, vol. 1, 2010, pp. 277-280.
Jeffrey et al., "Minor groove binder antibody conjugates employing a water soluble β-glucuronide linker", Bioorganic & Medicinal Chemistry Letter, vol. 17, 2007, pp. 2278-2280.
Johnson et al., "A Vindesine-Anti-Cea Conjugate Cytotoxic for Human Cancer Cells In Vitro", British Journal of Cancer, vol. 44, No. 372, 1981, pp. 472-475.
Joto et al., "DX-8951f, a Water-Soluble Camptothecin Analog, Exhibits Potent Antitumor Activity against a Human Lung Cancer Cell Line and Its SN-38-Resistant Variant", International Journal of Cancer, vol. 72, 1997, pp. 680-686.
Kabraji et al., "Preclinical and Clinical Efficacy of Trastuzumab Deruxtecan in Breast Cancer Brain Metastases", Clinical Cancer Research, vol. 29, No. 1, Jan. 1, 2023, pp. 174-182.
Kammerer et al., "Coevolution of activating and inhibitory receptors within mammalian carcinoembryonic antigen families", BMC Biology, vol. 8, No. 12, 2010, pp. 1-21.
Karol Michal Kacprzak, "Chemistry and Biology of Camptothecin and its Derivatives", Springer-Verlag Berlin Heidelberg, 2013, pp. 643-682.
Khongorzul et al., "Antibody-Drug Conjugates: A Comprehensive Review", Molecular Cancer Research, vol. 18, No. 1, Jan. 2020, pp. 3-19.
Kimio Yonesaka, "HER2-/HER3-Targeting Antibody-Drug Conjugates for Treating Lung and Colorectal Cancers Resistant to EGFR Inhibitors", Cancers, vol. 13, No. 1047, 2021, pp. 1-13.
Koganemaru et al. "U3-1402, a Novel HER3-Targeting Antibody-Drug Conjugate, for the Treatment of Colorectal Cancer", Molecular Cancer Therapeutics, vol. 18, No. 11, 2019, pp. 2043-2050.
Koyama et al., "Patritumab deruxtecan (HER3-DXd), a novel HER3 directed antibody drug conjugate, exhibits in vitro activity against breast cancer cells expressing HER3 mutations with and without HER2 overexpression", PLOS ONE, May 3, 2022, pp. 1-10.
Kumazawa et al., "DE-310, a Novel Macromolecular Carrier System for the Camptothecin Analog DX-8951f: Potent Antitumor Activities in Various Murine Tumor Models", Cancer Science, vol. 95, No. 2, Feb. 2004, pp. 168-175.
Kumazawa et al., "Potent and Broad Antitumor Effects of DX-8951f, a Water-Soluble Camptothecin Derivative, against Various Human Tumors Xenografted in Nude Mice", Cancer Chemotherapy and Pharmacology, vol. 42, 1998, pp. 210-220.
Lau et al., "Lactone Stabilization is Not a Necessary Feature for Antibody Conjugates of Camptothecins", Molecular Pharmaceutics, American Chemical Society, Aug. 1, 2018, 10 pages.
Lawrence et al., "Comparison of DX-8951f and topotecan effects on tumor colony formation from freshly explant adult and pediatric human tumor cells", Anti-Cancer Drugs, vol. 10, 1999, pp. 655-661.
L. Nathan Tumey, "Next Generation Payloads for ADCs", M.Damelin, (ed.) Innovations for Next-Generation Antibody-Drug Conjugates. Cancer Drug Discovery and Development. Humana Press, Cham., 2018, pp. 187-214.
Lee et al., "Quantification of an Antibody-Conjugated Drug in Fat Plasma by an Affinity Capture LC-MS/MS Method for a Novel Prenyl Transferase-Mediated Site-Specific Antibody-Drug Conjugate", Molecules, vol. 25, No. 1515, 2020, pp. 1-10.
Lerchen et al., "Antibody-Prodrug Conjugates with KSP Inhibitors and Legumain-Mediated Metabolite Formation", Chemistry European Journal, vol. 25, 2019, pp. 8208-8213.
Lerchen et al., "Tailored Linker Chemistries for the Efficient and Selective Activation of ADCs with KSPi Payloads" Bioconjugate Chemistry, 2020, vol. 31, pp. 1893-1898.
Lewēn et al., "A Legumain-based minigene vaccine targets the tumor stroma and suppresses breast cancer growth and angiogenesis", Cancer Immunol Immunother., vol. 57, 2008, pp. 507-515.
Na Li et al., "Effects of legumain as a potential prognostic factor on gastric cancers" Medical Oncology, vol. 30, No. 621, 2013, pp. 1-12.

(56) References Cited

OTHER PUBLICATIONS

Bob T. Li et al., "Trastuzumab Deruxtecan in HER2-Mutant Non-Small-Cell Lung Cancer", The New England Journal of Medicine, vol. 386, 2022, pp. 241-251.
Fu Li et al., "Intracellular Released Payload Influences Potency and Bystander-Killing Effects of Antibody-Drug Conjugates in Preclinical Models", Cancer Research, vol. 76, No. 9, May 1, 2016, pp. 2710-2719.
Yang Li et al., "Tailor-made legumain/pH dual-responsive doxorubicin prodrug-embedded nanparticales for efficient anticancer drug delivery and in situ monitoring of drug release", Nanoscale, vol. 12, 2020, pp. 2673-2685.
Hongcheng Liu et al., "Disulfide bond structures of IgG molecules—Structural variations, chemical modifications and possible impacts to stability and biological function", Landes Bioscience, vol. 4, No. 1, Jan./Feb. 2012, pp. 17-23.
Ze Liu et al., "Legumain protease-activated TAT-liposome cargo for targeting tumours and their microenvironment", Nature Communications, vol. 5, Issue 4280, Jun. 27, 2014, pp. 1-11.
Lyon et al., "Reducing hydrophobicity of homogeneous antibody-drug conjugates improves pharmacokinetics and therapeutic index", Nature Biotechnology, vol. 33, No. 7, Jul. 2015, pp. 733-736.
Lyski et al., "Development of Novel Antibody-Camptothecin Conjugates", Molecular Cancer Therapeutics, vol. 20, Issue 2, Feb. 2021, pp. 329-339.
Manoury et al., "Asparagine Endopeptidase can Initiate the Removal of the MHC Class II Invariant Chain Chaperone" Immunity, Humana Press, vol. 18, Apr. 2003, pp. 489-498.
Marc Damelin, "Innovations for Next-Generation Antibody-Drug Conjugates" Cancer Drug Discovery and Development 2018, Humana Press, Cham., 2018, 358 pages.
Marcin Poreba et al., "Recent advances in the development of legumain-selective chemical probes and peptide prodrugs", Biological Chemistry vol. 400, No. 12, 2019, pp. 1529-1550.
Masters et al., "Clinical toxicity of antibody drug conjugates: a meta-analysis of payloads", Invest. New Drugs, 2018, vol. 36, pp. 121-135.
Masubuchi et al., "A Predictive Model of Human Myelotoxicity Using Five Camptothecin Derivatives and the in Vitro Colony-Forming Unit Granulocyte/Macrophage Assay", Clincal Cancer Research, vol. 10, Oct. 1, 2004, pp. 6722-6731.
Mattock et al., "Legumain and cathepsin-L expression in human unstable carotid plaque" Atherosclerosis, vol. 208, 2010, pp. 83-89.
Mauricio et al., "Trastuzumab deruxtecan (DS-8201a), a HER2-targeting antibody-drug conjugate with topoisomerase I inhibitor payload, shows antitumor activity in uterine and ovarian carcinosarcoma with HER2/neu expression", Gynecologic Oncology, vol. 170, pp. 38-45.
Bodet-Milin et al., "Clinical Result in Medullary Thyroid Carcinoma Suggest High Potential of Pretargeted Immuno-PET for Tumor Imaging and Theranostic Approaches", Frontiers in Medicine, vol. 6, Article 124, Jun. 2019, pp. 1-7.
Miller et al., "Enzyme-Agnostic Lysosomal Screen Indentifies New Legumain-Cleavable ADC Linkers", Bioconjugate Chemistry, vol. 32, 2021, pp. 842-858.
Minami et al., "Phase I and Pharmacological Study of a New Camptothecin Derivative, Exatecan Mesylate (DX-8951f), Infused over 30 Minutes Every Three Weeks" Clinical Cancer Research, vol. 7, Oct. 2001, pp. 3056-3064.
Mitsui et al., "A New Water-Soluble Camptothecin Derivative, DX-8951f, Exhibits Potent Antitumor Activity against Human Tumors in Vitro and in Vivo" Japanese Journal of Cancer Research, vol. 86, Aug. 1995, pp. 776-782.
Modi et al., "Antitumor Activity and Safety of Trastuzumab Deruxtecan in Patients with HER2-Low-Expressing Advanced Breast Cancer: Results From a Phase Ib Study", Journal of Clinical Oncology, vol. 38, Issue 17, 2020, pp. 1887-1896.
Modi et al., "Trastuzumab Deruxtecan in Previously Treated HER2-Low Advanced Breast Cancer", The New England Journal of Medicine, vol. 387, No. 1, Jul. 7, 2022, pp. 9-20.
Morita et al., "Legumain/asparaginyl endopeptidase controls extracellular matrix remodeling through the degradation of fibronectin in mouse renal proximal tubular cells", FEBS Letters, vol. 581, 2007, pp. 1417-1424.
Murakami et al., "A reference of the GOLD classification of monoclonal antibodies against carcinoembryonic antigen to the domain structure of the carcinoembryonic antigen molecule", Hybridoma, vol. 14, No. 1, 1995, pp. 19-28.
Nagai et al., "Comprehensive preclinical pharmacokinetic evaluations of trastuzumab deruxtecan(DS-8201a), a HER2-targeting antibody-drug conjugate, in cynomolgus monkeys", Xenobiotica, vol. 49, No. 9, 2019, pp. 1086-1096.
Nakada Takashi et al., "Novel antibody drug conjugates containing exatecan derivative-based cytotoxic payloads", Bioorganic & Medicinal Chemistry Letters, vol. 26, 2016, pp. 1542-1545.
Nakada et al., "The Latest Research and Development into the Antibody-Drug Conjugate, [fam-] Trastuzumab Deruxtecan (DS-8201a), for HER2 Cancer Therapy", Chem. Pharm Bull, vol. 67, No. 3, 2019, pp. 173-185.
Nielsen et al., "Carcino-Embryonic Antigen (Cea) In Gastric Adenocarcinomas", Acta. Path. Microbiol. Immunil. Scand. Sect. A, vol. 90, 1982, pp. 393-396.
Nomoto et al., "Characterization of a Human Small-Cell Lung Cancer Cell Line Resistant to a New Water-Soluble Camptothecin Derivative, DX-8951f", Japanese Journal of Cancer Research, vol. 89, Nov. 1998, pp. 1179-1186.
Ochi et al., "A Possible Mechanism for the Long-Lasting Antitumor Effect of the Macromolecular Conjugate DE-310: Mediation by Cellular Uptake and Drug Release of Its Active Camptothecin Analog DX-8951", Cancer Chemotherapy and Pharmacology, vol. 55, 2005, pp. 323-332.
Ogitani et al., "Bystander killing effect of DS-8201a, a novel anti-human epidermal growth factor receptor 2 antibody-drug conjugate, in tumors with human epidermal growth factor receptor 2 heterogeneity", Cancer Science, Jul. 2016, vol. 107, No. 7, pp. 1039-1046.
Ogitani et al., "DS-8201a, A Novel HER2-Targeting ADC with a Novel DNA Topoisomerase I Inhibitor, Demonstrates a Promising Antitumor Efficacy with Differentiation from T-DM1", Clinical Cancer Research, vol. 22, No. 20, Oct. 15, 2016, pp. 5097-5108.
Oguma et al., "High-Performance Liquid Chromatographic Analysis of Lactone and Hydroxy Acid of New Antitumor Drug, DX-8951 (Exatecan), in Mouse Plasma",Biological & Pharmaceutical Bulletin, vol. 24, No. 2, 2001, pp. 176-180.
Oguma et al., "Sensitive High-Performance Liquid Chromatographic Method for the Determination of the Lactone Form and the Lactone plus Hydroxy-Acid Forms of the New Camptothecin Derivative DX-8951 in Human Plasma Using Fluorescence Detection", Journal of Chromatography B, vol. 740, 2000, pp. 237-245.
Oguma et al., "Validation Study of Assay Method for DX-8951 and Its Metabolite in Human Plasma and Urine by High-Performance Liquid Chromatography/Atmospheric Pressure Chemical Ionization Tandem Mass Spectrometry ", Biomedical Chromatography, vol. 15, 2001, vol. 108-115.
Okajima et al., "Datopotamab Deruxtecan, a Novel TROP2-directed Antibody-drug Conjugate, Demonstrates Potent Antitumor Activity by Efficient Drug Delivery to Tumor Cells", Molecular Cancer Therapeutics, vol. 20, No. 12, Dec. 2021, pp. 2329-2340.
P. Maxwell, "Carcinoembryonic antigen: cell adhesion molecule and useful diagnostic marker" British Journal of Biomedical Science, vol. 56, 1999, pp. 209-214.
Panousis et al., "Monoclonal Antibody-Directed Cytotoxic Therapy", Drugs & Aging, vol. 15, No. 1, Jul. 1999, pp. 1-13.
Peng et al., "The CEA/CD3-bispecific antibody MEDI-565 (MT111) binds a nonlinear epitope in the full-length but not a short splice variant of CEA", PLOS ONE, vol. 7, No. 5, e36412, May 2012, pp. 1-14.
Poreba et al., "Counter Selection Substrate Library Strategy for Developing Specific Protease Substrates and Probes", Cell Chemical Biology, vol. 23, Aug. 18, 2016, pp. 1023-1035.
Poreba et al., "Unnatural amino acids increase sensitivity and provide for the design of highly selective caspase substrates" Cell Death and Differentiation, vol. 21, 2014, pp. 1482-1492.

(56) References Cited

OTHER PUBLICATIONS

Pouzin et al., "Integrated multiple analytes and semi-mechanistic population pharmacokinetic model of tusamitamab ravtansine, a DM4 anti-CEACAM5 antibody-drug conjugate", Journal of Pharmacokinetics and Pharmacodynamics, 2022, 14 pages.
Pouzin et al., "Covariate analysis of tusamitamab ravtansine, a DM4 anti-CEACAM5 antibody-drug conjugate, based on first-in-human study", CPT Pharmacometrics & Systems Pharmacology, vol. 11, 2022, pp. 384-394.
Reichardt et al., "Exatecan in Pretreated Adult Patients with Advanced Soft Tissue Sarcoma: Results of a Phase II-Study of the EORTC Soft Tissue and Bone Sarcoma Group", European Journal of Cancer, vol. 43, 2007, pp. 1017-1022.
Rijpkema et al., "SPECT—and Fluorescence Image-Guided Surgery Using a Dual-Labeled Carcinoembryonic Antigen-Targeting Antibody", Journal of Nuclear Medicine, vol. 55, No. 9, Sep. 2014, pp. 1519-1524.
Riva et al., "Treatment of Metastatic Colorectal Cancer by Means of Specific Monoclonal Antibodies Conjugated with Iodine-131: a Phase II Study", Nuclear Medicine and Biology, vol. 18, No. 1, 1991, pp. 109-119.
Rivault et al., "A new linker for glucuronylated anticancer prodrugs", Bioorganic & Medicinal Chemistry, vol. 12, No. 4, 2004, pp. 675-682.
Paula Rivas Lopez et al., "β-Glucuronidase triggers extracellular MMAE release from an integrin-targeted conjugate", Organic & Biomolecular Chemistry, vol. 17, 2019, pp. 4705-4710.
Rowinsky et al., "DX-8951f, a Hexacyclic Camptothecin Analog, on a Daily—Times—Five Schedule: A Phase I and Pharmacokinetic Study in Patients with Advanced Solid Malignancies", Journal of Clinical Oncology: Official Journal of the American Society of Clinical Oncology, vol. 18, No. 17, Sep. 2000 pp. 3151-3163.
Royce et al., "A Phase II Study of Intravenous Exatecan Mesylate (DX-8951f) Administered Daily for Five Days Every Three Weeks to Patients with Metastatic Adenocarcinoma of the Colon or Rectum", Investigational New Drugs, vol. 22, 2004, pp. 53-61.
Royce et al., "Phase I and Pharmacokinetic Study of Exatecan Mesylate (DX-8951f): A Novel Camptothecin Analog", Journal of Clinical Oncology, vol. 19, No. 5 Mar. 1, 2001, pp. 1493-1500.
Martinez-Sabadell et al., "The target antigen determines the mechanism of acquired resistance to T cell-based therapies", Cell Reports, vol. 41, No. 111430, 2022, 22 pages.
Sahlmann et al., "Repeated Adjuvant Anti-CEA Radioimmunotherapy After Resection of Colorectal Liver Metastases: Safety, Feasibility, and Long-Term Efficacy Results of a Prospective Phase 2 Study", Cancer, Feb. 15, 2017,pp. 638-649.
Schlothauer et al., "Novel human IgG1 and IgG4 Fc-engineered antibodies with completely abolished immune effector functions", Protein Engineering, Design & Selection, vol. 29, No. 10, 2016, pp. 457-466.
Schmidt et al., "Kinetics of anti-carcinoembryonic antigen antibody internalization: effects of affinity, bivalency, and stability", Cancer Immunol Immunother, vol. 57, 2008, pp. 1879-1890.
Sharkey et al., "Selective and Concentrated Accretion of SN-38 with a CEACAM5-Targeting Antibody-Drug Conjugate (ADC), Labetuzumab Govitecan (IMMU-130)", Molecular Cancer Therapeutics, vol. 17, No. 1, Jan. 2018, pp. 196-203.
Sharkey et al., "Clinical Evaluation of Tumor Targeting with a High-Affinity Anticarcinoembryonic-Antigen-Specific, Murine Monoclonal Antibody, MN-14", Cancer, vol. 71, No. 6, Mar. 15, 1993, pp. 2082-2096.
Sharkey et al., "Evaluation of a Complementarity-Determining Region-Grafted (Humanized) Anti-Carcinoembryonic Antigen Monoclonal Antibody in Preclinical and Clinical Studies", Cancer Research (Suppl.), vol. 55, Dec. 1, 1995, pp. 5935s-5945s.
Sharkey et al., "Murine Monoclonal Antibodies against Carcinoembryonic Antigen: Immunological, Pharmacokinetic, and Targeting Properties in Humans", Cancer Research, vol. 50, May 1, 1990, pp. 2823-2831.
Sharkey et al., "Radioimmunotherapy of Human Colonic Cancer Xenografts with $^{90}$Y-labeled Monoclonal Antibodies to Carcinoembryonic Antigen[1]", Cancer Research, vol. 48, Jun. 1, 1988, pp. 3270-3275.
Sharma et al., "Phase I Study of Topoisomerase I Inhibitor Exatecan Mesylate (DX-8951f) given as Weekly 24-Hour Infusions Three of Every Four Weeks", Clinical Cancer Research, vol. 7, Dec. 2001, pp. 3963-3970.
Shastry et al., "Antibody-drug conjugates targeting TROP-2: Clinical development in metastatic breast cancer", The Breast, vol. 66, 2022, pp. 169-177.
Shi et al., "Identification of CEACAM5 as a stemness-related inhibitory immune checkpoint in pancreatic cancer", BMC Cancer, vol. 22, No. 1291, 2022, pp. 1-14.
Shinmi et al., "Novel anticarcinoembryonic antigen-drug conjugates has antitumor activity in the existence of soluble antigen" Cancer Medicine, vol. 6, No. 4, 2017, pp. 798-808.
Shiose et al., "Quantitative Acid Hydrolysis of DE-310, a Macromolecular Carrier System for the Camptothecin Analog DX-8951f". Journal of Pharmaceutical and Biomedical Analysis, vol. 43, 2007, pp. 1290-1296.
Shiose et al., "Relationship between Drug Release of DE-310, Macromolecular Prodrug of DX-8951f, and Cathepsins Activity in Several Tumors" Biological and Pharmaceutical Bulletin, vol. 30, No. 12, 2007, pp. 2365-2370.
Shirahama-Noda et al., "Biosynthetic Processing of Cathepsins and Lysosomal Degradation Are Abolished in Asparaginyl Endopeptidase-deficient Mice" Journal of Biological Chemistry, vol. 278, No. 35, Aug. 29, 2003, pp. 33194-33199.
Shitara et al., "Trastuzumab Deruxtecan in Previously Treated HER2-Positive Gastric Cancer", The New England Journal Medicine, vol. 382, No. 25, Jun. 18, 2020, pp. 2419-2430.
Shitara et al., "Trastuzumab deruxtecan (DS-8201a) in patients with advanced HER2-positive gastric cancer: a dose-expansion, phase 1 study", Lancet Oncology, vol. 20, Jun. 2019, pp. 827-836.
Siena et al., "Trastuzumab deruxtecan (DS-8201) in patients with HER2-expressing metastatic colorectal cancer (DESTINY-CRC01): a multicentre, open-label, phase 2 trial", Lancet Oncology, vol. 22, 2021, pp. 779-789.
Soepenberg et al., "Phase I and Pharmacokinetic Study of DE-310 in Patients with Advanced Solid Tumors", Clinical Cancer Research, vol. 11, Jan. 15, 2005, pp. 703-711.
Starling, et al., "In Vivo Antitumor Activity of a Panel of Four Monoclonal Antibody-Vinca Alkaloid Immunoconjugates Which Bing to Three Distinct Epitopes of Carcinoembryonic Antigen", Bioconjugate Chemistry, vol. 3, 1992, pp. 315-322.
Stein et al., "A humanized monoclonal antibody to carcinoembryonic antigen, labetuzumab, inhibits tumor growth and sensitizes human medullary thyroid cancer xenografts to dacarbazine chemotherapy", Molecular Cancer Therapeutics, vol. 3, No. 12, Dec. 2004, pp. 1559-1564.
Stern et al., "A Novel Antitumor Prodrug Platform Designed to Be Cleaved by the Endoprotease Legumain", Bioconjugate Chem., vol. 20, 2009, pp. 500-510.
Steuer et al., "Efficacy and safety of patritumab deruxtecan (HER3-DXd) in advanced/metastatic non-small cell lung cancer (NSCLC) without EGFR-activating mutations", Lung Cancer—Non-Small Cell Metastatic, Journal of Clinical Oncology 2022, vol. 40, Nr. 16_suppl, 2022, pp. 9017.
Strickland et al., "Preclinical evaluation of carcinoembryonic cell adhesion molecule (CEACAM) 6 as potential therapy target for pancreatic adenocarcinoma", Journal of Pathology, vol. 218, 2009, pp. 380-390.
Sun et al., "Efficacy of Camptothecin Analog DX-8951f (Exatecan Mesylate) on Human Pancreatic Cancer in an Orthotopic Metastatic Model", Cancer Research, vol. 63, Jan. 1, 2003, pp. 80-85.
Takegawa et al., "[fam-] trastuzumab deruxtecan, antitumor activity is dependent on HER2 expression level rather than on HER2 amplification", International Journal of Cancer, vol. 145, 2019, pp. 3414-3424.
Takegawa et al., "DS-8201a, a new HER2-targeting antibody-drug conjugate incorporating a novel DNA topoisomerase I inhibitor,

(56) References Cited

OTHER PUBLICATIONS overcomes HER2-positive gastric cancer T-DM1 resistance", International Journal of Cancer, vol. 141, 2017, pp. 1682-1689.
Takiguchi et al., "Antitumor Effect of DX-8951, a Novel Camptothecin Analog, on Human Pancreatic Tumor Cells and Their CPT-11-Resistant Variants Cultured in Vitro and Xenografted into Nude Mice", Japanese Journal of Cancer Research, vol. 88, Aug. 1997, pp. 760-769.
Tamura et al., "Trastuzumab deruxtecan (DS-8201a) in patients with advanced HER2-positive breast cancer previously treated with trastuzumab emtansine: a dose-expansion, phase 1 study", Lancet Oncology, vol. 20, Jun. 2019, pp. 816-826.
Thomas et al., "Targeting Topoisomerase I in the Era of Precision Medicine", published online Jun. 21, 2019, Clinical Cancer Research, 26 pages.
Tranoy-Opalinski et al., "β-Glucuronidase-responsive prodrugs for selective cancer chemotherapy: An update", European Journal of Medicinal Chemistry, vol. 74, 2014, pp. 302-313.
Tsai et al., "Growth Suppression of Human Colorectal Carcinoma in Nude Mice by Monoclonal Antibody C27-Abrin A Chain Conjugate" Dis Colon Rectum, vol. 38, No. 10, Oct. 1995, pp. 1067-1074.
Tsuchikama et al., "Antibody-drug conjugates: recent advances in conjugation and linker chemistries", Protein Cell, vol. 9, No. 1, 2018, pp. 33-46.
Tsurutani et al., "Targeting HER2 with Trastuzumab Deruxtecan: A Dose-Expansion, Phase I Study in Multiple Advanced Solid Tumors", Cancer Discovery, May 2020, pp. 688-701.
Turner et al., "The Use of Fluorescent Anti-CEA Antibodies to Label, Resect and Treat Cancers: A Review", Biomolecules, vol. 11, No. 1819, 2021, pp. 1-16.
Uppal et al., "Potential Mechanisms for Thrombocytopenia Development with Trastuzumab Emtansine (T-DM1)", Clinical Cancer Research, vol. 21, No. 1, Jan. 1, 2015, pp. 123-133.
Ichiro Uyama et al., "Improvement of Therapeutic Effect by Using Fab Fragment in the Treatment of Carcinoembryonic Antigen-positive Human Solid Tumors with Adriamycin-entrapped Immunoliposomes", Japan Journal of Cancer Research, vol. 85, Apr. 1994, pp. 434-440.
Verschraegen et al., "A Phase II Study of Intravenous Exatecan Mesylate (DX-8951f) Administered Daily for 5 Days Every 3 Weeks to Patients with Advanced Ovarian, Tubal or Peritoneal Cancer Resistant to Platinum, Taxane and Topotecan", Cancer Chemotherapy and Pharmacology, vol. 53, 2004, pp. 1-7.
Verschraegen et al., "Phase II Study of Intravenous DX-8951f in Patients with Advanced Ovarian, Tubal, or Peritoneal Cancer Refractory to Platinum, Taxane, and Topotecan", Annals New York Academy of Sciences, 2000, pp. 349-351.
Vey et al., "The Topoisomerase I Inhibitor DX-8951f Is Active in a Severe Combined Immunodeficient Mouse Model of Human Acute Myelogenous Leukemia", Clinical Cancer Research, vol. 6, Feb. 2000, pp. 731-736.
Viricel et al., "Monodisperse polysarcosine-based highly-loaded antibody-drug conjugates", Chemical Science, vol. 10, 2019, pp. 4048-4053.
Wang et al., "CEACAM5 inhibits the lymphatic metastasis of head and neck squamous cell carcinoma by regulating epithelial-mesenchymal transition via inhibiting MDM2", Clinical Science, vol. 136, 2022, pp. 1691-1710.
Webley et al., "Measurement of the critical DNA lesions produced by antibody-directed enzyme prodrug therapy (ADEPT) in vitro, in vivo and in clinical material", British Journal of Cancer, vol. 84, No. 12, 2001, pp. 1671-1676.
Wente et al., "DE-310, a Macromolecular Prodrug of the Topoisomerase-I-Inhibitor Exatecan (DX-8951), in Patients with Operable Solid Tumors" Investigational New Drugs, vol. 23, 2005, pp. 339-347.
Written Opinion issued Nov. 16, 2021, in PCT/EP2021/072595, 7 pages.
Yamaguchi et al., "Trastuzumab Deruxtecan in Anti-Human Epidermal Growth Factor Receptor 2 Treatment—Native Patients With Human Epidermal Growth Factor Receptor 2—Low Gastric or Gastroesophageal Junction Adenocarcinoma: Exploratory Cohort Results in a Phase II Trial", Journal of Clinical Oncology, vol. 41, No. 4, 2022, pp. 816-825.
Yazaki et al., "Tumor Targeting of Radiometal Labeled Anti-CEA Recombinant T84.66 Diabody and T84.66 Minibody: Comparison to Radioiodinated Fragments", Bioconjugte Chemistry, vol. 12, 2001, pp. 220-228.
Zalcberg et al., "A Phase I/II Study of the Intralesional Injection of Ricin-Monoclonal Antibody Conjugates in Patients with Hepatic Metastases", European Journal of Cancer, vol. 30A, No. 9, 1994, pp. 1227-1231.
Linshu Zhao et al., "An enzyme-linked immunosorbent assay for human carcinoembryonic antigen-related cell adhesion molecule 8, a biological marker of granulocyte activities in vivo", Journal of Immunological Methods, vol. 293, 2004, pp. 207-214.
Hui Zhao et al., "A Potential Mechanism for ADC-Induced Neutropenia: Role of Neutrophils in Their Own Demise", Molecular Cancer Therapeutics, vol. 16, No. 9, Sep. 2017, pp. 1866-1876.
Zheng et al., "A Novel Anti-CEACAM5 Monoclonal Antibody, CC4, Suppresses Colorectal Tumor Growth and Enhances NK Cells-Mediated Tumor Immunity", PLOS ONE, vol. 6, No. 6, Jun. 2011, e21146, pp. 1-11.
Singer, M. et al., Genes and Genomes, Moscow, Mir (1998), vol. 1, pp. 63-64 (w/ English translation) 6 pgs.
Roit, A. et al., Immunology (2000), Moscow, 'Mir', pp. 110-111 (w/ English translation) 8 pgs.
Edwards, B. M. et al., "The Remarkable Flexibility of the Human Antibody Repertoire; Isolation of Over One Thousand Different Antibodies to a Singler Protein, BLyS", JMB (2003), vol. 334, pp. 103-118.
Lloyd, C. et al., "Modelling the Human Immune Response: Performance of the 10 Human Antibody Repertoire against a Broad Panel of Therapeutically Relevant Antigens", Protein Engineering, Design & Selection (2009), vol. 22:3, pp. 159-168.
Office Action dated Jul. 17, 2026 issued in related Russian Application No. 2023107684 (w/ English translation) 22 pgs.

* cited by examiner

ANTI-CEACAM5 ANTIBODIES AND CONJUGATES AND USES THEREOF

CROSS-REFERENCE TO RELATED APPLICATIONS

This application is the National Stage entry under § 371 of International Application No. PCT/EP2021/072595, filed on Aug. 13, 2021, and which claims the benefit of priority to European Application No. 20194711.6, filed on Sep. 4, 2020, and European Application No. 20195559.8, filed on Sep. 10, 2020. The content of each of these applications is hereby incorporated by reference in its entirety.

REFERENCE TO A SEQUENCE LISTING

The present application is accompanied by an ASCII text file as a computer readable form containing the sequence listing entitled, 005071USPCT_SL_ST25.txt", created on Jan. 27, 2023, with a file size of 67,858 bytes, the content of which is hereby incorporated by reference in its entirety.

BACKGROUND OF THE INVENTION

Field of the Invention

The present invention relates to antibodies which bind human CEACAM5 protein, as well as to isolated nucleic acids and host cells comprising a sequence encoding said antibodies. The invention also relates to immunoconjugates comprising said antibodies linked to a growth-inhibitory agent, and to pharmaceutical compositions comprising antibodies or immunoconjugates of the invention. The invention also relates to the use of the antibodies, immunoconjugates and pharmaceutical compositions of the invention for the treatment of cancer or for diagnostic purposes.

Description of Related Art

Carcino-embryonic antigen (CEA) is a glycoprotein involved in cell adhesion. CEA was first identified in 1965 (Gold and Freedman, J Exp Med, 121, 439, 1965) as a protein normally expressed by fetal gut during the first six months of gestation and found in many cancers such as colorectal cancer or pancreatic cancer. The CEA family belongs to the immunoglobulin superfamily. The CEA family, which consists of 18 genes, is sub-divided in two sub-groups of proteins: the carcinoembryonic antigen-related cell adhesion molecule (CEACAM) sub-group and the pregnancy-specific glycoprotein subgroup (Kammerer & Zimmermann, BMC Biology 2010, 8:12).

In humans, the CEACAM sub-group consists of 7 members: CEACAM1, CEACAM3, CEACAM4, CEACAM5, CEACAM6, CEACAM7 and CEACAM8. CEACAM5, identical to the originally identified CEA, has been reported to be highly expressed on the surface of cancer cells such as e.g. colorectal, gastric, lung, and pancreatic tumor cells, and expression in normal tissues is limited to a few normal epithelial cells such as colon and esophagus epithelial cells. Thus, CEACAM5 may constitute a therapeutic target suitable for tumor-specific targeting approaches, such as immunoconjugates.

The extracellular domains of CEACAM family members are composed of repeated immunoglobulin-like (Ig-like) domains which have been categorized in 3 types, A, B and N, according to sequence homologies. CEACAM5 contains seven such domains, namely N, A1, B1, A2, B2, A3 and B3.

CEACAM5 A1, A2 and A3 domains, on the one hand, and B1, B2 and B3 domains, on the other hand, show high sequence homologies, the A domains of human CEACAM5 presenting from 84 to 87% pairwise sequence similarity, and the B domains from 69 to 80%. Furthermore, other human CEACAM members presenting A and/or B domains in their structure, namely CEACAM1, CEACAM6, CEACAM7 and CEACAM8, show homology with human CEACAM5. In particular, the A and B domains of human CEACAM6 protein display sequence homologies with A1 and A3 domains and any of B1 to B3 domains of human CEACAM5, respectively, which are even higher than those observed among the A domains and the B domains of human CEACAM5.

Anti-CEA antibodies have been generated for CEA-targeted diagnostic or therapeutic purposes. Specificity towards related antigens has always been mentioned as a concern in this field, e.g. by Sharkey et al (1990, Cancer Research 50, 2823). Due to the above-mentioned homologies, some of the previously described antibodies may demonstrate binding e.g. to repetitive epitopes of CEACAM5 present in the different immunoglobulin domains and show cross-reactivity to other CEACAM family members such as CEACAM1, CEACAM6, CEACAM7, or CEACAM8, thus lacking specificity for CEACAM5. Specificity of an anti-CEACAM5 antibody, however, is desired for CEA-targeted therapies, such that it binds to human CEACAM5-expressing tumor cells but does not bind to certain normal tissues expressing the other CEACAM family members. It is noteworthy that CEACAM1, CEACAM6 and CEACAM8 have been described as being expressed by neutrophils of human and non-human primates (Ebrahimmnejad et al, 2000, Exp Cell Res, 260, 365; Zhao et al, 2004, J Immunol Methods 293, 207; Strickland et al, 2009 J Pathol, 218, 380) where they have been shown to regulate granulopoiesis and to play a role in the immune response. For therapeutic purposes, cross-reactivity of an anti-CEACAM5 antibody with CEACAM1, CEACAM6, CEACAM7, or CEACAM8 may thus decrease the therapeutic index of the compound due to increased toxicity in normal tissues. Accordingly, there is a need for antibodies specifically directed to CEACAM5 that do not cross-react with other molecules of the CEACAM family, e.g. for use as part of an antibody drug conjugate (ADC) or for use in any other way resulting in killing the target cell.

Moreover, as CEACAM5 is described to be expressed in some normal cell tissues, it is desirable to develop anti-CEACAM5 antibodies capable of binding to human CEACAM5 as well as to cynomolgus monkey (*Macaca fascicularis*) CEACAM5, as such antibodies may be readily tested in preclinical toxicological studies in cynomolgus monkeys to evaluate their safety profile.

Combining the need for a) species cross-reactivity with b) the specificity for human and *Macaca fascicularis* CEACAM5, i.e. no cross reactivity with other *Macaca fascicularis* and human CEACAM family members, adds a further degree of complexity to the development of novel anti-CEACAM5 antibodies, not least in view of the overall sequence homologies between human and *Macaca fascicularis* CEACAM proteins.

Also, CEACAM5 is described in literature as a poorly internalizing surface protein (reviewed in Schmidt et al, 2008, Cancer Immunol. Immunother. 57, 1879), presenting a further challenge for antibody drug conjugates directed to this target protein.

Known anti-CEACAM5 antibodies include Immunomedics' labetuzumab (also known as hMN14; Sharkey et al, 1995, Cancer Research 55, 5935). This antibody has been shown not to bind to related antigens, but is also not cross-reacting with CEACAM5 from *Macaca fascicularis*. Labetuzumab has also been used as part of an antibody-drug conjugate (ADC), namely as labetuzumab govitecan. Labetuzumab govitecan is an ADC composed of the cytotoxic drug SN38 conjugated to the anti-CEACAM5 antibody labetuzumab via a linker (called CL2A) comprising a pH-sensitive carbonate and a short polyethylene glycol (PEG) chain. Labetuzumab govitecan is characterized by a significant instability of the linker structure used, resulting in an early systemic loss of the cytotoxic payload after parenteral application. This degradation process might limit antitumor activity and increases risks of side effects. Another known anti-CEACAM5 ADC is Sanofi's SAR408701 (tusamitamab ravtansine), comprising the anti-CEACAM5 antibody SAR408377 (tusamitamab; also referred to as huMab2-3) covalently linked to the cytotoxic agent DM4, a potent microtubule-destabilizing maytansinoid, via an N-succinimidyl 4-(2-pyridyldithio) butyrate (SPDB) linker. SAR408701 is associated with toxic side effects on several organs and tissues including the cornea of the eye (including keratitis and keratopathy). Also, effectiveness of microtubule inhibitor-based ADCs may be limited in certain cancer indications such as colorectal cancer. To date, no anti-CEACAM5 antibody or ADC has been approved for any therapeutic use in the clinic; in general, few ADCs have been approved for the treatment of solid tumors. There remains a need for new and improved therapeutic agents for the treatment of cancer, e.g. for different solid tumor indications including e.g. CRC, pancreatic cancer, gastric cancer, NSCLC, esophageal cancer and prostate cancer.

SUMMARY OF THE INVENTION

The present invention addresses this need and other needs in the art inter alia by providing monoclonal antibodies directed against CEACAM5 (reactive with both the human and *Macaca fascicularis* proteins) and by providing immunoconjugates (also referred to as antibody-drug conjugates (ADC) herein) comprising said antibodies; these immunoconjugates have a cytotoxic effect, killing tumor cells in vitro and inhibiting tumor growth in vivo. The present invention relates to embodiments described in the further description herein below.

In an attempt to produce new antibodies against CEACAM5 with optimal characteristics for therapeutic purposes, particularly in the format of an immunoconjugate, the inventors have performed extensive research and development, in order to select antibodies with an advantageous profile and to develop immunoconjugates on that basis.

The inventors were able to select and produce optimized IgGs that unexpectedly comprise several desired features. These antibodies bind to the A2-B2 domain of human CEACAM5 with a high affinity and do not recognize human CEACAM1, CEACAM6, CEACAM7 and CEACAM8 proteins. In a cellular context, these antibodies display high affinity for CEACAM5-expressing tumor cells and are internalized. Moreover, these antibodies also bind to *Macaca fascicularis* CEACAM5 protein, with affinities to the monkey and human proteins, respectively, within 10-fold of each other. Antibodies of the invention bind to the A2-B2 domain of *Macaca fascicularis* CEACAM5 but they do not recognize another *Macaca fascicularis* CEACAM protein, CEACAM6.

The inventors have also shown that the antibodies they have produced are able to induce cytotoxic effects on tumor cells in vitro when combined with a cytotoxic drug in an immunoconjugate. The antibodies conjugated to a cytotoxic drug (i.e. immunoconjugates of the invention) are also able to markedly inhibit tumor growth in mice bearing CEACAM5-expressing tumors. The linkers connecting drug and antibody were designed to maximize systemic stability after parenteral application. The release of exatecan from the immunoconjugates of the invention within target cells leads to very high potency and outstanding bystander effects. A potent bystander effect may be beneficial for the treatment of patients with heterogeneous target expression.

DETAILED DESCRIPTION OF THE INVENTION

Definitions

Figure 1:
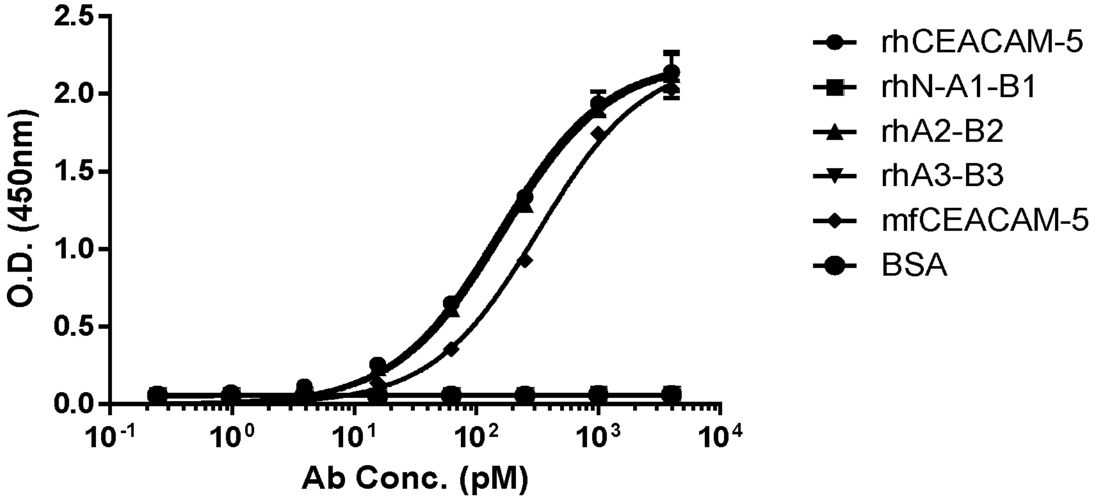
FIG. 1: Binding of mAb1 to recombinant human (rh) CEACAM5 ECD or its domains N-A1-B1, A2-B2, A3-B3 or to recombinant *Macaca fascicularis* (mf) CEACAM5 ECD in an ELISA assay.

As used herein "CEACAM5" designates the "carcinoembryonic antigen-related cell adhesion molecule 5", also known as "CD66e" (Cluster of Differentiation 66e) or CEA. CEACAM5 is a glycoprotein involved in cell adhesion. CEACAM5 is highly expressed especially on the surface of e.g. colorectal cancer, gastric cancer, non-small cell lung cancer, pancreatic cancer, esophageal cancer, prostate cancer and other solid tumors. A reference sequence of full length human CEACAM5, including signal peptide (positions 1-34) and propeptide (positions 686-702), is available from the GenBank database under accession number AAA51967.1; this amino acid sequence reads as follows:
MESPSAPPHRVCIPWVQRLLLTASLLTFWNPPTTAK-
LTIESTPFNVAEGKEVLLLVHNLPQHL
FGYSWYKGERVDGNRQIIGYVIGTQQATPGPAY-
SGREIIYPNASLLIQNIIQNDTGFYTLHVIK SDLVNEE-
ATGQFRVYPELPKPSISSNNSKPVEDKDAVAFTCE-
PETQDATYLWWVNNQSLPV
SPRLQLSNGNRTLTLFNVTRNDTA-
SYKCETQNPVSARRSDSVILNVLYGPDAPTISPLNTSY
RSGENLNLSCHAASNPPAQYSWFVNGTFQQSTQELF-
IPNITVNNSGSYTCQAHNSDTGLNR TTVTTITVYAE-
PPKPFITSNNSNPVEDEDAVALTCEPEIQNT-
TYLWWVNNQSLPVSPRLQLSN
DNRTLTLLSVTRNDVGPYECGIQNELSVDHSDPVI-
LNVLYGPDDPTISPSYTYYRPGVNLSLS CHAASNP-
PAQYSWLIDGNIQQHTQELFISNITEKNSG-
LYTCQANNSASGHSRTTVKTITVSAE LPKP-
SISSNNSKPVEDKDAVAFTCEPEAQNTTYLWWVNGQSLPVSPRLQL-
SNGNRTLTLFN
VTRNDARAYVCGIQNSVSANRSDPVTLDVLYGPDT-
PIISPPDSSYLSGANLNLSCHSASNPS PQYSWRING-
IPQQHTQVLFIAKITPNNNGTYACFVSNLATGRNN-
SIVKSITVSASGTSPGLSA GATVGIMIGVLVGVALI
(SEQ ID NO: 1). Five non-synonymous SNPs have been identified with a frequency higher than 2% in Caucasian population, four of them being localized in the N domain (at positions 80, 83, 112, 113), the last one in the A2 domain (at position 398) of human CEACAM5. GenBank AAA51967.1 contains the major haplotype (180, V83, 1112, 1113 and E398).

A "domain" or "region" may be any region of a protein, generally defined on the basis of sequence homologies and often related to a specific structural or functional entity. CEACAM family members are known to be composed of Ig-like domains. The term domain is used in this document to designate either individual Ig-like domains, such as "N-domain" or for groups of consecutive domains, such as "A2-B2 domain".

Domain organization of human CEACAM5 is as follows (based on GenBank AAA51967.1 sequence; SEQ ID NO: 1):

| Human CEACAM5 domains | Positions in SEQ ID NO: 1 |
|---|---|
| N | 35-142 |
| A1 | 143-237 |
| B1 | 238-320 |
| A2 | 321-415 |
| B2 | 416-498 |
| A3 | 499-593 |
| B3 | 594-685 |

Accordingly, the A2-B2 domain of human CEACAM5 consists of amino acids 321-498 of SEQ ID NO: 1.

A reference sequence of *Macaca fascicularis* CEACAM5 protein is available (NCBI Reference Sequence XP_005589491.1), and this amino acid sequence reads as follows: mgspsaphwcipwqtlltaslltfwnppttaqltiesrpfnvae-
gkevlllahnvsqnlfgyiwykgervdasrigscvirtqqitpg pahsgretidf-
nasllihnvtqsdtgsytiqvikedivnee-
atgqfrvypelpkpyissnnsnpvedkdavaltcepetqdttylwwv
nnqslpvsprlelssdnrtltvfnipmdttsykcetqnpvsvrrsdpvtlnvlygp-
daptisplntpyragenlnlschaasnptaqyf wfvngtfqqstqelf-
ipnitvnnsgsymcqahnsatglnrttvtaitvyaelpkpyitsnnsnpiedkdavtltcepetqdttylw
wvnnqslsvssrielsndnrtitvin-
ipmdttfyecetqnpvsvrrsdpvtlnvlygpdaptispintpyrageninlsch
aasnpaagyswfvngtfqqstqelfipnitvnnsgsymcqahn-
satgnrttvtaitvyvelpkpyissnnsnpiedkdav titcepvaent-
tylwwvnnqslsvsprlqlsngnriltllsvtmdtgpyecgiqns-
esakrsdpvtlnvtygpdtpiisppdlsyrsgan
lnlschsdsnpspqyswlingtirqhtqvlfiskitsnnngayacfvsnlatgmn-
sivknisvssgdsapgssglsar<u>atvgiiigmlv</u> <u>gvalm</u> (SEQ ID NO: 2) (signal peptide in italics; A2-B2 domain in bold letters; GPI anchor underlined; N-A1-B1 domain in regular font between signal peptide and A2-B2 domain; A3-B3 domain in regular font between A2-B2 domain and GPI anchor).

A "coding sequence" or a sequence "encoding" an expression product, such as a polypeptide, protein, or enzyme, is a nucleotide sequence that, when expressed, results in the production of that polypeptide, protein, or enzyme, i.e., the nucleotide sequence encodes an amino acid sequence for that polypeptide, protein or enzyme. A coding sequence for a protein may include a start codon (usually ATG) and a stop codon.

As used herein, references to specific proteins (e.g. antibodies) can include a polypeptide having a native amino acid sequence, as well as variants and modified forms regardless of their origin or mode of preparation. A protein which has a native amino acid sequence is a protein having the same amino acid sequence as obtained from nature. Such native sequence proteins can be isolated from nature or can be prepared using standard recombinant and/or synthetic methods. Native sequence proteins specifically encompass naturally occurring truncated or soluble forms, naturally occurring variant forms (e.g. alternatively spliced forms), naturally occurring allelic variants and forms including post-translational modifications. Native sequence proteins include proteins carrying post-translational modifications such as glycosylation, or phosphorylation, or other modifications of some amino acid residues.

The term "gene" means a DNA sequence that codes for, or corresponds to, a particular sequence of amino acids which comprises all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

Herein, a sequence "at least 85% identical" to a reference sequence is a sequence having, over its entire length, 85% or more, for instance 90%, 91%, 92%, 93%, 94%, 95%, 96%, 97%, 98% or 99% sequence identity with the entire length of the reference sequence. The percentage of "sequence identity" may thus be determined by comparing two such sequences over their entire length by global pairwise alignment using the algorithm of Needleman and Wunsch (J. Mol. Biol. 48:443 (1970)), e.g. using the program Needle (EMBOSS) with the BLOSUM62 matrix and the following parameters: gap open=10, gap extend=0.5, end gap penalty=false, end gap open=10, end gap extend=0.5 (which are standard settings).

A "conservative amino acid substitution" is one in which an amino acid residue is substituted by another amino acid residue having a side chain with similar chemical properties (e.g., charge, size or hydrophobicity). In general, a conservative amino acid substitution will not substantially change the functional properties of a protein. Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Conservative amino acid substitution groups can also be defined on the basis of amino acid size.

An "antibody" (also referred to as an "immunoglobulin") may e.g. be a natural or conventional type of antibody in which two heavy chains are linked to each other by disulfide bonds and each heavy chain is linked to a light chain by a disulfide bond. There are two types of light chain, lambda (l) and kappa (k). There are five main heavy chain classes (or isotypes) which determine aspects of the functional activity of an antibody molecule: IgM, IgD, IgG, IgA and IgE. Each antibody chain contains distinct sequence domains (or regions). The light chain of a typical IgG antibody includes two regions, a variable region (VL) and a constant region (CL). The heavy chain of a typical IgG antibody includes four regions, namely a variable region (VH) and a constant region (CH), the latter being made up of three constant domains (CH1, CH2 and CH3). The variable regions of both light and heavy chains determine binding and specificity to the antigen. The constant regions of the light and heavy chains can confer important biological properties, such as antibody chain association, secretion, trans-placental mobility, complement binding, and binding to Fc receptors (FcR). The Fv fragment is the N-terminal part of the Fab fragment of an antibody and consists of the variable portions of one light chain and one heavy chain.

The specificity of the antibody resides in the structural complementarity between the antibody combining site and the antigenic determinant. Antibody combining sites are made up of residues that are primarily from the so-called hypervariable or complementarity determining regions (CDRs). Complementarity determining regions (CDRs) therefore refer to amino acid sequences which together define the binding affinity and specificity of the Fv region of an antibody. The light (L) and heavy (H) chains of an antibody each have three CDRs, designated CDR1-L, CDR2-L, CDR3-L and CDR1-H, CDR2-H, CDR3-H, respectively. A conventional antibody's antigen-binding site, therefore, includes six CDRs, comprising the CDR set from each of a heavy and a light chain variable region.

"Framework regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively. As used herein, a "human framework region" is a framework region that is substantially identical (about 85%, or more, for instance 90%, 91%, 92%, 93%, 94%, 95%, 96%, 97%, 98% or 99%) to the framework region of a naturally occurring human antibody.

In the context of the invention, CDR/FR definition in an immunoglobulin light or heavy chain is determined based on the IMGT definition (Lefranc et al. Dev. Comp. Immunol., 2003, 27(1):55-77; www.imgt.org).

As used herein, the term "antibody" includes conventional antibodies and fragments thereof, as well as single domain antibodies and fragments thereof, such as variable heavy chain of single domain antibodies; the term "antibody" as used herein also includes chimeric, humanized, bispecific or multispecific antibodies, as well as other types of engineered antibodies. The term "antibody" includes monoclonal antibodies.

The term "monoclonal antibody" or "mAb" as used herein refers to an antibody molecule of a single amino acid sequence, which is directed against a specific antigen, and is not to be construed as requiring production of the antibody by any particular method. A monoclonal antibody may be produced e.g. by a single clone of B cells or hybridoma, but may also be recombinant, e.g. produced by methods involving genetic or protein engineering.

The term "chimeric antibody" refers to an engineered antibody which, in its broadest sense, contains one or more regions from one antibody and one or more regions from one or more other antibodies. In an embodiment, a chimeric antibody comprises a VH and a VL of an antibody derived from a non-human animal, in association with a CH and a CL of another antibody which is, in some embodiments, a human antibody. As the non-human animal, any animal such as mouse, rat, hamster, rabbit or the like can be used. A chimeric antibody may also denote a multispecific antibody having specificity for at least two different antigens.

The term "humanized antibody" refers to an antibody which is wholly or partially of non-human origin and which has been modified to replace certain amino acids, for instance in the framework regions of the VH and VL, in order to avoid or minimize an immune response in humans. The constant regions of a humanized antibody are typically human CH and CL regions.

"Fragments" of antibodies (e.g. of conventional antibodies) comprise a portion of an intact antibody such as an IgG, in particular an antigen binding region or variable region of the intact antibody. Examples of antibody fragments include Fv, Fab, F(ab')2, Fab', dsFv, (dsFv)2, scFv, sc(Fv)2, diabodies, as well as bispecific and multispecific antibodies formed from antibody fragments. A fragment of a conventional antibody may also be a single domain antibody, such as a heavy chain antibody or VHH.

The term "Fab" denotes an antibody fragment having a molecular weight of about 50,000 Da and antigen binding activity, in which about a half of the N-terminal side of the heavy chain and the entire light chain are bound together through a disulfide bond. It is usually obtained among fragments by treating IgG with a protease, papaine.

The term "F(ab')2" refers to an antibody fragment having a molecular weight of about 100,000 Da and antigen binding activity, which is slightly larger than 2 identical Fab fragments bound via a disulfide bond of the hinge region. It is usually obtained among fragments by treating IgG with a protease, pepsin.

The term "Fab'" refers to an antibody fragment having a molecular weight of about 50,000 Da and antigen binding activity, which is obtained by cutting a disulfide bond of the hinge region of the F(ab')2.

A single chain Fv ("scFv") is a covalently linked VH::VL heterodimer which is usually expressed from a gene fusion including VH and VL encoding genes linked by a peptide-encoding linker. The human scFv fragments of the invention include CDRs that are held in appropriate conformation, for instance by using gene recombination techniques. Divalent and multivalent antibody fragments can form either spontaneously by association of monovalent scFvs, or can be generated by coupling monovalent scFvs by a peptide linker, such as divalent sc(Fv)2. "dsFv" is a VH::VL heterodimer stabilised by a disulphide bond. "(dsFv)2" denotes two dsFv coupled by a peptide linker.

The term "bispecific antibody" or "BsAb" denotes an antibody which comprises two different antigen binding sites. Thus, BsAbs are able to e.g. bind two different antigens simultaneously. Genetic engineering has been used with increasing frequency to design, modify, and produce antibodies or antibody derivatives with a desired set of binding properties and effector functions as described for instance in EP 2 050 764 A1.

The term "multispecific antibody" denotes an antibody which comprises two or more different antigen binding sites.

The term "diabodies" refers to small antibody fragments with two antigen binding sites, which fragments comprise a heavy-chain variable domain (VH) connected to a light-chain variable domain (VL) in the same polypeptide chain (VH-VL). By using a linker that is too short to allow pairing between the two domains of the same chain, the domains are forced to pair with the complementary domains of another chain and create two antigen-binding sites.

The term "hybridoma" denotes a cell, which is obtained by subjecting a B cell prepared by immunizing a non-human mammal with an antigen to cell fusion with a myeloma cell derived from a mouse or the like which produces a desired monoclonal antibody having an antigen specificity.

By "purified" or "isolated" it is meant, when referring to a polypeptide (e.g. an antibody) or a nucleotide sequence, that the indicated molecule is present in the substantial absence of other biological macromolecules of the same type. The term "purified" as used herein means at least 75%, 85%, 95%, 96%, 97%, or 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

As used herein, the term "subject" denotes a mammal, such as a rodent, a feline, a canine, a primate or a human. In embodiments of the invention, the subject (or patient) is a human.

Antibodies of the Invention

The inventors have succeeded in generating, screening and selecting specific anti-CEACAM5 antibodies surprisingly displaying a combination of several characteristics that make them ideally suited for use in cancer therapy, in particular as part of an immunoconjugate (antibody-drug conjugate). For instance, the antibodies of the invention display high affinity for both human and *Macaca fascicularis* CEACAM5 protein, and they do not significantly cross-react with human CEACAM1, CEACAM6, CEACAM7 and CEACAM8 proteins, or with *Macaca fascicularis* CEACAM6 protein. The inventors have determined the amino acid sequence of such monoclonal antibodies according to the present invention.

The present invention provides an isolated antibody which binds to human CEACAM5 protein and which comprises a CDR1-H consisting of the amino acid sequence DGSVSRGGYY (SEQ ID NO: 3), a CDR2-H consisting of the amino acid sequence IYYSGST (SEQ ID NO: 4), a CDR3-H consisting of the amino acid sequence ARGIAVAPFDY (SEQ ID NO: 5), a CDR1-L consisting of the amino acid sequence QSVRSN (SEQ ID NO: 6), a CDR2-L consisting of the amino acid sequence AAS (SEQ ID NO: 7), and a CDR3-L consisting of the amino acid sequence QQYTNWPFT (SEQ ID NO: 8). This antibody can also bind to *Macaca fascicularis* CEACAM5 protein.

In embodiments of the invention, the antibody having the above-mentioned six CDR sequences comprises a heavy chain variable region (VH) comprising an amino acid sequence that is at least 85% identical to the amino acid sequence EVQLQESGPGLVKP- SQTLSLTCTVSDGSVSRGGYYLTWIRQHPGKGLEWI- GYIYYSGSTYF NPSLRSRVTMSVDTSKNQFSLKLSSVTAADTAVYY- CARGIAVAPFDYWGQGTLVTVSS (SEQ ID NO: 9) (CDRs shown in bold characters) and a light chain variable region (VL) comprising an amino acid sequence that is at least 85% identical to the amino acid sequence EIVLTQSPATLSVSPGERATLSCRTSQSVRSN- LAWYQQKPGQAPRLLIYAASTRATGIPARF SGSGSGTEFTLTISSLQSED- FAVYYCQQYTNWPFTFGPGTKVDIK (SEQ ID NO: 10) (CDRs shown in bold characters).

In embodiments of the invention, the antibody having the above-mentioned six CDR sequences comprises a heavy chain variable region (VH) comprising the amino acid sequence of SEQ ID NO: 9 and a light chain variable region (VL) comprising the amino acid sequence of SEQ ID NO: 10.

In embodiments of the invention, the antibody further comprises a heavy chain constant region (CH) comprising an amino acid sequence that is at least 85% identical to the amino acid sequence ASTKGPSVFPLAPSSKST- SGGTAALGCLVKDYFPEPVTVSWNSGALT- SGVHTFPAVLQSSG LYS- LSSVVTVPSSSLGTQTYICNVNHKPSNTKVDK- RVEPKSCDKTHTCPPCPAPPVAGPSVF LFPPKPKDTLMISRTPEVTCVVVDVSHEDPE- VKFNWYVDGVEVHNAKTKPREEQYNSTYRV VSVLTVLHQDWLNGKEYKCKVSNKA- LPSSIEKTISKAKGQPREPQVYTLPPSREEMTKNQV SLTCLVKGFYPSDIAVEWESNGQPEN- NYKTTPPVLDSDGSFFLYSKLTVDKSRWQQGNVFS CSVMHEALHNHYTQKSLSLSPG (SEQ ID NO: 11) and a light chain constant region (CL) comprising an amino acid sequence that is at least 85% identical to the amino acid sequence RTVAAPSVFIFPPSDEQLKSG- TASVVCLLNNFYPREAKVQWKVD- NALQSGNSQESVTEQDS KDSTYSLSSTLTL- SKADYEKHKVYACEVTHQGLSSPVTKSFNRGEC (SEQ ID NO: 12).

In embodiments of the invention, the antibody comprises a heavy chain constant region (CH) comprising the amino acid sequence of SEQ ID NO: 11 and a light chain constant region (CL) comprising the amino acid sequence of SEQ ID NO: 12.

In more specific embodiments, the antibody of the invention is an isolated antibody which binds to human CEACAM5 protein and which comprises a heavy chain (HC) comprising an amino acid sequence that is at least 85% identical to the amino acid sequence EVQLQESGPGLVKP- SQTLSLTCTVSDGSVSRGGYYLTWIRQHPGKGLEWI- GYIYYSGSTYF NPSLRSRVTMSVDTSKNQFSLKLSSVTAADTAVYY- CARGIAVAPFDYWGQGTLVTVSSAST KGPSVF- PLAPSSKSTSGGTAALGCLVKDYF- PEPVTVSWNSGALTSGVHTFPAVLQSSGLYS LSSVVTVPSSSLGTQTYICNVNHKPSNTKVDKRVE- PKSCDKTHTCPPCPAPPVAGPSVFLFP PKPKDTLMIS- RTPEVTCVVDVSHEDPE- VKFNWYVDGVEVHNAKTKPREEQYNSTYRVVSV LTVLHQDWLNGKEYKCKVSNKA- LPSSIEKTISKAKGQPREPQVYTLPPSREEMT- KNQVSLTC LVKGFYPSDIAVEWESNGQPEN- NYKTTPPVLDSDGSFFLYSKLTVDKSRWQQGNVF- SCSV MHEALHNHYTQKSLSLSPG (SEQ ID NO: 13) and a light chain (LC) comprising an amino acid sequence that is at least 85% identical to the amino acid sequence EIVLTQSPATLSVSPGERATLSCRTSQSVRSN- LAWYQQKPGQAPRLLIYAASTRATGIPARF SGSGSGTEFTLTISSLQSED- FAVYYCQQYTNWPFTFGPGTKVDIKRTVAAPSV- FIFPPSDEQ LKSGTASVVCLLNNFY- PREAKVQWKVDNALQSGNSQESVTEQDSKDSTYS- LSSTLTLSKAD YEKHKVYACE- VTHQGLSSPVTKSFNRGEC (SEQ ID NO: 14). In even more specific embodiments of the invention, the antibody comprises a heavy chain (HC) comprising the amino acid sequence of SEQ ID NO: 13 and a light chain (LC) comprising the amino acid sequence of SEQ ID NO: 14. In yet more specific embodiments of the invention, the antibody consists of two identical heavy chains (HC) comprising the amino acid sequence of SEQ ID NO: 13 and two identical light chains (LC) comprising the amino acid sequence of SEQ ID NO: 14.

In some embodiments, one or more individual amino acids of an antibody of the invention may be altered by substitution, in particular by conservative substitution, in one or more of the above-mentioned sequences, including the CDR sequences. Such an alteration may be intended for example to remove a glycosylation site or a deamidation site, e.g. in connection with humanization of the antibody.

In some embodiments, the antibody of the invention is an isolated antibody which binds to human CEACAM5 protein and which consists of two identical heavy chains (HC) consisting of the amino acid sequence of SEQ ID NO: 13 and two identical light chains (LC) consisting of the amino acid sequence of SEQ ID NO: 14; this particular antibody is also referred to as "mAb1" herein.

In some embodiments, the antibody of the invention binds to the A2-B2 domains of human and *Macaca fascicularis* CEACAM5. The invention also provides an antibody which competes for binding to A2-B2 domain of human and/or *Macaca fascicularis* CEACAM5 proteins with an antibody comprising the heavy and light chain variable regions of mAb1 (i.e. the VH and VL corresponding to SEQ ID NO: 9 and 10, respectively).

The ability of a candidate antibody to compete for binding to A2-B2 domain of human and/or *Macaca fascicularis* CEACAM5 proteins with an antibody comprising the VH and VL of mAb1 (hereafter, in the context of competition with a candidate antibody, referred to as a "reference" antibody) may be readily assayed, for instance, by competitive ELISA wherein the antigen (i.e. the A2-B2 domain of human or *Macaca fascicularis* CEACAM5, or a polypeptide comprising or consisting of a fragment of human or *Macaca fascicularis* CEACAM5 including the A2-B2 domain, in particular the extracellular domain of human or *Macaca fascicularis* CEACAM5) is bound to a solid support and two solutions containing the candidate antibody and the reference antibody, respectively, are added and the antibodies are allowed to compete for binding to the antigen. The amount of reference antibody bound to the antigen may then be measured, and compared to the amount of reference antibody bound to the antigen when measured against a negative control (e.g. solution containing no antibody). An amount of bound reference antibody in the presence of the candidate antibody decreased as compared to the amount of bound reference antibody in presence of the negative control indicates that the candidate antibody has competed with the reference antibody. Conveniently, the reference antibody may be labeled (e.g. fluorescently) to facilitate detection of bound reference antibody. Repeated measurements may be performed with serial dilutions of the candidate and/or reference antibody.

In some embodiments, the antibody of the invention does not bind to, or does not significantly cross-react with human CEACAM1, human CEACAM6, human CEACAM7, human CEACAM8 and *Macaca fascicularis* CEACAM6 proteins. In some embodiments, the antibody does not bind to, or does not significantly cross-react with the extracellular domain of the aforementioned human and *Macaca fascicularis* CEACAM proteins other than CEACAM5.

"Affinity" is defined, in theory, by the equilibrium association between the whole antibody and the antigen. It can be experimentally assessed by a variety of known methods, such as measuring association and dissociation rates with surface plasmon resonance or measuring the $EC_{50}$ (or apparent $K_D$) in an immunochemical assay (ELISA, FACS). In these assays, the $EC_{50}$ is the concentration of the antibody which induces a response halfway between the baseline and maximum after some specified exposure time on a defined concentration of antigen by ELISA (enzyme-linked immuno-sorbent assay) or cell expressing the antigen by FACS (Fluorescence Activated Cell Sorting).

A monoclonal antibody binding to an antigen 1 (Ag1) is "cross-reactive" to an antigen 2 (Ag2) when the $EC_{50}$s are in a similar range for both antigens. In the present application, a monoclonal antibody binding to Ag1 is cross-reactive to Ag2 when its affinity for Ag2 is within 10-fold or less (for instance within 5-fold) from its affinity of Ag1, affinities being measured with the same method for both antigens.

A monoclonal antibody binding to Ag1 is "not significantly cross-reactive" to Ag2 when the affinities are very different for the two antigens. Affinity for Ag2 may not be measurable if the binding response is too low. In the present application, a monoclonal antibody binding to Ag1 is not significantly cross-reactive to Ag2, when the binding response of the monoclonal antibody to Ag2 is less than 5% of the binding response of the same monoclonal antibody to Ag1 in the same experimental setting and at the same antibody concentration. In practice, the antibody concentration used can be the $EC_{50}$ or the concentration required to reach the saturation plateau obtained with Ag1. A monoclonal antibody "binds specifically" to (or "is specific for") Ag1 when it is not significantly cross-reactive to Ag2.

In some embodiments, an antibody according to the invention has an affinity for *Macaca fascicularis* CEACAM5 which is within 10-fold or less (for instance within 5-fold) from its affinity for human CEACAM5. Thus, the antibody according to the invention may be used in toxicological studies performed in monkeys because the toxicity profile observed in monkeys would be relevant to anticipate potential adverse effects in humans.

In some embodiments, the antibody of the invention has an affinity for human CEACAM5 or *Macaca fascicularis* CEACAM5, or both, which is ≤10 nM; for instance, the antibody of the invention may have an affinity for human CEACAM5 which is between 1 and 10 nM, such as an affinity for human CEACAM5 of about 6 nM.

Affinity for human CEACAM5 or for *Macaca fascicularis* CEACAM5 may be determined e.g. as the EC50 value in an ELISA using soluble recombinant CEACAM5 as capture antigen.

Alternatively, for the antibody of the invention, an apparent dissociation constant (apparent KD) may be determined by FACS analysis e.g. on tumor cell line MKN45 (DSMZ, ACC 409).

Additionally, antibodies according to the invention have been shown to be able to detect CEACAM5 expression by immunohistochemistry, e.g. in frozen and formalin-fixed and paraffin embedded (FFPE) tissue sections.

Any combination of the embodiments described herein above and below forms part of the invention.

In some embodiments, the antibody according to the invention is a conventional antibody, such as a conventional monoclonal antibody, or an antibody fragment, a bispecific or multispecific antibody.

In some embodiments, the antibody according to the invention comprises or consists of an IgG, or a fragment thereof.

In some embodiments, the antibody of the invention may be e.g. a murine antibody, a chimeric antibody, a humanized antibody, or a human antibody. Numerous methods for humanization of an antibody sequence are known in the art; see e.g. the review by Almagro & Fransson (2008) Front Biosci. 13: 1619-1633. One commonly used method is CDR grafting, or antibody reshaping, which involves grafting of the CDR sequences of a donor antibody, generally a mouse antibody, into the framework scaffold of a human antibody of different specificity. Since CDR grafting may reduce the binding specificity and affinity, and thus the biological activity, of a CDR grafted non-human antibody, back mutations may be introduced at selected positions of the CDR grafted antibody in order to retain the binding specificity and affinity of the parent antibody. Identification of positions for possible back mutations can be performed using information available in the literature and in antibody databases. Amino acid residues that are candidates for back mutations are typically those that are located at the surface of an antibody molecule, while residues that are buried or that have a low degree of surface exposure will not normally be altered. An alternative humanization technique to CDR grafting and back mutation is resurfacing, in which non-surface exposed residues of non-human origin are retained, while surface residues are altered to human residues. Another alternative technique is known as "guided selection" (Jespers et al. (1994) Biotechnology 12, 899) and can be used to derive from a murine antibody a fully human antibody conserving the epitope and binding characteristics of the parental antibody.

For chimeric antibodies, humanization typically involves modification of the framework regions of the variable region sequences.

Amino acid residues that are part of a CDR will typically not be altered in connection with humanization, although in certain cases it may be desirable to alter individual CDR amino acid residues, for example to remove a glycosylation site, a deamidation site or an undesired cysteine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, for instance by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, for instance Asn-Gly, is present in a CDR sequence, it may therefore be desirable to remove the site, typically by conservative substitution to remove one of the implicated residues. Substitution in a CDR sequence to remove one of the implicated residues is also intended to be encompassed by the present invention.

In a humanized antibody or fragment thereof, the variable domains of heavy and light chains may comprise human acceptor framework regions. A humanized antibody may further comprise human constant heavy and light chain domains, where present.

In some embodiments, the antibody according to the invention may be an antibody fragment (for instance a humanized antibody fragment) selected from the group consisting of Fv, Fab, F(ab')2, Fab', dsFv, (dsFv)2, scFv, sc(Fv)2, and diabodies.

In some embodiments, the antibody according to the invention may be a bispecific or multispecific antibody formed from antibody fragments, at least one antibody fragment being a fragment of an antibody according to the present invention. Multispecific antibodies are polyvalent protein complexes as described for instance in EP 2 050 764 A1 or US 2005/0003403 A1.

Bispecific or multispecific antibodies according to the invention can have specificity for (a) the human and *Macaca fascicularis* CEACAM5 proteins and (b) at least one other antigen. In some embodiments, the at least one other antigen is not a human or *Macaca fascicularis* CEACAM family member. In other embodiments, the at least one other antigen may be an epitope on human or *Macaca fascicularis* CEACAM5 other than the epitope targeted by mAb1.

The antibodies of the invention can be produced by any technique known in the art. Antibodies according to the invention can be used e.g. in an isolated (e.g. purified) form or contained in a vector, such as a membrane or lipid vesicle (e.g. a liposome).

Nucleic Acids and Host Cells of the Invention

A further aspect of the invention relates to an isolated nucleic acid comprising or consisting of a nucleic acid sequence encoding an antibody of the invention as defined above.

Typically, said nucleic acid is a DNA or RNA molecule, which may be included in any suitable vector, such as a plasmid, cosmid, episome, artificial chromosome, phage or a viral vector.

The terms “vector”, “cloning vector” and “expression vector” mean the vehicle by which a DNA or RNA sequence (e.g. a foreign gene) can be introduced into a host cell, so as to transform the host and promote expression (e.g. transcription and translation) of the introduced sequence.

Accordingly, a further aspect of the invention relates to a vector comprising a nucleic acid of the invention as defined above.

Such vectors may comprise regulatory elements, such as a promoter, enhancer, terminator and the like, to cause or direct expression of said polypeptide upon administration to a subject.

Examples of promoters and enhancers used in the expression vector for an animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cells can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O’Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vectors include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a host cell which has been transfected, infected or transformed by a nucleic acid and/or a vector according to the invention.

The term “transformation” means the introduction of a “foreign” (i.e. extrinsic) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been “transformed”.

The nucleic acids of the invention may be used to produce an antibody of the invention in a suitable expression system. The term “expression system” means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as “DHFR gene”) is defective (Urlaub G et al; 1980), rat YB2/3HL.P2.G11.16Ag.20 cell (ATCC CRL1662, hereinafter referred to as “YB2/0 cell”), and the like. In some embodiments, the YB2/0 cell is used, since ADCC activity of chimeric or humanized antibodies is enhanced when expressed in this cell.

For expression of a humanized antibody, the expression vector may be either of a type in which a gene encoding an antibody heavy chain and a gene encoding an antibody light chain exists on separate vectors or of a type in which both genes exist on the same vector (tandem type).

In respect of easiness of construction of a humanized antibody expression vector, easiness of introduction into animal cells, and balance between the expression levels of antibody H and L chains in animal cells, a humanized antibody expression vector is of the tandem type Shitara K et al. J Immunol Methods. 1994 Jan. 3; 167(1-2):271-8).

Examples of tandem type humanized antibody expression vector include pKANTEX93 (WO 97/10354), pEE18 and the like.

The present invention also relates to a method of producing a recombinant host cell expressing an antibody according to the invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody.

Such recombinant host cells can be used for the production of antibodies of the invention.

Methods of Producing Antibodies of the Invention

Antibodies of the invention may be produced by any technique known in the art, such as, without limitation, any chemical, biological, genetic or enzymatic technique, either alone or in combination.

Knowing the amino acid sequence of a desired antibody, one skilled in the art can readily produce said antibodies or immunoglobulin chains using standard techniques for production of polypeptides. For instance, they can be synthesized using well-known solid phase methods using a commercially available peptide synthesis apparatus (such as that made by Applied Biosystems, Foster City, California) and following the manufacturer's instructions. Alternatively, antibodies and immunoglobulin chains of the invention can be produced by recombinant DNA techniques, as is well-known in the art. For example, these polypeptides (e.g. antibodies) can be obtained as DNA expression products after incorporation of DNA sequences encoding the desired polypeptide into expression vectors and introduction of such vectors into suitable eukaryotic or prokaryotic hosts that will express the desired polypeptide, from which they can be later isolated using well-known techniques.

For instance, the present invention provides the following DNA sequences encoding the antibody mAb1:

mAb1 heavy chain nucleotide sequence
wherein mVk signal peptide is underlined,
start and stop codons are in italics,
VH region sequence in boldface, and
CDRs are indicated with double underlining:

(SEQ ID NO: 15)

*ATG*GAGACCGACACCCTGCTGCTGTGGGTGCTGCTGCTGTGGGTGCCCGGGTCGACC

GGTGAGGTGCAGCTGCAGGAGTCGGGCCCAGGACTGGTGAAGCCTTCACAGACCCT

GTCCCTCACCTGCACTGTCTCTGATGGCTCCGTCAGCAGGGGTGGTTACTACTTGACC

TGGATCCGCCAGCACCCAGGGAAGGGCCTGGAGTGGATTGGGTACATCTATTACAGT

GGGAGCACCTACTTCAACCCGTCCCTCAGGAGTCGGGTTACCATGTCAGTAGACACG

TCTAAGAACCAGTTCTCCCTGAAGCTGAGCTCTGTGACTGCCGCGGACACGGCCGTG

TATTACTGTGCGAGAGGGATAGCAGTGGCTCCCTTTGACTACTGGGGCCAGGGAACC

CTGGTCACCGTCTCTTCAGCTAGCACCAAGGGCCCCAGCGTGTTCCCCCTGGCCCCCA

GCAGCAAGTCCACAAGCGGAGGAACAGCCGCCCTGGGCTGCCTGGTGAAGGACTACT

TCCCCGAGCCCGTGACCGTGTCCTGGAACAGCGGAGCCCTGACCTCCGGCGTGCACA

CCTTCCCCGCCGTGCTGCAGAGCAGCGGCCTGTACAGCCTGAGCAGCGTGGTGACAG

TGCCAAGCAGCAGCCTGGGAACCCAGACCTACATCTGCAACGTGAACCACAAGCCCAG

CAACACCAAGGTGGACAAGAGAGTGGAGCCCAAGAGCTGCGACAAGACCCATACCTGT

CCACCCTGCCCAGCCCCCCCAGTGGCCGGACCCTCCGTGTTCCTGTTCCCCCCCAAGC

CCAAGGACACCCTGATGATCAGCAGGACCCCCGAGGTGACCTGCGTGGTGGTGGACG

TGAGCCACGAGGACCCAGAGGTGAAGTTCAATTGGTATGTGGACGGCGTGGAGGTGCA

CAACGCCAAGACCAAGCCCAGAGAGGAACAGTACAACAGCACCTACAGGGTGGTGTCC

GTGCTGACCGTGCTGCACCAGGACTGGCTGAACGGCAAGGAATACAAGTGCAAGGTCT

CCAACAAGGCCCTGCCCTCCAGCATCGAGAAAACCATCAGCAAGGCCAAGGGCCAGCC

ACGGGAGCCCCAGGTGTACACACTGCCCCCATCTCGGGAAGAAATGACCAAGAACCAG

GTGTCCCTGACCTGTCTGGTGAAGGGCTTTTACCCCAGCGACATCGCCGTGGAGTGGG

AGAGCAACGGCCAGCCCGAGAACAACTACAAGACCACCCCCCCTGTGCTGGACAGCGA

CGGCAGCTTCTTCCTGTACAGCAAGCTGACCGTGGACAAGTCCAGGTGGCAGCAGGGC

AACGTGTTCAGCTGCAGCGTGATGCACGAGGCCCTGCACAACCACTACACACAGAAGA

GCCTGAGCCTGTCCCCCGGC*TGA*

-continued mAb1 light chain nucleotide sequence
wherein uPA signal peptide is underlined
start and stop codons are in italics,
VL region sequence in boldface, and
CDRs are indicated with double underlining:

(SEQ ID NO: 16)

*ATG*AGGGCCCTGCTGGCTAGACTGCTGCTGTGCGTGCTGGTCGTGTCCGACAGCAAGG

GCGAAATCGTACTCACGCAGTCTCCAGCCACCCTGTCTGTGTCTCCAGGGGAAAGAG

CCACCCTCTCCTGCAGGACCAGTCAGAGTGTTCGCAGCAACTTAGCCTGGTACCAGC

AGAAGCCTGGCCAGGCTCCCAGGCTCCTCATCTATGCTGCATCCACCAGGGCCACTG

GTATCCCAGCCAGGTTCAGTGGCAGTGGGTCTGGGACAGAGTTCACTCTCACCATCA

GCAGCCTGCAGTCTGAAGATTTTGCAGTTTATTACTGTCAGCAGCAGTATACTAACTGGCC

ATTCACTTTCGGCCCTGGGACCAAAGTGGACATCAAACGTACGGTGGCTGCACCATCT

GTCTTCATCTTCCCGCCATCTGATGAGCAGTTGAAATCTGGAACTGCCTCTGTTGTGTG

CCTGCTGAATAACTTCTATCCCAGAGAGGCCAAAGTACAGTGGAAGGTGGATAACGCCC

TCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGGG

GAGAGTGTTGA*TAG*

The invention further relates to a method of producing an antibody of the invention, which method comprises the steps consisting of: (i) culturing a transformed host cell according to the invention; (ii) expressing the antibody; and (iii) recovering the expressed antibody.

Antibodies of the invention can be suitably separated from the culture medium by conventional immunoglobulin purification procedures such as, for example, protein A-Sepharose, hydroxyapatite chromatography, gel electrophoresis, dialysis, or affinity chromatography.

In some embodiments, a humanized chimeric antibody of the present invention can be produced by obtaining nucleic acid sequences encoding humanized VL and VH regions as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, any region which belongs to human immunoglobulin heavy chains may be used, for instance those of IgG class are suitable and any one of subclasses belonging to IgG class, such as IgG1, IgG2, IgG3 and IgG4, can be used. Also, as the CL of a human chimeric antibody, any region which belongs to human immunoglobulin light chains may be used, and those of kappa class or lambda class can be used.

Methods for producing humanized or chimeric antibodies may involve conventional recombinant DNA and gene transfection techniques are well known in the art (see e.g. Morrison S L. et al. (1984) and patent documents U.S. Pat. Nos. 5,202,238; and 5,204,244).

Methods for producing humanized antibodies based on conventional recombinant DNA and gene transfection techniques are well known in the art (see, e.g., Riechmann L. et al. 1988; Neuberger M S. et al. 1985). Antibodies can be humanized using a variety of techniques known in the art including, for example, the technique disclosed in the application WO2009/032661, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

A Fab of the present invention can be obtained by treating an antibody of the invention (e.g. an IgG) with a protease, such as papaine. Also, the Fab can be produced by inserting DNA sequences encoding both chains of the Fab of the antibody into a vector for prokaryotic expression, or for eukaryotic expression, and introducing the vector into prokaryotic or eukaryotic cells (as appropriate) to express the Fab.

A F(ab')2 of the present invention can be obtained treating an antibody of the invention (e.g. an IgG) with a protease, pepsin. Also, the F(ab')2 can be produced by binding a Fab' described below via a thioether bond or a disulfide bond.

A Fab' of the present invention can be obtained by treating F(ab')2 of the invention with a reducing agent, such as dithiothreitol. Also, the Fab' can be produced by inserting DNA sequences encoding Fab' chains of the antibody into a vector for prokaryotic expression, or a vector for eukaryotic expression, and introducing the vector into prokaryotic or eukaryotic cells (as appropriate) to perform its expression.

A scFv of the present invention can be produced by taking sequences of the CDRs or VH and VL domains as previously described for the antibody of the invention, then constructing a DNA encoding a scFv fragment, inserting the DNA into a prokaryotic or eukaryotic expression vector, and then introducing the expression vector into prokaryotic or eukaryotic cells (as appropriate) to express the scFv. To generate a humanized scFv fragment, a well-known technology called CDR grafting may be used, which involves selecting the complementary determining regions (CDRs) according to the invention, and grafting them onto a human scFv fragment framework of known three dimensional structure (see, e.g., WO98/45322; WO 87/02671; U.S. Pat. Nos. 5,859,205; 5,585,089; 4,816,567; EP0173494).

Modification of the Antibodies of the Invention

Amino acid sequence modification(s) of the antibodies described herein are contemplated. For example, it may be desirable to improve the binding affinity and/or other biological properties of the antibody.

Modifications and changes may be made in the structure of the antibodies of the present invention, and in the DNA sequences encoding them, and still result in a functional antibody or polypeptide with desirable characteristics.

In making the changes in the amino sequences of polypeptide, the hydropathic index of amino acids may be considered. The importance of the hydropathic amino acid index for the interactive biologic function of a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further aspect of the present invention also encompasses function-conservative variants of the polypeptides of the present invention.

For example, certain amino acids may be substituted by other amino acids in a protein structure without appreciable loss of activity. Since the interactive capacity and nature of a protein define its biological functional activity, certain amino acid substitutions can be made in a protein sequence, and of course in its encoding DNA sequence, while nevertheless obtaining a protein with like properties. It is thus contemplated that various changes may be made in the antibody sequences of the invention, or corresponding DNA sequences which encode said polypeptides, without appreciable loss of their biological activity.

It is known in the art that certain amino acids may be substituted by other amino acids having a similar hydropathic index or score and still result in a protein with similar biological activity, i.e. still obtain a biological functionally equivalent protein. It is also possible to use well-established technologies, such as alanine-scanning approaches, to identify, in an antibody or polypeptide of the invention, all the amino acids that can be substituted without significant loss of binding to the antigen. Such residues can be qualified as neutral, since they are not involved in antigen binding or in maintaining the structure of the antibody. One or more of these neutral positions can be substituted by alanine or by another amino acid can without changing the main characteristics of the antibody or polypeptide of the invention.

Neutral positions can be seen as positions where any amino acid substitution could be incorporated. Indeed, in the principle of alanine-scanning, alanine is chosen since it this residue does not carry specific structural or chemical features. It is generally admitted that if an anlanine can be substituted for a specific amino acid without changing the properties of a protein, many other, if not all amino acid substitutions are likely to be also neutral. In the opposite case where alanine is the wild-type amino acid, if a specific substitution can be shown as neutral, it is likely that other substitutions would also be neutral.

As outlined above, amino acid substitutions are generally based on the relative similarity of the amino acid side-chain substituents, for example, their hydrophobicity, hydrophilicity, charge, size, and the like. Exemplary substitutions which take any of the foregoing characteristics into consideration are well known to those of skill in the art and include: arginine and lysine; glutamate and aspartate; serine and threonine; glutamine and asparagine; and valine, leucine and isoleucine.

It may be also desirable to modify the antibody of the invention with respect to effector function, e.g. so as to enhance antigen-dependent cell-mediated cytotoxicity (ADCC) and/or complement dependent cytotoxicity (CDC) of the antibody, or e.g. to alter the binding to Fc receptors. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. 1992; and Shopes B. 1992). In some embodiments, an antibody of the invention may be an antibody with a modified amino acid sequence that results in reduced or eliminated binding to most Fcγ receptors, which can reduce uptake and toxicity in normal cells and tissues expressing such receptors, e.g. macrophages, liver sinusoidal cells etc. An example for such an antibody is one including substitutions of two leucine (L) residues to alanine (A) at position 234 and 235 (i.e. LALA); this double substitution has been demonstrated to reduce Fc binding to FcγRs and consequently to decrease ADCC as well to reduce complement binding/activation. Another example for such an antibody is one including the substitution P329G in addition to the LALA double substitution (i.e. PG-LALA; see e.g. Schlothauer et al., Novel human IgG1 and IgG4 Fc-engineered antibodies with completely abolished immune effector functions, Protein Engineering, Design and Selection, Volume 29, Issue 10, October 2016, Pages 457-466). In some embodiments, an antibody of the invention may thus be an antibody having an amino acid sequence that (i) contains e.g. the LALA or the PG-LALA set of substitutions and (ii) is otherwise identical to the amino acid sequence of one of the antibodies of the invention described herein above with reference to the respective SEQ ID NOs.

Another type of amino acid modification of the antibody of the invention may be useful for altering the original glycosylation pattern of the antibody, i.e. by deleting one or more carbohydrate moieties found in the antibody, and/or adding one or more glycosylation sites that are not present in the antibody. The presence of either of the tripeptide sequences asparagine-X-serine, and asparagine-X-threonine, where X is any amino acid except proline, creates a potential glycosylation site. Addition or deletion of glycosylation sites to the antibody can conveniently be accomplished by altering the amino acid sequence such that it contains one or more of the above-described tripeptide sequences (for N-linked glycosylation sites).

Another type of modification involves the removal of sequences identified, either in silico or experimentally, as potentially resulting in degradation products or heterogeneity of antibody preparations. As examples, deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in an antibody or polypeptide, it may therefore be considered to remove the site, typically by conservative substitution to remove one of the implicated residues. Such substitutions in a sequence to remove one or more of the implicated residues are also intended to be encompassed by the present invention.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antibody comprises linking the antibody to one of a variety of non-proteinaceous polymers, e.g. polyethylene glycol, polypropylene glycol, or polyoxyalkylenes, e.g. in the manner set forth in U.S. Pat. Nos. 4,640,835; 4,496,689; 4,301,144; 4,670,417; 4,791,192 or 4,179,337.

Other amino acid sequence modifications known in the art may also be applied to an antibody of the invention.

Immunoconjugates of the Invention

The present invention provides immunoconjugates, also referred to herein as antibody-drug conjugates or, more briefly, conjugates. As used herein, all these terms have the same meaning and are interchangeable. Suitable methods for preparing immunoconjugates are known in the art. The immunoconjugates of the invention may be prepared by in vitro methods, e.g. as described herein.

The present invention provides an immunoconjugate comprising an antibody of the invention (such as e.g. mAb1, or an antibody with the same six CDRs as mAb1) covalently linked via a linker to at least one growth inhibitory agent.

The term "growth inhibitory agent" (also referred to as an "anti-proliferative agent") refers to a molecule or compound or composition which inhibits growth of a cell, such as a tumor cell, in vitro and/or in vivo.

In some embodiments, the growth inhibitory agent is a cytotoxic drug (also referred to as a cytotoxic agent). In some embodiments, the growth inhibitory agent is a radioactive moiety.

The term "cytotoxic drug" as used herein refers to a substance that directly or indirectly inhibits or prevents the function of cells and/or causes destruction of the cells. The term "cytotoxic drug" includes e.g. chemotherapeutic agents, enzymes, antibiotics, toxins such as small molecule toxins or enzymatically active toxins, toxoids, vincas, taxanes, maytansinoids or maytansinoid analogs, tomaymycin or pyrrolobenzodiazepine derivatives, cryptophycin derivatives, leptomycin derivatives, auristatin or dolastatin analogs, prodrugs, topoisomerase I inhibitors, topoisomerase II inhibitors, DNA alkylating agents, anti-tubulin agents, CC-1065 and CC-1065 analogs.

Topoisomerase I inhibitors are molecules or compounds that inhibit the human enzyme topoisomerase I which is involved in altering the topology of DNA by catalyzing the transient breaking and rejoining of a single strand of DNA. Topoisomerase I inhibitors are highly toxic to dividing cells e.g. of a mammal. Examples of suitable topoisomerase I inhibitors include camptothecin (CPT) and analogs thereof such as topotecan, irinotecan, silatecan, cositecan, exatecan, lurtotecan, gimatecan, belotecan and rubitecan.

In some embodiments, the immunoconjugates of the invention comprise the cytotoxic drug exatecan as the growth inhibitory agent. Exatecan has the chemical name (1S,9S)-1-Amino-9-ethyl-5-fluoro-1,2,3,9,12,15-hexahydro-9-hydroxy-4-methyl-10H,13H-benzo(de)pyrano(3',4':6,7)indolizino(1,2-b)quinoline-10,13-dione. Exatecan is represented by the following structural formula (I):

(I)

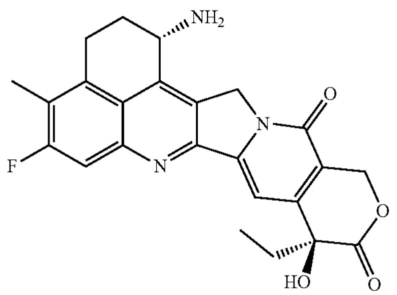

In further embodiments of the invention, other CPT analogs and other cytotoxic drugs may be used, e.g. as listed above. Examples of some cytotoxic drugs and of methods of conjugation are further given in the application WO2008/010101 which is incorporated by reference.

The term "radioactive moiety" refers to a chemical entity (such as a molecule, compound or composition) that comprises or consists of a radioactive isotope suitable for treating cancer, such as $At^{211}$, $Bi^{212}$, $Er^{169}$, $I^{131}$, $I^{125}$, $Y^{90}$, $In^{111}$, $P^{32}$, $Re^{186}$, $Re^{188}$, $Sm^{153}$, $Sr^{89}$, or radioactive isotopes of Lu. Such radioisotopes generally emit mainly beta-radiation. In some embodiments, the radioactive isotope is an alpha-emitter isotope, for example Thorium 227 which emits alpha-radiation. Immunoconjugates can be prepared e.g. as described in the application WO2004/091668.

In an immunoconjugate of the present invention, an antibody of the present invention is covalently linked via a linker to the at least one growth inhibitory agent. "Linker", as used herein, means a chemical moiety comprising a covalent bond and/or any chain of atoms that covalently attaches the growth inhibitory agent to the antibody. Linkers are well known in the art and include e.g. disulfide groups, thioether groups, acid labile groups, photolabile groups, peptidase labile groups and esterase labile groups. Conjugation of an antibody of the invention with cytotoxic drugs or other growth inhibitory agents may be performed e.g.

using a variety of bifunctional protein coupling agents including but not limited to N-succinimidyl pyridyldithiobutyrate (SPDB), butanoic acid 4-[(5-nitro-2-pyridinyl)dithio]-2,5-dioxo-1-pyrrolidinyl ester (nitro-SPDB), 4-(Pyridin-2-yldisulfanyl)-2-sulfo-butyric acid (sulfo-SPDB), N-succinimidyl (2-pyridyldithio) propionate (SPDP), succinimidyl (N-maleimidomethyl) cyclohexane-1-carboxylate (SMCC), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)-hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987). Carbon labeled 1-isothiocyanatobenzyl methyldiethylene triaminepentaacetic acid (MX-DTPA) is an exemplary chelating agent for conjugation of radionucleotide to an antibody (WO 94/11026).

In embodiments of the present invention, the linker may be a "cleavable linker", which may facilitate release of the cytotoxic drug or other growth inhibitory agent inside of or in the vicinity of a cell, e.g. a tumor cell. In some embodiments, the linker is a linker cleavable in an endosome of a mammalian cell. For example, an acid-labile linker, a peptidase-sensitive linker, an esterase labile linker, a photolabile linker or a disulfide-containing linker (see e.g. U.S. Pat. No. 5,208,020) may be used.

When referring to a structural formula representing an immunoconjugate, the following nomenclature is also used herein: a growth inhibitory agent and a linker, taken together, are also referred to as a [(linker)-(growth inhibitory agent)] moiety; for instance, an exatecan molecule and a linker, taken together, are also referred to as a [(linker)-(exatecan)] moiety.

In some specific embodiments of the present invention, the linker is a linker cleavable by the human enzyme glucuronidase. For example, an immunoconjugate of the present invention may thus have the following formula (II) which includes a linker cleavable by glucuronidase:

(II)

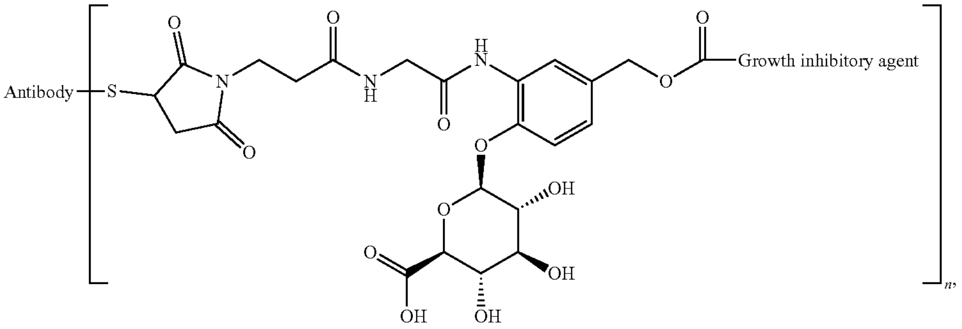

wherein the antibody is the antibody of the invention, wherein S is a sulfur atom of the antibody, and wherein n is a number of [(linker)-(growth inhibitory agent)] moieties covalently linked to the antibody. The number n may be e.g. between 1 and 10; in more specific embodiments, n is between 7 and 8; in even more specific embodiments, n is between 7.5 and 8.0 (i.e. about 8). In some embodiments, S is a sulfur atom of a cysteine of the antibody. In some embodiments, the antibody is mAb1.

The number n is also referred to as "drug-to-antibody ratio" (or "DAR"); this number n is always to be understood as an average number for any given (preparation of an) immunoconjugate.

In other specific embodiments of the present invention, the linker is a linker cleavable by the human enzyme legumain. For example, an immunoconjugate of the present invention may thus have the following formula (III) which includes a linker cleavable by legumain:

(III)

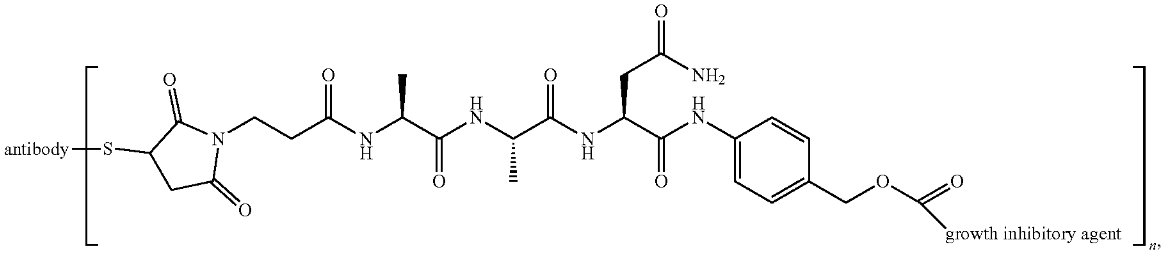

wherein the antibody is the antibody of the invention, wherein S is a sulfur atom of the antibody, and wherein n is a number of [(linker)-(growth inhibitory agent)] moieties covalently linked to the antibody. The number n (also referred to as the DAR) may be e.g. between 1 and 10; in more specific embodiments, n is between 7 and 8; in even more specific embodiments, n is between 7.5 and 8.0 (i.e. about 8). In some embodiments, S is a sulfur atom of a cysteine of the antibody. In some embodiments, the antibody is mAb1.

In each of the above formulae (II) and (III), the chemical structure between the sulfur atom of the antibody and the growth inhibitory agent is a linker. One of these linkers is also contained in each of the formulae (IV) to (IX) depicted further below.

In any one of the embodiments with linkers cleavable by glucuronidase or legumain, as described above, the growth inhibitory agent may be exatecan, for example.

Accordingly, in some embodiments, the present invention provides an immunoconjugate comprising an antibody according to the invention covalently linked via a linker to exatecan, wherein the conjugate has the following formula (IV):

(IV)

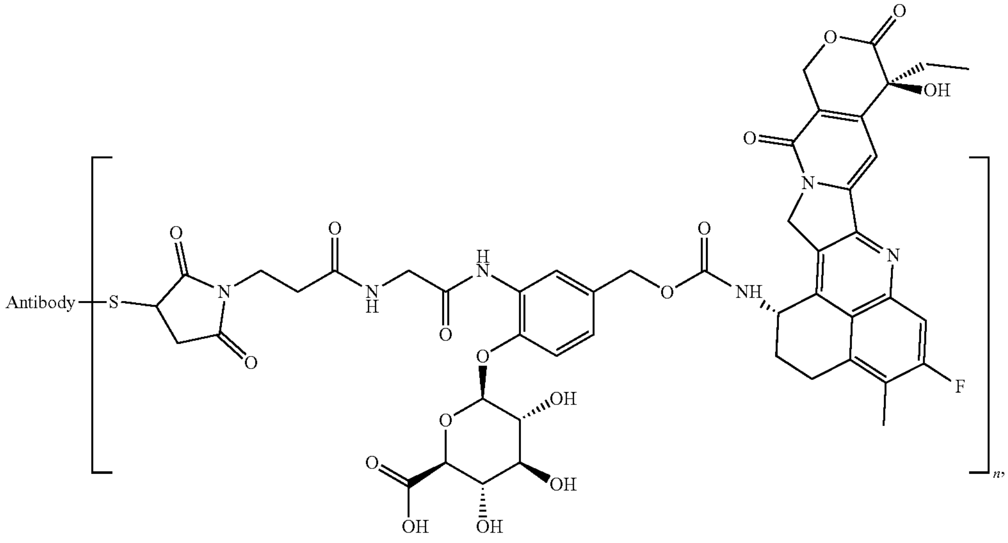

wherein S is a sulfur atom of the antibody, and wherein n is a number of [(linker)-(exatecan)] moieties covalently linked to the antibody. The number n (also referred to as the DAR) may be e.g. between 1 and 10; in more specific embodiments, n is between 7 and 8; in even more specific embodiments, n is between 7.5 and 8.0 (i.e. about 8). In some embodiments, the antibody is mAb1.

In some embodiments, in an immunoconjugate of the invention such as the exatecan conjugates with glucuronidase- or legumain-cleavable linkers as described above, the linker is covalently attached to the antibody at a sulfur atom of a cysteine residue of the antibody. For example, this cysteine residue of the antibody may be one of the cysteine residues capable of forming an interchain disulfide bond (also referred to herein as an interchain disulfide bridge).

As there are four interchain disulfide bonds in an IgG1 antibody, involving a total of eight cysteine residues, attachment of the linker to the antibody at a sulfur atom of such cysteine residues provides that the DAR may be up to 8 and, in such cases, the DAR is typically between 7 and 8, such as between 7.5 and 8.0 (i.e. about 8), provided that the antibody is an IgG1 or has the same number of interchain disulfide bonds as an IgG1.

wherein S is a sulfur atom of the antibody, and wherein n is a number of [(linker)-(exatecan)] moieties covalently linked to the antibody. The number n (also referred to as the DAR) may be e.g. between 1 and 10; in more specific embodiments, n is between 7 and 8; in even more specific embodiments, n is between 7.5 and 8.0 (i.e. about 8). In some embodiments, the antibody is mAb1.

In other embodiments, the present invention provides an immunoconjugate comprising an antibody according to the invention covalently linked via a linker to exatecan, wherein the conjugate has the following formula (V):

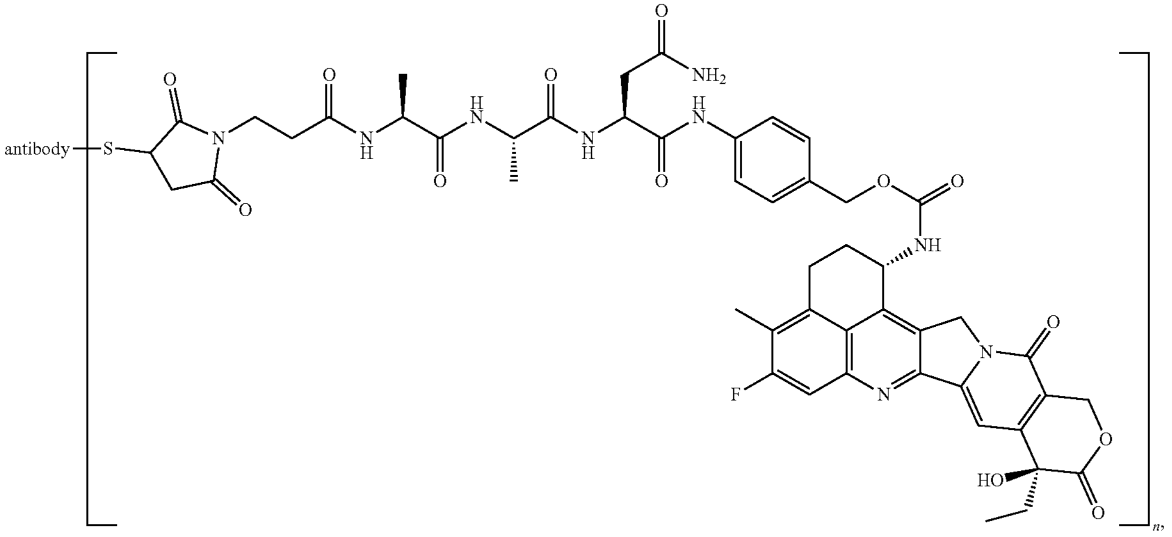

Accordingly, in some embodiments, the present invention provides an immunoconjugate comprising an antibody according to the invention covalently linked via a linker to exatecan, wherein the conjugate has the following formula (VI):

(VI)

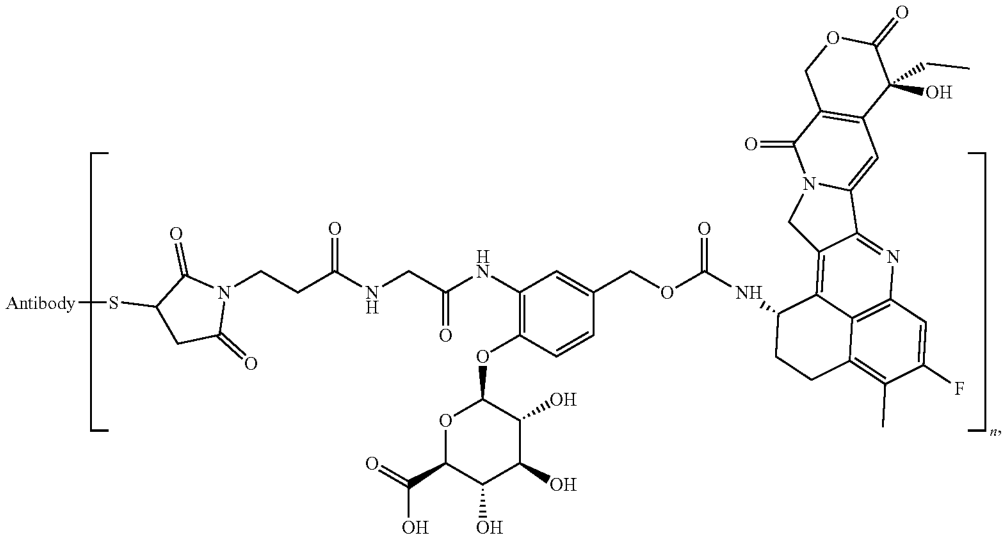

wherein S is a sulfur atom of a cysteine of the antibody, and wherein n is a number of [(linker)-(exatecan)] moieties covalently linked to the antibody. The number n (also referred to as the DAR) may be e.g. between 1 and 10; in more specific embodiments, n is between 7 and 8; in even more specific embodiments, n is between 7.5 and 8.0 (i.e. about 8).

In other embodiments, the present invention provides an immunoconjugate comprising an antibody according to the invention covalently linked via a linker to exatecan, wherein the conjugate has the following formula (VII):

(VII)

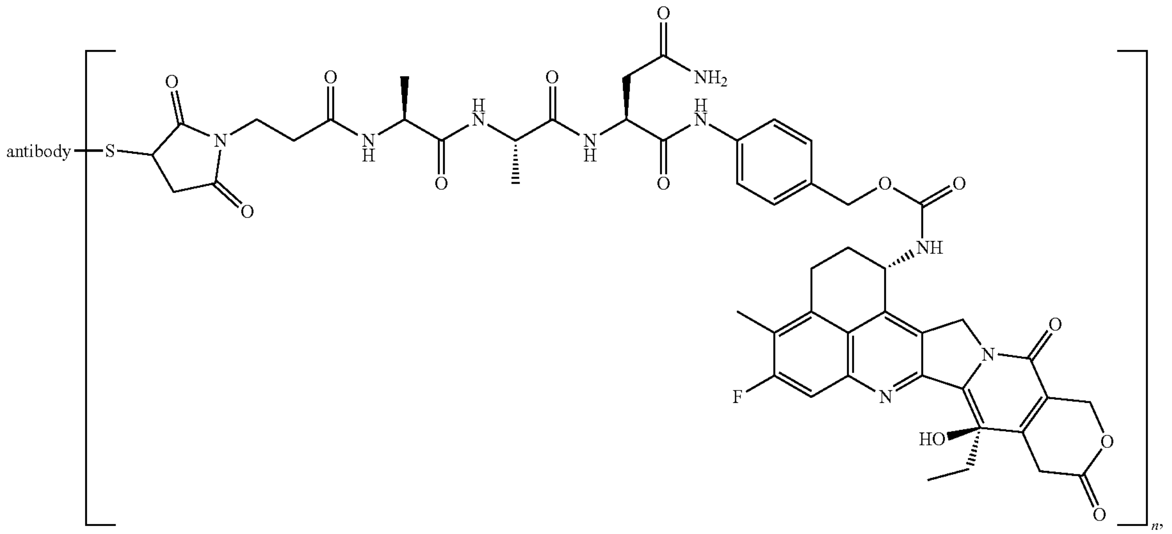

wherein S is a sulfur atom of a cysteine of the antibody, and wherein n is a number of [(linker)-(exatecan)] moieties covalently linked to the antibody. The number n (also referred to as the DAR) may be e.g. between 1 and 10; in more specific embodiments, n is between 7 and 8; in even more specific embodiments, n is between 7.5 and 8.0 (i.e. about 8).

In any of the immunoconjugates described above, any antibody of the invention (as described herein above and below) may be used. In some embodiments, the immunoconjugate of the invention comprises mAb1 as the antibody.

Accordingly, in some embodiments, the present invention provides an immunoconjugate comprising mAb1 covalently linked via a linker to exatecan, wherein the conjugate has the following formula (VIII):

(VIII)

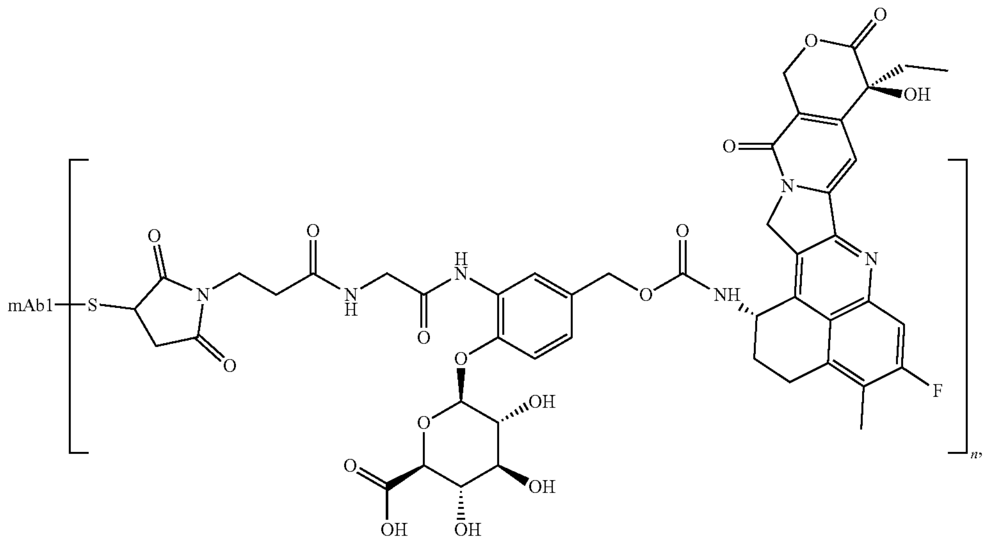

wherein S is a sulfur atom of a cysteine of the antibody mAb1, and wherein n is a number of [(linker)-(exatecan)] moieties covalently linked to mAb1. The number n (also referred to as the DAR) may be e.g. between 1 and 10; in more specific embodiments, n is between 7 and 8; in even more specific embodiments, n is between 7.5 and 8.0 (i.e. about 8). In some embodiments, S is a sulfur atom of a cysteine of mAb1 capable of forming an interchain disulfide bridge and the DAR is about 8. An example of such an immunoconjugate (namely "ADC1") is further described in the Examples.

In other embodiments, the present invention provides an immunoconjugate comprising mAb1 covalently linked via a linker to exatecan, wherein the conjugate has the following formula (IX):

moieties covalently linked to mAb1. The number n (also referred to as the DAR) may be e.g. between 1 and 10; in more specific embodiments, n is between 7 and 8; in even more specific embodiments, n is between 7.5 and 8.0 (i.e. about 8). In some embodiments, S is a sulfur atom of a cysteine of mAb1 capable of forming an interchain disulfide bridge and the DAR is about 8. An example of such an immunoconjugate (namely "ADC2") is further described in the Examples.

In other embodiments of the present invention, the linker may be a "non-cleavable linker" (for example an SMCC linker). Release of the growth inhibitory agent from the antibody can occur upon lysosomal degradation of the antibody.

(IX)

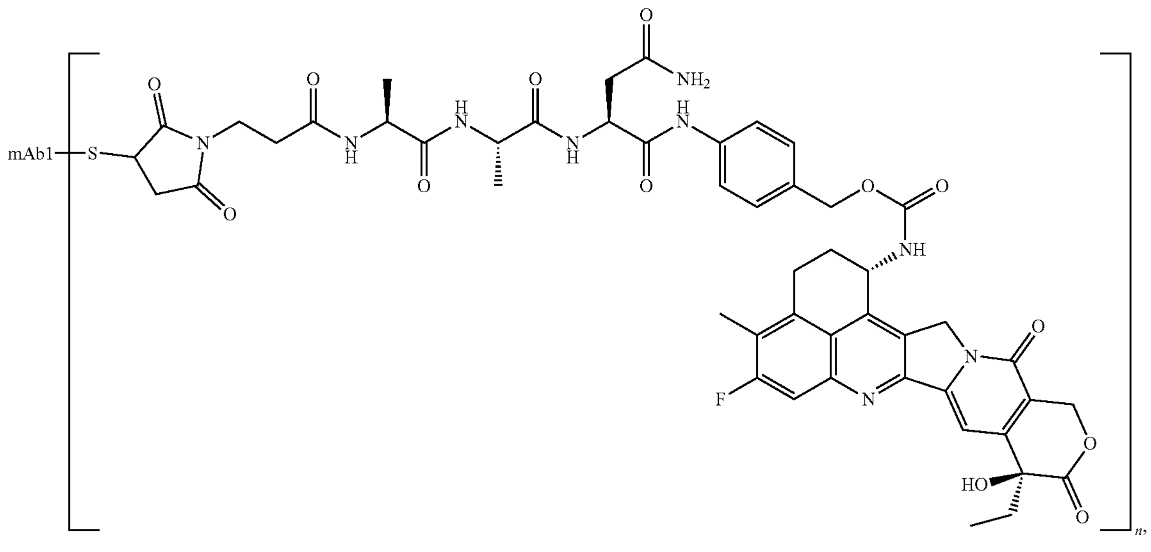

wherein S is a sulfur atom of a cysteine of the antibody mAb1, and wherein n is a number of [(linker)-exatecan)]

In other embodiments of the invention, the immunoconjugate may be a fusion protein comprising an antibody of the invention and a cytotoxic or growth inhibitory polypeptide (as the growth inhibitory agent); such fusion proteins may be made by recombinant techniques or by peptide synthesis, i.e. methods well known in the art. A molecule of encoding DNA may comprise respective regions encoding the two portions of the conjugate (antibody and cytotoxic or growth inhibitory polypeptide, respectively) either adjacent to one another or separated by a region encoding a linker peptide.

The antibodies of the present invention may also be used in directed enzyme prodrug therapy such as antibody-directed enzyme prodrug therapy by conjugating the antibodies to a prodrug-activating enzyme which converts a prodrug (e.g. a peptidyl chemotherapeutic agent, see WO081/01145) to an active cytotoxic drug (see, for example, WO 88/07378 and U.S. Pat. No. 4,975,278). The enzyme component of an immunoconjugate useful for ADEPT may include any enzyme capable of acting on a prodrug in such a way as to convert it into its more active, cytotoxic form. Enzymes that are useful in this context include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anticancer drug 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs.

The enzymes can be covalently bound to the antibodies of the invention by techniques well known in the art, such as the use of the linkers discussed above.

Suitable methods for preparing an immunoconjugate of the invention are well known in the art (see e.g. Hermanson G. T., Bioconjugate Techniques, Third Edition, 2013, Academic Press). For instance, methods of conjugating a cytotoxic drug to an antibody via a linker that attaches covalently to cysteine residues of interchain disulfide bridges of the antibody are well known.

In general, an immunoconjugate of the present invention can be obtained e.g. by a process comprising the steps of:

(i) preparing a compound comprising the linker and the growth inhibitory agent (e.g. cytotoxic drug), also referred to herein as a "drug-linker compound";
(ii) bringing into contact an optionally buffered aqueous solution of an antibody according to the invention with a solution of the drug-linker compound;
(iii) then optionally separating the conjugate which was formed in (ii) from the unreacted antibody and/or drug-linker compound.

The aqueous solution of antibody can be buffered with buffers such as e.g. histidine, potassium phosphate, acetate, citrate or N-2-Hydroxyethylpiperazine-N'-2-ethanesulfonic acid (Hepes buffer). The buffer may be chosen depending upon the nature of the antibody. The drug-linker compound can be dissolved e.g. in an organic polar solvent such as dimethyl sulfoxide (DMSO) or dimethylacetamide (DMA).

For conjugation to the cysteine residues of an antibody, the antibody is subjected to reduction (e.g. using TCEP) before step (ii). Suitable reduction conditions to reduce only the interchain disulfide bonds are known in the art.

The reaction temperature for conjugation is usually between 20 and 40° C. The reaction time can vary and is typically from 1 to 24 hours. The reaction between the antibody and the drug-linker compound can be monitored by size exclusion chromatography (SEC) with a refractometric and/or UV detector. If the conjugate yield is too low, the reaction time can be extended.

A number of different chromatography methods can be used by the person skilled in the art in order to perform the separation of step (iii): the conjugate can be purified e.g. by SEC, adsorption chromatography (such as ion exchange chromatography, IEC), hydrophobic interaction chromatography (HIC), affinity chromatography, mixed-support chromatography such as hydroxyapatite chromatography, or high performance liquid chromatography (HPLC) such as reverse-phase HPLC. Purification by dialysis or filtration or diafiltration can also be used.

After step (ii) and/or (iii), the conjugate-containing solution can be subjected to an additional step (iv) of purification e.g. by chromatography, ultrafiltration and/or diafiltration. Such an additional step of purification e.g. by chromatography, ultrafiltration and/or diafiltration can also be performed with the antibody-containing solution after the reduction reaction, in cases where reduction is performed prior to conjugation.

The conjugate is recovered at the end of such a process in an aqueous solution. The drug-to-antibody ratio (DAR) is a number that can vary with the nature of the antibody and of the drug-linker compound used along with the experimental conditions used for the conjugation (such as the ratio (drug-linker compound)/(antibody), the reaction time, the nature of the solvent and of the cosolvent if any). Thus, the contact between the antibody and the drug-linker compound can lead to a mixture comprising several conjugates differing from one another by different drug-to-antibody ratios. The DAR that is determined is thus an average value.

Performing conjugation at the cysteine residues of interchain disulfide bridges using an antibody that has four interchain disulfide bridges (e.g. mAb1 or any IgG1 antibody)—which is a method well known in the art—offers the advantage that a relatively homogeneous DAR of about 8 can be achieved by choosing reaction conditions that allow conjugation to proceed to completion (or at least close to completion).

An exemplary method which can be used to determine the DAR consists of measuring spectrophotometrically the ratio of the absorbance at of a solution of purified conjugate at $\lambda_D$ and 280 nm. 280 nm is a wavelength generally used for measuring protein concentration, such as antibody concentration. The wavelength $\lambda_D$ is selected so as to allow discriminating the drug from the antibody, i.e. as readily known to the skilled person, $\lambda_D$ is a wavelength at which the drug has a high absorbance and $\lambda_D$ is sufficiently remote from 280 nm to avoid substantial overlap in the absorbance peaks of the drug and antibody. For instance, $\lambda_D$ may be selected as being 370 nm for exatecan (or for camptothecin or other camptothecin analogs), or 252 nm for maytansinoid molecules.

A method of DAR calculation may be derived e.g. from Antony S. Dimitrov (ed), LLC, 2009, Therapeutic Antibodies and Protocols, vol 525, 445, Springer Science: The absorbances for the conjugate at $\lambda_D$ ($A_{\lambda D}$) and at 280 nm ($A_{280}$) are measured either on the monomeric peak of the size exclusion chromatography (SEC) analysis (allowing to calculate the "DAR(SEC)" parameter) or using a classic spectrophotometer apparatus (allowing to calculate the "DAR(UV)" parameter). The absorbances can be expressed as follows:

$$A_{\lambda D}=(C_D\times\varepsilon_{D\lambda D})+(C_A\times\varepsilon_{A\lambda D})$$

$$A_{280}=(C_D\times\varepsilon_{D280})+(C_A\times\varepsilon_{A280})$$

wherein:

$C_D$ and $C_A$ are respectively the concentrations in the solution of the drug and of the antibody $\varepsilon_{D\lambda D}$ and $\varepsilon_{D280}$ are respectively the molar extinction coefficients of the drug at $\lambda_D$ and 280 nm $\varepsilon_{A\lambda D}$ and $\varepsilon_{A280}$ are respectively the molar extinction coefficients of the antibody at $\lambda_D$ and 280 nm.

Resolution of these two equations with two unknowns leads to the following equations:

$$C_D=[(\varepsilon_{A280}\times A_{\lambda D})-(\varepsilon_{A\lambda D}\times A_{280})]/[(\varepsilon_{D\lambda D}\times\varepsilon_{A280})-(\varepsilon_{A\lambda D}\times\varepsilon_{D280})]$$

$$C_A=[A_{280}-(C_D\times\varepsilon_{D280})]/\varepsilon_{A280}$$

The average DAR is then calculated from the ratio of the drug concentration to that of the antibody: DAR=$C_D/C_A$.

Exemplary methods for preparing an immunoconjugate of the invention are described in the Examples.

Drug-Linker Compounds

The present invention also provides compounds comprising a linker and a growth inhibitory agent (e.g. a cytotoxic drug), also referred to herein as "drug-linker compounds". For instance, the present invention provides a compound of the following formula (X):

(X)

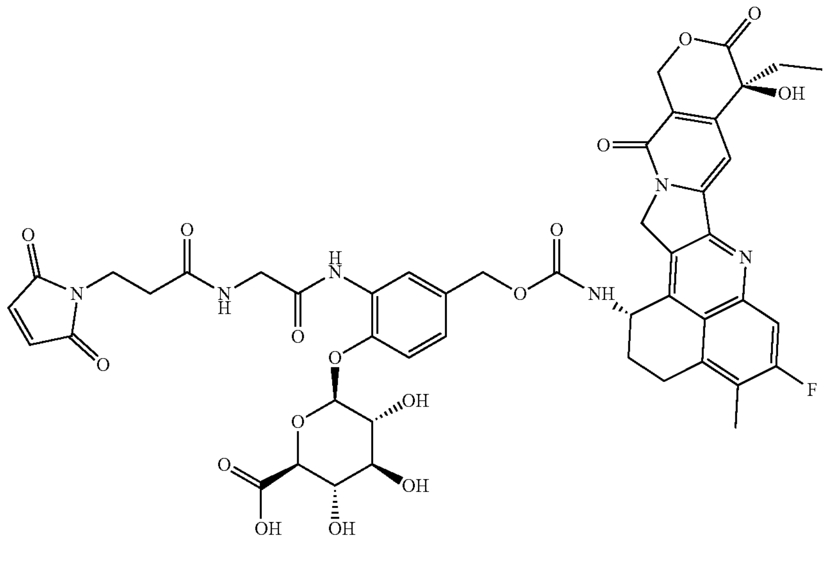

or a physiologically acceptable salt thereof; this compound is also referred to herein as "drug-linker compound 1", "compound DL1" or "DL1".

The present invention also provides a compound of the following formula (XI):

(XI)

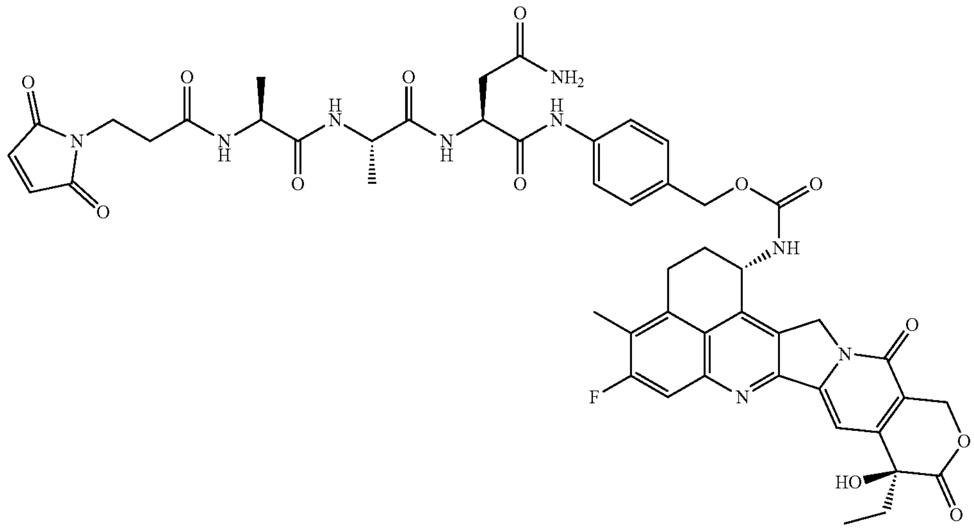

or a physiologically acceptable salt thereof; this compound is also referred to herein as "drug-linker compound 2", "compound DL2" or "DL2".

These drug-linker compounds may be used to prepare immunoconjugates of the invention as described herein above and below.

The drug-linker compounds of the invention (e.g. those of formula (X) or (XI) depicted above) may be prepared by chemical synthesis, for instance as described in the Examples further below.

Pharmaceutical Compositions

The antibodies or immunoconjugates of the invention may be combined with pharmaceutically acceptable carriers, diluents and/or excipients, and optionally with sustained-release matrices including but not limited to the classes of biodegradable polymers, non-biodegradable polymers, lipids or sugars, to form pharmaceutical compositions.

Thus, another aspect of the invention relates to a pharmaceutical composition comprising an antibody or an immunoconjugate of the invention and a pharmaceutically acceptable carrier, diluent and/or excipient.

"Pharmaceutical" or "pharmaceutically acceptable" refers to molecular entities and compositions that do not produce an adverse, allergic or other unwanted reaction when administered to a mammal, especially a human, as appropriate. A pharmaceutically acceptable carrier, diluent or excipient refers to a non-toxic solid, semi-solid or liquid filler, diluent, encapsulating material or formulation auxiliary of any type.

As used herein, "pharmaceutically acceptable carriers" include any and all solvents, dispersion media, coatings, antibacterial and antifungal agents, and the like that are physiologically compatible. Examples of suitable carriers, diluents and/or excipients include, but are not limited to, one or more of water, amino acids, saline, phosphate buffered saline, buffer phosphate, acetate, citrate, succinate; amino acids and derivates such as histidine, arginine, glycine, proline, glycylglycine; inorganic salts such as NaCl or calcium chloride; sugars or polyalcohols such as dextrose, glycerol, ethanol, sucrose, trehalose, mannitol; surfactants such as polysorbate 80, polysorbate 20, poloxamer 188; and the like, as well as combination thereof.

In many cases, it will be useful to include isotonic agents, such as sugars, polyalcohols, or sodium chloride in a pharmaceutical composition, and the formulation may also contain an antioxidant such as tryptamine and/or a stabilizing agent such as Tween 20.

The form of the pharmaceutical compositions, the route of administration, the dosage and the regimen naturally depend upon the condition to be treated, the severity of the illness, the age, weight, and gender of the patient, etc.

The pharmaceutical compositions of the invention can be formulated for a topical, oral, parenteral, intranasal, intravenous, intramuscular, subcutaneous or intraocular administration and the like.

In an embodiment, the pharmaceutical compositions contain vehicles which are pharmaceutically acceptable for a formulation for injection. These may be isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical composition can be administrated through drug combination devices.

The doses used for the administration can be adapted as a function of various parameters, and for instance as a function of the mode of administration used, of the relevant pathology, or alternatively of the desired duration of treatment.

To prepare pharmaceutical compositions, an effective amount of the antibody or immunoconjugate of the invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions; in all such cases, the form must be sterile and injectable with the appropriate device or system for delivery without degradation, and it must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant. Dispersions can also be prepared in glycerol, liquid polyethylene glycols, and mixtures thereof and in oils. Under ordinary conditions of storage and use, these preparations may contain a preservative to prevent the growth of microorganisms.

An antibody or immunoconjugate of the invention can be formulated into a pharmaceutical composition in a neutral or salt form. Pharmaceutically acceptable salts include the acid addition salts (formed with the free amino groups of the protein) which are formed with inorganic acids such as, for example, hydrochloric or phosphoric acids, or such organic acids as acetic, oxalic, tartaric, or mandelic acid, and the like. Salts formed with the free carboxyl groups can also be derived from inorganic bases such as, for example, sodium, potassium, ammonium, calcium, or ferric hydroxides, and such organic bases as isopropylamine, trimethylamine, glycine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In some cases, it may be desirable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions can be prepared by incorporating the active compounds in the required amount in the appropriate solvent with any of the other ingredients enumerated above, as required, followed by filtered sterilization. Generally, dispersions can be prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

The preparation of more concentrated, or highly concentrated solutions for direct injection is also contemplated, where the use of DMSO as solvent is envisioned to result in extremely rapid penetration, delivering high concentrations of the active agents to a small tumor area.

Upon formulation, solutions can be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution can be suitably buffered if necessary and the liquid diluent first rendered isotonic with sufficient saline or glucose. These aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibody or immunoconjugate of the invention may be formulated within a therapeutic mixture to comprise e.g. about 0.01 to 100 milligrams per dose or so.

In addition to the antibody or immunoconjugate formulated for parenteral administration, such as intravenous or intramuscular injection, other pharmaceutically acceptable forms include e.g. tablets or other solids for oral administration, time release capsules, and any other form currently used.

In some embodiments, the use of liposomes and/or nanoparticles is contemplated for the introduction of polypeptides into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles, or biodegradable polylactide or polylactide coglycolide nanoparticles that meet these requirements are contemplated for use in the present invention, and such particles may be easily made by those of skill in the art.

Liposomes can be formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 A, containing an aqueous solution in the core. The physical characteristics of liposomes depend on pH, ionic strength and the presence of divalent cations.

Besides the above-mentioned examples, further pharmaceutical forms such as nanoparticles, microparticles and -capsules, implants (e.g. lipid implants), or self-solidifying or -emulsifying systems, are also contemplated.

Therapeutic Methods and Uses

The inventors have found that an antibody of the invention (e.g. mAb1) is able to internalize as part of the CEACAM5-antibody complex after binding. Furthermore, they have shown that such an antibody, conjugated to a cytotoxic drug (exatecan), mediates a cytotoxic effect on tumor cells in vitro. The inventors have also shown that these immunoconjugates of the invention induce a marked anti-tumor activity in vivo e.g. in murine xenograft models of human colorectal carcinoma derived from a patient, when used at a dose of 10 mg/kg, with a single injection. In fact, the immunoconjugates of the invention show broad activity in a large set of in vitro and in vivo models. Cytotoxic potency correlates well with target (CEACAM5) expression and is much lower in target-negative cells. In several cell-line-derived xenograft (CDX) and patient-derived xenograft (PDX) models of different cancer types a very good antitumor activity was demonstrated. The immunoconjugates were well tolerated in a non-human primate dose-range finding study with a side effect profile which is typical for a topoisomerase-I inhibitor chemotherapy. The preclinical data indicate a good therapeutic window for later clinical testing. The antibodies, immunoconjugates and pharmaceutical compositions of the invention may thus be useful for treating cancer.

Accordingly, the present invention provides the antibody, immunoconjugate or pharmaceutical composition of the invention for use as a medicament. For instance, the invention provides the antibody, immunoconjugate or pharmaceutical composition of the invention for use in the treatment of cancer. The invention further provides a method of treating cancer, comprising administering the antibody, immunoconjugate or pharmaceutical composition of the invention to a subject in need thereof.

The cancer to be treated with antibodies, immunoconjugates, or pharmaceutical compositions of the invention is preferably a cancer expressing CEACAM5, more preferably a cancer overexpressing CEACAM5 as compared to normal (i.e. non-tumoral) cells of the same tissue origin. Expression of CEACAM5 by cells may be readily assayed for instance by using an antibody according to the invention (or a commercially available anti-CEACAM5 antibody), for instance as described in the following section "Diagnostic uses", and e.g. by an immunohistochemical method.

In some embodiments, the cancer to be treated with antibodies, immunoconjugates, or pharmaceutical compositions of the invention is a colorectal cancer, non-small-cell lung carcinoma, pancreatic cancer, gastric cancer, cervical cancer, esophageal cancer (e.g. esophageal adenocarcinoma), cholangiocarcinoma, breast cancer, prostate cancer, ovarian cancer, urothelial cancer, bladder cancer, or cancer of the stomach, uterus, endometrium, thyroid, or skin. In some specific embodiments, the cancer to be treated with antibodies, immunoconjugates, or pharmaceutical compositions of the invention is colorectal cancer, gastric cancer, non-small cell lung cancer, pancreatic cancer, esophageal cancer or prostate cancer.

The antibodies or immunoconjugates of the invention may be used in cancer therapy alone or in combination with any suitable growth inhibitory agent.

The antibodies of the invention may be conjugated (linked) to a growth inhibitory agent, as described above. Antibodies of the invention may thus be useful for targeting said growth inhibitory agent to cancerous cells expressing or over-expressing CEACAM5 on their surface.

It is also well known that therapeutic monoclonal antibodies can lead to the depletion of cells bearing the antigen specifically recognized by the antibody. This depletion can be mediated through at least three mechanisms: antibody mediated cellular cytotoxicity (ADCC), complement dependent lysis, and direct inhibition of tumor growth through signals mediated by the antigen targeted by the antibody.

"Antibody-dependent cell-mediated cytotoxicity" or "ADCC" refers to a form of cytotoxicity in which antibodies bound to Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell. To assess ADCC activity of a molecule of interest, an in vitro ADCC assay, such as that described in U.S. Pat. No. 5,500,362 or 5,821,337 may be performed.

"Complement dependent cytotoxicity" or "CDC" refers to the lysis of a target cell in the presence of complement. Activation of the classical complement pathway is initiated by the binding of the first component of the complement system to antibodies which are bound to their cognate antigen. To assess complement activation, a CDC assay, e.g. as described in Gazzano-Santoro et al. (Journal of Immunological Methods. 1997 March; 202(2):163-171) may be performed.

In some embodiments, an antibody of the invention may be an antibody with a modified amino acid sequence that results in reduced or eliminated binding to most Fcγ receptors, which can reduce uptake and toxicity in normal cells and tissues expressing such receptors, e.g. macrophages, liver sinusoidal cells etc.

An aspect of the invention relates to a method of treating cancer, comprising administering a therapeutically effective amount of the antibody, immunoconjugate or pharmaceutical composition of the invention to a subject in need thereof.

In the context of the invention, the term "treating" or "treatment", as used herein, means reversing, alleviating, inhibiting the progress of, or preventing the disorder or condition to which such term applies, or one or more symptoms of such disorder or condition. By the term "treating cancer" as used herein is meant the inhibition of the growth of malignant cells of a tumor and/or the progression of metastases from said tumor. Such treatment can also lead to the regression of tumor growth, i.e., the decrease in size of a measurable tumor. For instance, such treatment can lead to the complete regression of the tumor or metastasis.

In the context of the therapeutic applications of the present invention, the term "subject" or "patient" or "subject in need thereof" or "patient in need thereof" refers to a subject (e.g. a human or non-human mammal) affected or likely to be affected by a tumor. For instance, said patient may be a patient who has been determined to be susceptible to a therapeutic agent targeting CEACAM5, in particular to an antibody or immunoconjugate according to the invention, for instance according to a method as described herein below.

By a "therapeutically effective amount" is meant a sufficient amount to treat said cancer disease at a reasonable benefit/risk ratio applicable to any medical treatment. It will be understood, however, that the total daily usage of the antibodies, immunoconjugates and pharmaceutical compositions (collectively referred to as the "therapeutic agent") of the present invention will be decided by the attending physician within the scope of sound medical judgment. The specific therapeutically effective dose level for any particular patient will depend upon a variety of factors including the disorder being treated and the severity of the disorder; activity of the specific therapeutic agent employed; the age, body weight, general health, sex and diet of the patient; the time of administration, route of administration, and rate of excretion of the specific therapeutic agent employed; the duration of the treatment; drugs used in combination or coincidental with the specific therapeutic agent employed; and like factors well known in the medical arts. For example, it is well known within the skill of the art to start doses of the compound at levels lower than those required to achieve the desired therapeutic effect and to gradually increase the dosage until the desired effect is achieved.

The antibody, immunoconjugate or pharmaceutical composition of the invention may also be used for inhibiting the progression of metastases of a cancer.

Antibodies, immunoconjugates or pharmaceutical compositions of the invention may also be used in combination with any other therapeutic intervention for treating a cancer (e.g. adjuvant therapy) and/or for reducing the growth of a metastatic cancer. For instance, the other therapeutic intervention for such combination may be a standard-of-care (SOC) therapeutic agent for the cancer to be treated.

Efficacy of the treatment with an antibody or immunoconjugate or pharmaceutical composition according to the invention may be readily assayed in vivo, for instance in a mouse model of cancer and by measuring e.g. changes in tumor volume between treated and control groups, % tumor regression, partial regression or complete regression.

Diagnostic Uses

CEACAM5 has been reported to be highly expressed on the surface of cancer cells such as e.g. colorectal, gastric, lung, and pancreatic tumor cells, and expression in normal tissues is limited to a few normal epithelial cells such as colon and esophagus epithelial cells.

Therefore, CEACAM5 constitutes a cancer marker and has the potential to be used e.g. to indicate the effectiveness of an anti-cancer therapy or to detect recurrence of the disease.

In an embodiment, the antibody of the invention can be used as component of an assay in the context of a therapy targeting CEACAM5 expressing tumors, in order to determine susceptibility of the patient to the therapeutic agent, monitor the effectiveness of the anti-cancer therapy or detect recurrence of the disease after treatment. In some embodiments, the same antibody of the invention can be used both as component of the therapeutic agent and as component of the diagnostic assay.

Thus, a further aspect of the invention relates to a use of an antibody according to the invention for detecting CEACAM5 expression ex vivo in a biological sample from a subject. Another aspect of the invention relates to the use of an antibody of the invention for detecting CEACAM5 expression in vivo in a subject. When used for detection of CEACAM5, the antibody may be labelled with a detectable molecule such as e.g. a fluorophore or an enzyme.

Detection of CEACAM5 may be intended for e.g.

a) diagnosing the presence of a cancer in a subject, or b) determining susceptibility of a patient having cancer to a therapeutic agent targeting CEACAM5, in particular an antibody or immunoconjugate according to the invention, or c) monitoring effectiveness of an anti-CEACAM5 cancer therapy or detecting a cancer relapse after anti-CEACAM5 cancer therapy, in particular wherein said therapy is therapy with an antibody or immunoconjugate according to the invention;

by detecting expression of the surface protein CEACAM5 on tumor cells.

In embodiments, the antibody is intended for an in vitro or ex vivo diagnostic use. For example, CEACAM5 may be detected using an antibody of the invention in vitro or ex vivo in a biological sample obtained from a subject. Use according to the invention may also be an in vivo use. For example, an antibody according to the invention can be administered to the subject and antibody-cell complexes can be detected and/or quantified, whereby the detection of said complexes is indicative of a cancer.

The invention further relates to an in vitro or ex vivo method of detecting the presence of a cancer in a subject, comprising the steps of (a) contacting a biological sample from a subject with an antibody according to the invention, in particular in conditions suitable for the antibody to form complexes with said biological sample;

(b) measuring the level of antibody bound to said biological sample; and (c) detecting the presence of a cancer by comparing the measured level of bound antibody with a control, an increased level of bound antibody compared to control being indicative of a cancer.

The invention also relates to an in vitro or ex vivo method of determining susceptibility of a patient having cancer to a therapeutic agent targeting CEACAM5, in particular an antibody or immunoconjugate according to the invention, which method comprises the steps of:

(a) contacting a biological sample from a patient having cancer with an antibody according to the invention, in particular in conditions suitable for the antibody to form complexes with said biological sample;

(b) measuring the level of antibody bound to said biological sample; and (c) comparing the measured level of bound antibody to said biological sample with the level of antibody bound to a control;

wherein an increased level of bound antibody to said biological sample compared to control is indicative of a patient susceptible to a therapeutic agent targeting CEACAM5.

In the above methods, said control can be a normal, non-cancerous biological sample of the same type, or a reference value determined as representative of the antibody binding level in a normal biological sample of the same type.

In an embodiment, the antibodies of the invention are useful for diagnosing a CEACAM5 expressing cancer, such as a colorectal cancer, gastric cancer, non-small cell lung cancer, pancreatic cancer, esophageal cancer, prostate cancer or other solid tumors expressing CEACAM5.

The invention further relates to an in vitro or ex vivo method of monitoring effectiveness of anti-CEACAM5 cancer therapy, comprising the steps of:

(a) contacting a biological sample from a subject undergoing anti-CEACAM5 cancer therapy with an antibody according to the invention, in particular in conditions suitable for the antibody to form complexes with said biological sample;

(b) measuring the level of antibody bound to said biological sample; and (c) comparing the measured level of bound antibody with the level of antibody bound to a control;

wherein a decreased level of bound antibody to said biological sample compared to control is indicative of effectiveness of said anti-CEACAM5 cancer therapy. In said method, an increased level of bound antibody to said biological sample compared to control would be indicative of ineffectiveness of said anti-CEACAM5 cancer therapy. In an embodiment of this method of monitoring effectiveness, said control is a biological sample of the same type as the biological sample submitted to analysis, but which was obtained from the subject at an earlier time point during the course of the anti-CEACAM5 cancer therapy.

The invention further relates to an in vitro or ex vivo method of detecting cancer relapse after anti-CEACAM5 cancer therapy, comprising the steps of (a) contacting a biological sample from a subject, the subject having completed anti-CEACAM5 cancer therapy, with an antibody according to the invention, in particular in conditions suitable for the antibody to form complexes with said biological sample;

(b) measuring the level of antibody bound to said biological sample; and (c) comparing the measured level of bound antibody with the level of antibody bound to a control;

wherein an increased level of bound antibody to said biological sample compared to control is indicative of cancer relapse after anti-CEACAM5 cancer therapy. Said control may be, in particular, a biological sample of the same type as the biological sample submitted to analysis, but which was obtained from the subject previously, namely upon or after completion of the anti-CEACAM5 cancer therapy.

Said anti-CEACAM5 cancer therapy is e.g. a therapy using an antibody or immunoconjugate according to the invention. Said anti-CEACAM5 cancer therapy targets a CEACAM5 expressing cancer, such as a colorectal cancer, gastric cancer, non-small cell lung cancer, pancreatic cancer, esophageal cancer, prostate cancer or other solid tumors expressing CEACAM5.

In some embodiments, antibodies of the invention may be labelled with a detectable molecule or substance, such as a fluorescent molecule or fluorophore, a radioactive molecule, an enzyme or any other labels known in the art that provide (either directly or indirectly) a signal.

As used herein, the term "labeled", with regard to the antibody according to the invention, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the polypeptide, as well as indirect labeling of the polypeptide by reactivity with a detectable substance.

An antibody of the invention may be labelled with a radioactive molecule by any method known to the art. For example, radioactive molecules include but are not limited to radioactive atoms for scintigraphic studies such as $I^{123}$, $I^{124}$, $In^{111}$, $Re^{186}$, $Re^{188}$, $Tc^{99}$. Antibodies of the invention may also be labelled with a spin label for nuclear magnetic resonance (NMR) imaging (also known as magnetic resonance imaging, MRI), such as iodine-123, indium-111, fluorine-19, carbon-13, nitrogen-15, oxygen-17, gadolinium, manganese or iron.

A "biological sample" encompasses a variety of sample types obtained from a subject that can be used in a diagnostic or monitoring assay. Biological samples include but are not limited to blood and other liquid samples of biological origin, solid tissue samples such as a biopsy specimen or tissue cultures or cells derived therefrom, and the progeny thereof. Therefore, biological samples encompass clinical samples, cells in culture, cell supernatants, cell lysates, serum, plasma, biological fluid, and tissue samples, such as tumor samples.

In some embodiments, the biological sample may be a formalin-fixed and paraffin-embedded (FFPE) tissue sample.

The invention also relates to an in vivo method of detecting the presence of a cancer in a subject, comprising the steps of:

a) administering an antibody according to the invention to a patient, wherein the antibody is labelled with a detectable molecule;

b) detecting localization of said antibody in the patient by imaging, e.g. by detecting the detectable molecule.

In said method, the cancer may be a CEACAM5 expressing cancer, such as a colorectal cancer, gastric cancer, non-small cell lung cancer, pancreatic cancer, esophageal cancer, prostate cancer or other solid tumors expressing CEACAM5.

Antibodies of the invention may also be useful for staging of cancer (e.g., in radioimaging). They may be used alone or in combination with other cancer markers.

The terms "detection" or "detected" as used herein include qualitative and/or quantitative detection (i.e. measuring levels) with or without reference to a control.

In the context of the invention, the term "diagnosing", as used herein, means the determination of the nature of a medical condition, intended to identify a pathology which affects the subject, based on a number of collected data.

Kits

Finally, the invention also provides kits comprising at least one antibody or immunoconjugate of the invention. Kits containing antibodies of the invention can find use in detecting the surface protein CEACAM5, or in therapeutic or diagnostic assays. Kits of the invention can contain an antibody coupled to a solid support, e.g., a tissue culture plate or beads (e.g., sepharose beads). Kits can be provided which contain antibodies for detection and quantification of the surface protein CEACAM5 in vitro, e.g. in an ELISA or a Western blot. Such an antibody useful for detection may be provided with a label such as a fluorescent or radiolabel.

BRIEF DESCRIPTION OF THE SEQUENCES

Amino Acid Sequences:

- SEQ ID NO: 1 Human CEACAM5 protein sequence according to GenBank accession number AAA51967.1
- SEQ ID NO: 2 *Macaca fascicularis* CEACAM5 protein sequence (NCBI Reference Sequence XP_005589491.1)
- SEQ ID NO: 3 CDR1-H of mAb1
- SEQ ID NO: 4 CDR2-H of mAb1
- SEQ ID NO: 5 CDR3-H of mAb1
- SEQ ID NO: 6 CDR1-L of mAb1
- SEQ ID NO: 7 CDR2-L of mAb1
- SEQ ID NO: 8 CDR3-L of mAb1
- SEQ ID NO: 9 VH of mAb1
- SEQ ID NO: 10 VL of mAb1
- SEQ ID NO: 11 CH of mAb1
- SEQ ID NO: 12 CL of mAb1
- SEQ ID NO: 13 HC of mAb1
- SEQ ID NO: 14 LC of mAb1

Nucleic Acid Sequences:

- SEQ ID NO: 15 DNA sequence encoding HC of mAb1
- SEQ ID NO: 16 DNA sequence encoding LC of mAb1

Amino Acid Sequences:

- SEQ ID NO: 17 HC of antibody hu8G4
- SEQ ID NO: 18 LC of antibody hu8G4
- SEQ ID NO: 19 HC of optimized antibody Variant 1
- SEQ ID NO: 20 LC of optimized antibody Variant 1
- SEQ ID NO: 21 LC of optimized antibody Variant 2
- SEQ ID NO: 22 LC of optimized antibody Variant 4
- SEQ ID NO: 23 LC of optimized antibody Variant 5
- SEQ ID NO: 24 HC of optimized antibody Variant 6
- SEQ ID NO: 25 HC of huMab2-3 (allotype)
- SEQ ID NO: 26 LC of huMab2-3
- SEQ ID NO: 27 HC of hmn-14
- SEQ ID NO: 28 LC of hmn-14
- SEQ ID NO: 29 HC of rb8G4
- SEQ ID NO: 30 LC of rb8G4

EXAMPLES

Example 1: Anti-CEACAM5 Antibodies 1.1 Immunization of Transgenic Rats and Isolation of Hybridomas To generate monoclonal antibodies to human CEACAM5 protein (Carcinoembryonic antigen-related cell adhesion molecule 5; CD66e), human immunoglobulin gene transgenic rats (OmniRat™) were obtained from CHARLES RIVER LABORATORIES INTERNATIONAL INC. (WILMINGTON, MA). 5 animals were immunized 4 times with CEACAM5 cDNA (encoding amino acids 35-675 of the human CEACAM5 protein sequence with UniProt ID no. P06731; the sequence of P06731 is identical to SEQ ID NO: 1 except for the substitution of E398 of SEQ ID NO: 1 by K398) cloned into an Aldevron proprietary immunization vector (pB8-CEA-hum-MC) and was transiently transfected into the OMT Rats cells using a Gene gun.

Anti-CEACAM5 titers were evaluated by a cell-based ELISA (CELISA) assay using cells that express CEACAM5 on their cell membrane (titer results presented below). The immunized animal serum was taken at day 31 of the immunization protocol, after 4 rounds of genetic material immunization (IS31d-4). Sera, diluted in PBS+3% FBS, were tested by flow cytometry on mammalian cells transiently transfected with the CEACAM5 cDNA cloned into an Aldevron proprietary expression vector (pB1-CEA-hum-MC). A goat anti-rat IgG R-phycoerythrin conjugate (Southern Biotech, #3030-09) was used as a secondary antibody at 10 μg/ml.

All animals were sacrificed and lymphocytes from lymphnodes were pooled and cryo-preserved for future use. Cells were fused with the Ag8 mouse myeloma cell line to create viable hybridomas. Hybridoma cells from this fusion were then transferred to ten 96 well plates.

1.2 CEACAM5 Specificity

Hybridoma supernatants were screened using a cell-based ELISA (CELISA) assay for the detection of ant-CEACAM5 antibodies that did not bind CEACAM1 (BGP), CEACAM3 (CGM1a), CEACAM4 (CGM7), CEACAM6 (NCA) and CEACAM8 (NCA-95). A goat anti-rat IgG R-phycoerythrin conjugate (Southern Biotech, #3030-09) was used as a secondary antibody at 10 μg/ml.

Clones that showed specificity to human CEACAM5 and not to its related proteins were transferred to one 96 well plate and the hybridoma supernatant was evaluated for specificity and cross reactivity in ELISA assay. In this assay the 8G4 hybridoma clone and its subclones showed specificity to human CEACAM5 and cross reactivity to *Macaca fascicularis* CEACAM5.

1.3 Detection of Antibody Sequence and Cloning

Total RNA was prepared from each hybridoma clone according to the RNeasy 96 Protocol, Qiagen. Subsequently total RNA was transcribed into cDNA using Random Hexamers and SuperScript® III.

The resultant cDNA was quality-controlled by qPCR and VH and Vk were amplified by PCR. The PCR products were purified using AMpure XP PCR clean-up kit in combination with a KingFisher instrument.

The VH and Vk genes of 8G4 subclones were cloned into destination vectors hi00_pTT5_VH_ccdB and hh00_pTT5_Vk_ccdB, respectively, using the procedure of homologous recombination (so called "Lucigen-Cloning"). The reaction mixes were transformed in One Shot® Mach1™-T1R Chemically Competent *E. coli*. Correctly recombined clones were confirmed by Sanger sequencing.

1.4 Humanization and Biochemical Characterization of Hits, and Candidate Selection 8G4 and other clones were reformatted and expressed as human IgG1 molecules. They were assessed by SDS-PAGE, size exclusion chromatography (SEC), selectivity, affinity, cell binding and potency. Based on the results, one humanized candidate antibody, designated as hu8G4, was selected for amino acid sequence optimization to improve manufacturability and affinity.

The amino acid sequence of the humanized candidate antibody hu8G4 is as follows:

```
Heavy chain:
                                       (SEQ ID NO: 17)
EVQLVESGPGLVKPSQTLSLTCTVSDGSVSRGGYYLTWIRQHPGKGLEW

IGYIYYSGSTYFNPSLRSRLTMSVDTSKNQFSLKLSSVTAADTAVYYCA

RGIAVAPFDYWGQGTLVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQK

SLSLSPGK

Light chain:
                                       (SEQ ID NO: 18)
ETTLTQSPATLSVSPGERATLSCRTSQSVRSNLAWYQQKPGQAPRLLIY

AASTRATGIPARFSGSGSGTEFTLTIGSLQSEDFAVYFCQQYTNWPFTF

GPGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFN RGEC
```

1.5 Biophysical Improvement Strategy for hu8G4 Leading Inter Alia to mAb1

An assessment of the variable region sequences of hu8G4 identified six non-germline amino acid residues in the light chain framework and two non-germline amino acid residues in the heavy chain framework. An assessment of amino acids and sequence motifs potentially prone to post-translational modification, such as deamidation motifs, surface-accessible methionines, and free cysteines, did not identify any amino acid residues with increased liability. Several designed antibody sequences were generated in which certain amino acids were replaced with the germline-associated amino acid at that position. The different VH and VL optimization designs were then co-expressed in HEK 293 6E cells as Fab and full IgG1 molecules, purified and tested (see e.g. the optimized Variants 1-10 below).

The amino acid sequences of 10 optimized antibody variants in full IgG1 format were as follows:

```
Variant 1 (VH1.00/VL 1.00)

HC:
                                                          (SEQ ID NO: 19)
EVQLQESGPGLVKPSQTLSLTCTVSDGSVSRGGYYLTWIRQHPGKGLEWIGYIYYSGSTYF

NPSLRSRLTMSVDTSKNQFSLKLSSVTAADTAVYYCARGIAVAPFDYWGQGTLVTVSSAST
```

-continued

KGPSVFPLAPSSKSTSGGTAALGCLVKDYFPEPVTVSWNSGALTSGVHTFPAVLQSSGLYS

LSSVVTVPSSSLGTQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPSREEMTKNQVSLT

CLVKGFYPSDIAVEWESNGQPENNYKTTPPVLDSDGSFFLYSKLTVDKSRWQQGNVFSCS

VMHEALHNHYTQKSLSLSPGK

LC:

(SEQ ID NO: 20)

ETTLTQSPATLSVSPGERATLSCRTSQSVRSNLAWYQQKPGQAPRLLIYAASTRATGIPARF

SGSGSGTEFTLTIGSLQSEDFAVYFCQQYTNWPFTFGPGTKVEIKRTVAAPSVFIFPPSDEQ

LKSGTASVVCLLNNFYPREAKVQWKVDNALQSGNSQESVTEQDSKDSTYSLSSTLTLSKAD

YEKHKVYACEVTHQGLSSPVTKSFNRGEC

Variant 2 (VH1.00/VL1.01)

HC: SEQ ID NO: 19

LC:

(SEQ ID NO: 21)

EIVLTQSPATLSVSPGERATLSCRTSQSVRSNLAWYQQKPGQAPRLLIYAASTRATGIPARF

SGSGSGTEFTLTISSLQSEDFAVYFCQQYTNWPFTFGPGTKVDIKRTVAAPSVFIFPPSDEQ

LKSGTASVVCLLNNFYPREAKVQWKVDNALQSGNSQESVTEQDSKDSTYSLSSTLTLSKAD

YEKHKVYACEVTHQGLSSPVTKSFNRGEC

Variant 3 (VH1.00/VL1.02)

HC: SEQ ID NO: 19

LC: SEQ ID NO: 14

Variant 4 (VH1.00/VL1.03)

HC: SEQ ID NO: 19

LC:

(SEQ ID NO: 22)

EIVMTQSPATLSVSPGERATLSCRTSQSVRSNLAWYQQKPGQAPRLLIYAASTRATGIPARF

SGSGSGTEFTLTISSLQSEDFAVYFCQQYTNWPFTFGPGTKVDIKRTVAAPSVFIFPPSDEQ

LKSGTASVVCLLNNFYPREAKVQWKVDNALQSGNSQESVTEQDSKDSTYSLSSTLTLSKAD

YEKHKVYACEVTHQGLSSPVTKSFNRGEC

Variant 5 (VH1.00/VL1.04)

HC: SEQ ID NO: 19

LC:

(SEQ ID NO: 23)

EIVMTQSPATLSVSPGERATLSCRTSQSVRSNLAWYQQKPGQAPRLLIYAASTRATGIPARF

SGSGSGTEFTLTISSLQSEDFAVYYCQQYTNWPFTFGPGTKVDIKRTVAAPSVFIFPPSDEQ

LKSGTASVVCLLNNFYPREAKVQWKVDNALQSGNSQESVTEQDSKDSTYSLSSTLTLSKAD

YEKHKVYACEVTHQGLSSPVTKSFNRGEC

Variant 6 (VH1.02/VL 1.00)

HC:

(SEQ ID NO: 24)

EVQLQESGPG LVKPSQTLSL TCTVSDGSVS RGGYYLTWIR QHPGKGLEWI GYIYYSGSTY

FNPSLRSRVT MSVDTSKNQF SLKLSSVTAA DTAVYYCARG IAVAPFDYWG QGTLVTVSSA

STKGPSVFPL APSSKSTSGG TAALGCLVKD YFPEPVTVSW NSGALTSGVH

-continued

```
TFPAVLQSSG LYSLSSVVTV PSSSLGTQTY ICNVNHKPSN TKVDKRVEPK SCDKTHTCPP

CPAPELLGGP SVFLFPPKPK DTLMISRTPE VTCVVVDVSH EDPEVKFNWY

VDGVEVHNAK TKPREEQYNS TYRVVSVLTV LHQDWLNGKE YKCKVSNKAL PAPIEKTISK

AKGQPREPQV YTLPPSREEM TKNQVSLTCL VKGFYPSDIA VEWESNGQPE

NNYKTTPPVL DSDGSFFLYS KLTVDKSRWQ QGNVFSCSVM HEALHNHYTQ KSLSLSPGK

LC: SEQ ID NO: 20

Variant 7 (VH1.02/VL1.01)

HC: SEQ ID NO: 24

LC: SEQ ID NO: 21

Variant 8 (VH1.02/VL1.02)

HC: SEQ ID NO: 24

LC: SEQ ID NO: 14

Variant 9 (VH1.02/VL1.03)

HC: SEQ ID NO: 24

LC: SEQ ID NO: 22

Variant 10 (VH1.02/VL1.04)

HC: SEQ ID NO: 24

LC: SEQ ID NO: 23
```

All of the optimized Variants 1 to 10 performed similarly well in terms of maintenance of quality as assayed by percent aggregate by size exclusion chromatography, maintained stability based on Fluorescence Monitored Thermal Unfolding (FMTU), retained binding to MKN-45 cancer cell line and maintained selectivity toward the target. Variant 8 (i.e. the variant including VH1.02 and VL1.02) was selected for further development as an optimized variant with a sequence particularly similar to germline.

Further sequence optimization of the selected Variant 8 was then performed inter alia in order to reduce IgG Fc effector functions. Compared to the parent clone, the resulting final sequence-optimized (so) clone, designated so8G4 (also referred to as mAb1 herein), shows improved affinity and improved manufacturability and, also, shows reduced or no binding to FcγRI, FcγRIIa, FcγRIIIa, FcγRIIIa/complex, C1q, FcγRIIb and FcγRIIIb, while maintaining the affinity to CEACAM5 and FcRn. The amino acid sequence of this final sequence-optimized antibody so8G4 (also referred to as mAb1 herein) is as follows:

- Heavy chain (HC): SEQ ID NO: 13 (as defined herein above)
- Light chain (LC): SEQ ID NO: 14 (as defined herein above)

1.6 In-Vitro Characterization of mAb1

Antibody mAb1 was characterized with in vitro assays for several properties including: binding affinity, selectivity, and internalization.

1.6.1 Binding Affinity

To determine the binding affinity of soluble antibody analyte to captured target protein CEACAM5 (human or cynomolgus monkey *Macaca fascicularis*). The following experimental conditions were used on Octet Red instrument:

Biosensor coated with StreptAvidin.

Biotinylated target protein concentration (where ECD stands for extracellular domain):

- human_CEACAM5_ECD-his-biotin R&D Systems (biotinylated using routine methods) were captured at 2.5 μg/ml for 900 seconds at 1000 rpm.
- Recombinant *Macaca fascicularis* CEACAM5_ECD-His-biotin obtained from Syngene (biotinylated using routine methods) were captured at 5 μg/ml for 900 seconds at 1000 rpm.

Analyte Antibody Concentrations: 200, 100, 50, 25, 12.5, 6.25, 0 nM.

Binding affinity KD (equilibrium dissociation constant) values were determined with Octet Evaluation software from the measured binding kinetics association (ka) and dissociation (kd) rate constants, where KD=kd/ka Antibody was used in Fab format Results for Fab Generated from mAb1:

Binding affinity KD for human CEACAM5 was 6.3±1.98 nM.

Binding affinity KD for cynomolgus_monkey-CEACAM5 was 14.1±2.53 nM 1.6.2. Selectivity a) Species and Domains Selectivity determination for mAb1 was done by titrating the antibody from 4 nM to 0.25 pM and applying it on 1 μg/ml bound recombinant human (rh) CEACAM5 ECD or its domains N-A1-B1, A2-B2, A3-B3 or bound recombinant *Macaca fascicularis* (mf) CEACAM5 ECD, all obtained from Syngene, in an ELISA assay. Results are shown in FIG. 1 and summarized below:

Binding EC50 to rhCEACAM5 is 153.4 pM.

Binding EC50 to rhA2-B2 domain is 166.9 pM.

Binding EC50 to mfCEACAM5 is 324.3 pM.

No binding to rhN-A1-B1 or rhA3-B3 or BSA (bovine serum albumin, serving as negative control) was detected.

b) Different CEACAM Proteins

Selectivity determination for Fab of mAb1 to human CEACAM5 and other human CEACAM family members was done in ELISA assay. Proteins were coated on 96-well assay plates: huCEACAM5-His6 (R&D Systems #4128-CM), huCEACAM6-His6 (3934-CM R&D Systems and recombinant protein obtained from Syngene), huCEACAM1-His6 (2244-CM R&D Systems), huCEACAM3-His6 (C449 Novoprotein), huCEACAM7-His6 (C926 Novoprotein), huCEACAM8-His6 (C583 Novoprotein), huPSG1-His6 (CC66 Novoprotein), each protein was coating the plate at 12 nM concentration.

Results:

Fab of mAb1 bound human CEACAM5 (EC50 of 3.04 nM), but did not bind the other human CEACAM family members in ELISA assay even when using 1000 nM Fab of mAb1 which is a more than 300-fold higher concentration than the EC50 for binding to human CEACAM5.

Fab of mAb1 also did not bind to unrelated protein (BSA) in ELISA assay, at all concentrations tested.

1.6.3 Cellular Binding of mAb1

The antibody's ability to bind its target protein on cells was determined by titrating the antibody on cells that express the target (e.g. human CEACAM5) and measuring the fluorescence MFI of the cells. Model cells for antibody binding comparison were the MKN45 cell line expressing human CEACAM5 as well as a CHO cell line expressing mfCEACAM5. Titration was done with 10-point×4 dilution, curve starting concentration 2000 nM in assay buffer (PBS×1 containing 1% BSA).

Exemplary Data:

mAb1 binding to human CEACAM5-expressing MKN-45 cell line with EC50=10.62±1.6 nM.

mAb1 binding to mfCEACAM5-expressing CHO cell line with EC50=4.8±0.6 nM.

1.6.4 Cellular Binding Comparison to Known Antibodies

Cellular binding of our lead antibody mAb1 was compared to ADC-related known antibodies huMab2-3 (as in the known ADC SAR408701) and hMN14 (also referred to as hmn-14 herein) (as in the known ADC labetuzumab govitecan or IMMU-130) on MKN45 cell line which expresses CEACAM5.

The following amino acid sequences were used for the above-mentioned known antibodies in the experiments described herein below:

```
huMab2-3:
HC (allotype):
                                          (SEQ ID NO: 25)
EVQLQESGPGLVKPGGSLSLSCAASGFVFSSYDMSWVRQTPERGLEWVA

YISSGGGITYAPSTVKGRFTVSRDNAKNTLYLQMNSLTSEDTAVYYCAA

HYFGSSGPFAYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK
```

-continued

```
LC:
                                          (SEQ ID NO: 26)
DIQMTQSPASLSASVGDRVTITCRASENIFSYLAWYQQKPGKSPKLLVY

NTRTLAEGVPSRFSGSGSGTDFSLTISSLQPEDFATYYCQHHYGTPFTF

GSGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

hmn-14:
HC:
                                          (SEQ ID NO: 27)
EVQLVESGGGVVQPGRSLRLSCSASGFDFTTYWMSWVRQAPGKGLEWIG

EIHPDSSTINYAPSLKDRFTISRDNAKNTLFLQMDSLRPEDTGVYFCAS

LYFGFPWFAYWGQGTPVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQK

SLSLSPGK

LC:
                                          (SEQ ID NO: 28)
DIQLTQSPSSLSASVGDRVTITCKASQDVGTSVAWYQQKPGKAPKLLIY

WTSTRHTGVPSRFSGSGSGTDFTFTISSLQPEDIATYYCQQYSLYRSFG

QGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC
```

Figure 2:
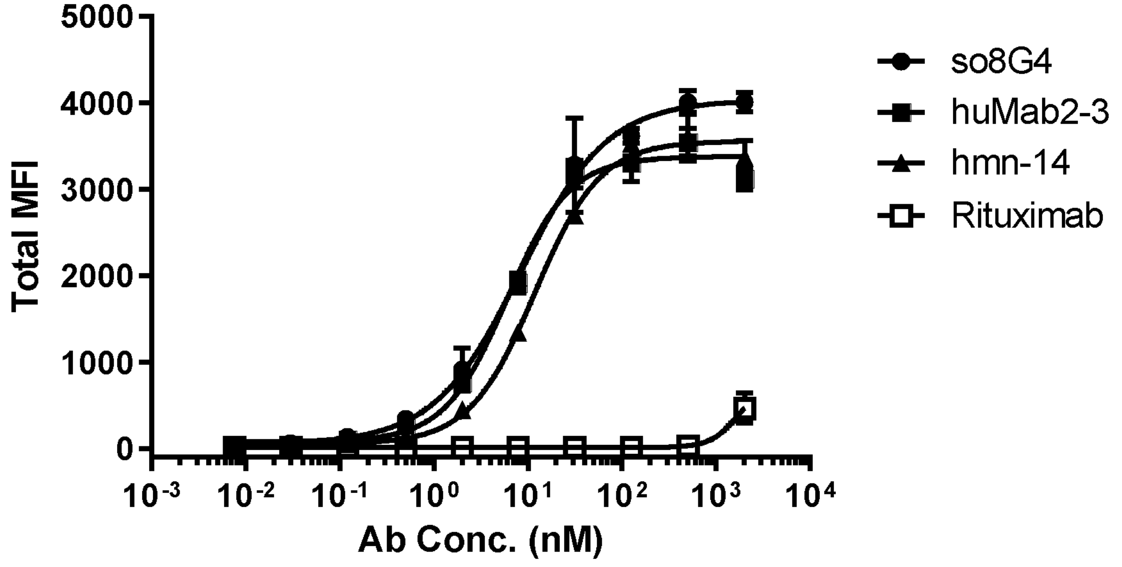
FIG. 2: EC50 of anti CEACAM5 antibodies binding to MKN-45 cells: Cellular binding of mAb1 compared to antibodies huMab2-3 and hmn-14 on MKN45 cell line which expresses CEACAM5.

Rituximab was included in the comparison as a control. Results for antibodies binding to the cells are shown in FIG. 2 and summarized below:

mAb1 (so8G4)=8.3 nM huMab2−3=6 nM hmn-14=11.8 nM

Average of Several Experiments (EC50):

mAb1 (so8G4)=10.4 nM±1.6 nM (n=12)

huMab2−3=4.9 nM±1.6 nM (n=3)

hmn-14=16 nM (n=2)

Cellular binding of anti CEACAM5 antibodies to MKN45 cell line show that the binding of mAb1 and the known antibodies is similar.

1.6.5 Internalization Assay Using Cell Discoverer

A relevant characteristic of an ADC is its internalization into a target-expressing cell and lysosomes, and thus internalization is a relevant property of antibodies to be used as part of ADCs. Antibody internalization rate into the late endosome and lysosome (low pH vesicles) can be monitored by directly labeling the antibodies with a pH-sensitive dye (pHrodo) which emits strong fluorescence at a pH lower than 6.0 upon excitation. This fluorescence can be imaged in the Cell-Discoverer7 (Zeiss) and internalization rate can be calculated.

To analyze the internalization rates of several antibodies, MKN45 cells were seeded in a 96 well, dark, flat clear bottom plate (Cellvis) at 25,000 cells/well. Cells were cultivated over night with 100 μl/well of RMPI-1640+10%

FBS (Thermo). Cell media was removed, and cells were stained with 100 μl of 10 μg/ml Hoechst dye diluted in PBS×1 for 15 min at room temperature (RT) in the dark. Cells were then washed twice with PBS×1.

Anti-CEACAM5 human IgG antibodies (so8G4 (i.e. mAb1), humab2-3, hmn-14), and an anti-MerTK antibody (Merck) were directly labeled with pHrodo, were diluted to a concentration of 100 nM in warm RPM11640+10% FBS without phenol red and were added to their respective wells. Plate was incubated in the Cell Discoverer at 37° C., 5% $CO_2$, for 20 hours, and images were acquired every 20 minutes, as further described below.

Internalization of pHrodo labeled antibodies into the late endosomes and lysosomes of cells was imaged by Cell-Discoverer7 (Zeiss) using fluorescence at excitation of 567 nm and emission detector of 592/25 nm. Cell nuclei were labeled with Hoechst and imaged at excitation of 385 nm and emission detector of 425/30 nm.

Fluorescence of each well was recorded every 20 min for 20 h. Analysis of Sum Fluorescence Intensity per cell (SFI) was calculated by the Zen Software (ZEN3.1) and Excel analysis of linear regression.

Figure 3:
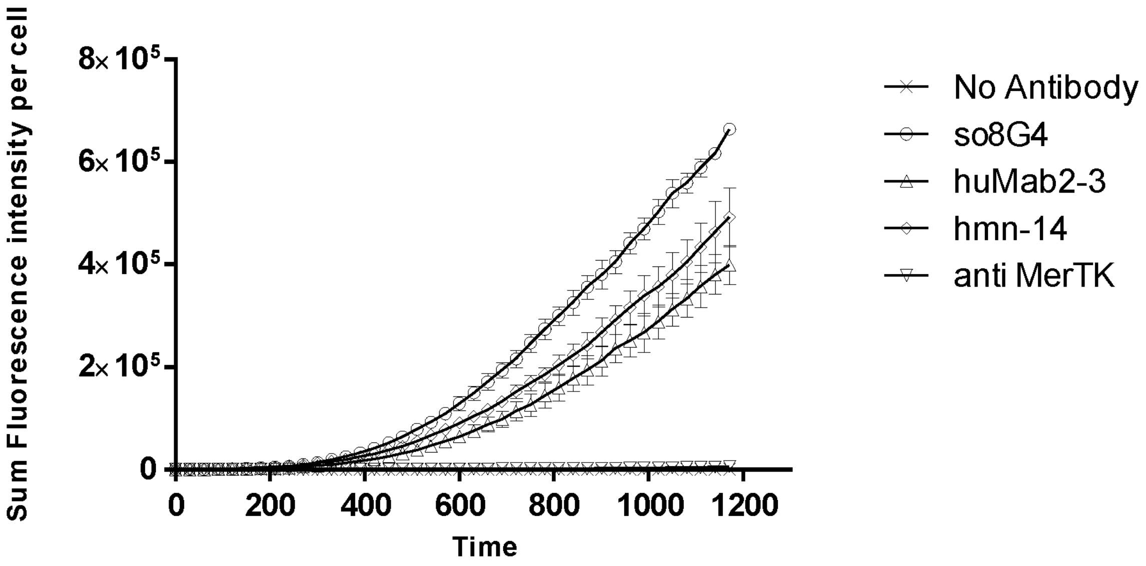
FIG. 3: Internalization of pHrodo labeled antibodies into the late endosomes and lysosomes of cells (sum fluorescence intensity per cell, average of triplicates).
Figure 4:
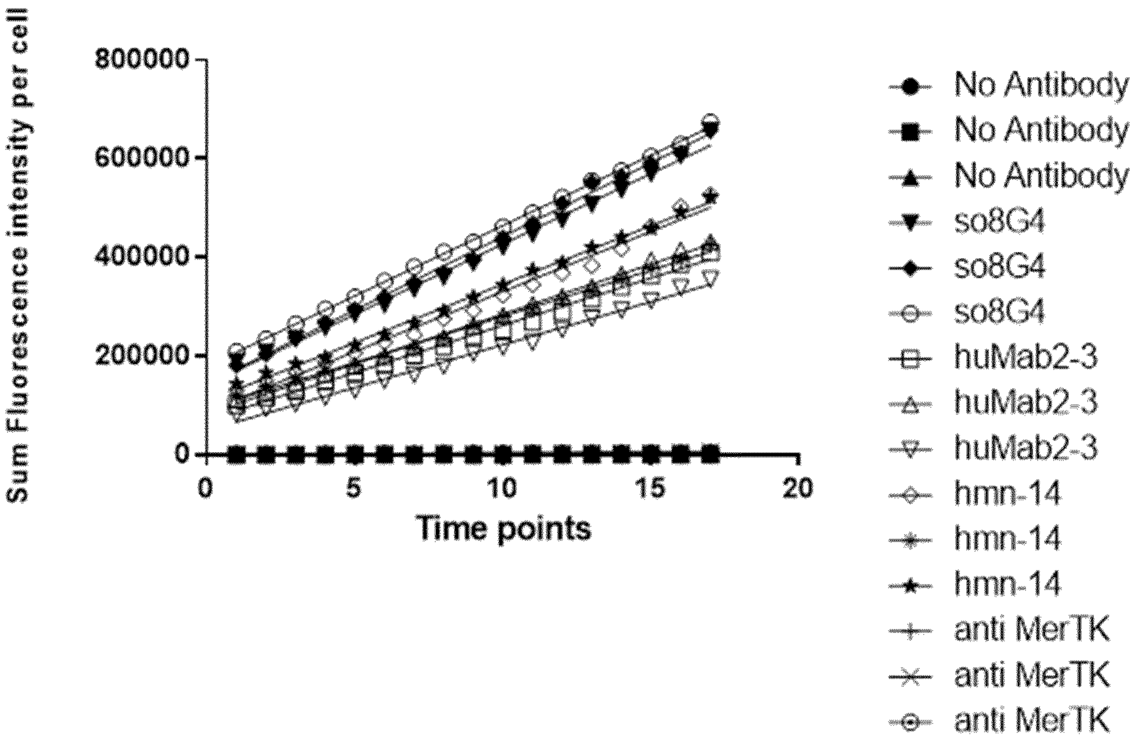
FIG. 4: Fluorescence intensity per cell from time of 700 minutes to 1200 minutes, which is the linear part of the curve. Linear slope was measured and compared between samples (see Example 1.6.5).

Results are shown in FIG. 3 and FIG. 4 and the slope of the linear part of the curves (see FIG. 4) is also summarized in the table below:

| Sample | Slope of Curve | R^2 |
|---|---|---|
| so8G4 | 28519 | 99.41 |
| so8G4 | 29844 | 99.66 |
| so8G4 | 28513 | 99.92 |
| humab2-3 | 19154 | 99.42 |
| humab2-3 | 17398 | 99.19 |
| humab2-3 | 20201 | 99.68 |
| hmn-14 | 24350 | 98.61 |
| hmn-14 | 18754 | 99.56 |
| hmn-14 | 23701 | 99.58 |

Conclusions:
1. so8G4 (mAb1) has a higher average binding rate (28958 ± 766) than humab2-3 (18917 ± 1416) and hmn-14 (22268 ± 3060).
2. so8G4 (mAb1) also has a higher internalization intensity compared to humab2-3 and hmn-14.

1.7 Exemplary Method of Producing mAb1 e.g. for Use in Conjugation to Drug-Linker Compounds Anti-CEACAM5 antibody mAb1 was produced in recombinant CHO-K1Sv cell line. Cell cultures were conducted in batch mode in a 200 l single-use bioreactor. Cells were grown in proprietary CHO fed-batch growth media supplemented with glucose at 37° C. The cultures were fed with a mixture of proprietary feed components on days 3, 5, 7 and 10 post inoculation.

Crude conditioned media from the bioreactor runs were clarified using 3×1.1 $m^2$ Millistak+ Pod DOHC (Millipore MDOHC10FS1) and 1.1 $m^2$ Millistak+ Pod XOHC (Millipore #MX0HC01 FS1) filters, followed by terminal filtration with a Millipore Opticap XL3 0.5/0.2 μm filter (Millipore #KHGES03HH3).

Following clarification, the antibody mAb1 was purified using a standard antibody purification process consisting of Protein A capture step and ion exchange chromatographic steps. The anti-CEACAM5 antibody mAb1 served as an intermediate for generation of ADC molecules.

1.8 Expression and Purification of Human/Rabbit Chimeric Variant of mAb1 and its Use in Immunohistochemistry (IHC) on Formaldehyde Fixed and Paraffin Embedded Cell Lines and Human Tumor Tissues A human/rabbit chimeric variant of mAb1 was generated by routine recombinant methods. The human/rabbit chimeric variant of mAb1 (also referred to as "rb8G4" herein) had the following amino acid sequence:

```
Heavy chain
                                        (SEQ ID NO: 29)
EVQLQESGPGLVKPSQTLSLTCTVSDGSVSRGGYYLTWIRQHPGKGLEW

IGYIYYSGSTYFNPSLRSRVTMSVDTSKNQFSLKLSSVTAADTAVYYCA

RGIAVAPFDYWGQGTLVTVSSQPKAPSVFPLAPCCGDTPSSTVTLGCLV

KGYLPEPVTVTWNSGTLTNGVRTFPSVRQSSGLYSLSSVVSVTSSSQPV

TCNVAHPATNTKVDKTVAPSTCSKPTCPPPELLGGPSVFIFPPKPKDTL

MISRTPEVTCVVVDVSEDDPEVQFTWYINNEQVRTARPPLREQQFNSTI

RVVSTLPIAHEDWLRGKEFKCKVHNKALPAPIEKTISKARGQPLEPKVY

TMGPPREELSSRSVSLTCMINGFYPSDISVEWEKNGKAEDNYKTTPAVL

DSDGSYFLYSKLSVPTSEWQRGDVFTCSVMHEALHNHYTQKSISRSPGK

Light chain
                                        (SEQ ID NO: 30)
EIVLTQSPATLSVSPGERATLSCRTSQSVRSNLAWYQQKPGQAPRLLIY

AASTRATGIPARFSGSGSGTEFTLTISSLQSEDFAVYYCQQYTNWPFTF

GPGTKVDIKRDPVAPSVLLFPPSKEELTTGTATIVCVANKFYPSDITVT

WKVDGTTQQSGIENSKTPQSPEDNTYSLSSTLSLTSAQYNSHSVYTCEV

VQGSASPIVQSFNRGDC
```

rb8G4 was expressed in HEK cells (Expi 293 suspension cells) by transient transfection and purified using MabSelect SuRe and citrate buffers. rb8G4 was then used for IHC on formaldehyde fixed and paraffin embedded cell lines and human tumor tissues:

Material and Methods

Cell Lines and Tissues

Human cancer cell lines were cultivated from the Merck cell bank, fixed in 4% buffered formaldehyde, and embedded in paraffin (FFPE). The paraffin embedded cell lines were arranged into cell line microarrays (CMAs) (Zytomed). FFPE tissue sections of a tissue microarray (TMA) with human organs were from amsbio (FDA Standard Tissue Array, T8234701). FFPE human tumor samples were provided by BiolVT and Indivumed GmbH.

Methods

For the IHC staining with the anti-CEACAM-5 antibody rb8G4, sections of 4 μm from formaldehyde fixed paraffin embedded (FFPE) cancer cell line microarrays (CMAs) and human tumor tissues were mounted on charged slides (SuperFrost Ultra Plus, Thermo Fisher Scientific or TOMO, Matsunami). The staining procedure was performed using a Discovery XT (Roche Diagnostics) staining platform. Following deparaffinization, the sections were heated for epitope retrieval in Tris-EDTA buffer pH 8 (CC1, Roche Diagnostics). The sections were incubated with the primary monoclonal antibody rb8G4 diluted to 0.5 or 0.7 μg/ml in phosphate-buffered saline (PBS) or antibody diluent buffer (DCS). The clone DA1E (rabbit monoclonal IgG, NEB) served as isotype control antibody. The primary antibodies were followed by the HQ anti-rabbit IgG detection kit (Roche Diagnostics). Slides were counterstained with hematoxylin, washed in tap water, dehydrated, and mounted on glass coverslips in Entellan Neu (VWR) permanent mounting media.

CMAs and the TMA with human organ tissue were stained and scanned with the NanoZoomer (Hamamatsu) with a resolution of 0.46 μm/pixel. Human tumor sections were stained and scanned using an AxioScan.Z1 (Zeiss) instrument with a resolution of 0.44 μm/pixel. The scans of the CMAs were analyzed with the image analysis software HALO (Indica Labs, USA). For the determination of the amount of antigen present, positive brown stained area was calculated as percent area of the viable tissue area. Staining (arbitrary units) is calculated as Antibody staining (AU)=% positive tissue area*Average optic density (OD ranges from 0 to 1)

of the brown colour. The maximum value of the antibody staining is 100=100% of the tissue area is black (the grey scale OD value is 1).

CEACAM-5 mRNA data of cancer cell lines were obtained from the Cancer Cell Line Encyclopedia (CCLE; Broad Institute of MIT & Harvard).

Results

Validation on Cancer Cell Lines and Human Normal Tissue

Figure 5:
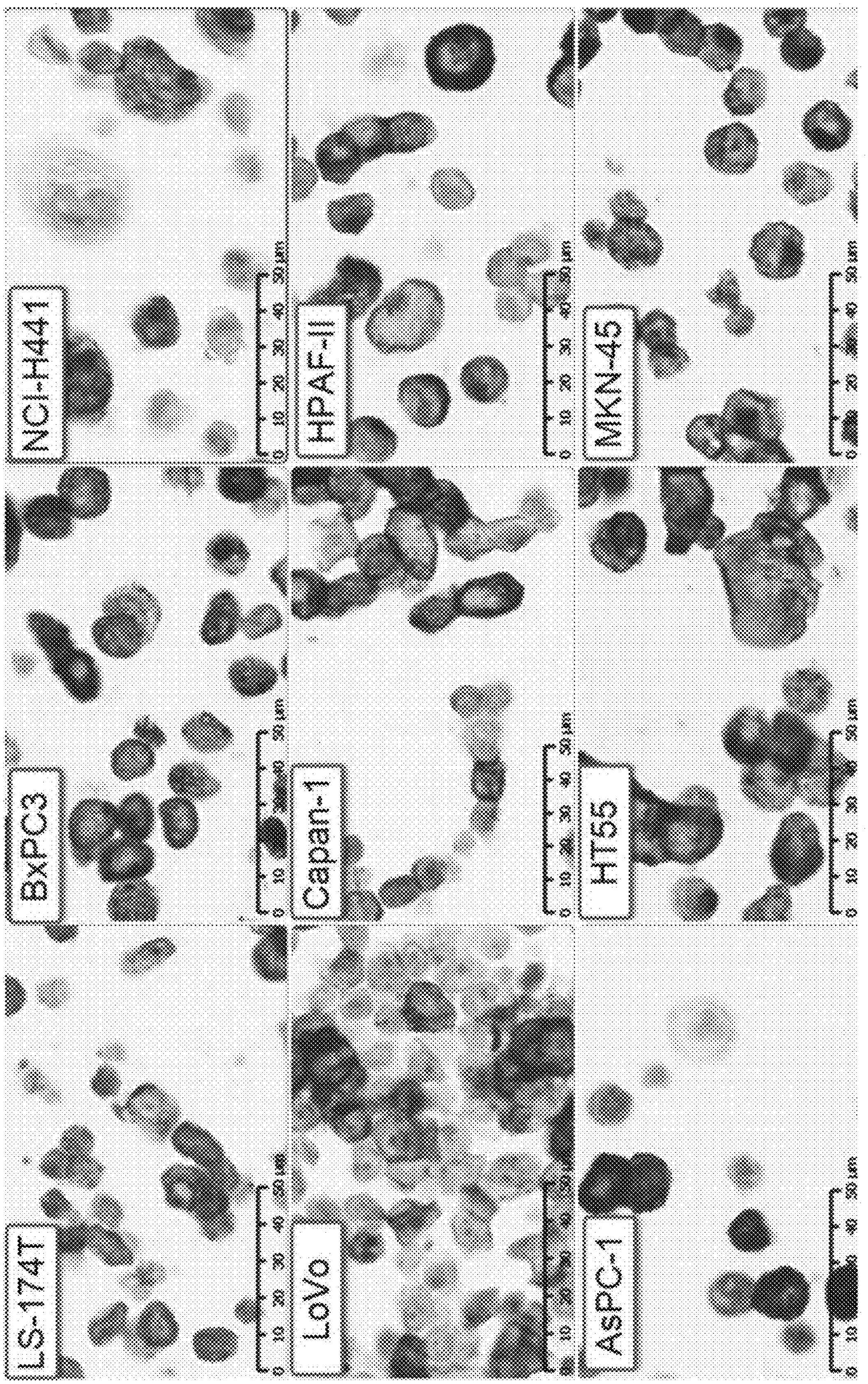
FIG. 5: IHC staining with antibody rb8G4 on FFPE cancer cell lines.

The antibody rb8G4 showed on FFPE cancer cell lines a signal in the cytoplasm and the plasma membrane (FIG. 5).

Figure 6:
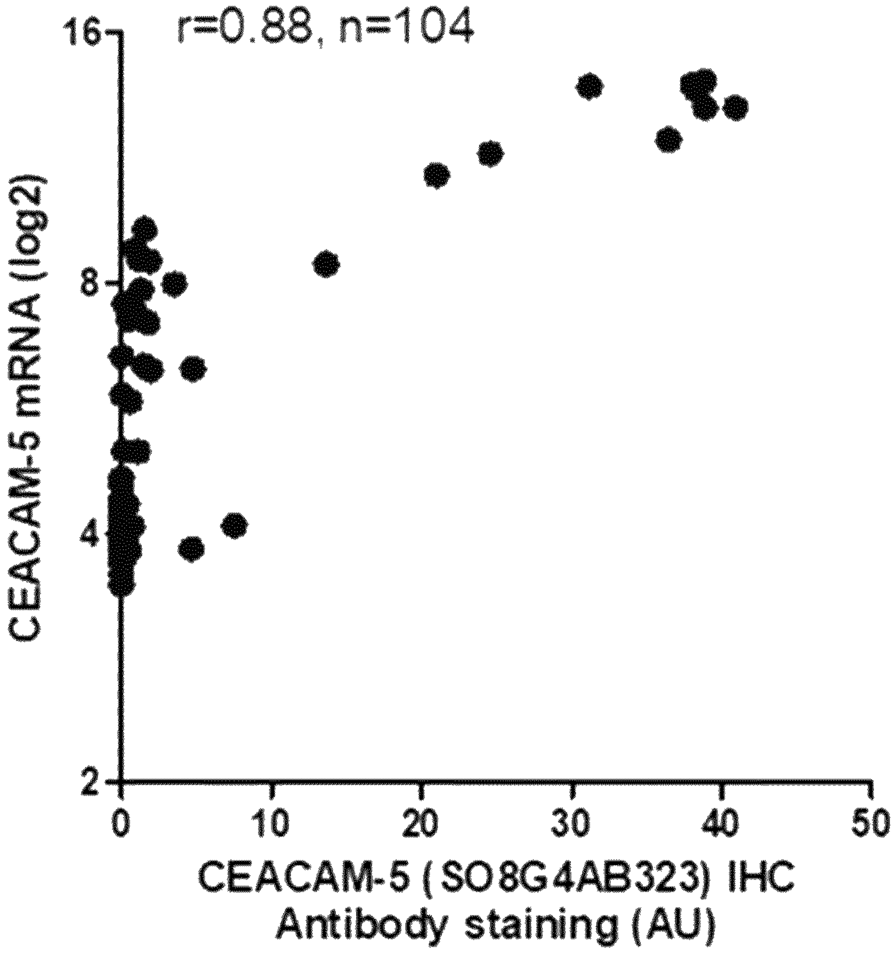
FIG. 6: Correlation of CEACAM5 mRNA expression and IHC staining for 104 cancer cell lines.

The specificity of the antibody rb8G4 on FFPE tissue/cells was shown by comparing the staining signal on 104 cancer cell lines with the mRNA expression (CCLE dataset) of these cell lines. The resulting Pearson correlation coefficient of r=0.88 supports the conclusion that the antibody rb8G4 (also referred to as S08G4AB323) detects a CEACAM-5 epitope in FFPE tissues/cells (FIG. 6). This cancer cell line microarray and individually selected positive and negative cell lines served as control matrices in staining runs with human normal and tumor tissue.

Figure 7:
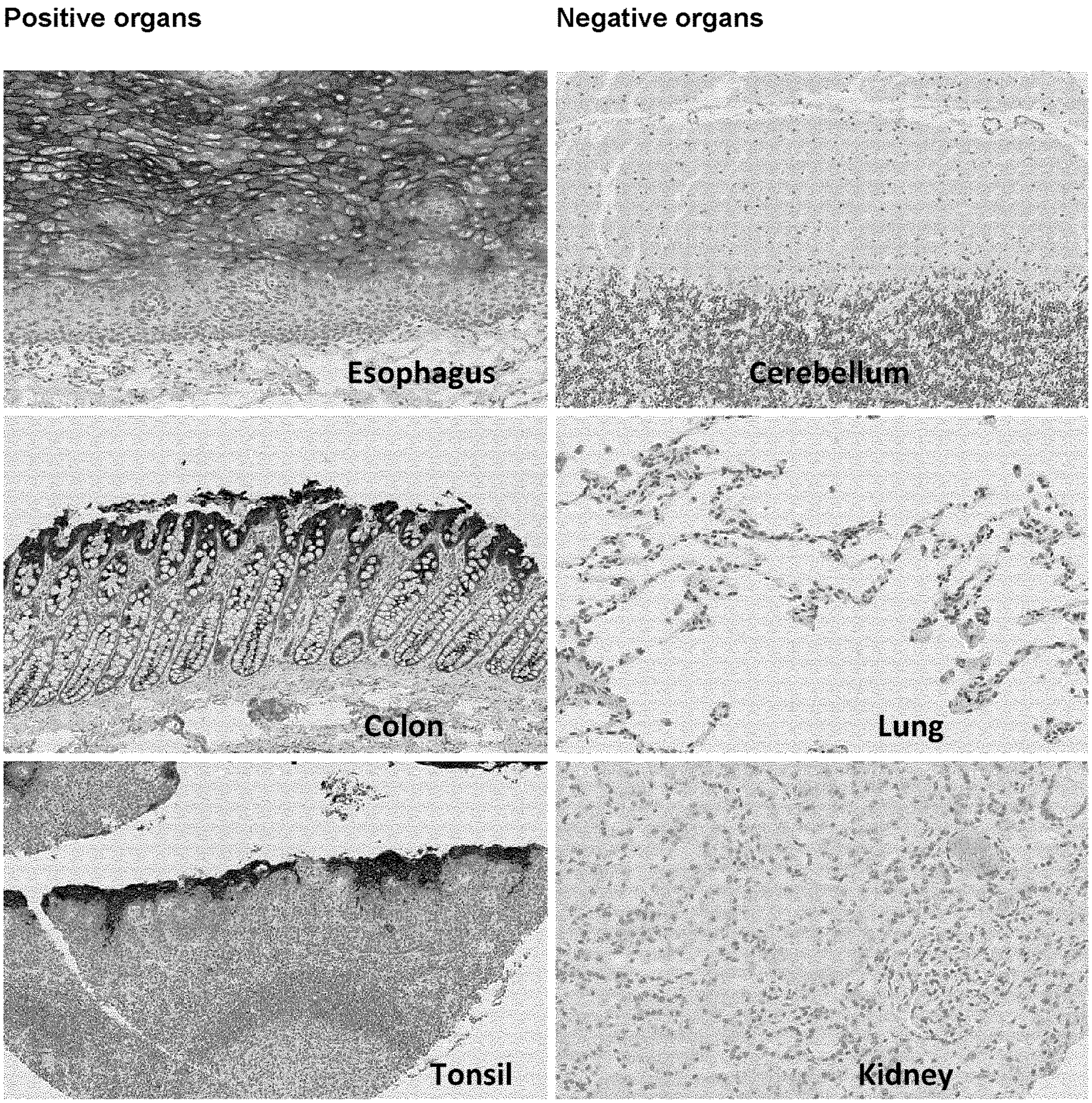
FIG. 7: IHC staining with the antibody rb8G4 on normal human tissue.
Figure 8:
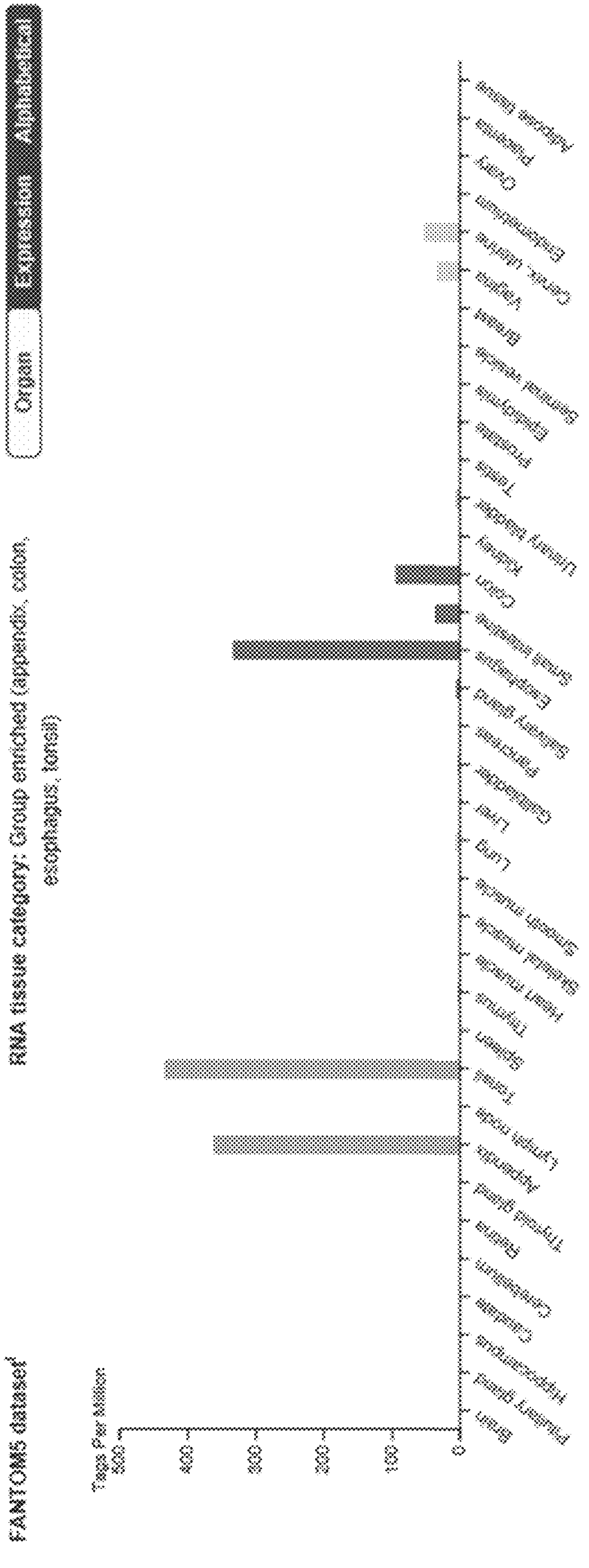
FIG. 8: CEACAM5 mRNA expression in normal human tissues.

The staining with the antibody rb8G4 in normal human tissue (FIG. 7) is in agreement with the CEACAM-5 mRNA expression (FIG. 8) (Source: http://www.proteinatlas.org/ENSG00000105388-CEACAM5/tissue), further supporting the specificity of the antibody for CEACAM-5.

Human Tumor Tissue

Figure 9:
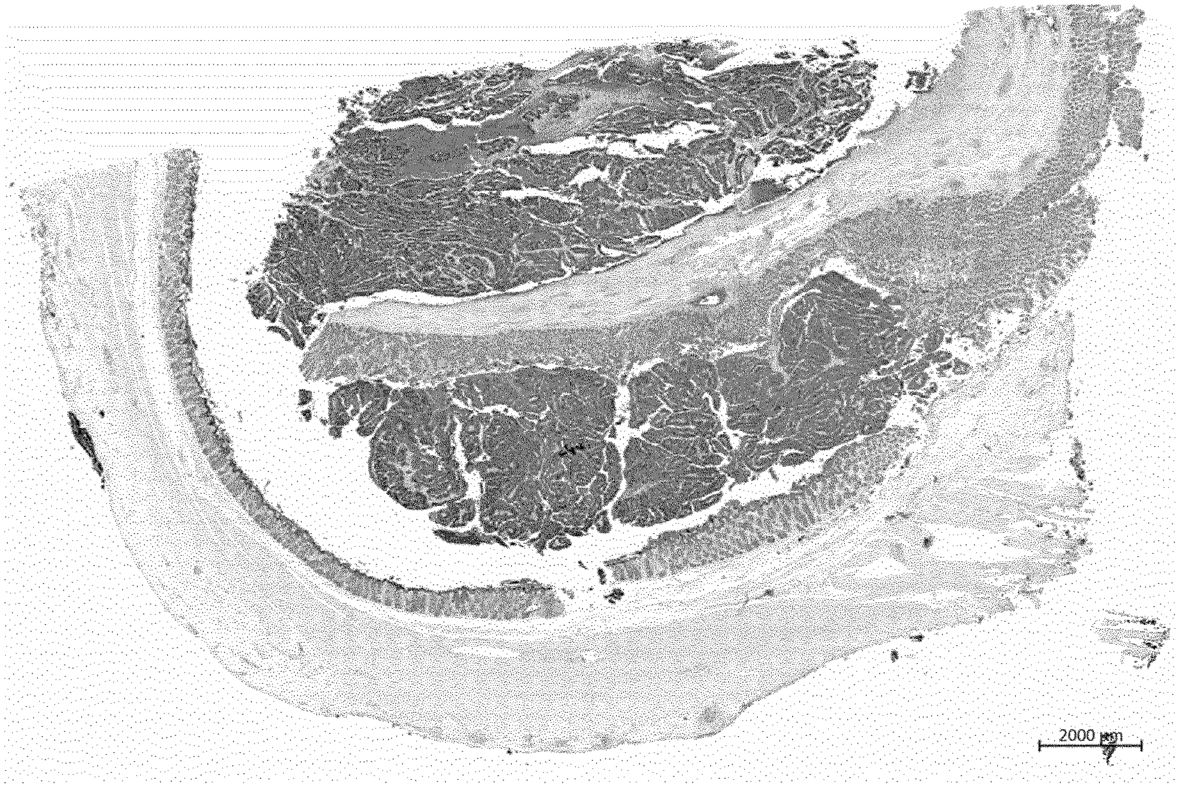
FIG. 9: IHC staining with the antibody rb8G4 on human colorectal cancer tissue.
Figure 9:
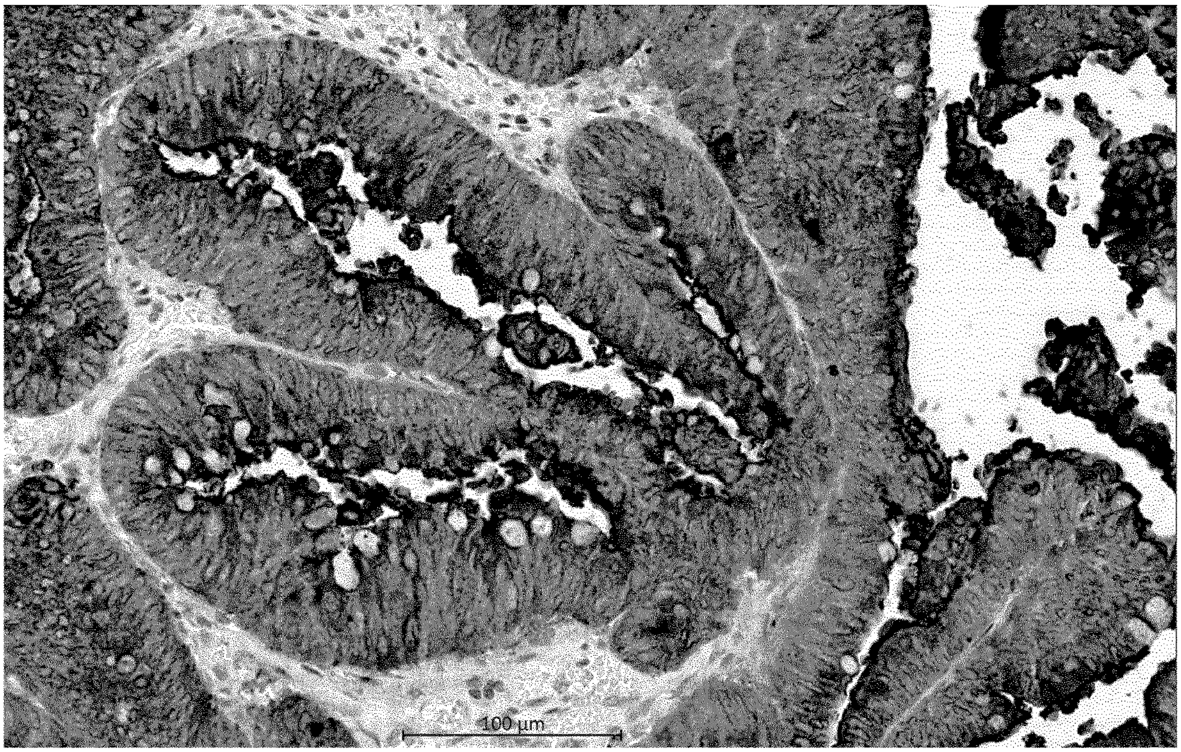
Figure 10:
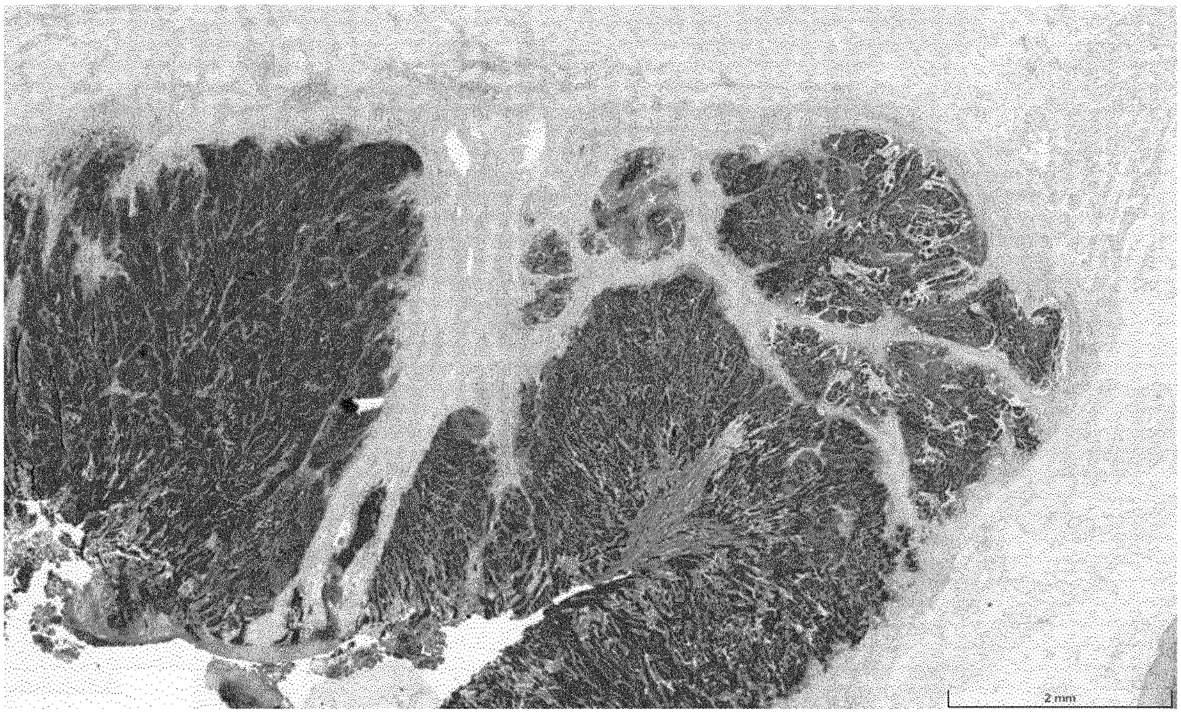
FIG. 10: IHC staining with the antibody rb8G4 on human gastric cancer tissue.
Figure 10:
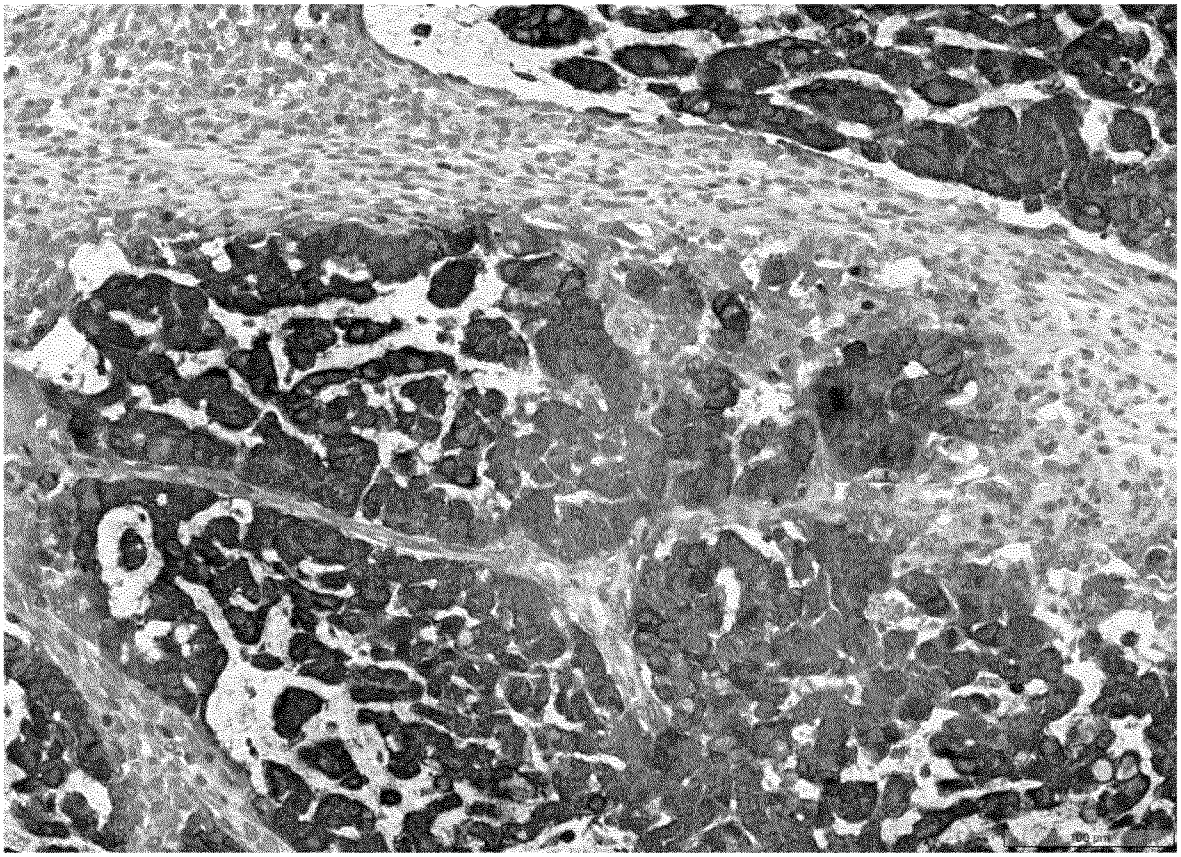
Figure 11:
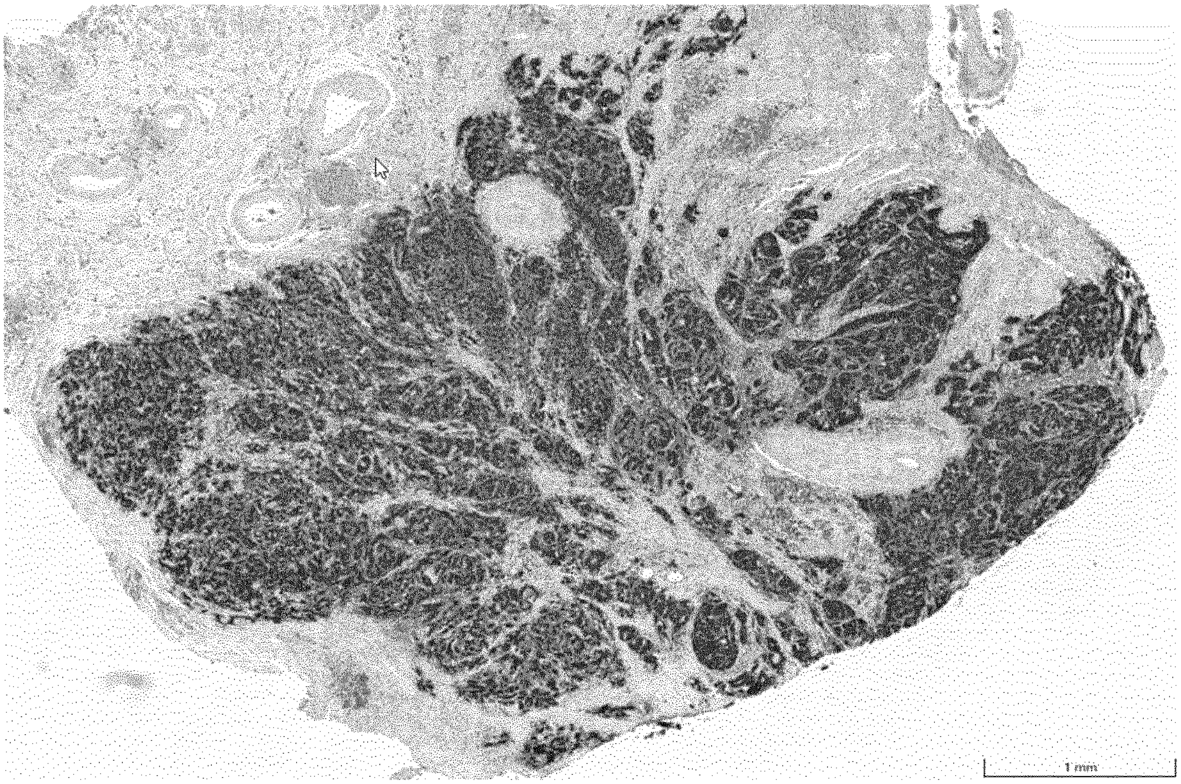
FIG. 11: IHC staining with the antibody rb8G4 on human esophageal cancer tissue.
Figure 11:
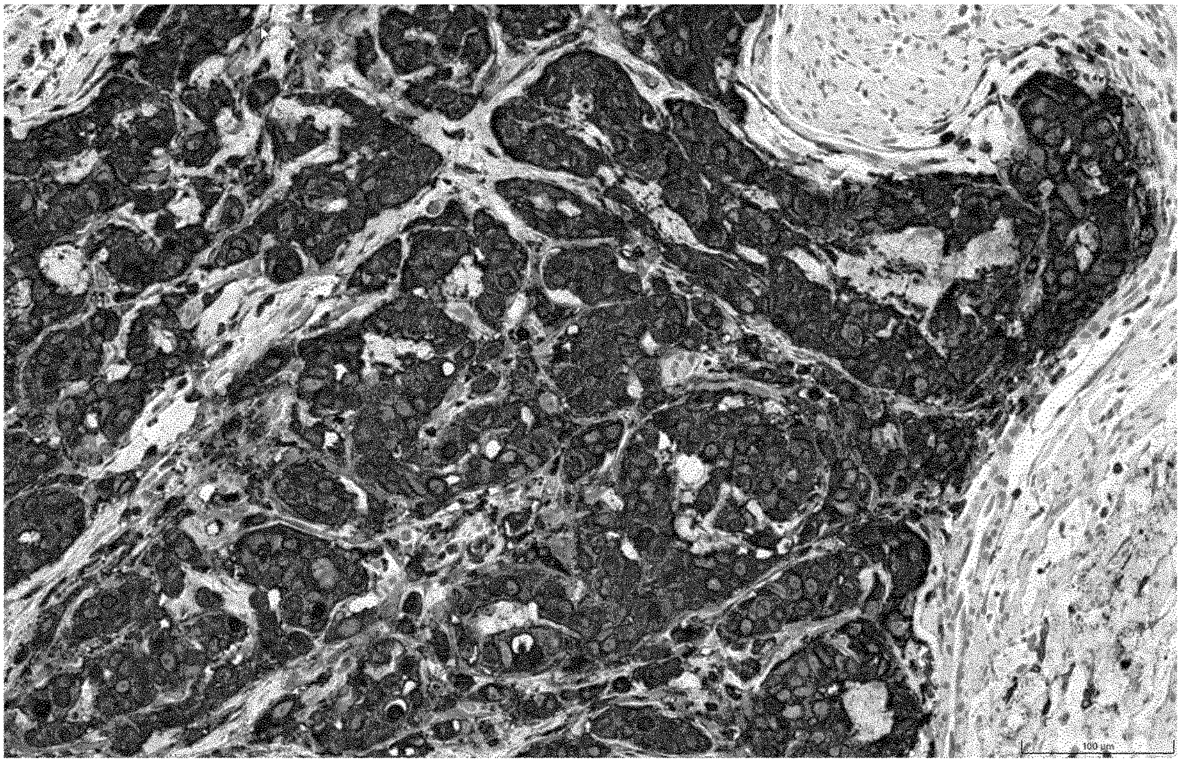
Figure 12:
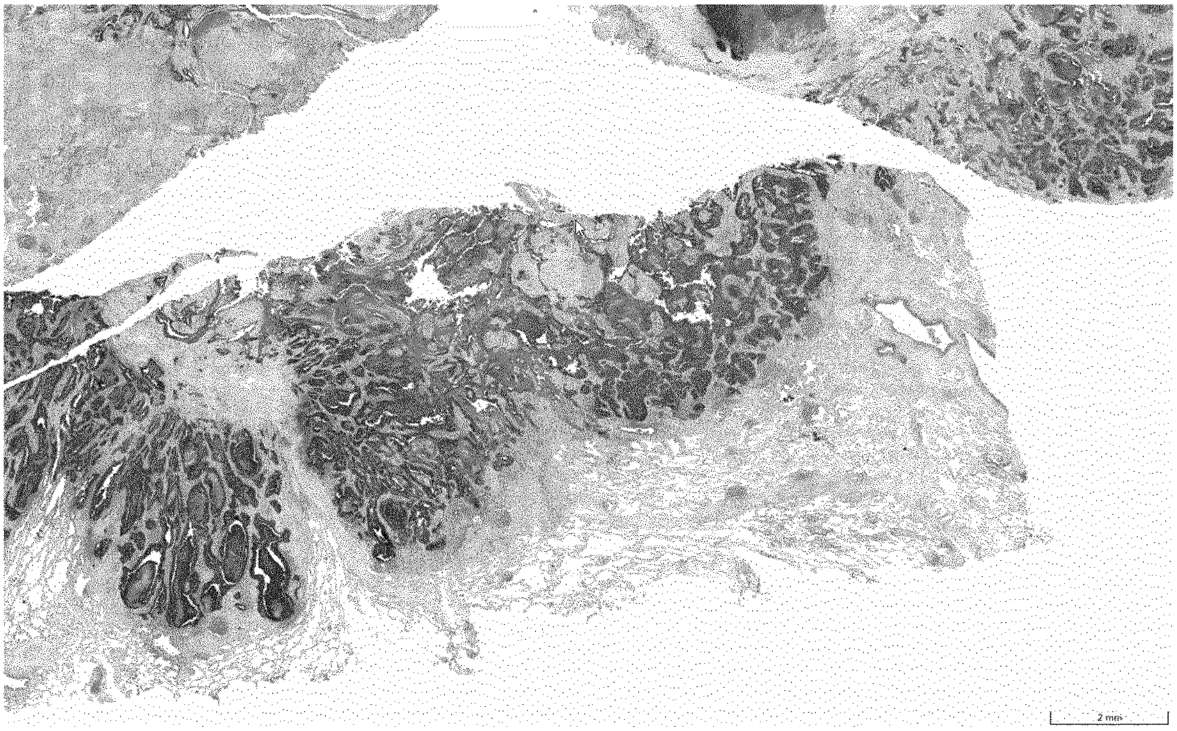
FIG. 12: IHC staining with the antibody rb8G4 on human non-small cell lung cancer tissue.
Figure 12:
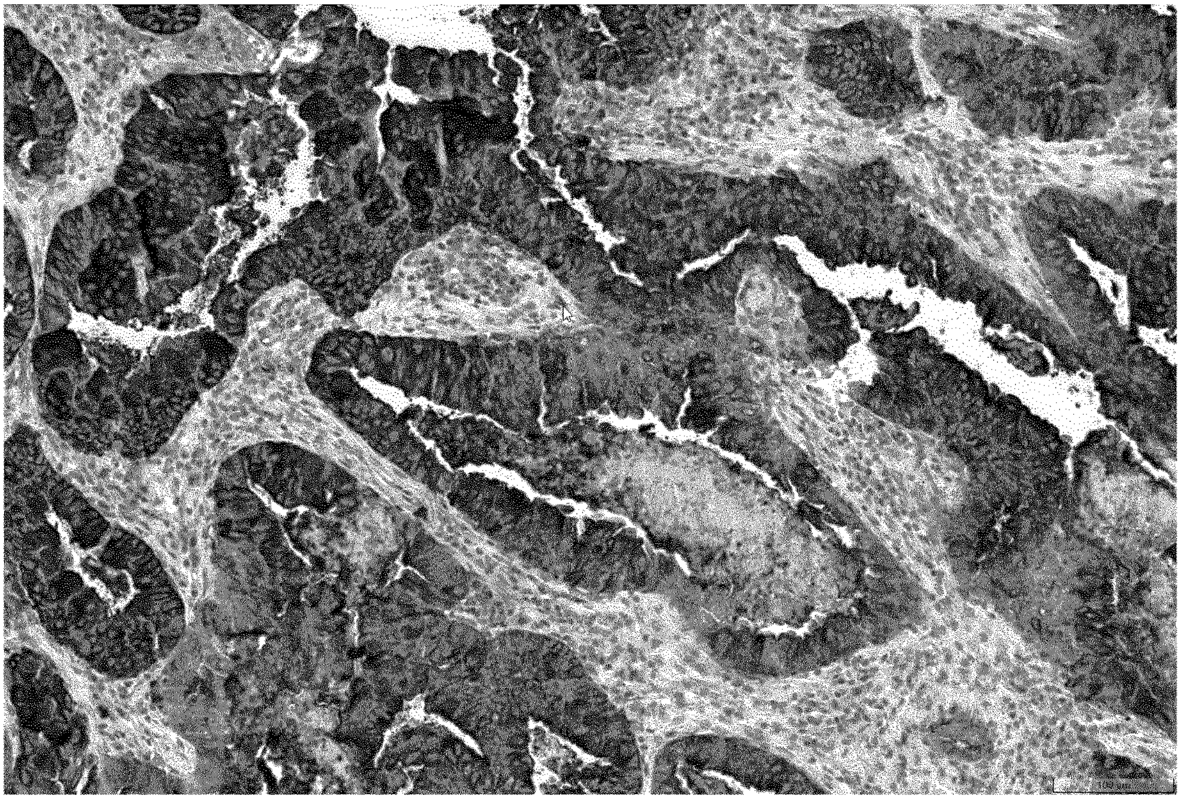

The antibody rb8G4 stained positive in several human tumor indications, as shown in colorectal cancer (FIG. 9), gastric cancer (FIG. 10), esophageal cancer (FIG. 11), and non-small cell lung cancer (FIG. 12). The signal is localized in the cytoplasm and at the plasma membrane.

1.9 Flow Cytometry and Western Blot Using mAb1 and rb8G4

Binding of mAb1, rb8G4 and a commercially available anti-CEACAM5 antibody to CEACAM5-positive and -negative cell lines was compared.

Method used: 5E5 to 1E6 cells were used for flow cytometry analyses using a BD FACSCanto II (BD Biosciences) in 5 mL polystyrene tubes. Staining with 10 μg/mL primary antibodies (mAb1, rb8G4, mouse monoclonal Agilent Dako #M7072 clone #1L7) and respective fluorescently labeled secondary antibodies (donkey anti-human IgG Jackson-Dianova #709-116-149; donkey anti-mouse IgG Jackson ImmunoResearch #715-116-150, donkey anti-rabbit IgG Jackson-Dianova #711-116-152) were conducted in 50 μL 1% PBS/BSA for 20 to 30 min at 4° C. Between and after staining steps, cells were washed thrice with 1% PBS/BSA and resuspended in 500 μL 1% PBS/BSA (including 0.2 μg/mL DAPI for live cell gating) for flow cytometry analyses. For data evaluation, FlowJo software (BD Biosciences) was used.

Results: mAb1 and rb8G4 showed binding corresponding to mRNA expression level data on CEACAM5-positive cell lines only (Table 1 below; MKN-45, NCI-H441). In contrast, for the commercial antibody, binding was weaker and limited to a CEACAM5-high cell line (Table 1 below; MKN-45). In conclusion, mAb1 and rb8G4 specifically detect CEACAM5-positive cancer cells and can be utilized as a detection agent.

TABLE 1

Binding of different antibodies to CEACAM5-positive and CEACAM5-negative cell lines. Quotients of median fluorescent intensity (MFI) of respective antibodies divided by MFI of secondary antibody only controls are listed per cell line.

| CELL LINE | MAB1 | RB8G4 | AGILENT/DAKO M7072 CLONE IL7 |
|---|---|---|---|
| MKN-45 | 23.2 | 36.2 | 3.8 |
| NCI-H441 | 2.2 | 3.2 | 1.1 |
| A549 | 1.1 | 1.1 | 1.0 |
| MDA-MB-468 | 1.1 | 1.0 | 1.0 |

Binding of human mAb1 and rb8G4 to CEACAM5-positive and -negative cell line lysates was also investigated by Western Blots.

Method used: Western blots were performed according to standard protocols (Sambrook, J. & Russell, D. W., 2001. Molecular Cloning: A Laboratory Manual, Volume 1, CSHL Press). For SDS-PAGE followed by membrane wet blotting, 15 μg total protein of RIPA cell lysates quantified by BCA kit (Thermo Scientific, #23227) were loaded per lane. Criterion XT 4-12% gels (Bio-Rad, #3450125) using MOPS running buffer (Bio-Rad #1610788) were used in a Criterion electrophoresis cell (Bio-Rad, #1656001). Transfer of proteins was confirmed by Ponceau staining. Membranes were washed before and in-between staining with 0.5 μg/mL to 1 μg/mL primary (mAb1 or rb8G4) and secondary antibodies (anti-human IgG, Jackson ImmunoResearch #109-035-098 or anti-rabbit IgG, CellSignaling #7074) was conducted. Stained membranes were visualized by ECL detection reagent using a Fusion FX imaging system (Vilber).

Figure 13A:
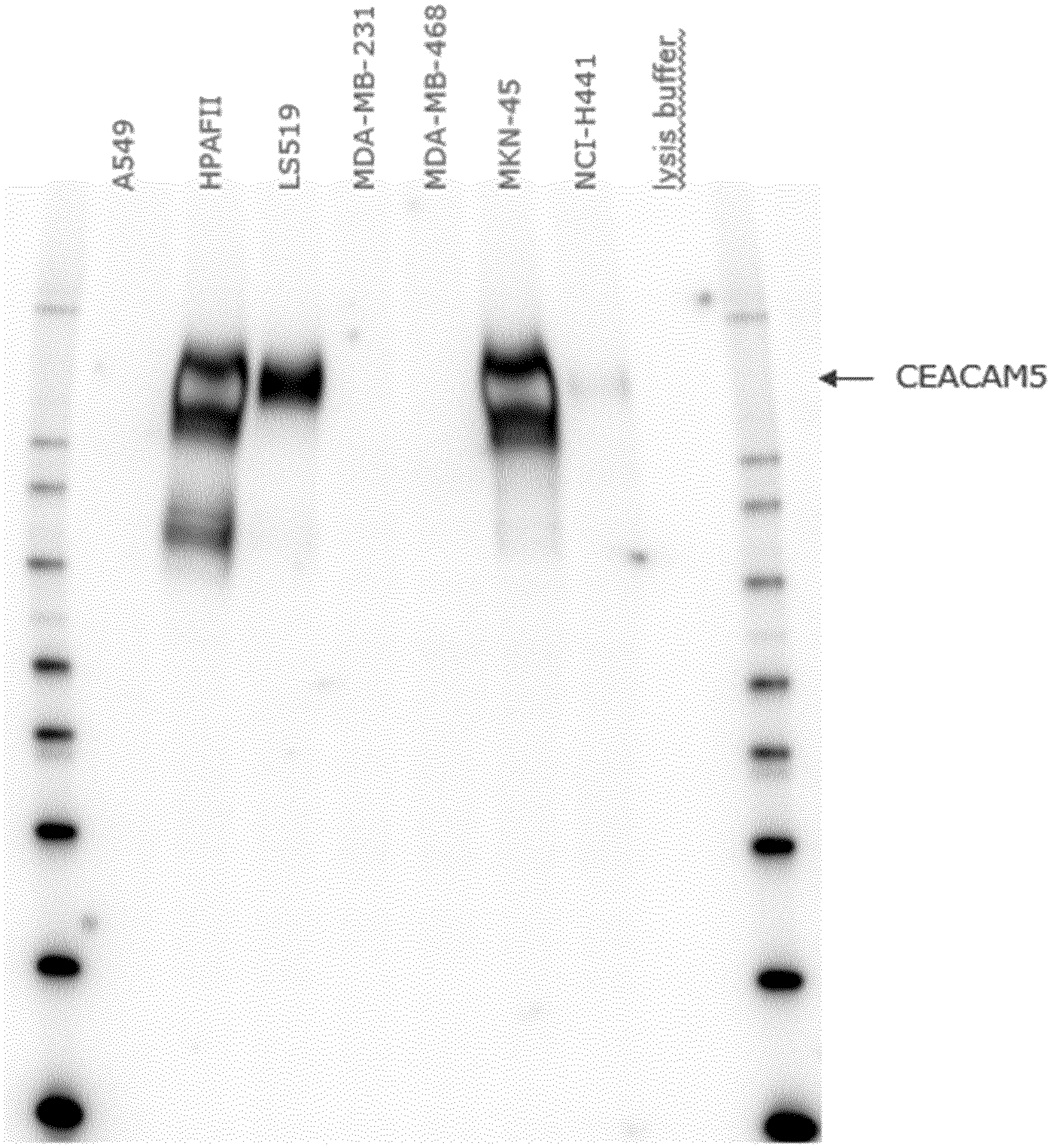
FIGS. 13A and 13B: Binding of mAb1 (FIG. 13A) and rb8G4 (FIG. 13B) to CEACAM5 in cancer cell line lysates investigated by Western Blots.
Figure 13B:
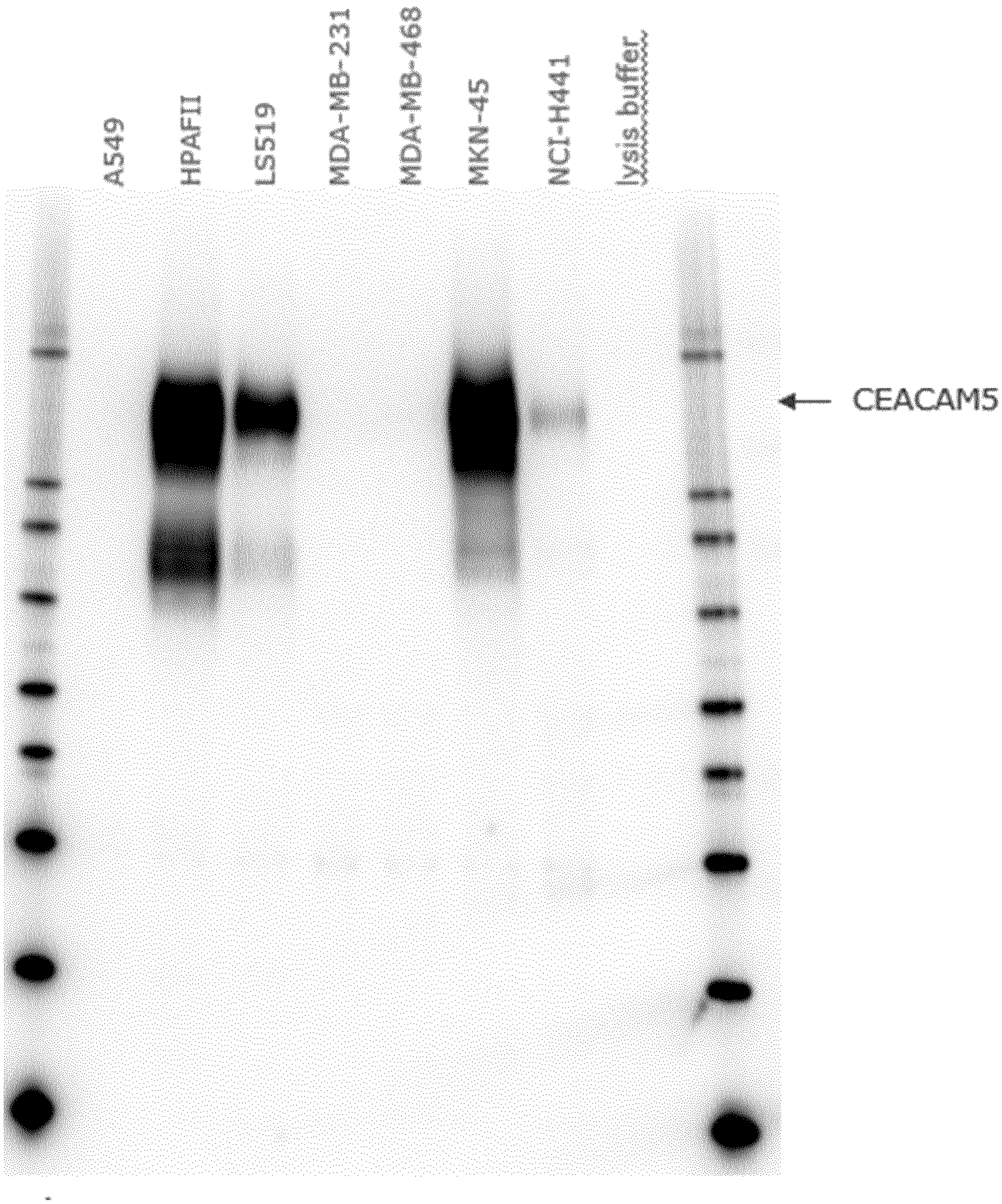

Results are shown in FIG. 13A and FIG. 13B: Both antibodies bound in a comparable pattern corresponding to the expected migration speed of highly glycosylated CEACAM5. CEACAM5 detection by mAb1 (FIG. 13A) and rb8G4 (FIG. 13B) was specific to CEACAM5-positive cell lines, and intensity correlated with mRNA expression levels. A secondary band observed with lower intensity corresponds to a potential second isoform previously described (Hatakeyama et al.: Novel protein isoforms of carcinoembryonic antigen are secreted from pancreatic, gastric and colorectal cancer cells. BMC Research Notes 2013 6:381).

Example 2: Synthesis of a Drug-Linker Compound with Glucuronide-Based Linker: Drug-Linker Compound 1 (DL1)
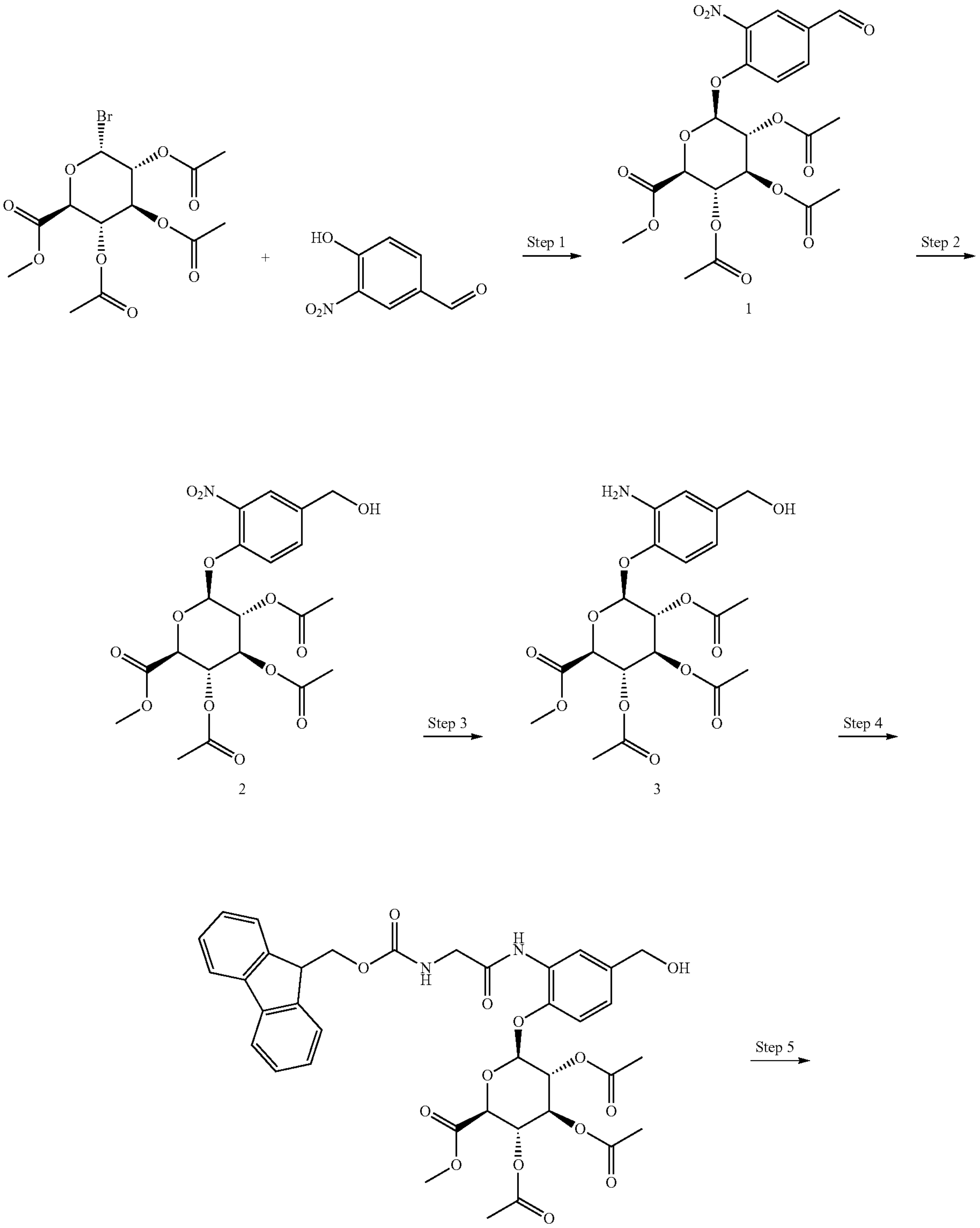
1
2
3
4

-continued
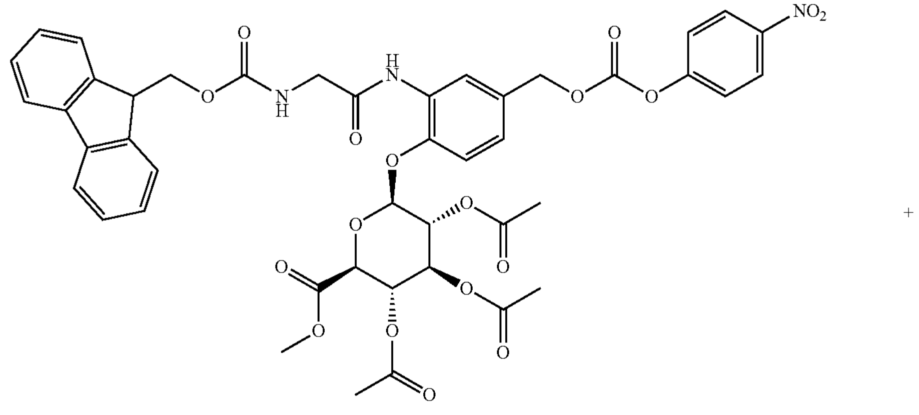
5
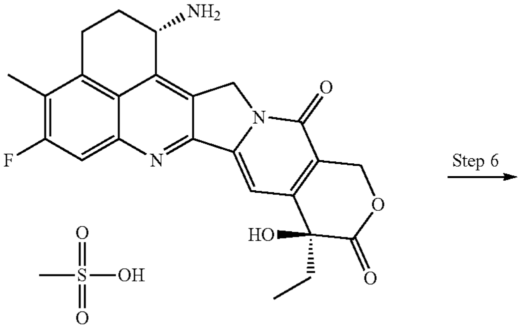
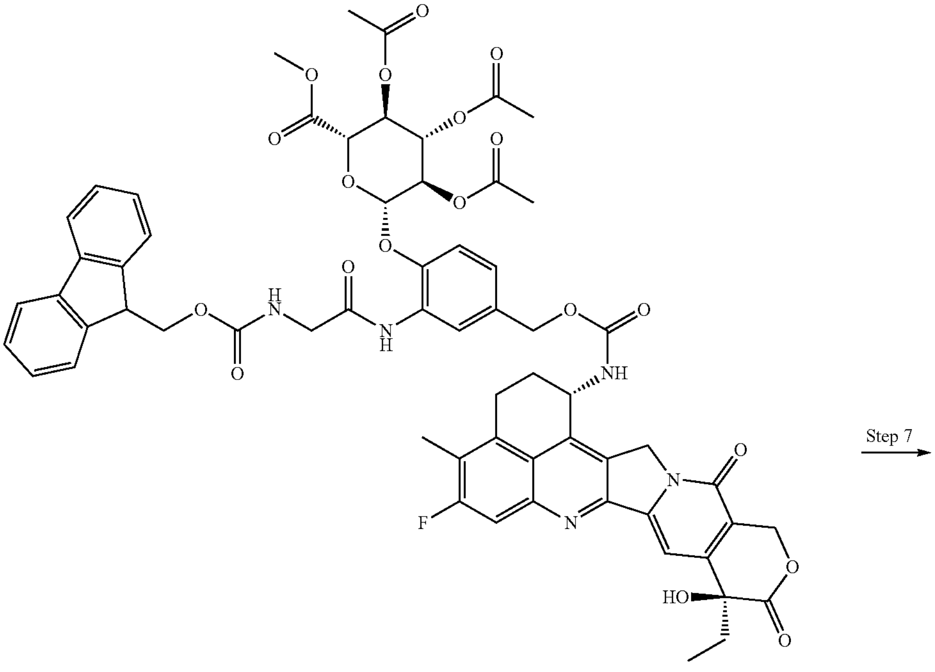
6

-continued
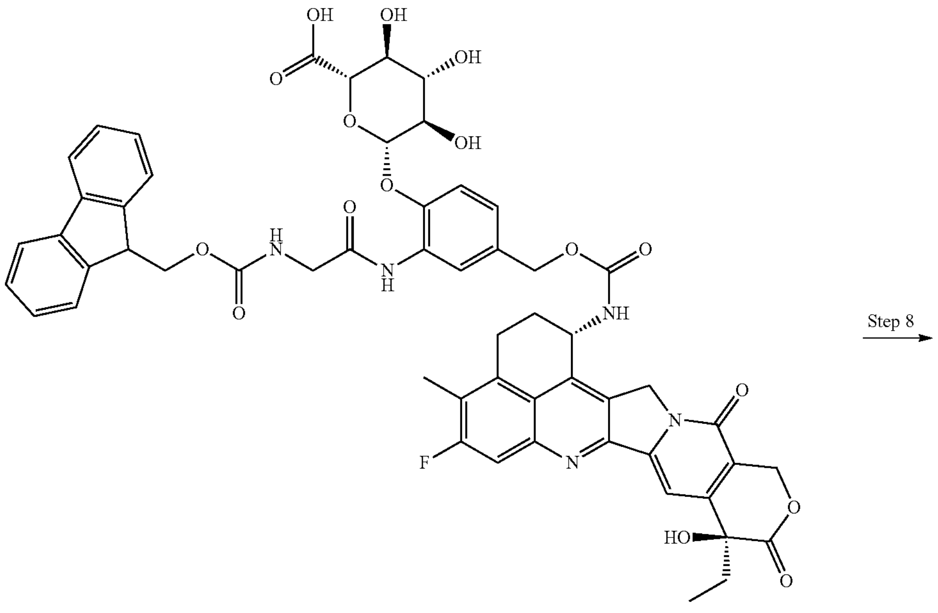
7
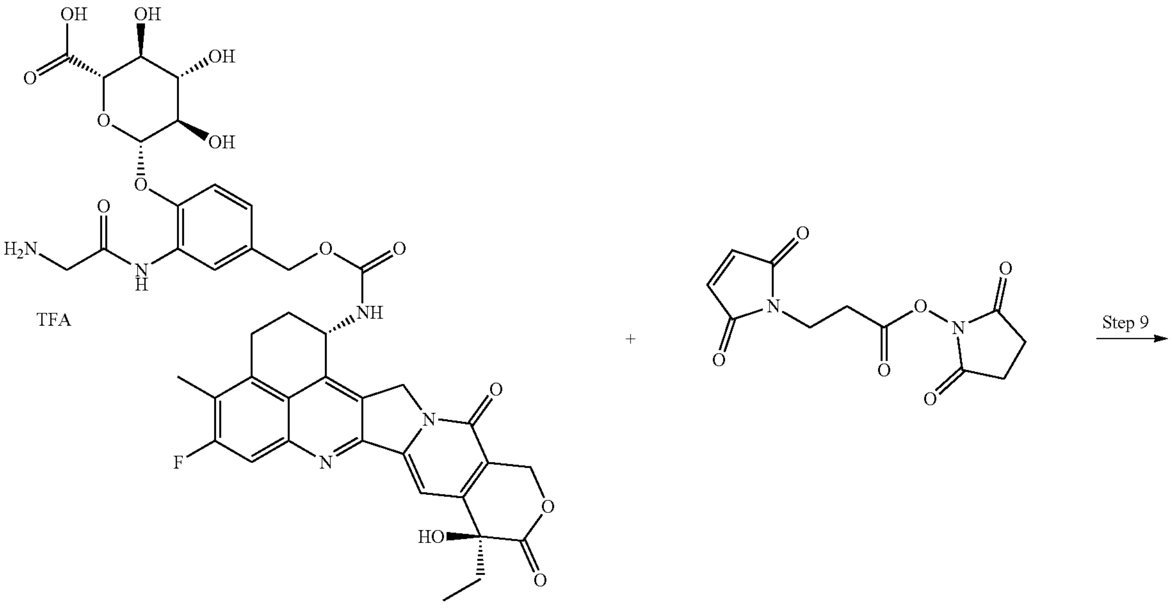
8

-continued

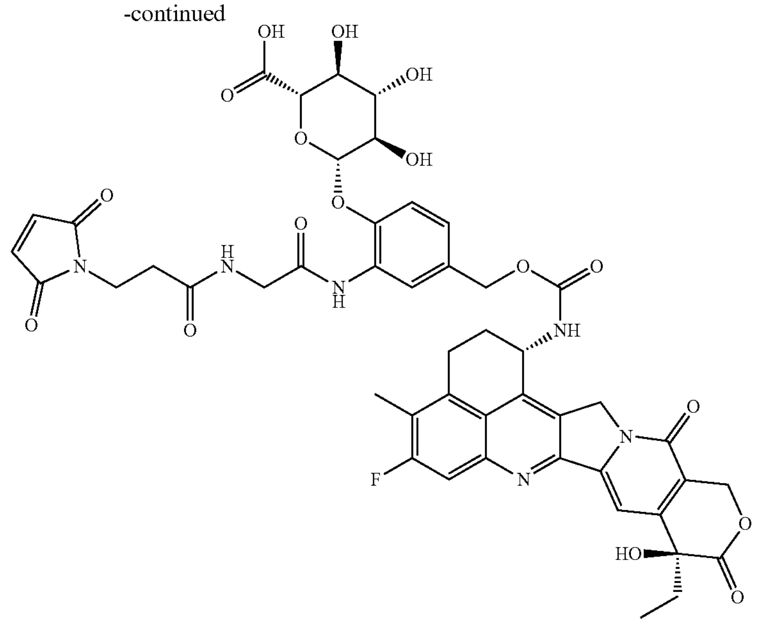

9

The synthetic route to compound 9 (also referred to herein as drug-linker compound 1 (DL1)).

Protocol of Chemical Preparation

Step 1: Compound 1

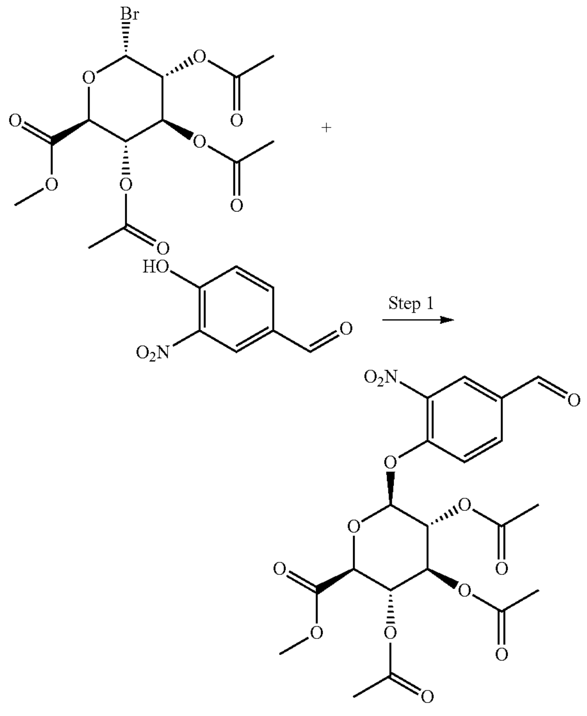

1

To a stirred solution of (2S,3S,4S,5R,6R)-3,4,5-Triacetoxy-6-bromo-tetrahydro-pyran-2-carboxylic acid methyl ester (8.30 g; 20.90 mmol; 1.00 eq.) and 4-Hydroxy-3-nitro-benzaldehyde (5.24 g; 31.35 mmol; 1.50 eq.) in Acetonitrile (83.00 ml; 10.00 V) was added Silver(I) oxide (9.69 g; 41.80 mmol; 2.00 eq.). The reaction mixture was stirred at RT for 16 h. The reaction mixture was filtered through celite. The filtrate was concentrated under vacuum to get solid. The solid was dissolved in EtOAc and washed with 10% aqueous solution of $NaHCO_3$ to remove excess 4-Hydroxy-3-nitro-benzaldehyde. The organic layer was concentrated under vacuum to get compound 1 as sand colour solid.

Yield: 9.0 g

Percentage Yield: 89.1%

Analytical Data:

NMR: $^1$H-NMR (400 MHz, DMSO-d6): 9.98 (s, 1H), 8.46 (s, 1H), 8.25-8.21 (m, 1H), 7.64 (d, J=11.60 Hz, 1H), 5.94 (d, J=10.00 Hz, 1H), 5.51-5.44 (m, 1H), 5.20-5.09 (m, 2H), 4.80 (d, J=13.20 Hz, 1H), 3.64 (s, 3H), 2.09 (s, 9H).

Step 2: Compound 2

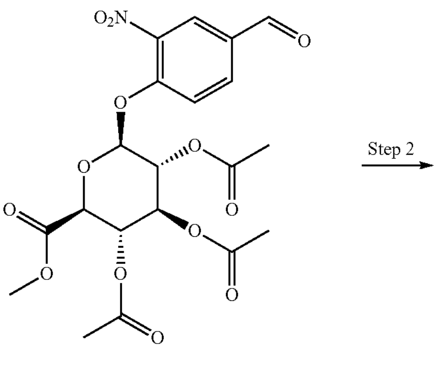

1

-continued

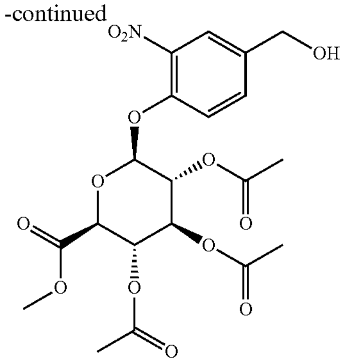

2

To a stirred solution of compound 1 (9.00 g; 18.62 mmol; 1.00 eq.) in Propan-2-ol (33.00 ml; 3.67 V) and $CHCl_3$ (167.00 ml; 18.56 V) were added silica gel 60-120 (3.60 g; 112.09 mmol; 6.02 eq.) followed by sodium borohydride (1.80 g; 46.55 mmol; 2.50 eq.). The reaction mixture was stirred for 1 h at RT. After completion, the reaction mixture was quenched with cooled $H_2O$ and filtered through celite. The filtrate was extracted with Dichloromethane and dried over $Na_2SO_4$. The solvent was concentrated to get compound 2 as off-white powder.

Yield: 8.70 g

Percentage Yield: 92.4%

Analytical Data

LCMS: Column: ATLANTIS dC18 (50×4.6 mm) 5 μm; Mobile phase A: 0.1% HCOOH in $H_2O$: ACN (95:5); B: ACN RT (min): 2.05: M+H: 503.2, Purity: 96.6%

Step 3: Compound 3

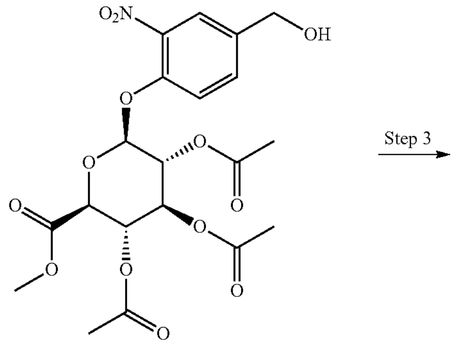

2

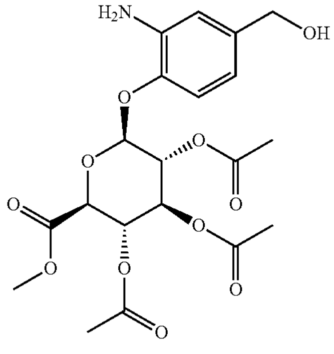

3

To a stirred solution of compound 2 (8.70 g; 17.21 mmol; 1.00 eq.) in ethyl acetate (100.00 ml; 11.49 V) and THF (100.00 ml; 11.49 V) was added Palladium on carbon (10% w/w) (2.50 g; 2.35 mmol; 0.14 eq.). The reaction mixture stirred for 3 h at RT under hydrogen atmosphere.

After completion, the reaction mixture was filtered off through celite. The solvent was concentrated under vacuum to get compound 3 as off-white solid.

Yield: 8.5 g

Percentage Yield: 100%

Analytical Data:

LCMS: Column: ATLANTIS dC18 (50×4.6 mm) 5 μm; Mobile phase A: 0.1% HCOOH in $H_2O$: ACN (95:5); B: ACN RT (min): 1.73; M+H: 456.10, Purity: 95.1%

Step 4: Compound 4

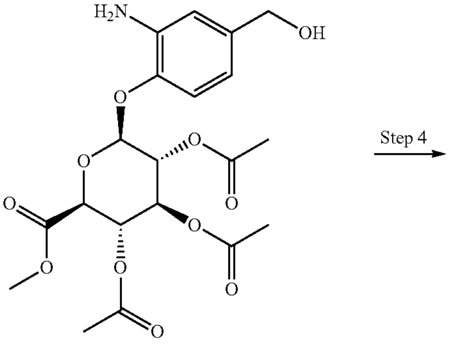

3

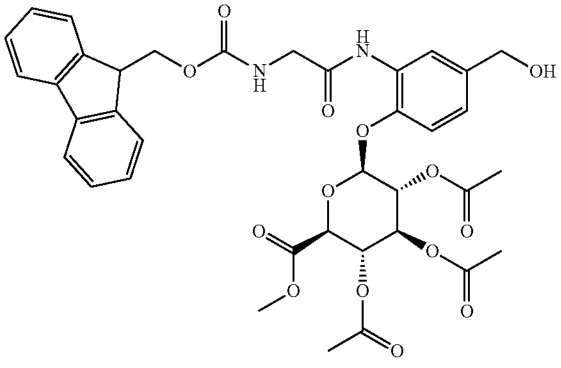

4

To a stirred solution of compound 3 (10.00 g; 20.89 mmol; 1.00 eq.) and (9H-Fluoren-9-ylmethoxycarbonylamino)-acetic acid (7.60 g; 25.06 mmol; 1.20 eq.) in DCM (250.00 ml; 25.00 V) was added 2-Ethoxy-2H-quinoline-1-carboxylic acid ethyl ester (15.65 g; 62.66 mmol; 3.00 eq.) at 0° C. The reaction mixture was stirred for 16 h at RT. After completion, solvent was removed under reduced pressure to get a crude product. The crude product was purified by column chromatography (56% EtOAc:petroleum ether) to get compound with purity 80%. The compound was purified further by washings with 30% EtOAc and pet ether to get compound 4 as white solid.

Yield: 8.5 g

Percentage Yield: 50.7%

Analytical Data:

LCMS: Column: ATLANTIS dC18 (50×4.6 mm) 5 μm; Mobile phase A: 0.1% HCOOH in $H_2O$: ACN (95:5); B: ACN RT (min): 3.03; M+H: 735.2, Purity: 81.9%

Step 5: Compound 5

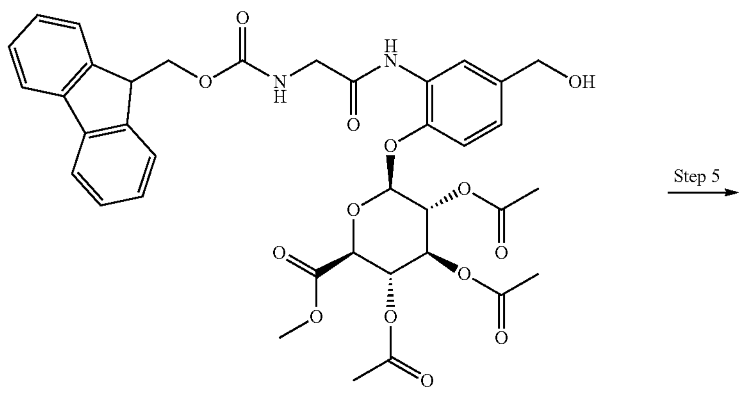

4

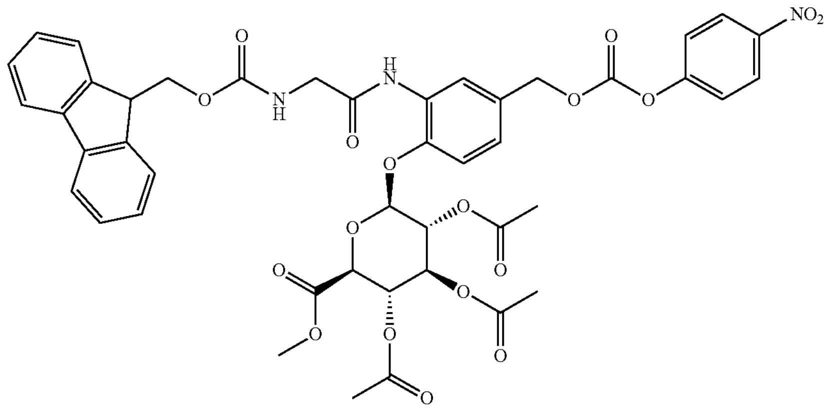

5

To a stirred solution of compound 4 (2.00 g; 2.49 mmol; 1.00 eq.) in THF (40.00 ml; 20.00 V) at 0° C., were added Carbonic acid bis-(4-nitro-phenyl) ester (3.06 g; 9.97 mmol; 4.00 eq.) and DIPEA (4.40 ml; 24.92 mmol; 10.00 eq.). The reaction mixture was stirred at RT for 12 h. After completion of the reaction, reaction mixture was concentrated under vacuum. The crude product was purified by column chromatography using silica gel (230-400) and pet ether/ethyl acetate as an eluent to afford compound 5 as pale yellow solid.

Yield: 2.0 g

Percentage Yield: 84.6%

Analytical Data:

LCMS: Column: X-Bridge C8(50×4.6) mm, 3.5 μm; Mobile phase: A: 0.1% TFA in MilliQ water; B: ACN RT (min): 3.24; M+H: 900.20, Purity: 94.9%

Step 6: Compound 6

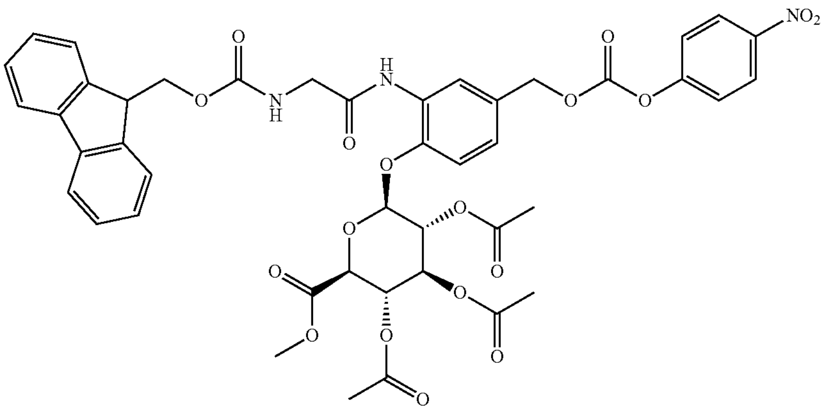

5

+

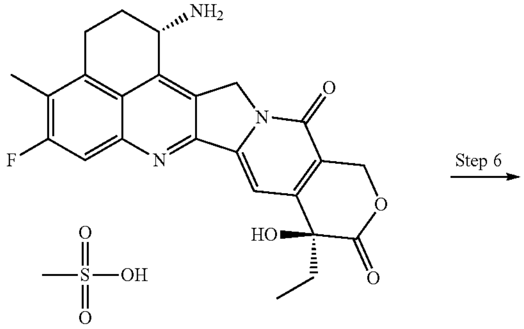

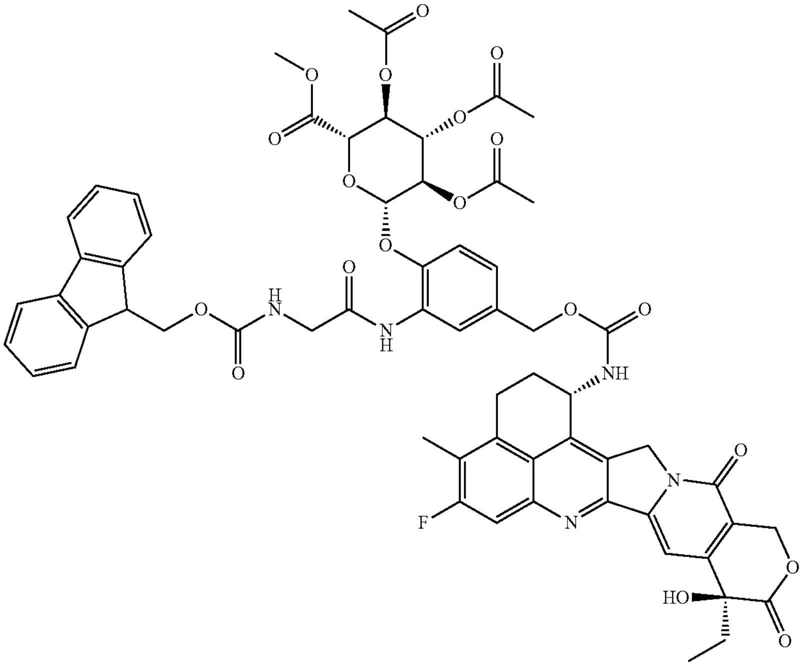

6

Compound 5 (1,369 g; 1.00 eq.) was dissolved in N,N-dimethylformamide (15.00 ml), Exatecan mesylate (679.7 mg; 1.00 eq.), 4-methylmorpholine for synthesis (0,422 ml; 3.00 eq.) and 1-Hydroxybenzotriazol (172.8 mg; 1.00 eq.) were added. The reaction mixture was stirred at room temperature for overnight. After the stirring time the reaction suspension was changed to a brown solution. The reaction was monitored by LC-MS, which showed a complete conversion of the starting material. The reaction mixture was purified via RP flash chromatography. The product containing fractions were combined, concentrated in vacuo and lyophilized overnight to afford compound 6 as an yellow solid.

Yield: 1.59 g

Percentage Yield: 87.5%

Analytical Data:

LCMS: Column: Chromolith HR RP-18e (50-4.6 mm); Mobile phase A: 0.05% HCOOH in $H_2O$; B: 0.04% HCOOH and 1% $H_2O$ in ACN; T: 40° C.; Flow: 3.3 m/min; MS: 100-2000, amu positive; 1%→100% B: 0→2.0 min; 100% B: 2.0→2.5 min RT (min): 1.95; M+H: 1196.40, Purity: 84.4%.

Step 7: Compound 7

Compound 6 (1,586 g; 1.00 eq.) was dissolved in tetrahydrofuran (50.00 ml) and a solution (0.1M) of LiOH (contains Lithium hydroxide hydrate (281.77 mg; 6.00 eq.) in water (67,100 ml)) was added dropwise at 0° C. The pH value was checked during the addition. The pH should not exceed 10. The addition of the solution of LiOH was completed after 1.5 hours. The reaction was monitored by LC-MS, which showed a complete conversion of the starting material. The reaction was quenched with citric acid solution, pH adjusted to 5. The reaction mixture was concen-

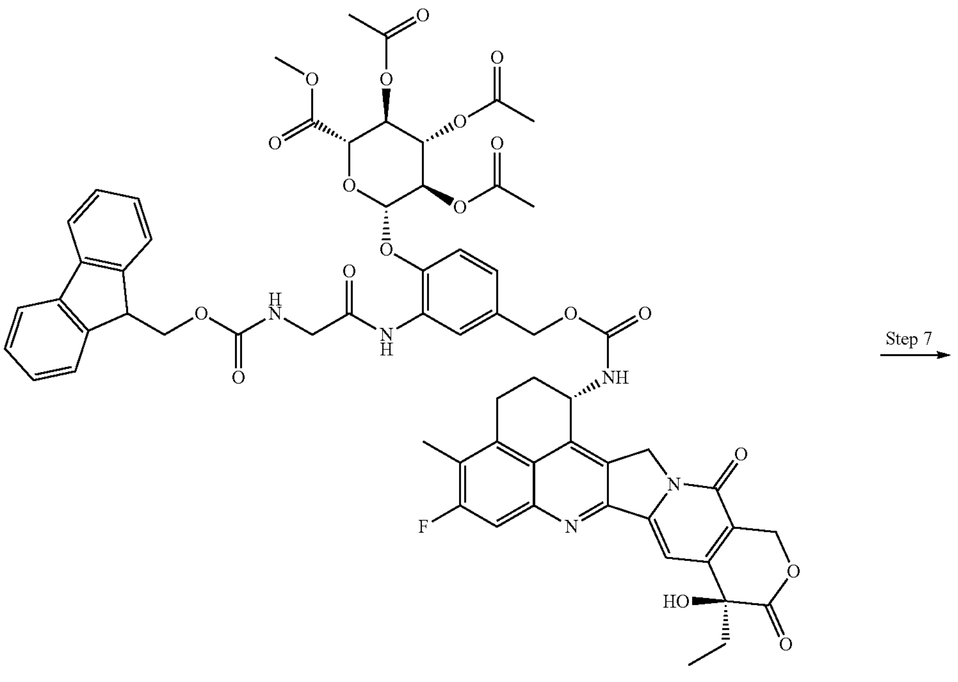

6

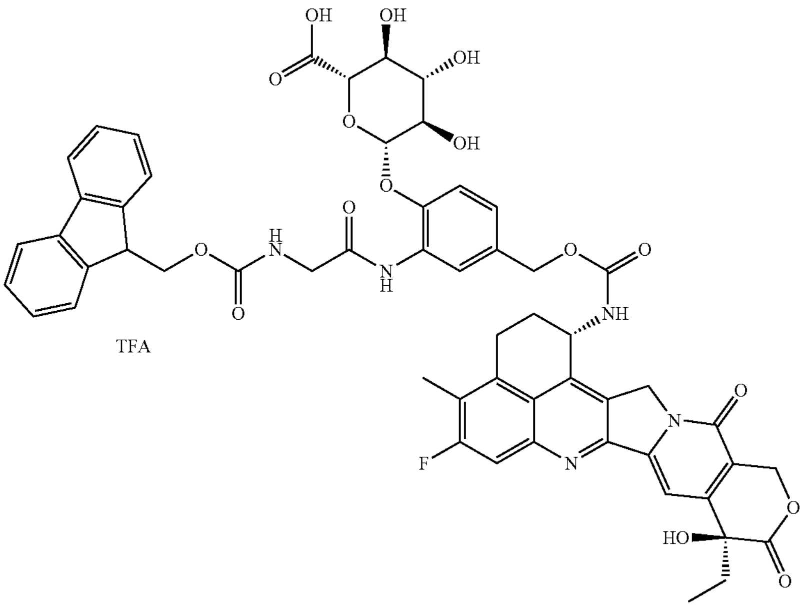

7 trated under reduced pressure. The crude was purified by prep. HPLC. The product containing fractions were combined and lyophilized to afford Compound 7 as a dark yellow solid.

Yield: 728 mg

Percentage Yield: 54.8%

Analytical Data:

LCMS: Column: Chromolith HR RP-18e (50-4.6 mm); Mobile phase A: 0.05% HCOOH in $H_2O$; B: 0.04% HCOOH and 1% $H_2O$ in ACN; T: 40° C.; Flow: 3.3 ml/min; MS: 100-2000, amu positive; 1%→100% B: 0→2.0 min; 100% B: 2.0→2.5 min RT (min): 1.68; M+H: 1056.30, Purity: 98.5%.

Step 8: Compound 8

Compound 7 (728,000 mg; 1.00 eq.) was dissolved in N,N-dimethylformamide (20.00 ml). Piperidine (136,513 μl; 2.00 eq.) was added and the solution was stirred at RT for totally 4 hours. The reaction was monitored by LC-MS, which showed a complete conversion of the starting material. The reaction mixture was concentrated under reduced pressure and the crude product was purified by RP flash chromatography. The product containing fractions were combined, the solvent was removed partially and it was lyophilized overnight to afford compound 8 as an yellow solid.

Yield: 706 mg

Percentage Yield: 100%

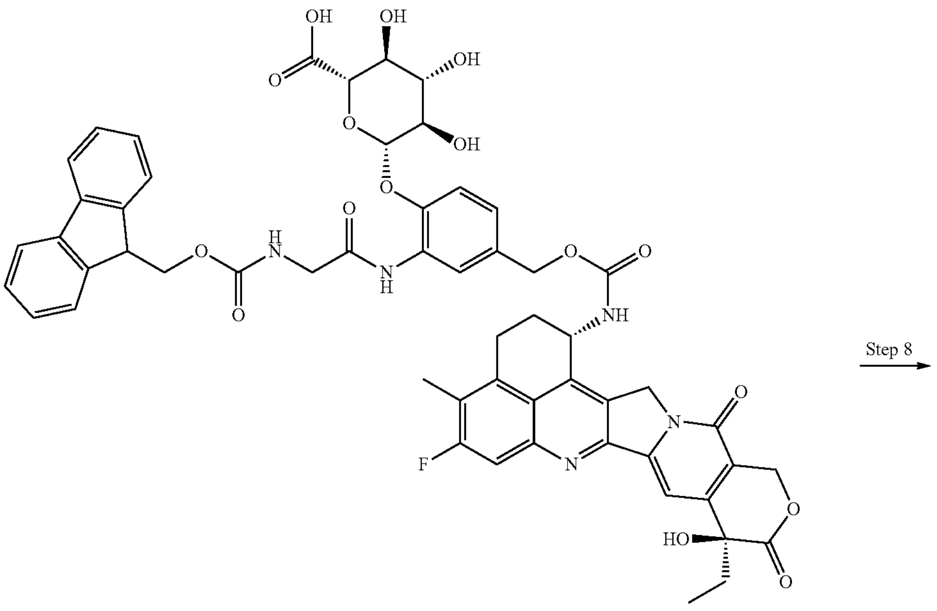

7

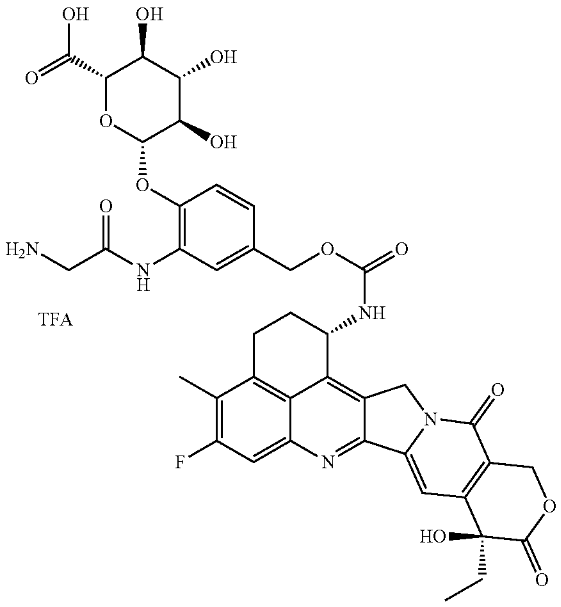

8

Analytical Data:

LCMS: Column: Chromolith HR RP-18e (50-4.6 mm); Mobile phase A: 0.05% HCOOH in $H_2O$; B: 0.04% HCOOH and 1% $H_2O$ in ACN; T: 40° C.; Flow: 3.3 m/min; MS: 100-2000, amu positive; 1%→100% B: 0→2.0 min; 100% B: 2.0→2.5 min RT (min): 1.22; M+H: 834.30, Purity: 97.6%.

Step 9: Compound 9

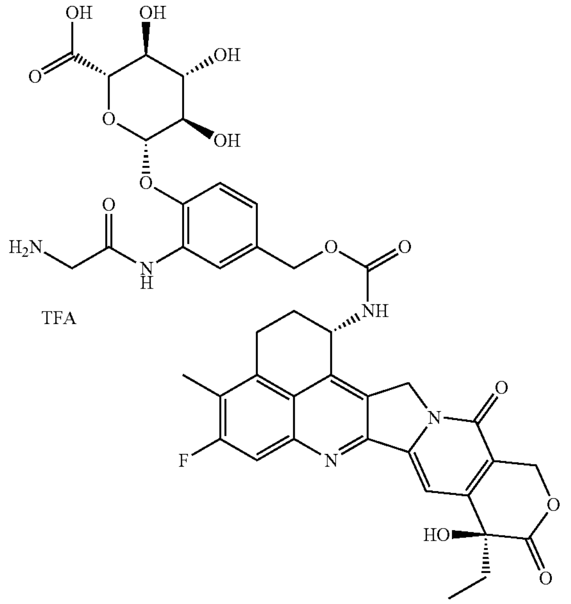

8

+

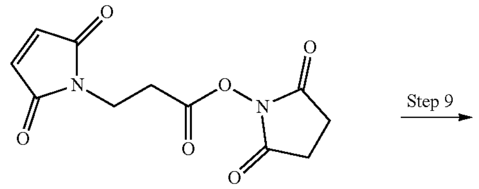

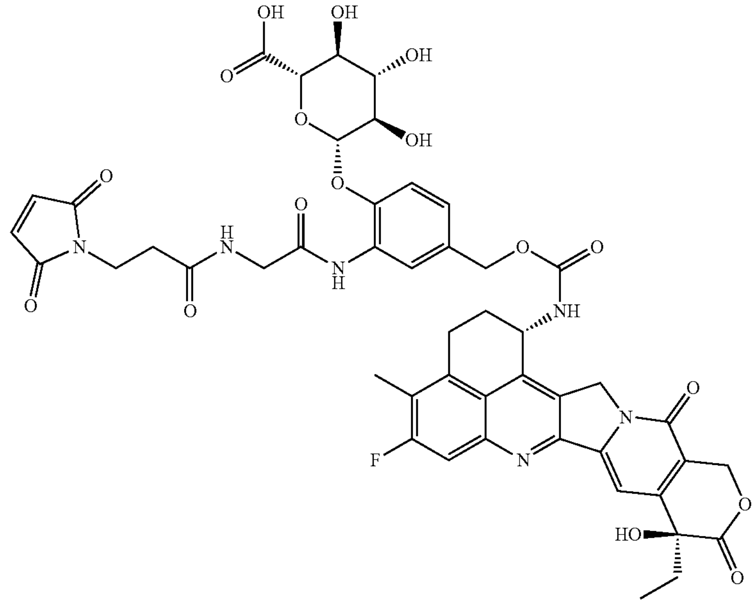

9

To a solution of compound 8 (854 mg; 1.00 eq.) in dimethylformamid (30.00 ml) were added N-ethyldiisopropylamine (149,234 μl: 1.00 eq.) and 3-(2,5-Dioxo-2,5-dihydro-pyrrol-1-yl)-propionic acid 2,5-dioxo-pyrrolidin-1-yl ester (233.61 mg; 1.00 eq.). The reaction mixture was stirred at RT for 3 hours. The reaction was monitored by LC-MS, which showed a complete conversion of the starting material. The reaction mixture was concentrated under reduced pressure and the crude product was by RP flash chromatography. The product containing fractions were combined, concentrated and lyophilized to give the desired produce with a purity of 91%. This material was again purified by RP chromatography to give compound 9 as an yellow solid.

Yield: 580 mg

Percentage Yield: 60.1%

Analytical Data:

LCMS: Column: Chromolith HR RP-18e (50-4.6 mm); Mobile phase A: 0.05% HCOOH in $H_2O$; B: 0.04% HCOOH and 1% $H_2O$ in ACN; T: 40° C.; Flow: 3.3 ml/min; MS: 100-2000, amu positive; 1%→100% B: 0→2.0 min; 100% B: 2.0→2.5 min RT (min): 1.38; M+H: 985.30, Purity: 90% (the other 10% of isomer can be removed by HPLC)
$^{1}H$ NMR (500 MHz, DMSO-$d_6$) 13.10-12.44 (m, 1H), 9.08 (s, 1H), 8.32 (t, J=5.8 Hz, 1H), 8.16 (s, 1H), 8.02 (d, J=8.8 Hz, 1H), 7.76 (d, J=10.9 Hz, 1H), 7.31 (s, 1H), 7.15-7.09 (m, 2H), 6.98 (s, 2H), 5.48-5.38 (m, 2H), 5.32-5.22 (m, 3H), 5.11-5.01 (m, 2H), 4.87 (d, J=7.6 Hz, 1H), 3.92-3.88 (m, 1H), 3.89-3.84 (m, 2H), 3.65-3.61 (m, 2H), 3.46-3.41 (m, 1H), 3.42-3.37 (m, 1H), 3.38-3.31 (m, 1H), 3.28-3.20 (m, 1H), 3.15-3.07 (m, 1H), 2.48-2.44 (m, 2H), 2.38 (s, 3H), 2.24-2.13 (m, 2H), 1.94-1.80 (m, 2H), 0.88 (t, J=7.3 Hz, 3H).
Example 3: Synthesis of a Drug-Linker Compound with Legumain-Cleavable Linker: Drug-Linker Compound 2 (DL2)
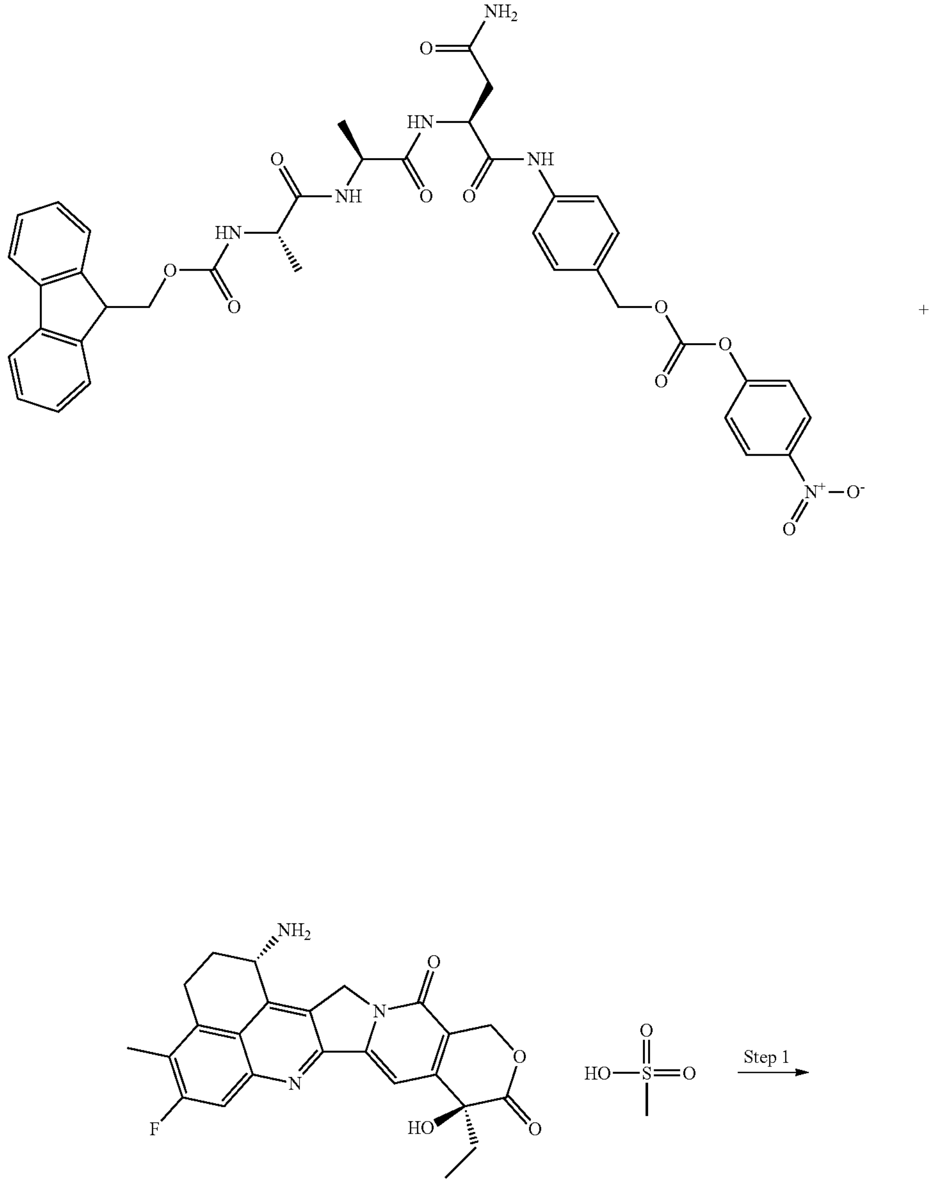

-continued

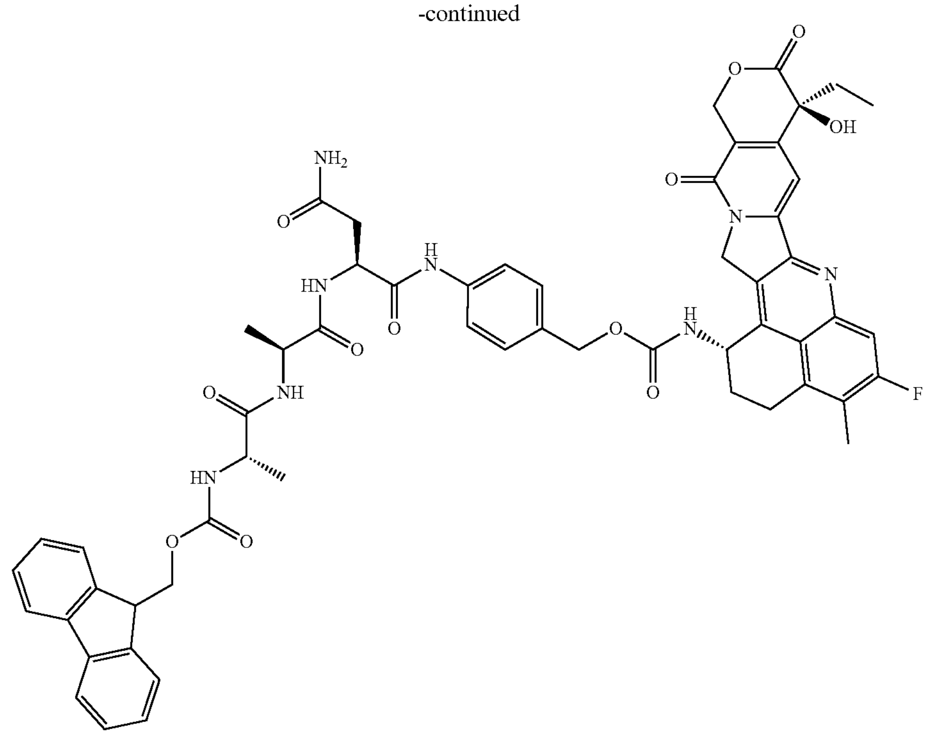

Step 1

{4-[(2S)-3-carbamoyl-2-[(2S)-2-[(2S)-2-({[(9H-fluoren-9-yl)methoxy]carbonyl}amino)propanamido]propanamido]propanamido]phenyl}methyl 4-nitrophenyl carbonate (400 mg; 0.52 mmol; 1.00 eq.) [commercially available from Levena Biopharma US] was dissolved in N,N-Dimethylformamide (5.00 ml). Exatecan mesylate (277.30 mg; 0.52 mmol; 1.00 eq.), N-Ethyldiisopropylamine (0.27 ml; 1.57 mmol; 3.00 eq.) and 1-Hydroxybenzotriazol (HOBT) (3.52 mg; 0.03 mmol; 0.05 eq.) were added. The reaction mixture was stirred at room temperature overnight. LC/MS indicated complete conversion.

The crude reaction mixture was purified via prep HPLC and lyophilized yielding 365 mg (0.343 mmol) of (9H-fluoren-9-yl)methyl ((S)-1-(((S)-1-(((S)-4-amino-1-((4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenyl)amino)-1,4-dioxobutan-2-yl)amino)-1-oxopropan-2-yl)amino)-1-oxopropan-2-yl)carbamate

LC/MS: [M+H]=1064.2

Prep HPLC:

Column: sunfire prep c18 obd—75.0 g (250 bar)

Solvent A: Wasser 0.1% TFA Solvent C:

Solvent B: Acetonitril 0.1% TFA

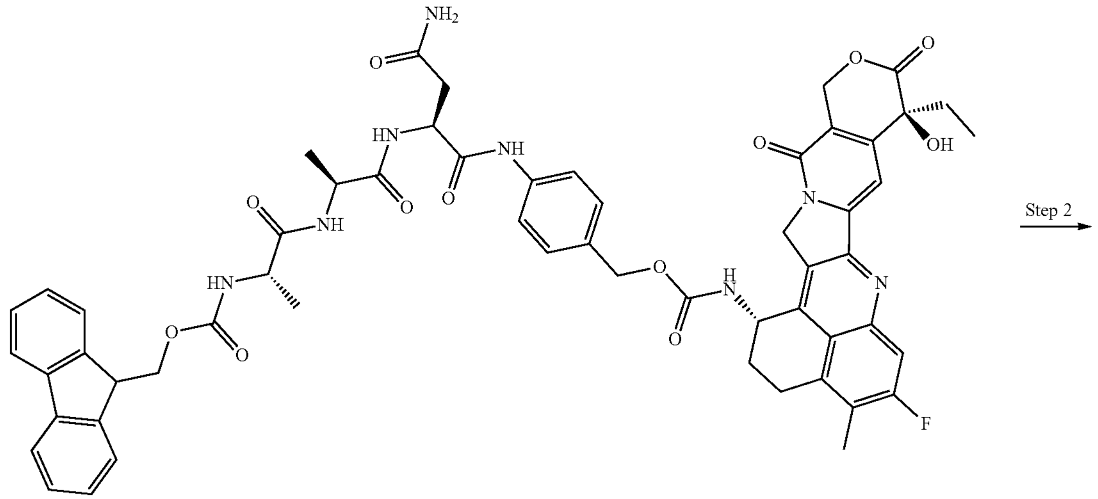

-continued

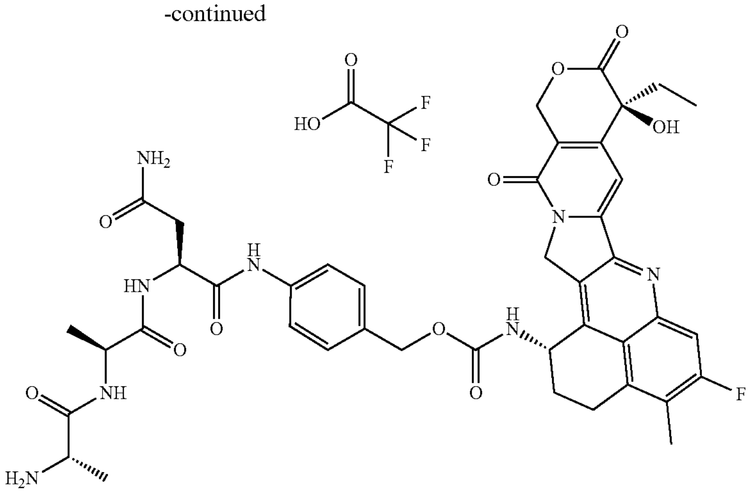

Step 2

(9H-fluoren-9-yl)methyl ((S)-1-(((S)-1-(((S)-4-amino-1-((4-(((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)oxy)methyl)phenyl)amino)-1,4-dioxobutan-2-yl)amino)-1-oxopropan-2-yl)amino)-1-oxopropan-2-yl)carbamate (365 mg; 0.34 mmol; 1.00 eq.) was dissolved in N,N— (4.00 ml). Piperidine for synthesis (0.07 ml; 0.69 mmol; 2.00 eq.) was added and the reaction solution was stirred at rt for 1 h.

The reaction mixture was purified via prep HPLC yielding 300 mg (0.314 mmol) of 4-((S)-4-amino-2-((S)-2-((S)-2-aminopropanamido)propanamido)-4-oxobutanamido)benzyl ((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamate.

LC/MS: [M+H]: 841.3

Prep HPLC for Purification:

RediSep Säule: C18 130 g

SN: E0410A0D24BE1 Lot: 262118923W

Flowrate: 75 ml/min

Condition—Volumen: 390.0 ml

Eluent: A1 WATER 0.1% TFA

Eluent: B1 ACETONITRILE 0.1% TFA

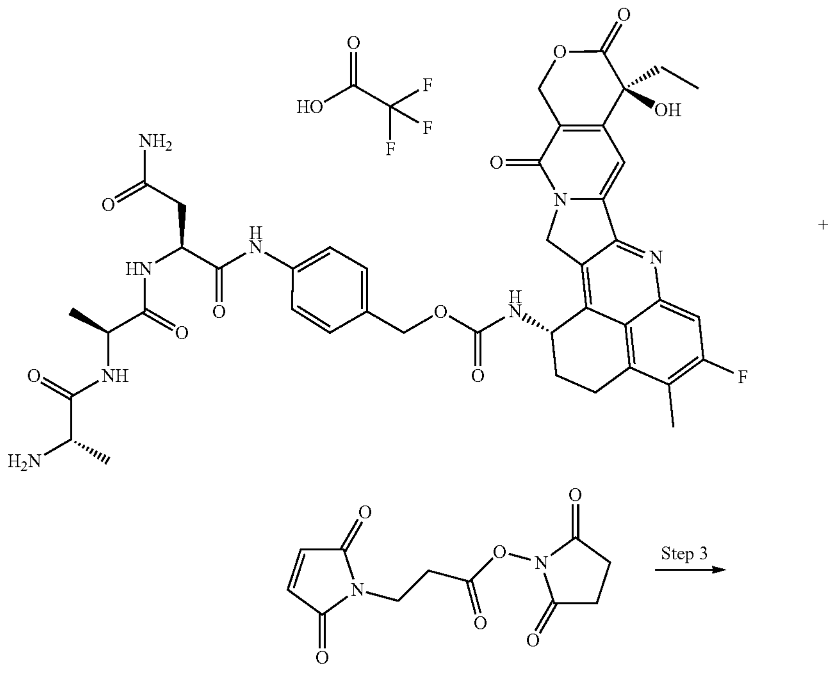

-continued

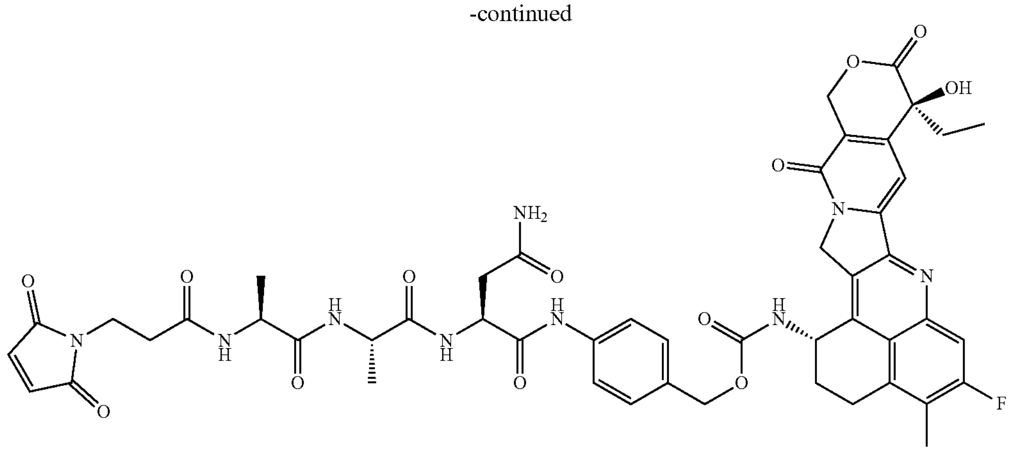

Step 3

To a solution of 4-((S)-4-amino-2-((S)-2-((S)-2-amino-propanamido)propanamido)-4-oxobutanamido)benzyl ((1S, 9S)-9-ethyl-5-fluoro-9-hydroxy-4-methyl-10,13-dioxo-2,3, 9,10,13,15-hexahydro-1H,12H-benzo[de]pyrano[3',4':6,7] indolizino[1,2-b]quinolin-1-yl)carbamate (571 mg; 0.60 mmol; 1.00 äq.) in N,N-Dimethylformamide (20 ml) was added N-Ethyldiisopropylamine (203 µl; 1.20 mmol; 2.00 eq.) and N-Succinimidyl 3-maleimidopropionate (162 mg; 0.60 mmol; 1.00 eq.). The reaction mixture was then stirred for 10 min and monitored via LC/MS.

The reaction mixture was purified via prep HPLC yielding 378 mg (0.35 mmol) of DL2.

LC/MS: [M+H]: 992.4

Prep HPLC for Purification:

RediSep column: C18 86 g

SN: E0410A8B46130 Lot: 281729189W

Flowrate: 60 ml/min

Conditon—Volumen: 264.0 ml

Eluent 1: A1 WATER 0.1% TFA

Eluent 2: B1 ACETONITRILE 0.1% TFA

Analytics for Sequence:

Method Info: A: $H_2O$+0.05% HCOOH|B: MeCN+0.04% HCOOH+1% $H_2O$

T: 40° C.|Flow: 3.3 ml/min|MS: 100-2000 amu positive

Column: Chromolith HR RP-18e 50-4.6 mm

0%→100% B: 0→2.0 min|100% B: 2.0→2.5 min

Example 4: Preparation of an Immunoconjugate: A Glucuronide-Based Conjugate of mAb1 (Referred to as ADC1)

4.1 Conjugation Process

Antibody Preparation

The antibody mAb1 (as defined herein above) was thawed at 2-8° C. up to 3 days prior to conjugation and stored at 2-8° C. until use. The mAb (>10 g) was equilibrated at room temperature on the day of conjugation prior to use. The mAb (9.6 mg/mL) was aliquoted (10.0 g, 1041.7 mL) and diluted to 5.59 mg/mL using conjugation buffer (200 mM Histidine, pH 6.5). The mAb solution was added into a 3 L Chemglass jacketed reactor and set to 25±2° C. while stirring at 50 rpm.

Reduction of Antibody

Added 7.0 mol eq. (9.7 mL) of 50 mM TCEP solution (50 mM TCEP in conjugation buffer) into the mAb solution vial and the reaction was allowed to proceed at 25±2° C. for 3 hours.

Conjugation

The drug-linker compound 1 (DL1) of formula (X) was weighed and dissolved in DMSO to prepare a 20 mM solution. 90% (148.6 mL) of the required DMSO was added to the reactor. Immediately after DMSO addition, 10.0 mol equivalents (38.2 mL) of 20 mM drug-linker solution was added to the reactor. Then, 10% (18.2 mL) of the remaining required DMSO was used to rinse the drug-linker vial to ensure total transfer. After final addition, the reaction was allowed to proceed at 25±2° C. for 1 hour. Total volume during conjugation was 1997.0 mL.

Note: Overall DMSO concentration of the reaction was 10% (v/v) (DMSO+Drug Linker solution).

Quench

Added 35 mol eq. (48.5 mL) of 50 mM NAC to the reactor and the reaction was allowed to proceed at 25±2° C. for 30 minutes.

Filtration

The filtered crude conjugate solution was transferred from the reactor and then filtered using a Millipak Gamma Gold 60 (MPGL06GH2) to give 1993.6 mL (Filter Load: 324.7 g/m2 [protein], 66.5 L/m2 [solution]) of filtered crude conjugate.

Diafiltration

The filtered crude conjugate solution was buffer exchanged (DV=1993.6 mL) with a Pellicon 3 (30 kDa) Biomax membrane (1×0.11 m2, 300 LMH (550 mL/min), 16 psi TMP, actual loading 88.5 g/m2). Diafiltration buffer (10 mM Histidine, pH 5.5) was used to buffer exchange the crude conjugate for 16 diavolumes. After buffer exchanging, the solution was concentrated to ≥25 mg/mL, transferred into a bottle, and the membrane flushed with diafiltration buffer. Total volume recovered from UF/DF was 361.5 mL.

Formulation

The concentrated ADC (i.e. ADC1) was diluted to 20.0 mg/mL with 112.1 mL of diafiltration buffer (10 mM Histidine, pH 5.5). The resulting solution was diluted to 15.0 mg/mL with 157.6 mL of 4× formulation buffer (10 mM Histidine, 12% (w/v) Trehalose Dihydrate, 400 mM NaCl, pH 5.5) for a final target bulk drug substance (BDS) concentration of 15.0 mg/mL.

Filtration

The final formulated ADC was filtered using a 0.2 µm Millipak Gamma Gold 40 (MPGL04GH2) filter to yield 619.6 mL (Filter Load: 464.6 g/m2 [protein], 31.0 L/m2 [solution]) ADC1 BDS. The material was packaged into HDPE bottles and stored at ≤−65° C.

4.2 Methods: Drug Substance Characterization: ADC1
Size Exclusion Chromatography (SEC) Method
SEC Method Parameters

| | |
|---|---|
| Wavelength | 280 nm |
| Column | Tosoh TSKgel 7.8 mm × 300 mm, 5 μm (P/N 0008541) |
| Mobile Phase | 0.14M Potassium Phosphate Monobasic<br>50 mM Sodium Phosphate Monobasic<br>0.06M Potassium Phosphate Dibasic<br>0.25M Potassium Chloride<br>5% IPA |
| Injection Volume | 20 μL |
| Temperature | 25° C. |
| Flow rate | 0.5 mL/min |
| Run Time | 30 min |

Figure 14:
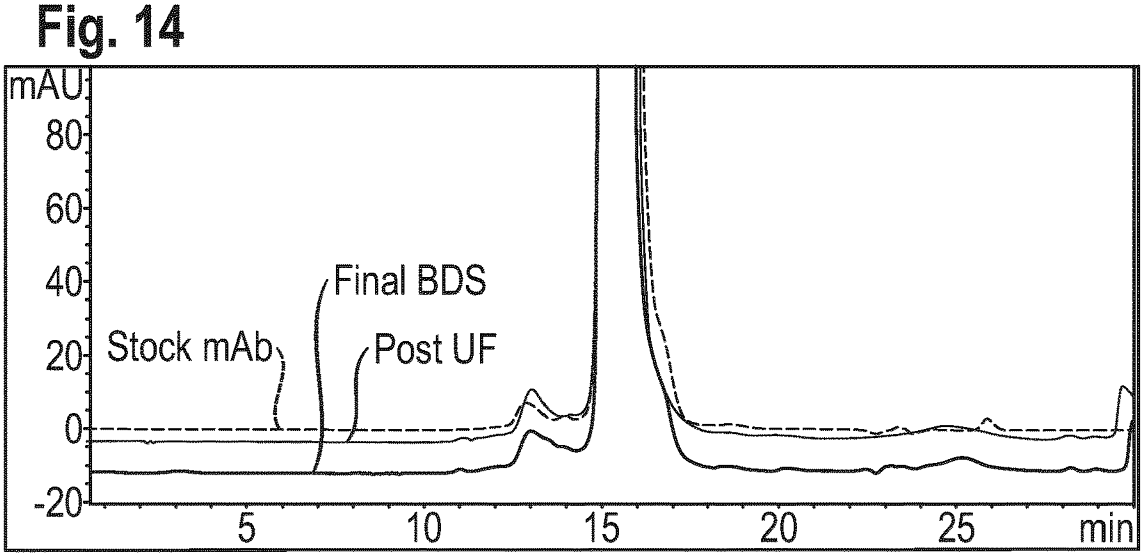
FIG. 14: Typical SEC chromatogram showing the purity of the stock mAb, the conjugate post UF and the final BDS.

Typical SEC chromatogram showing the purity of the stock mAb, the conjugate post UF and the final BDS: FIG. 14.

For the BDS material shown above, 1.7% HMWS and a monomeric purity of 96.9% have been reported.

Reversed-Phase HPLC (RP HPLC) Method
RP HPLC Method Parameters

| | |
|---|---|
| Wavelength | 280 nm |
| Column | PLRP-S 1000 Å (50 × 2.1 mm, 8 μm) column, Agilent (P/N PL1912-1802) |
| Mobile Phase A | 0.1% Formic Acid in Water with 0.01% TFA |
| Mobile Phase B | 0.1% Formic Acid in ACN with 0.01% TFA |

Gradient

| Time (min) | MP A (%) | MP B (%) |
|---|---|---|
| 0.00 | 80 | 20 |
| 3.00 | 80 | 20 |
| 20.00 | 0 | 100 |
| 22.00 | 80 | 20 |
| 26.00 | 0 | 100 |

4 min Equilabration to 80% A and 20% B

| | |
|---|---|
| Injection Volume | 10 μL |
| Column Temperature | 80° C. |
| Flow rate | 1.0 mL/min |
| Run Time | 30 min |

Sample Preparation Dilute sample to 2 mg/mL and add 40 μL to a micro centrifuge tube. Add 60 μL of the ~8 M Guanidine HCl, ~130 mM Tris, ~1 mM EDTA, pH 7.6 buffer. Add 2 μL of 500 mM DTT and vortex to mix. Incubate sample for 30±2 min at 37±2° C.

Figure 15:
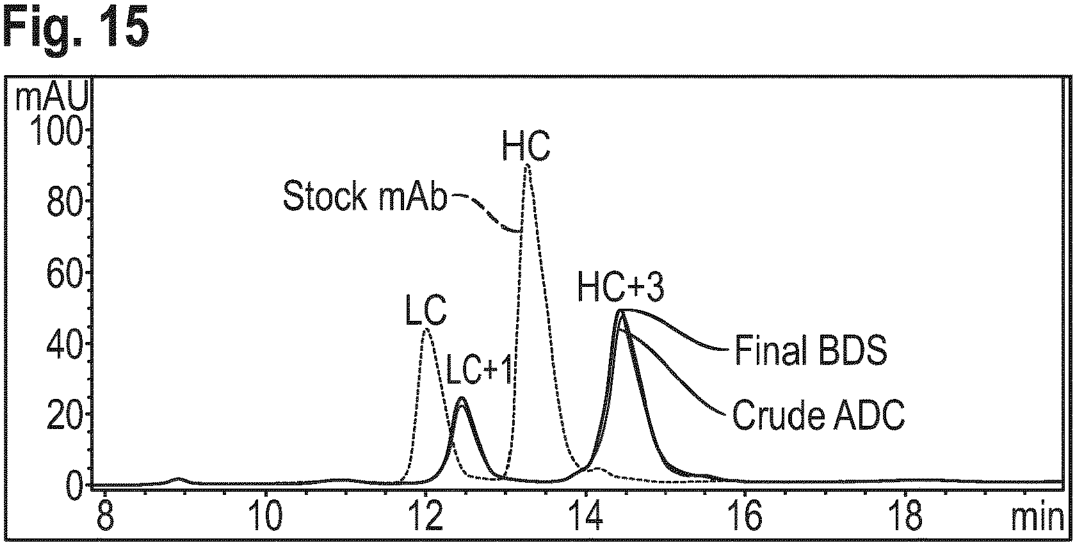
FIG. 15: Typical RP-HPLC chromatogram showing the separation of light and heavy chains. The chromatogram shows an overlay of the stock mAb, the crude ADC and the final BDS.

Typical RP-HPLC chromatogram showing the separation of light and heavy chains: FIG. 15. The chromatogram shows an overlay of the stock mAb, the crude ADC and the final BDS.

For the ADC1 BDS material above, a DAR of 7.9 was reported.

Free-Drug Method
Free-Drug Method Parameters

| | |
|---|---|
| Wavelength | 254 nm |
| Column | Phenomenex Gemini, C18, 2 × 150 mm, 3 μm (P/N 00F-4439-B0) |
| Mobile Phase A | 0.1% Formic acid in water |
| Mobile Phase B | 0.1% Formic acid in acetonitrile |

Gradient

| Time (min) | MP A (%) | MP B (%) |
|---|---|---|
| 0.00 | 95 | 5 |
| 1.00 | 95 | 5 |
| 12.00 | 0 | 100 |

3 min Equilabration to 95% A

| | |
|---|---|
| Injection Volume | 10.00 μL |
| Column Temperature | 50° C. |
| Flow rate | 0.75 mL/min |

Sample Preparation Protein drop: 100 μL of Drug Substance+250 μL of cold MeOH+50 μL of 3 M $MgCl_2$. Spin at 20,000 rpm for 10 min Standard Preparation Mix 20 μL of 20 mM DL1 (drug-linker compound 1 in DMSO)+20 μL DMSO+40 μL MeOH+20 μL of 200 mM NAC in Diafiltration buffer. Incubate overnight to afford 4 mM DL-NAC. Dilute 4 mM DL-NAC in MeOH to afford a 4 μM DL-NAC standard.

Figure 16:
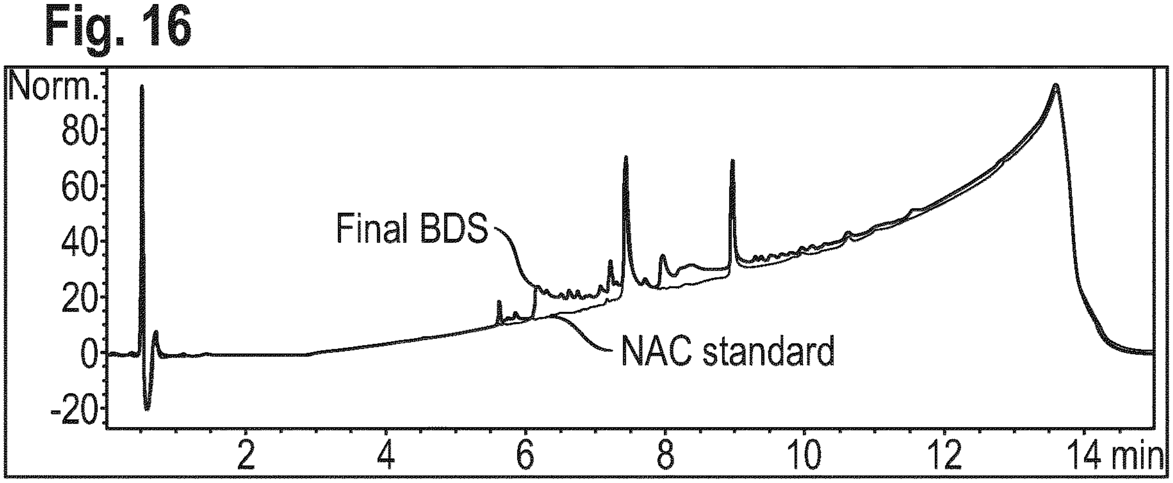
FIG. 16: Typical chromatogram showing the NAC standard and the free-drug levels of the final BDS.

Typical chromatogram showing the NAC standard and the free-drug levels of the final BDS: FIG. 16.

For the ADC1 BDS material shown above, residual free-drug levels below 2.4% (by molar ratio) have been reported.

Example 5: Preparation of an Immunoconjugate: A Peptide-Based Conjugate of mAb1 (Referred to as ADC2)

5.1 Conjugation Process
Antibody Preparation

The antibody mAb1 (as defined herein above) was thawed at 2-8° C. up to 3 days prior to conjugation and stored at 2-8° C. until use. The mAb (>9.5 g) was equilibrated at room temperature on the day of conjugation prior to use. The mAb (9.6 mg/mL) was aliquoted (9.5 g, 989.6 mL) and diluted to 5.59 mg/mL using conjugation buffer (200 mM Histidine, pH 6.5). The mAb solution was added to a 3 L Chemglass jacketed reactor and set to 25±2° C. while stirring at 50 rpm.

Reduction of Antibody

Added 8.0 mol eq. (10.5 mL) of 50 mM TCEP solution (50 mM TCEP in conjugation buffer) into the mAb solution vial and the reaction was allowed to proceed at 25±2° C. for 3 hours.

Diafiltration

The reduced mAb solution was buffer exchanged against 6 DVs (DV=1706.9 mL) using a Pellicon 3 (30 kDa) Biomax membrane (1×0.11 m2, 300 LMH (550 mL/min), 16 psi TMP, actual loading 86.3 g/m2. Conjugation buffer (200 mM Histidine, pH 6.5) was used to buffer exchange the reduced antibody. After buffer exchanging, the reduced mAb solution was recovered back into the reactor and the membrane flushed with conjugation buffer.

Conjugation

The drug-linker compound 2 (DL2) of formula (XI) was weighed and dissolved in DMSO to prepare a 20 mM drug-linker solution. 90% (142.6 mL) of the required DMSO was added to the reactor. Immediately after DMSO addition, 9.5 mol equivalents (31.2 mL) of the 20 mM drug-linker solution was added to the reactor. Then, 10% (15.8 mL) of the remaining required DMSO was used to rinse the drug-linker vial to ensure total transfer. After final addition, the reaction was allowed to proceed at 25±2° C. for 2 hours. Total volume during conjugation reaction was 1894.5 mL Quench Added 35 mol eq. (46 mL) of 50 mM NAC to the reactor and the reaction was allowed to proceed at 25±2° C. for 45 minutes.

Filtration

The crude conjugate solution was transferred from the reactor and filtered using a Millipak Gamma Gold 60 (MPGL06GH2) to give 1897.3 mL (Filter Load: 308.9 g/m2 [protein], 63.2 L/m2 [solution]) of filtered crude conjugate.

Diafiltration

The filtered crude conjugate solution was buffer exchanged (DV=1897.3 mL) with a Pellicon 3 (30 kDa) Biomax membrane (1×0.11 m2, 300 LMH (550 mL/min), 16 psi TMP, actual loading 84.2 g/m2). The initial 12 DVs were performed using conjugation buffer (200 mM Histidine, pH 6.5) and then switched to standard diafiltration buffer (10 mM Histidine, pH 5.5) for 8 additional DVs. After buffer completing the buffer exchange, the solution was then concentrated to a 25 mg/mL, transferred into a bottle and the membrane flushed with diafiltration buffer. Total pooled volume recovered from UF/DF was 335.7 mL.

Formulation

The concentrated ADC (i.e. ADC2) was diluted to 20.0 mg/mL with 84.7 mL of Diafiltration Buffer (10 mM Histidine, pH 5.5). The resulting solution was diluted with 138.6 mL of 4× Formulation Buffer (10 mM Histidine, 12% (w/v) Trehalose Dihydrate, 400 mM NaCl, pH 5.5) for a final target BDS concentration of 15.0 mg/mL.

Filtration

The final formulated ADC was aseptically filtered using a Millipak Gamma Gold 60 (MPGL06GH2) to yield 549.3 mL (Filter Load: 411.4 g/m2 [protein], 27.5 L/m2 [solution]) of ADC2 BDS. The material was packaged into HDPE bottles and stored at ≤−65° C.

5.2 Methods: Drug Substance Characterization: ADC2

Size Exclusion Chromatography (SEC) Method

SEC Method Parameters

| | |
|---|---|
| Wavelength | 280 nm |
| Column | Tosoh TSKgel 7.8 mm × 300 mm, 5 μm (P/N 0008541) |
| Mobile Phase | 50 mM Sodium Phosphate Monobasic 0.4M Sodium Perchlorate |
| pH | 6.3 |
| Injection Volume | 1 μL |
| Column Temperature | 25° C. |
| Flow rate | 0.5 mL/min |
| Run Time | 30 min |

Figure 17:
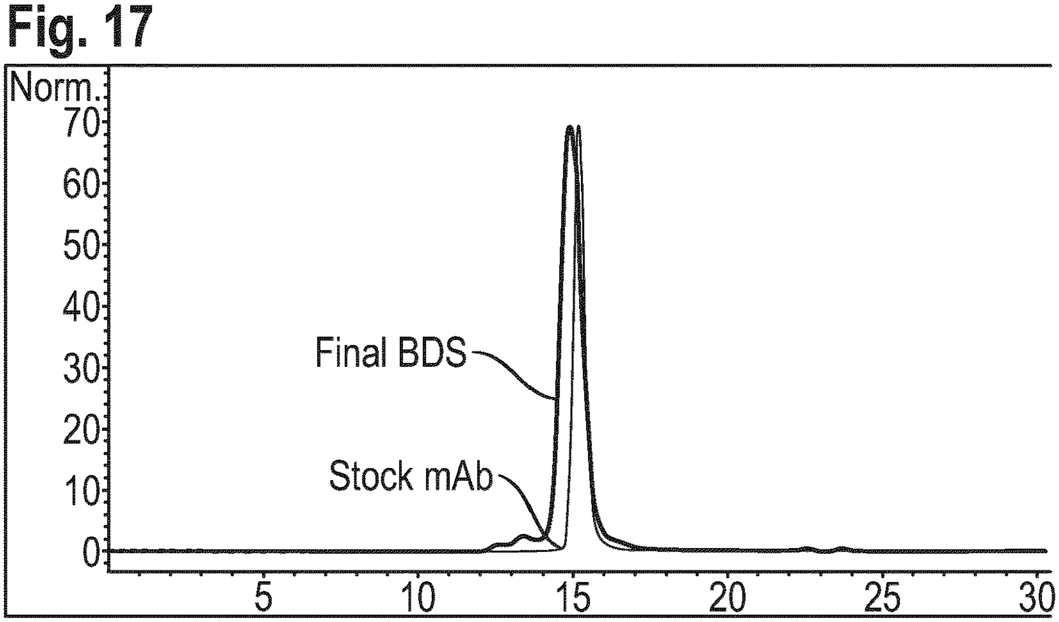
FIG. 17: Typical SEC chromatogram showing the purity of the stock mAb and the final BDS.

Typical SEC chromatogram showing the purity of the stock mAb and the final BDS: FIG. 17.

For the ADC2 BDS material shown above, 4.2% HMWS and a monomeric purity of 95.8% have been reported.

Reversed-Phase HPLC (RP HPLC) Method

RP HPLC Method Parameters

| | |
|---|---|
| Wavelength | 280 nm |
| Column | PLRP-S 1000 Å (50 × 2.1 mm, 8 μm) column, Agilent (P/N PL1912-1802) |
| Mobile Phase A | 0.1% Formic Acid in Water with 0.01% TFA |
| Mobile Phase B | 0.1% Formic Acid in ACN with 0.01% TFA |

Gradient

| Time (min) | MP A (%) | MP B (%) |
|---|---|---|
| 0.00 | 80 | 20 |
| 3.00 | 80 | 20 |
| 20.00 | 0 | 100 |
| 22.00 | 80 | 20 |
| 26.00 | 0 | 100 |

4 min Equilabration to 80% A and 20% B

| | |
|---|---|
| Injection Volume | 10 μL |
| Column Temperature | 80° C. |
| Flow rate | 1.0 mL/min |
| Run Time | 30 min |

Sample Preparation Dilute sample to 2 mg/mL and add 40 μL to a micro centrifuge tube. Add 60 μL of the ~8 M Guanidine HCl, −130 mM Tris, −1 mM EDTA, pH 7.6 buffer. Add 2 μL of 500 mM DTT and vortex to mix. Incubate sample for 30±2 min at 37±2° C.

Figure 18:
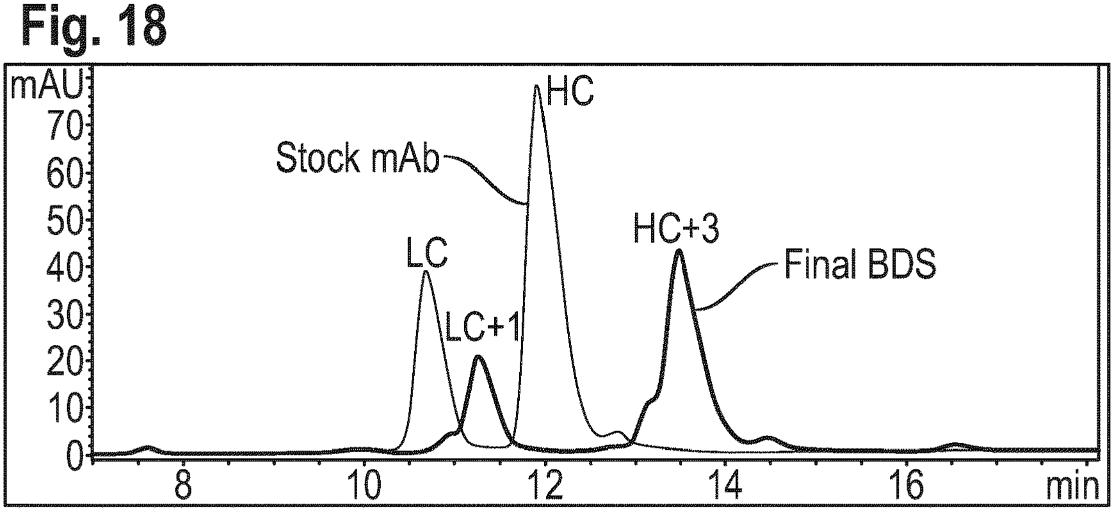
FIG. 18: Typical RP-HPLC chromatogram showing the separation of light and heavy chains. The chromatogram shows an overlay of the stock mAb and the final BDS.

Typical RP-HPLC chromatogram showing the separation of light and heavy chains: FIG. 18. The chromatogram shows an overlay of the stock mAb and the final BDS.

For the ADC2 BDS material above, a DAR of 7.6 was reported.

Free-Drug Method

Free-Drug Method Parameters

| | |
|---|---|
| Wavelength | 254 nm |
| Column | Phenomenex Gemini, C18, 2 × 150 mm, 3 μm (P/N 00F-4439-B0) |
| Mobile Phase A | 0.1% Formic acid in water |
| Mobile Phase B | 0.1% Formic acid in acetonitrile |

Gradient

| Time (min) | MP A (%) | MP B (%) |
|---|---|---|
| 0.00 | 95 | 5 |
| 1.00 | 95 | 5 |
| 12.00 | 0 | 100 |

3 min Equilabration to 95% A

| | |
|---|---|
| Injection Volume | 10.00 μL |
| Column Temperature | 50° C. |
| Flow rate | 0.75 mL/min |

Sample Preparation Protein drop: 100 μL of Drug Substance+250 μL of cold MeOH+50 μL of 3 M $MgCl_2$. Spin at 20,000 rpm for 10 min Standard Preparation Mix 20 μL of 20 mM DL2 (drug-linker compound 2 in DMSO)+20 μL DMSO+40 μL MeOH+20 μL of 200 mM NAC in Diafiltration buffer. Incubate overnight to afford 4 mM DL-NAC. Dilute 4 mM DL-NAC in MeOH to afford a 4 μM DL-NAC standard.

Figure 19:
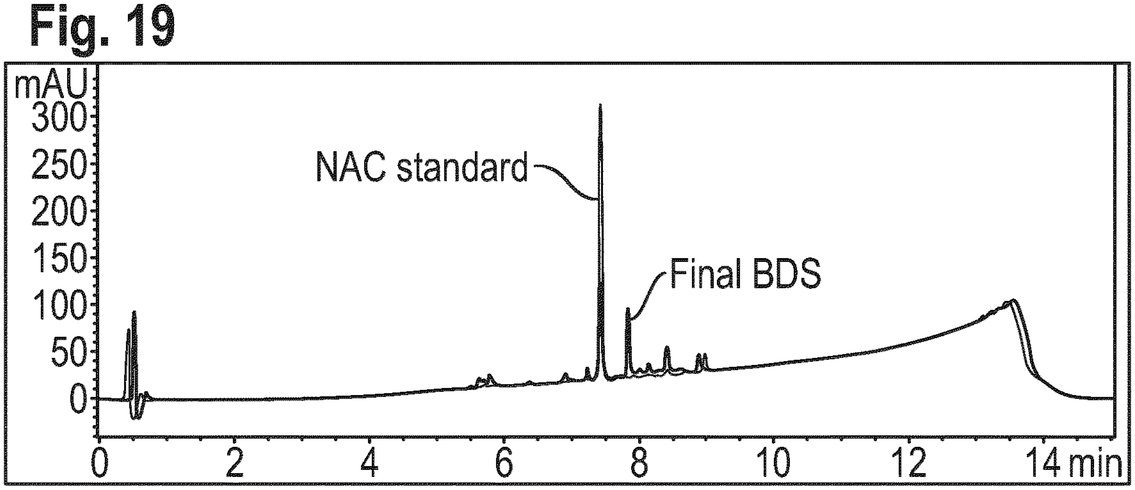
FIG. 19: Typical chromatogram showing the NAC standard and the free-drug levels of the final BDS.

Typical chromatogram showing the NAC standard and the free-drug levels of the final BDS: FIG. 19.

For the ADC2 BDS material shown above, residual free-drug levels below 1.9% (by molar ratio) have been reported.

Example 6: An Analog of the ADC SAR408701

6.1 The Antibody

For the purposes of further comparative experiments, an analog of Sanofi's anti-CEACAM5 ADC SAR408701 was prepared based on a monoclonal antibody having the following sequence:

Heavy chain: SEQ ID NO: 25

Light chain: SEQ ID NO: 26

6.2 The Drug-Linker Compound

As a drug-linker molecule to be conjugated to the above-mentioned antibody, SPDB-DM4 (obtained from Levena Biopharma) was used:

Product name: SPDB-DM4

Structure:

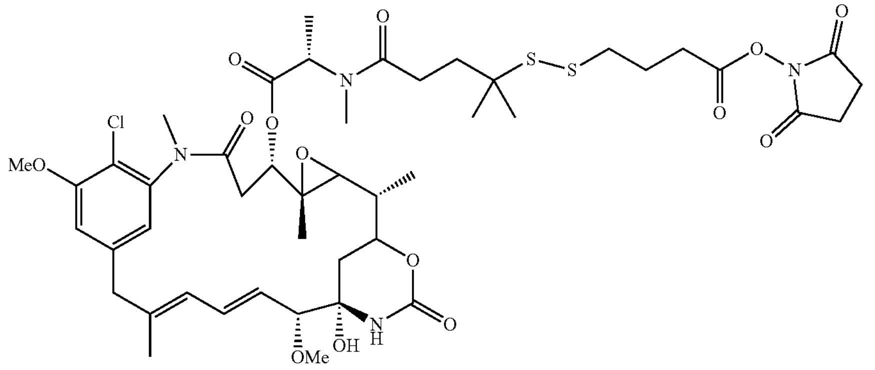 [SMILES: COc1cc2cc(c1Cl)N(C)C(=O)C[C@H](OC(=O)[C@H](C)N(C)C(=O)CCC(C)(C)SSCCCC(=O)ON1C(=O)CCC1=O)[C@]1(C)OC1[C@H](C)C1C[C@@](O)(NC(=O)O1)[C@H](OC)/C=C/C=C(\C)C2]

Expected mass: 994.35

Observed average mass: 995.5 ($Ms+H^+$)

Mass spectral analysis: consistent, exhibited correct MW

HPLC analysis: purity>95%

Appearance: white powder 6.3 Conjugation

The antibody was thawed at 2-8° C. up to 3 days prior to conjugation and stored at 2-8° C. until use. The antibody (175 mg) was equilibrated at room temperature on the day of conjugation prior to use. The antibody (7.9 mg/mL) was diluted to 5 mg/mL using conjugation buffer (PBS pH 7.4) and a 5 mM DMSO solution (8 mol equivalents relative to the antibody) of SPDB-DM4 (Levena Biopharma). The reaction solution was mixed and incubated at 25° C. for 4 h.

6.4 Preparative Size Exclusion Chromatography, Desalting and Filtration

The reaction mixture was purified using preparative size-exclusion chromatography. A Superdex 200 µg (50/60) column was connected to an Äkta Avant 25 system (GE Healthcare) and equilibrated with PBS pH 7.4 according to the manufacturer's instructions. Subsequently, the reaction mixture was injected and run through the column with a flowrate of 10 ml/min and PBS pH 7.4 as running buffer. ADC containing fractions were determined via UV light absorption at 280 nm, pooled and concentrated. ADC material was concentrated using 15 ml Amicon Ultra 50 kDa cutoff centrifugal devices (Merck Millipore) according to manufactures instructions. The concentrated ADC material was transferred into formulation buffer (10 mM Histidine, 130 mM Glycine, 5% Sucrose. pH 5.5) using HiPrep 26/10 desalting columns (GE Healthcare) at a flowrate of 10 ml/min on an Äkta Avant 25 system (GE Healthcare) according to the manufactures instructions. The resulting ADC material was filtered using a 0.2 µm filter (Merck Millipore), aliquoted and subsequently shock frozen in liquid nitrogen. The final concentration of the ADC material was 5.82 mg/ml and the material was kept at −80° C. until further use. The ADC resulting from this work is also referred to herein as "ADC SAR DM4" or, briefly, as "ADC SAR"; this ADC is an analog of SAR408701.

Example 7: An ADC Based on mAb1 and SPDB-DM4

Another ADC was prepared based on the antibody mAb1 (as described herein above) and the drug-linker compound SPDB-DM4, i.e. the same drug-linker compound as in ADC SAR DM4 described above. The ADC resulting from this work is referred to herein as "ADC mAb1 DM4" and was prepared as follows:

7.1 Materials Used:

Antibody: mAb1, 1 mg/mL in 10 mM HEPES, pH 5.8

Conjugation Buffer. 10 mM HEPES, pH 5.8

Drug-linker compound: SPDB-DM4, 2 mg/mL in DMF 7.2 Method:

Conjugation: about 30-fold molar excess of drug-linker molecule was used for conjugation (75 mL antibody+7.1 mL SPDB-DM4 drug-linker), incubated at room temperature for 5 h with slow rocking Purification: ADC was buffer exchanged to 20 mM Histidine, 150 mM NaCl, pH 6.0 to remove free drug Formulation Buffer: 20 mM Histidine, 150 mM NaCl, pH 6.0

7.3 Purified ADC Analysis Details:

Final Yield: 40 mg

Concentration: 2.2 mg/mL

DAR: 4.4

Example 8: Characterization of Drug Release from ADC1 and ADC2

8.1 Materials and Methods 8.1.1 Test Articles

| ADC number | Brief description of ADC |
|---|---|
| ADC1 | mAb1-glucuronid-exatecan (see also Example 4 above) |
| ADC2 | mAb1-AAN-exatecan (see also Example 5 above) |

-continued

| ADC number | Brief description of ADC |
|---|---|
| ADC3 | Anti-CEACAM5-CL2A-SN-38 ADC (Creative Biolabs, CAT#: ADC-091LCT, a humanized IgG1 monoclonal anti-CEACAM5 antibody like labetuzumab conjugated to SN38 via a CL2A linker) |

8.1.2 Materials

All reagents and buffers were stored according to the instructions of the manufacturers and used before the batch expiration date.

| Abbreviated name | Origin and contents |
|---|---|
| Human Liver Lysosomes | Sekisui Xenotech, H0610.L |
| Legumain Assay Buffer | 50 mM MES, 250 mM NaCl |
| 10 × Catabolism Buffer | Sekisui Xenotech |
| Human serum | Biowest, S4200-100, Lot # S15594 S4200 |
| Mouse serum | Biowest, S2160-100, Lot # S18169 S2160 |
| Cynomolgus serum | Abcam, cat: ab155109, lot: GR316568-1 |
| HEPES | Sigma, cat: H3784-100 g lot: SLBR6536V |
| PIC III | Calbiochem, Protease Inhibitor Cocktail Set III, EDTA-Free, #539134 |
| Methanol | Merck, cat: 1060092500 |

8.1.3 Instruments

| Instrument | Supplier |
|---|---|
| CO2-Incubator | Heraeus |
| Thermomixer compact | Eppendorf |
| HTC PAL Autosampler | CTC Analytics |
| 1200 HPLC | Agilent Technologies |
| API4000 Triple Quadrupole | Sciex |

8.1.4 Procedures 8.1.4.1 Serum Sample Preparation

2 M HEPES solution: 52.1 g HEPES were dissolved in 75 mL MiliQ-water and 15 mL HCl 25%, adjusted to pH 7.55 and added up to 100 mL. This solution was mixed as 15% v/v with serum to obtain a stabilized serum with pH 7.3-7.4. Human serum from Biowest (Lot. no. S1559454200) was thawed. 100 mL serum were mixed with 15 mL 2 M HEPES buffer. Mouse serum from Biowest (Lot. no. S18169S2160) was thawed. 100 mL serum were mixed with 15 mL 2 M HEPES buffer. Cynomolgus serum was thawed and 8.5 mL serum were mixed with 1.5 mL 2 M HEPES buffer. The pH was measured (7.37) and serum was sterile filtered. 2 mL aliquots were frozen at −20° C.

The prepared serum was thawed at RT. The desired ADC protein concentration was prepared as triplicated with 180 µg/mL for subsequent free payload analytics via LC-MS. After adding the ADCs to the serum, the individual batches were mixed and separated into 20 µL aliquots. Additionally, one 96 h sample with 20 µL for each ADC was pipetted and was used to for total work up analyses to measure recovery. 0 h samples were directly frozen at −80° C., remaining samples were incubated at 37° C. and 5% CO2 and reactions were stopped at 2/4/6/24/48/72, 96 hours incubation via storage at −80° C.

8.1.4.2 Human Liver Lysosome Sample Preparation pH was adjusted either to pH 5.0 or pH 4.0 using assay buffer. Lysosomal stability preparations: 80 µL Human Liver Lysosomes were prepared for triplicate measurements as exemplary shown for ADC1 (n=3): 2.76 µL ADC1+6 µL Human Liver Lysosomes+71.2 µL Legumain Assay Buffer. Preparation of MeOH+PIC (1:200): 10 µL PIC III+1990 µL MeOH. The reactions were started upon transferring the Eppendorf tubes to a Thermomix that was preheated to 37° C. Subsequently, 10 µL aliquots were drawn after 0, 1, 2, 4, 24 and 48 hours and mixed with 40 µL PIC III (1:200).

8.2 Results

Figure 20:
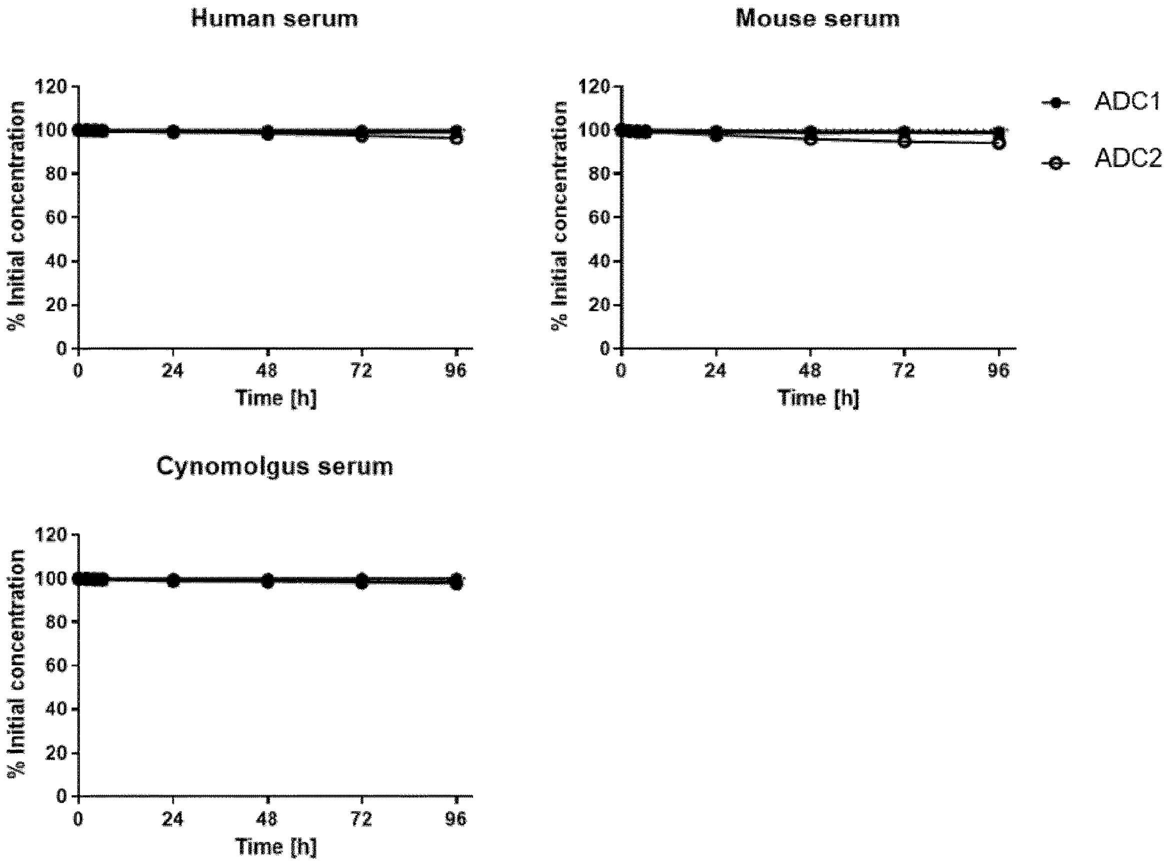
FIG. 20: ADC stability for human, mouse and cynomolgus sera. Conjugated Exatecan concentrations were calculated (initial dose~10 μM) using free Exatecan (normalized data).

ADC stability for human, mouse and cynomolgus sera (FIG. 20). Conjugated Exatecan concentrations were calculated (initial dose ~10 µM) using free Exatecan (normalized data). Similar profiles were obtained for human, cynomolgus and mouse sera. Only minor warhead release observed, most pronounced in mouse serum for ADC2 (5.9% free of initial conj. payload at 96 h) and ADC1 (1.4%).

Figure 21:
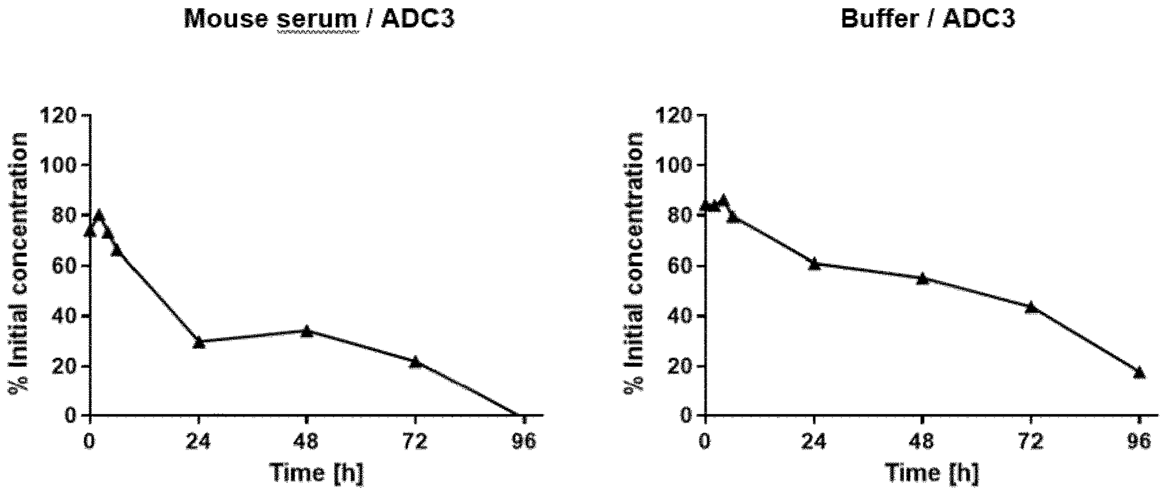
FIG. 21: ADC3 control stability for mouse serum and buffer. Conjugated SN38 concentrations were calculated (initial dose 50 μg/mL ADC protein concentration) using free SN38 (not normalized).

ADC3 control stability for mouse serum and buffer (FIG. 21). Conjugated SN38 concentrations were calculated (initial dose 50 µg/mL ADC protein concentration) using free SN38 (not normalized). For both matrices, pronounced SN-38 release observed.

Figure 22:
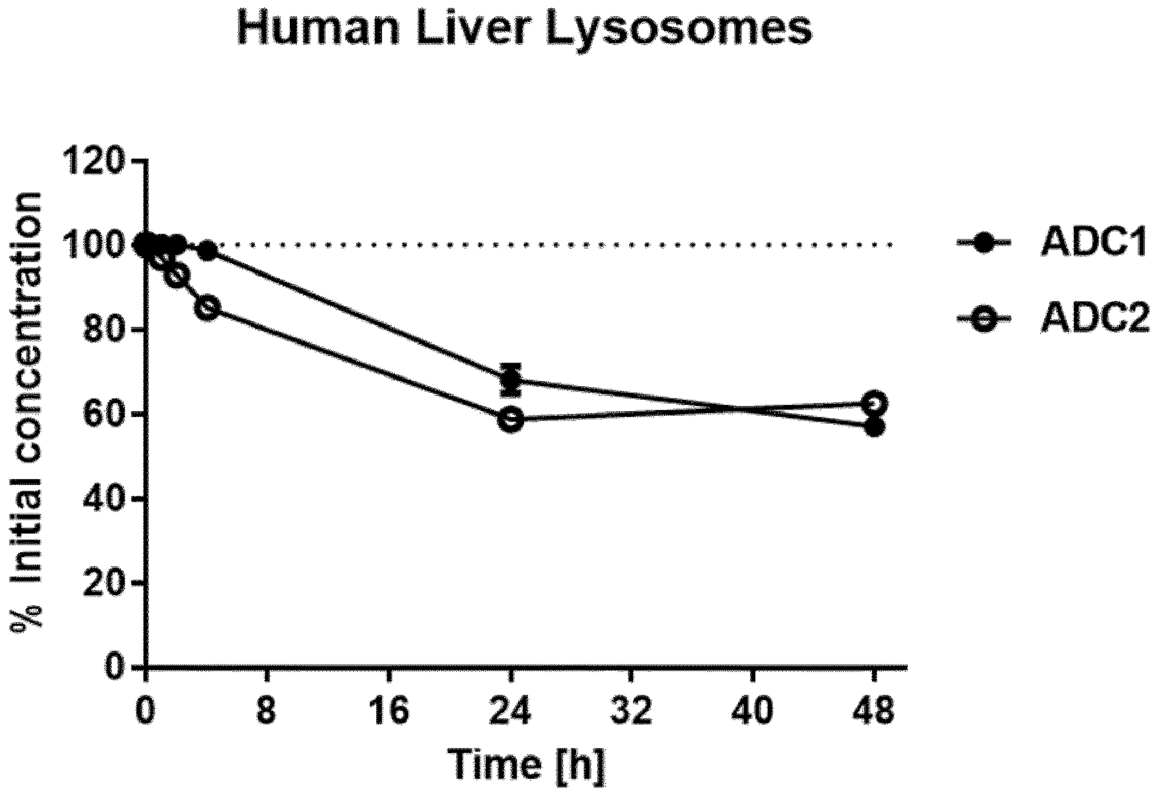
FIG. 22: Payload liberation profiles for ADC1 and ADC2 in human liver lysosomes (pH 5.0). Conjugated drug concentrations were calculated using e.g. free Exatecan (initial conc. ~10 μM Exatecan), normalized data.
Figure 23A:
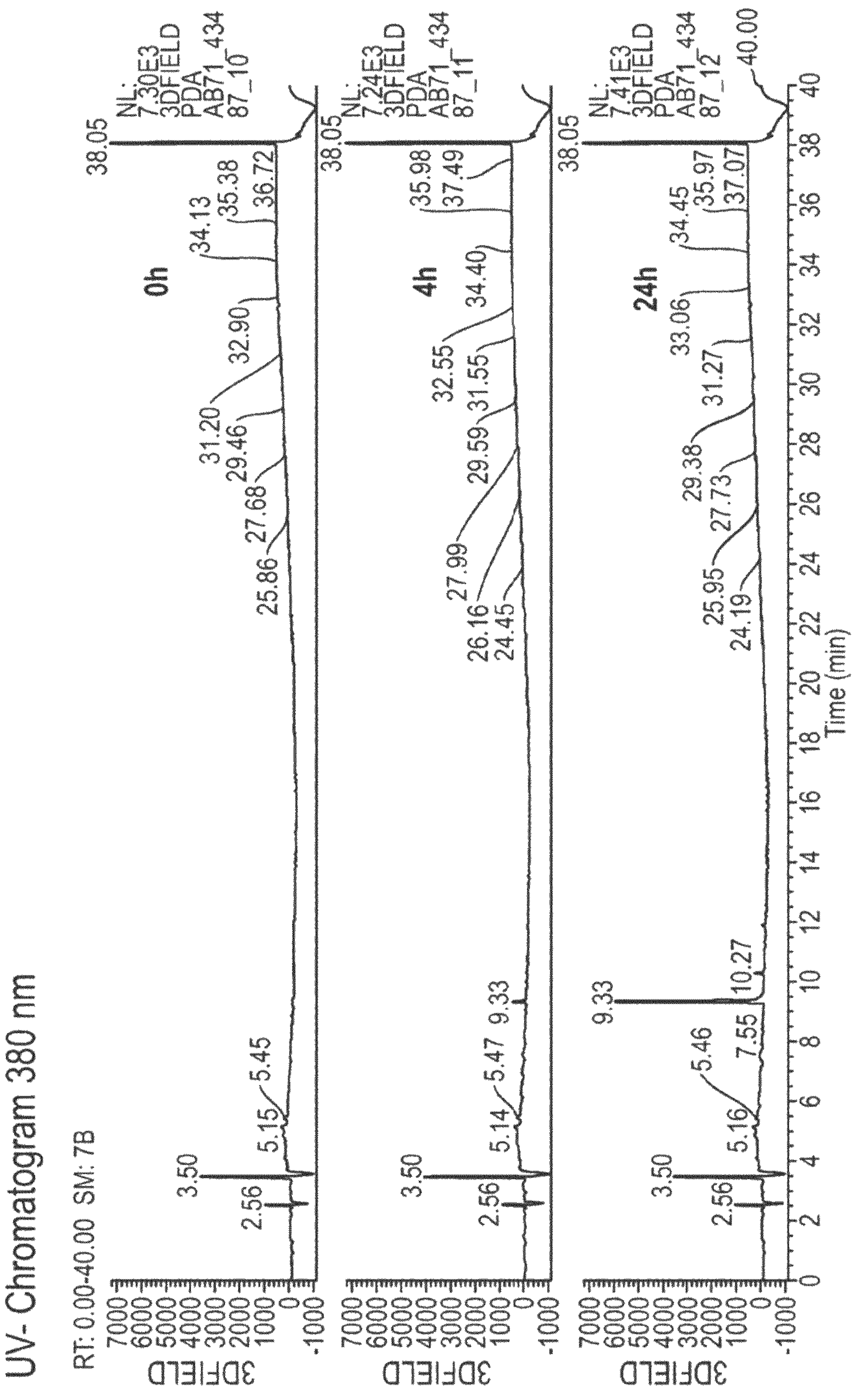
FIGS. 23A and 23B: ADC catabolite profiling with comparison of extracted ion chromatograms (FIG. 23A) and TIC-MS (FIG. 23B) confirms free exatecan as lysosomal release product.
Figure 23B:
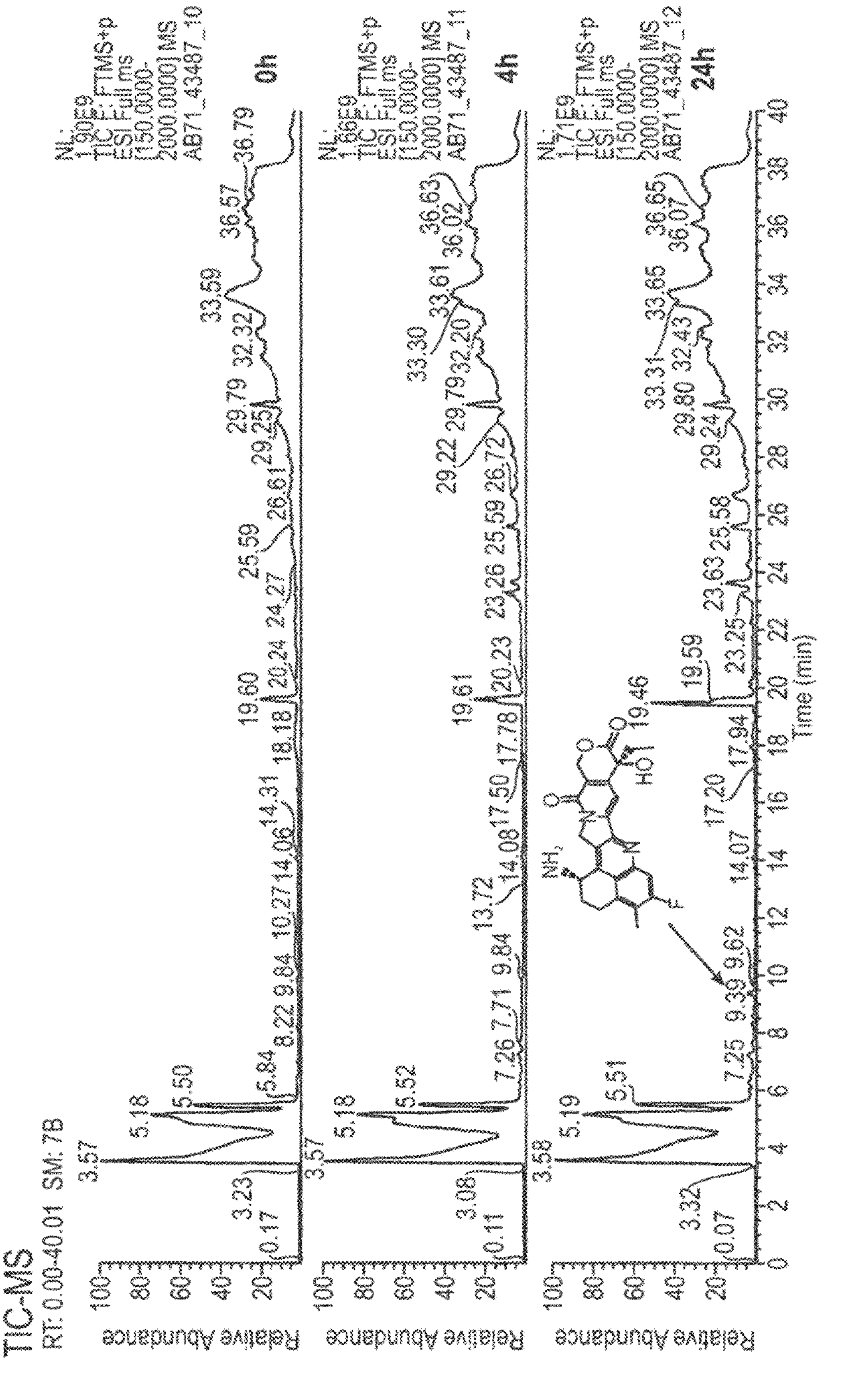

Payload liberation profiles for ADC1 and ADC2 in human liver lysosomes (pH 5.0) (FIG. 22). Conjugated drug concentrations were calculated using e.g. free Exatecan (initial conc. ~10 µM Exatecan), normalized data. Intermediate levels of payload release were observed for ADC1- and ADC2-cleavage mediated payload liberation (both~40% of initial total conj. Payload). ADC catabolite profiling confirms free exatecan as lysosomal release product (FIGS. 23A and 23B). To confirm exatecan as major release product, ADC1 catabolite profiling study was performed in human lysosomal extracts. At this, comparison of the TIC-MS (FIG. 23B) and extracted ion chromatograms (FIG. 23A) at various timepoints showed that the expected exatecan catabolite was subsequently released from ADC1 during incubation (0 h, 4 h, 24 h). The retention time 9.33 min, the detected mass m/z 436.1671 ($[M+H]^+$, $C_{24}H_{23}O_4N_4F$) and the MS/MS spectrum of the detected catabolite are consistent with those of exatecan.

Figure 24A:
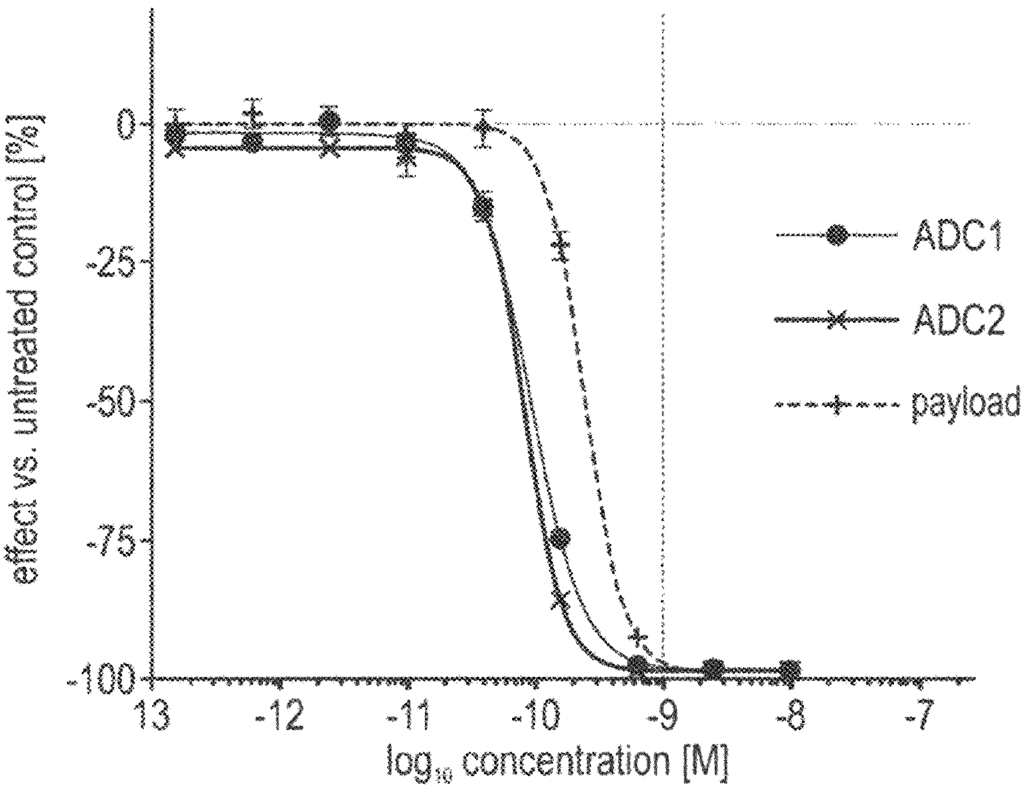
FIGS. 24A-24C: In vitro potency of ADC1, ADC2 and free payload against antigen-positive SK-CO-1 (FIG. 24A) and SNU-16 (FIG. 24B) cell lines in comparison to antigen-negative MDA-MB-231 (FIG. 24C) cell line. One representative experiment is shown, mean of triplicates±SD.
Figure 24B:
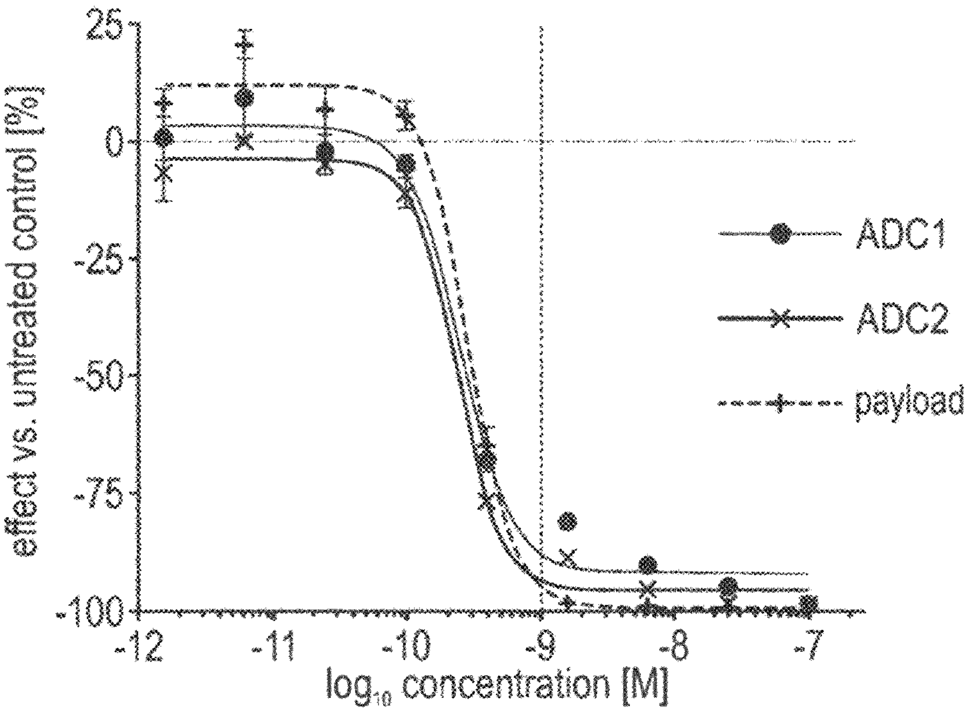
Figure 24C:
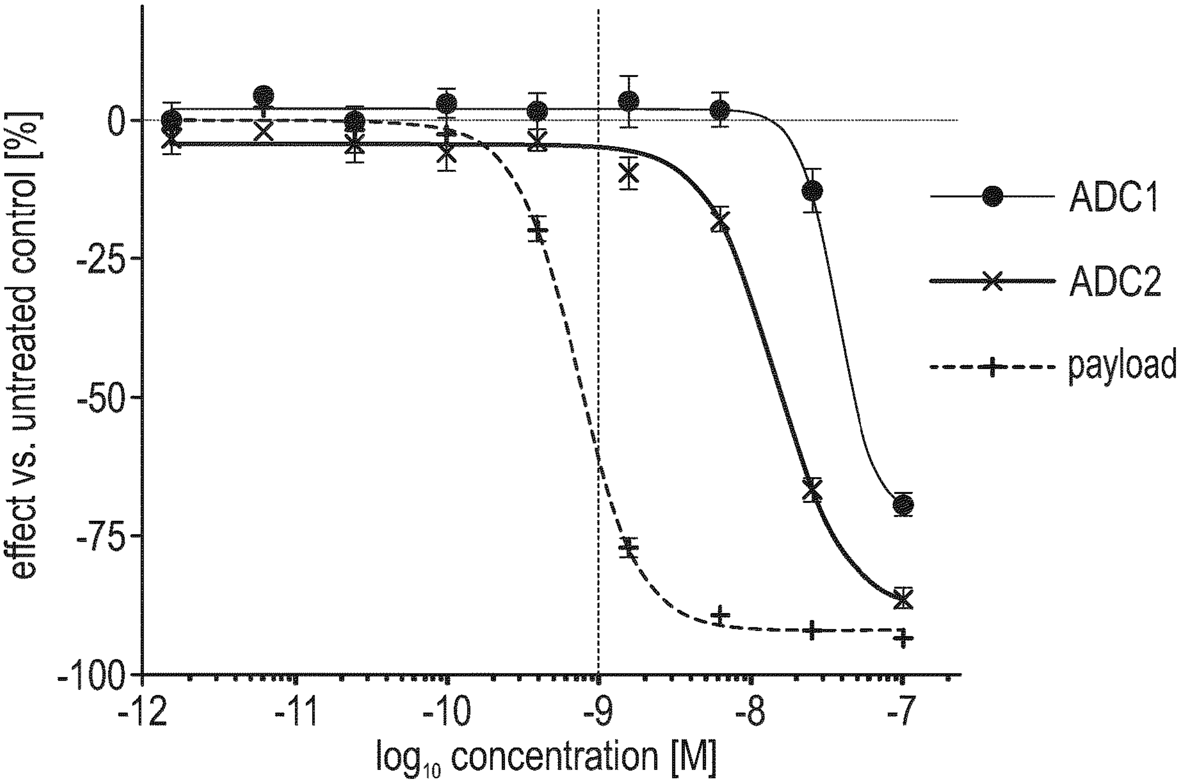

Example 9: ADC1 and ADC2 Specifically Kill Cancer Cells In Vitro with High Potency Human cancer cell lines were used to assess the potential of ADC1 and ADC2 to kill cancer cells. ADC1 and ADC2 showed sub-nanomolar in vitro potency against different CEACAM5-positive and minor effect on CEACAM5-negative cell lines (Table 2 below). As shown in exemplary dose-response curves (FIG. 24A/B), ADC1 and ADC2 were very potent against CEACAM5-positive cell lines SK-CO-1 and SNU-16. In contrast, effects of ADC1 and ADC2 on antigen-negative MDA-MB-231 were limited to the highest concentrations tested (FIG. 24C).

Figure 25:
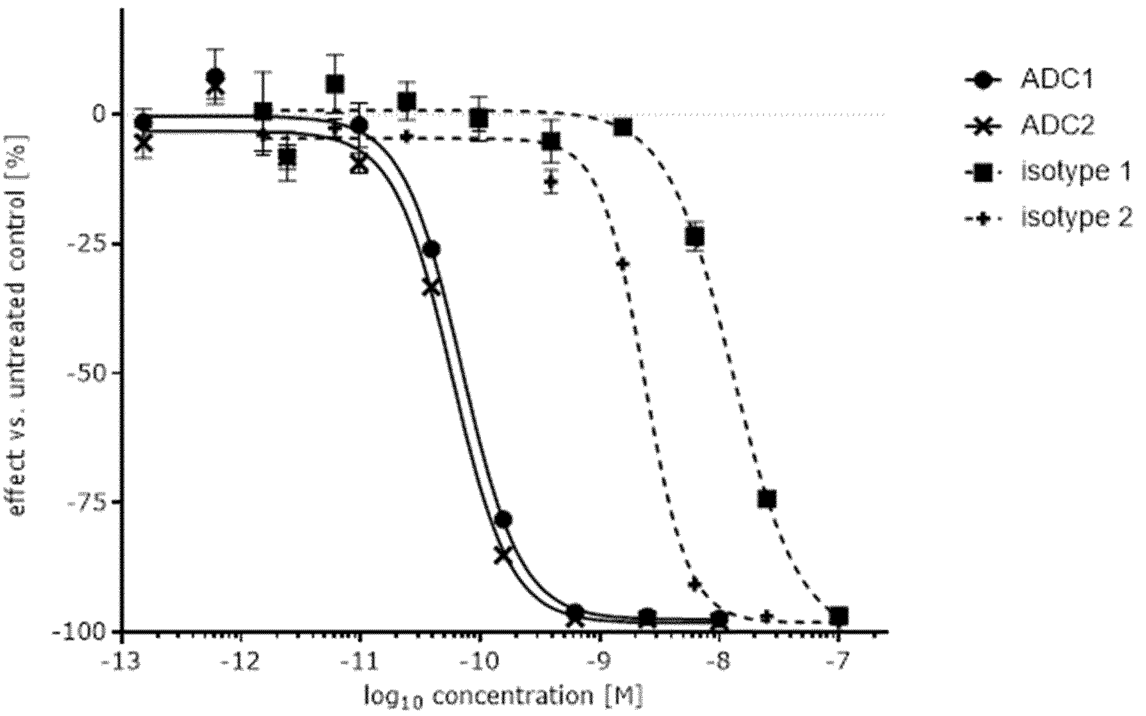
FIG. 25: Comparison of ADC1 and ADC2 with respective isotype controls on SK-CO-1 cell line. One representative experiment is shown, mean of triplicates±SD.

Isotype control ADCs utilizing the same linker payloads as ADC1 and ADC2 showed much lower effects on SK-CO-1 cell line (FIG. 25).

In conclusion, ADC1 and ADC2 specifically kill CEACAM5 expressing human cancer cell lines in vitro with high potency.

TABLE 2

Potency of ADC1, ADC2 and free payload against multiple human cell lines. Maximal effects compared to untreated controls at the highest tested compound concentration are indicated in brackets. For each cell line, CEACAM5 expression is indicated.

| | MKN-45 IC50 [M]; N ≥ 3 | SNU-16 IC50 [M]; N ≥ 3 | SK-CO-1 IC50 [M]; N ≥ 4 | LS174T IC50 [M]; N ≥ 3 | MDA-MB-468 IC50 [M]; N ≥ 2 | MDA-MB-231 IC50 [M]; N ≥ 3 |
|---|---|---|---|---|---|---|
| ADC1 | 6.2E−10 (−78%) | 3.2E−10 (−91%) | 8.5E−11 (−97%) | 3.8E−10 (−72%) | >1E−08 (−85%) | >1E−08 (−67%) |
| ADC2 | 4.7E−10 (−90%) | 2.8E−10 (−96%) | 6.9E−11 (−98%) | 2.8E−10 (−81%) | 6.7E−09 (−97%) | 1.5E−08 (−84%) |
| PAYLOAD | 8.9E−10 (−96%) | 4.4E−10 (−99%) | 2.5E−10 (−99%) | 5.3E−10 (−88%) | 2.1E−10 (−99%) | 9.3E−10 (−92%) |
| CEACAMS | Positive | Positive | Positive | Positive | Negative | Negative |

Method—Viability Assay:

Cytotoxicity effects of the ADC on the cancer cell lines were measured by cell viability assays. Cells were seeded in a volume of 90 μL in 96-well plates the day before treatment. Test compounds (ADCs or free payloads) were formulated at 10-fold the starting concentration in cell culture medium. Test compounds were serial diluted (1:4) and 10 μL of each dilution was added to the cells in triplicates. Plates were cultured at 37° C. in a CO2 incubator for six days. For cell viability measurement, Cell Titer-Glo® reagent (Promega™ Corp, Madison, WI) was added to each well, and plates processed according to the manufacturer's instructions. Luminescence signals were measured using a Varioskan plate reader (Thermo Fisher). Luminescence readings were converted to % viability relative to untreated cells. Data was fitted with non-linear regression analysis, using log (inhibitor) vs. response, variable slope, 4-parameter fit equation using GraphPad Prism. Data is shown as % relative cell viability vs. molar compound concentration, error bars indicating standard deviation (SD) of triplicates. Geometric mean values of IC50s derived from multiple experiments were calculated.

Figure 26A:
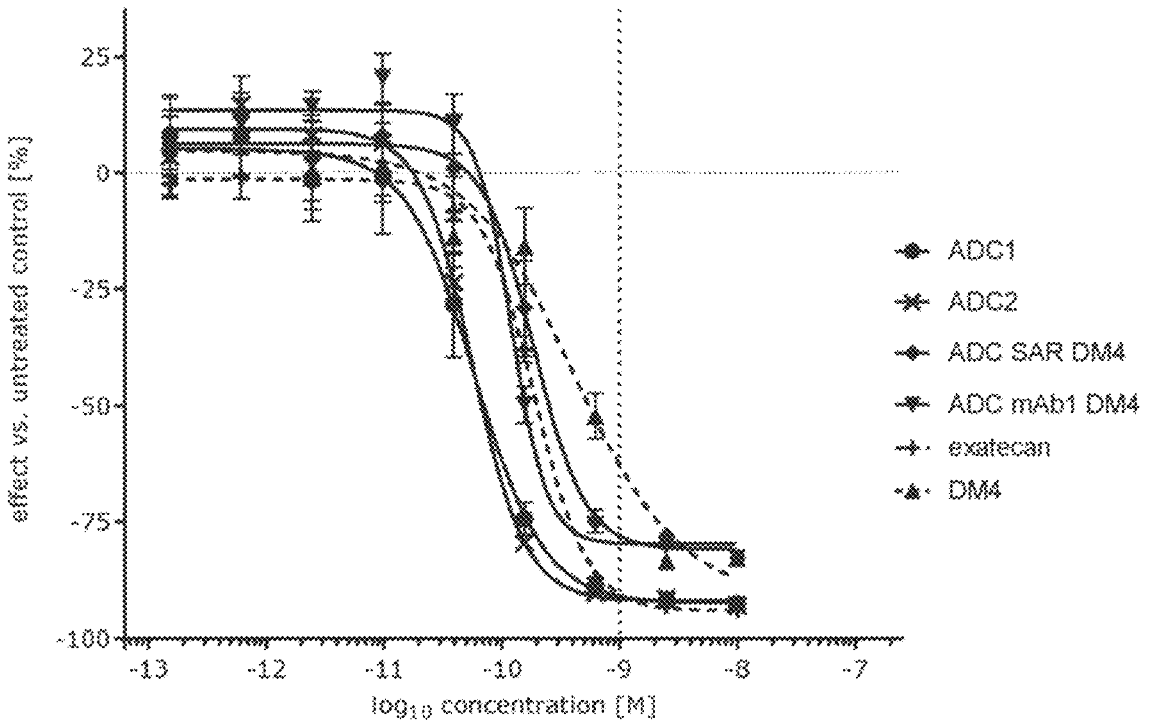
FIGS. 26A and 26B: In vitro potency of ADC1, ADC2, ADC SAR DM4, ADC mAb1 DM4 and free payloads against antigen-positive SK-CO-1 (FIG. 26A) in comparison to antigen-negative MDA-MB-231 (FIG. 26B) cell line. One representative experiment is shown, mean of triplicates±SD.
Figure 26B:
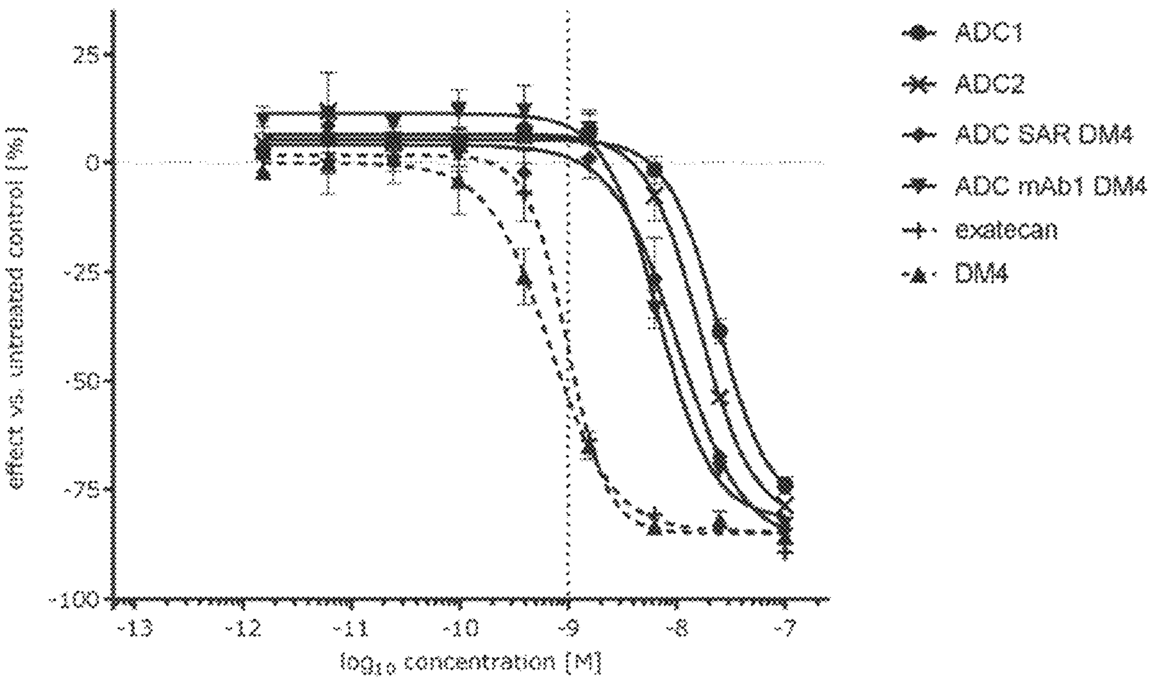

Using the same method as above, ADC1 and ADC2 were also compared to ADC SAR DM4 in terms of their cytotoxic effects on antigen-positive SK-CO-1 and antigen-negative MDA-MB-231 cell line. ADC1 and ADC2 showed 2.9- and 2.7-fold higher potencies than ADC SAR DM4 against SK-CO-1 cancer cells, respectively (FIG. 26A). Non-specific effects against antigen-negative MDA-MB-231 were slightly higher for ADC SAR DM4 compared to ADC1 and ADC2 (FIG. 26B). ADC SAR DM4 and ADC mAb1 DM4 showed comparable potencies against SK-CO-1, with a slight tendency for higher potency of ADC mAb1 DM4 (FIG. 26A).

Figure 27A:
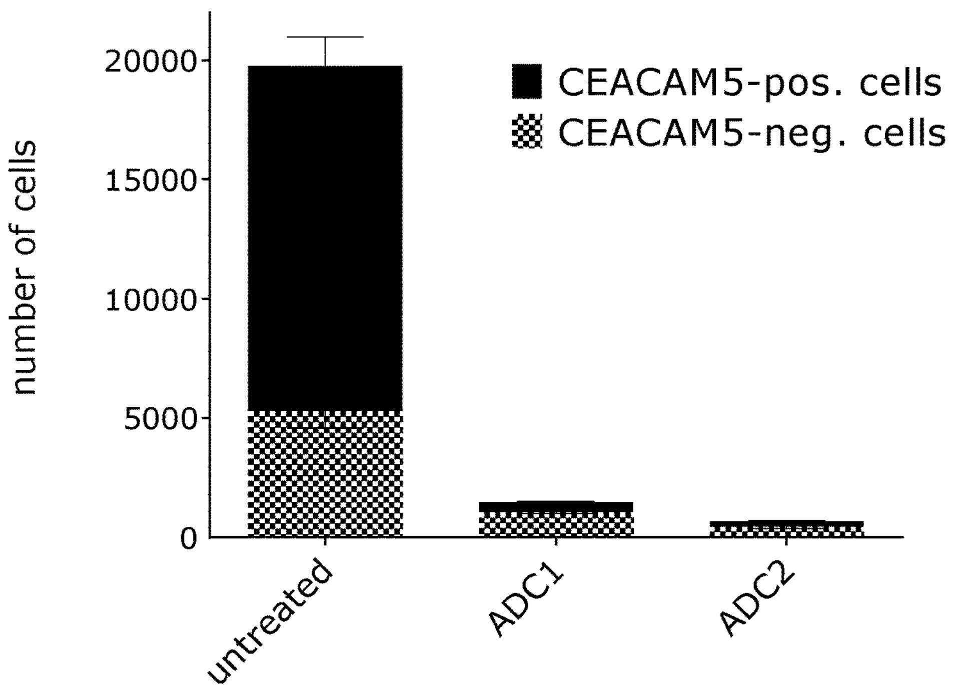
FIGS. 27A and 27B: Potent bystander effect of ADC1 and ADC2 on antigen-negative MDA-MB-231 cells in co-culture with antigen-positive SK-CO-1 cells (FIG. 27A). No unspecific effects of ADC1 or ADC2 on MDA-MB-231 cells alone (FIG. 27B). One representative experiment is shown, mean of duplicates ±SD.
Figure 27B:
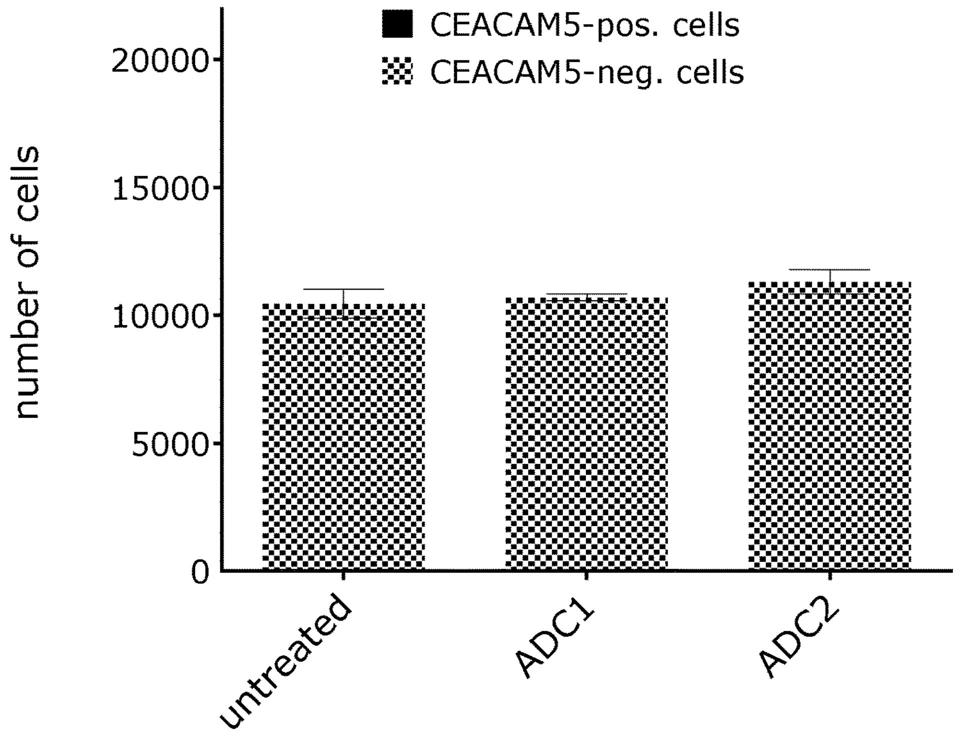

Example 10: ADC1 and ADC2 Mediate Potent Bystander Effect Against Antigen-Negative Cells in Co-Culture with Antigen-Positive Cells The potential of ADC1 and ADC2 to mediate a bystander effect against antigen-negative cells in close proximity to antigen-positive cells was evaluated in bystander assays. ADC1 and ADC2 showed a potent bystander effect against CEACAM5-negative MDA-MB-231 cells in the presence of CEACAM5-positive SK-CO-1 (FIG. 27A). At the tested concentration of 1E-9 M in mono-culture viability assays, ADC1 and ADC2 treatment resulted in maximal effects on SK-CO-1 cells (FIG. 26A) while no effect on MDA-MB-231 (FIG. 26B) was observed. In line with these findings, no non-specific effect of ADC1 or ADC2 was observed in the bystander assay setup for MDA-MB-231 only controls (FIG. 27B).

In conclusion, ADC1 and ADC2 mediate a potent bystander effect against antigen-negative cancer cells in co-culture with antigen-positive cells. These findings indicate the potential to effectively target tumors with heterogeneous target expression.

Figure 28A:
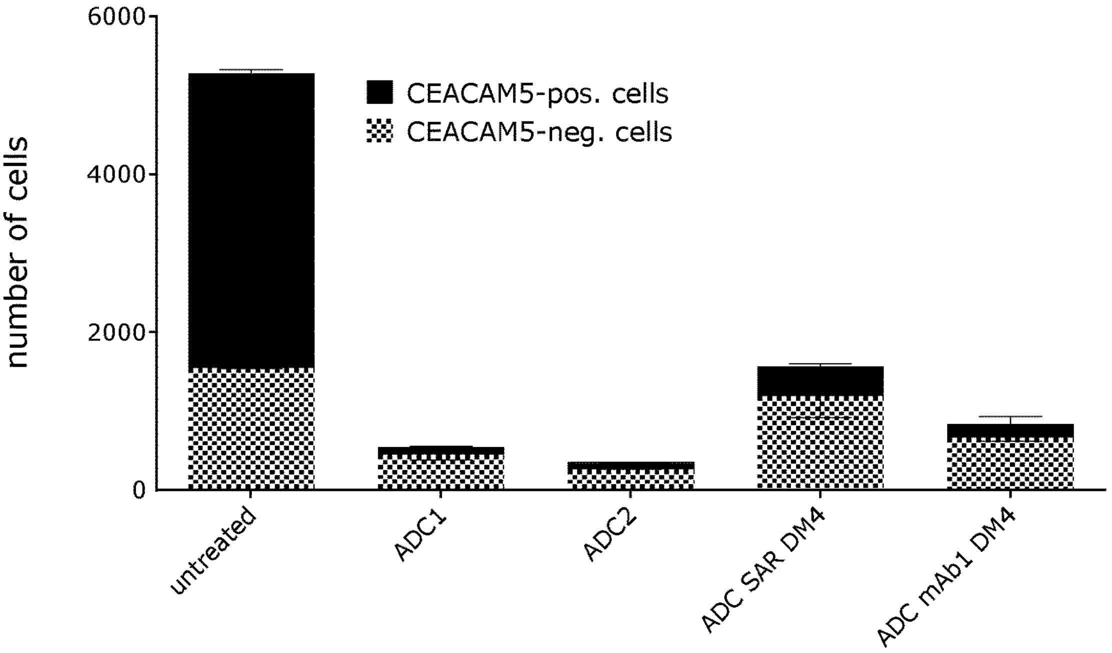
FIGS. 28A-28C: Bystander effect of ADC1 and ADC2 on antigen-negative MDA-MB-231 cells in co-culture with antigen-positive SK-CO-1 cells is more potent than for ADC SAR DM4 (FIG. 28A and FIG. 28B). No non-specific effects of tested ADCs on MDA-MB-231 cells alone (FIG. 28C). One representative experiment is shown, mean of duplicates ±SD.
Figure 28B:
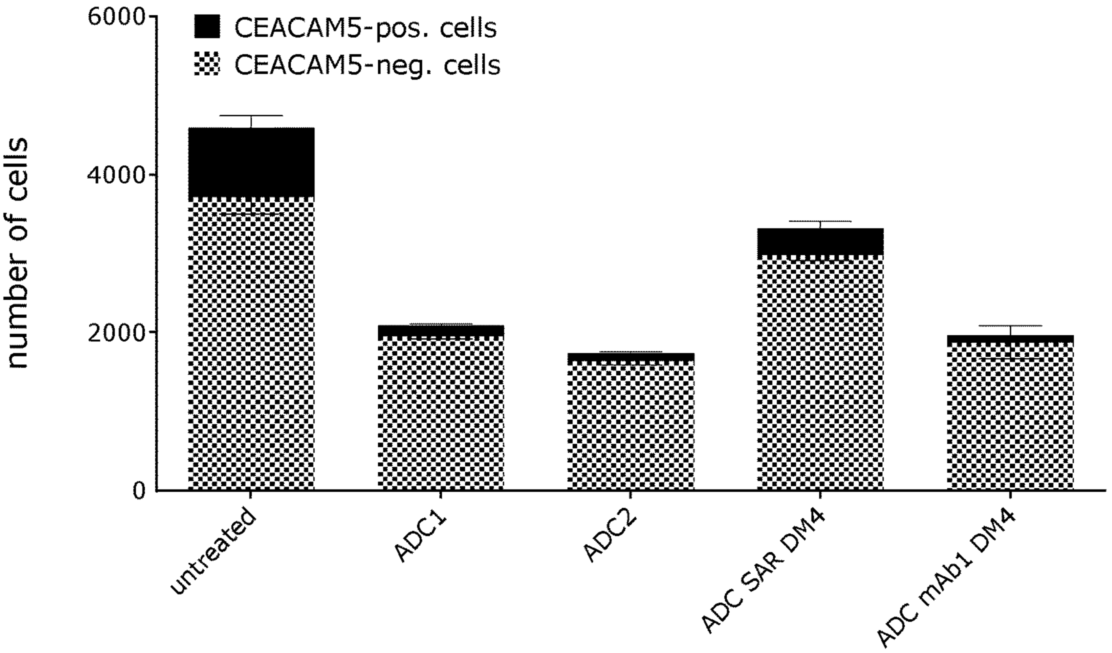

Compared to ADC SAR, ADC1 and ADC2 mediated a much more potent bystander effect on antigen-negative cells in co-culture with antigen-positive cells (FIG. 28A, FIG. 28B). ADC mAb1 DM4 utilizing the same antibody as in ADC1 and ADC2 (i.e. mAb1) with the drug-linker molecule utilized in ADC SAR DM4 (i.e. SPDB-DM4) also showed a more pronounced bystander effect than ADC SAR DM4 (FIG. 28A, FIG. 28B). This indicated that mAb1 contributes to the higher bystander effect observed for ADC1 and ADC2 in comparison with ADC SAR utilizing a different antibody.

For all ADCs tested, the extent of bystander effect increased with increasing the number of antigen-positive cells added to a constant number of antigen-negative cells (compare FIG. 28A and FIG. 28B). This indicates that more ADC is processed by the antigen-positive cells to release free payload which is responsible for the bystander effect on antigen-negative cells.

Figure 28C:
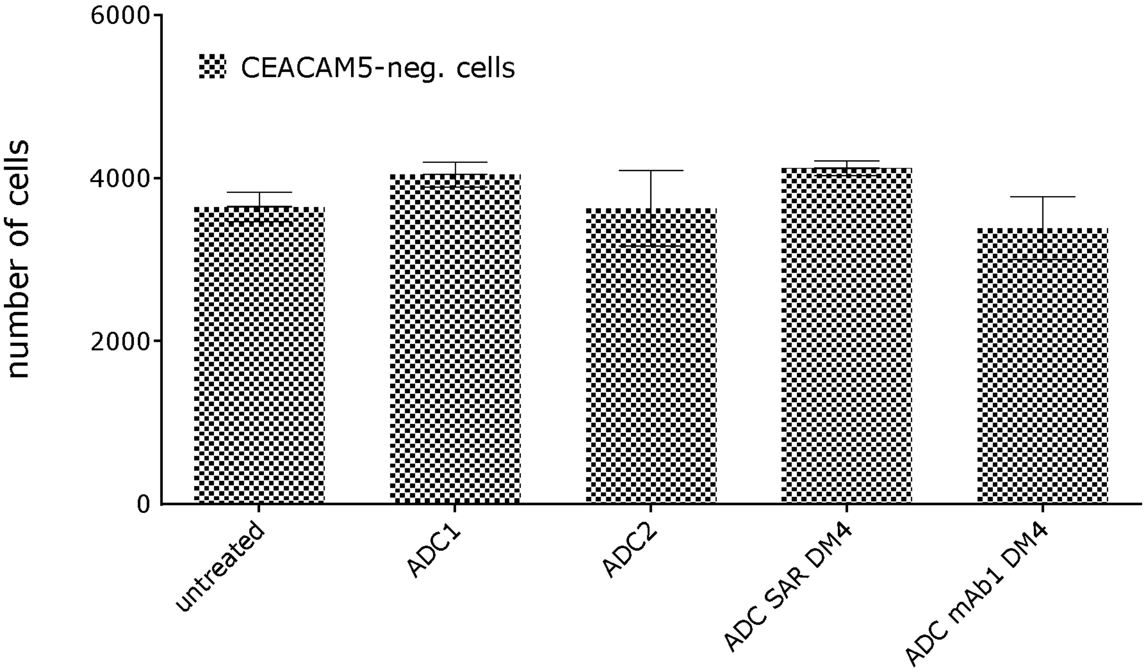

No non-specific effects of tested ADCs were observed on MDA-MB-231 cells alone (FIG. 28C).

Method—Bystander Assay

Cytotoxicity effects of ADCs on antigen-negative cancer cell lines in co-culture with antigen-positive cancer cell lines were measured by bystander assays. One thousand CEACAM5-negative MDA-MB-231 cells were seeded in co-culture experiments with 750 or 3000 CEACAM5-positive SK-CO-1 cells per well. As a control, 1000 MDA-MB-231 cells only were seeded in parallel. Cells were seeded in a total volume of 90 μL in 96-well plates the day before treatment. Test compounds were formulated at 10-fold the final concentration of 1E-9 M in cell culture medium and 10 μL was added to the cells in duplicates. Plates were cultured at 37° C. in a CO2 incubator for six days.

Prior to immunofluorescence staining, medium was removed and cells were treated with 100% methanol (−20° C.) for 30 minutes. After methanol removal and one PBS wash step, cells were treated with 2.5% paraformaldehyde (PFA) with 0.2% Triton X-100 in PBS for 15 minutes at room temperature. After solution removal and one PBS wash step, cells were treated with 1% BSA/0.1% Tween/0.1% sodium azide in PBS for at least one hour at room temperature. Antigen-positive and antigen-negative cells were discriminated by immunofluorescence staining with 10 μg/mL human anti-CEACAM5 (mAb1) primary antibody and 1:2000 dilution of donkey anti-human IgG fluorescently (phycoerythrin) labeled secondary antibody (Jackson ImmunoResearch #709-116-149). Cells were identified by nuclei staining using 1 μg/mL Hoechst 33342 (Life technologies, cat #$H_{3570}$) dye. Staining was carried out in 1% BSA/0.1% sodium azide PBS solutions for 30 minutes at room temperature. Secondary antibody staining was combined with Hoechst dye staining. Between and after staining steps, cells were washed thrice with PBS.

Plates were imaged with the confocal quantitative image cytometer CQ1 (Yokogawa® Electric Corporation, Tokyo, Japan). Analysis was adapted from the CQ1 software (Yokogawa) template "Nucleus and pseudo-Cell body" and FCS export files were analyzed using FlowJo (BD). Based on staining or absence of staining with fluorescently labeled antibody around the nucleus, antigen-positive and antigen-negative cells were distinguished and quantified. Bar graphs show the number of identified antigen-positive and antigen-negative cells per treatment condition.

Example 11: Efficacy of ADC1 and ADC2 in a Colorectal Cancer (CRC) Patient-Derived Xenograft (PDX) Mouse Model Anti-tumor efficacy in vivo has been evaluated in the human patient-derived CRC xenograft model COPF217 (Shanghai LideBiotech CO., LTD). COPF217 tumor fragments were transplanted subcutaneously into the right flank of six to eight weeks old immunodeficient female mice (NU-Foxn1nu, Charles River). When tumors reached a mean volume of 165 $mm^3$, 6 mice/group were treated once intravenously with vehicle (saline solution) or with ADC1 or ADC2 (each at a dose of 10 mg/kg; day 0). Tumor length (L) and width (W) were measured with calipers and tumor volumes were calculated using the formula L×(W^2)/2.

Figure 29:
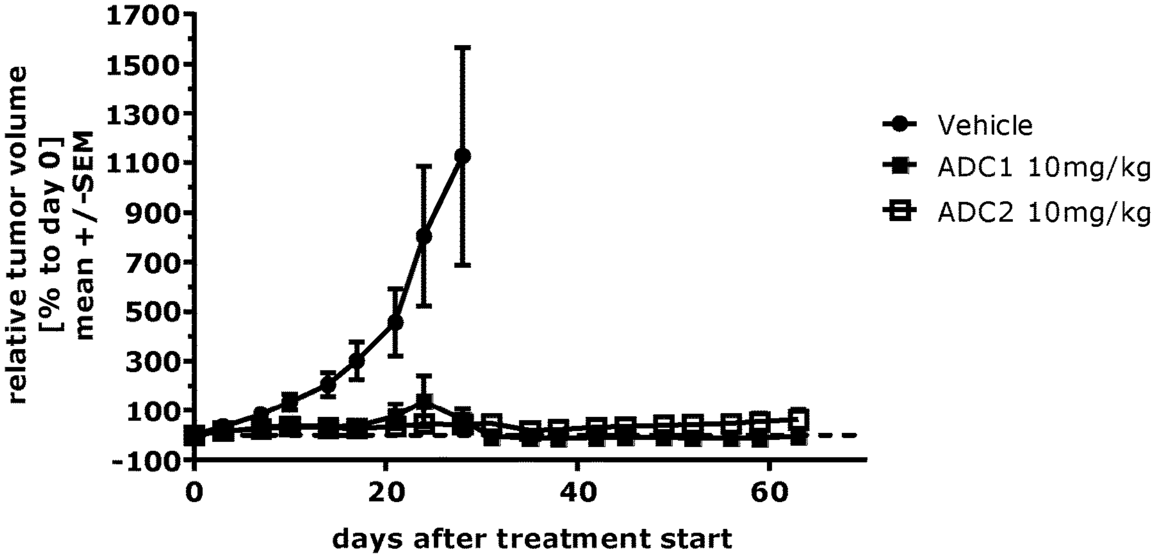
FIG. 29: Efficacy of ADC1 and ADC2 in a CRC PDX model (COPF217) after single treatment.

The single treatment with ADC1 or ADC2 at a dose of 10 mg/kg led to a significant anti-tumor effect. The two substances show a comparable effect leading to tumor stasis (FIG. 29). Treatment with ADC1 or ADC2 had no significant impact on body weight (data not shown).

Further experiments with other CRC PDX models:

In additional experiments corresponding to the one above described for COPF217, a single treatment with ADC1 also resulted in tumor stasis or tumor regression in 12 other CRC PDX models with high CEACAM5 expression.

Example 12: Efficacy of ADC1 in a Non-Small Cell Lung Cancer (NSCLC) PDX Mouse Model Anti-tumor efficacy in vivo has been evaluated in the human patient-derived NSCLC xenograft model LUPF160151 (Shanghai LideBiotech CO., LTD). LUPF160151 tumor fragments were transplanted subcutaneously into the right flank of six to eight weeks old immunodeficient female mice (NU-Foxn1nu, Charles River). When tumors reached a mean volume of 180 $mm^3$, 5 mice/group were treated once intravenously with vehicle (saline solution) or with ADC1 (6 mg/kg; day 0). Tumor length (L) and width (W) were measured with calipers and tumor volumes were calculated using the formula L×(W¨2)/2.

Figure 30:
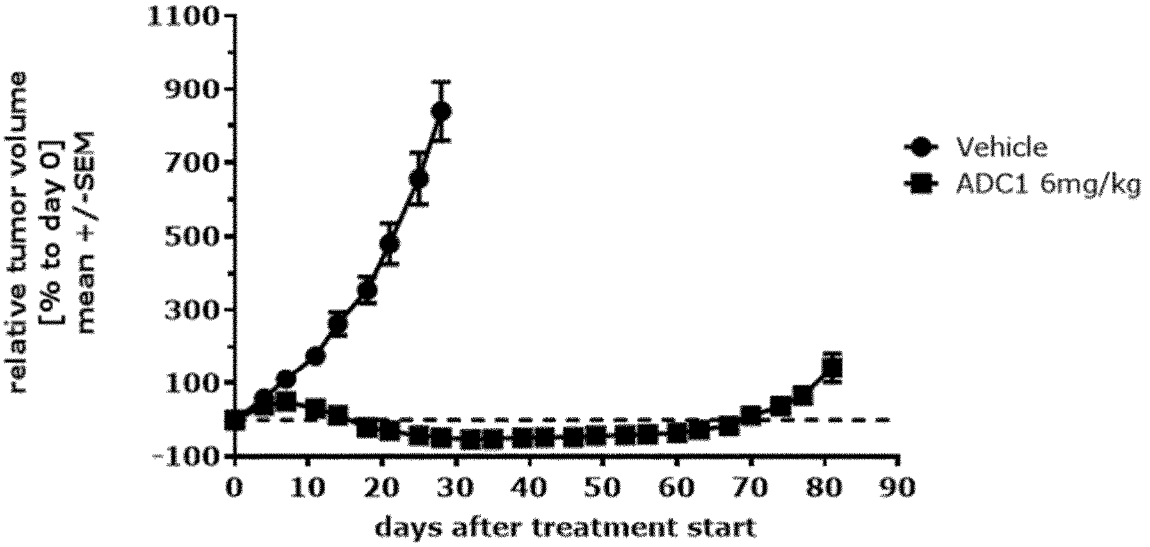
FIG. 30: Efficacy of ADC1 in a NSCLC PDX model (LUPF160151) after single treatment.

The single treatment with ADC1 at a dose of 6 mg/kg led to a significant anti-tumor effect (FIG. 30) with no impact on body weight (data not shown). The model LUPF160151 showed a heterogeneous CEACAM5 expression with CEACAM5 negative tumor cells adjacent to CEACAM5 positive tumor cells. The good efficacy of ADC1 in this model thus indicates a potent bystander effect of the ADC.

Example 13: Efficacy of ADC1 in Gastric Cancer PDX Mouse Model

Anti-tumor efficacy in vivo was evaluated in the human patient-derived gastric cancer xenograft model GAX066 (Shanghai ChemPartner Co., Ltd). Tumor fragments were transplanted subcutaneously into the right flank of immunodeficient female mice (Nu/Nu mice, Beijing Vital River Lab Animal Technology Co. Ltd, 18-22 g). When tumors reached a mean volume of 220 $mm^3$, 6 mice/group were treated once intravenously with vehicle (saline solution) or with ADC1 (3 or 10 mg/kg; Day 0). Tumor length (L) and width (W) were measured with calipers and tumor volumes were calculated using the formula L×(W^2)/2.

Figure 31:
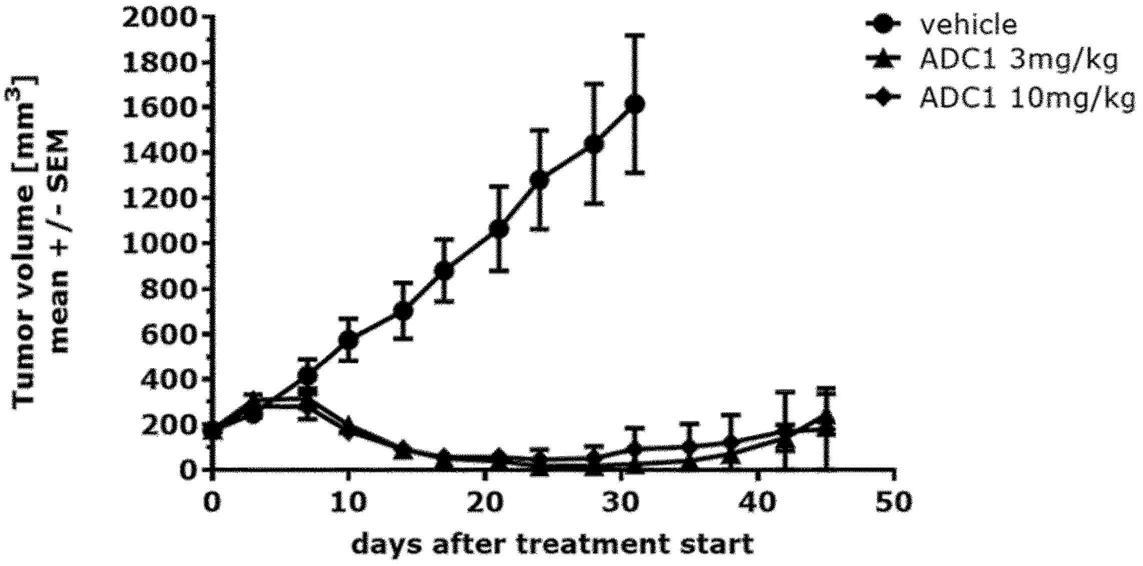
FIG. 31: Efficacy of ADC1 in a gastric cancer PDX model (GAX066) after single treatment

The single treatment with 3 or 10 mg/kg ADC1 caused a significant anti-tumor effect (FIG. 31) with no impact on body weight (data not shown). In five of six tumors, treatment with 10 mg/kg resulted in complete tumor regression.

Example 14: Efficacy of ADC1 Compared to ADC3 in a Pancreatic Cell Line Derived Tumor Model Efficacy of ADC1 in comparison to ADC3 has been evaluated in the human pancreatic cell line derived xenograft model HPAF-II (ATCC, CRL-1997). $5\times10^6$ HPAF-II cells were injected subcutaneously into the right flank of six to eight weeks old immunodeficient female mice (Hsd: Athymic Nude-Foxn1nu, Envigo). When tumors reached a mean volume of 150 $mm^3$, 10 mice/group were treated once intravenously with vehicle (saline solution) or ADC1 (1 mg/kg or 6 mg/kg; day 0) or with ADC3 (1 mg/kg or 6 mg/kg; day 0). Tumor length (L) and width (W) were measured with calipers and tumor volumes were calculated using L×(W^2)/2.

Figure 32:
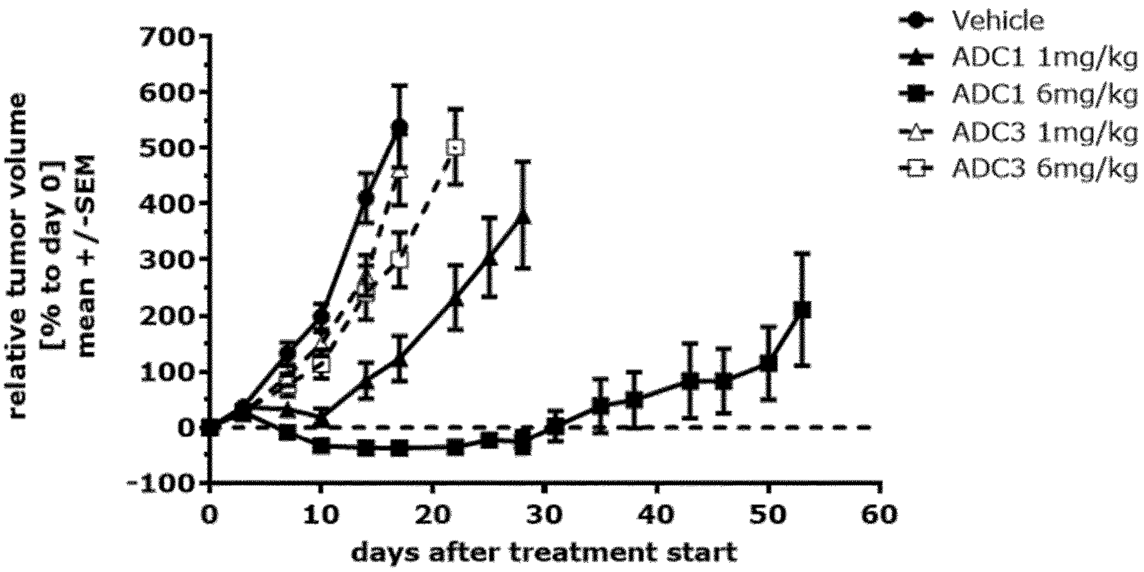
FIG. 32: Efficacy of ADC1 compared to ADC3 in a pancreatic xenograft model (HPAF-II).

The single treatment with ADC1 at a dose of 6 mg/kg led to a significant anti-tumor effect. The effect is dose-dependent, as the single treatment with 1 mg/kg only led to a mild but significant, transient anti-tumor effect. In contrast, the single treatment with same doses of ADC3 showed no significant anti-tumor effect at either dose (FIG. 32). All treatments had no significant effect on body weight (data not shown).

Example 15: Efficacy of ADC1 Compared to ADC SAR DM4 in Two CRC PDX Mouse Models Anti-tumor efficacy in vivo was evaluated in the human patient-derived CRC xenograft models COPF230 and REPF210 (Shanghai LideBiotech CO., LTD). Tumor fragments were transplanted subcutaneously into the right flank of six to eight weeks old immunodeficient female mice (NU-Foxn1nu, Charles River). When tumors reached a mean volume of about 170 $mm^3$, 6 mice/group were treated once (Day 0) intravenously with vehicle (saline solution), ADC1 (6 mg/kg) or ADC SAR DM4 (6 mg/kg). Tumor length (L) and width (W) were measured with calipers and tumor volumes were calculated using the formula L×(W^2)/2.

Figure 33:
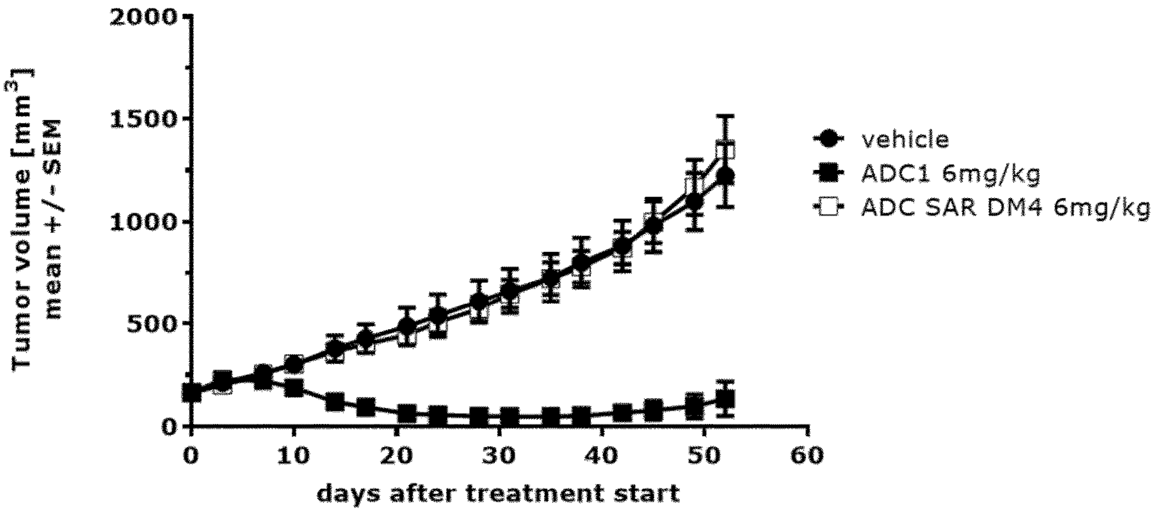
FIG. 33: Efficacy of ADC1 compared to ADC SAR DM4 in a CRC PDX model (COPF230)
Figure 34:
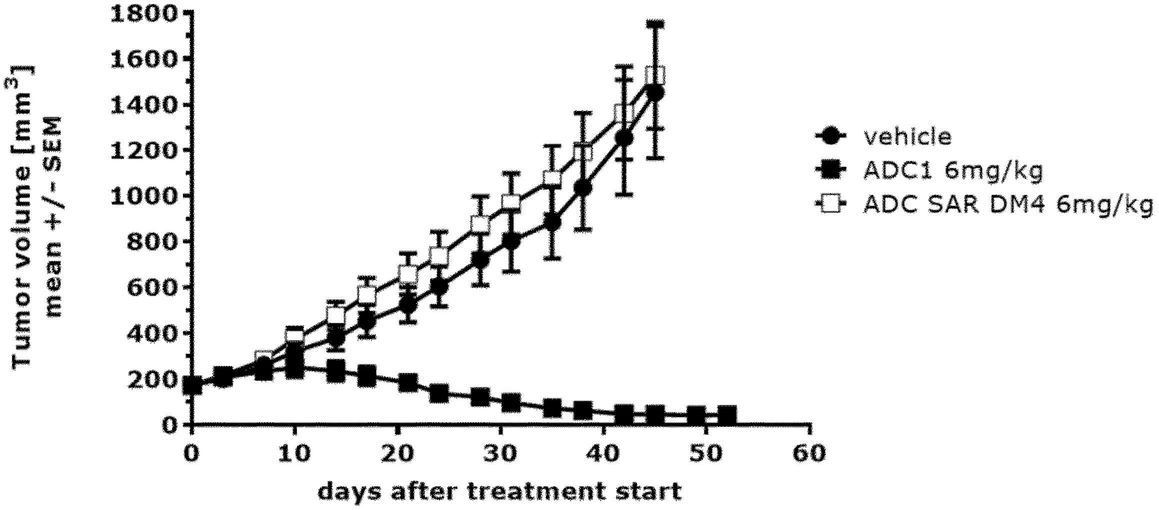
FIG. 34: Efficacy of ADC1 compared to ADC SAR DM4 in a CRC PDX model (REPF210)

Single treatment with ADC1 led to a significant anti-tumor effect in both PDX models COPF230 (FIG. 33) and REPF210 (FIG. 34). In contrast, a single treatment with the same dose of ADC SAR DM4 showed no anti-tumor effect in either of the CRC PDX models (FIG. 33, FIG. 34). No significant effect on body weight was observed in any of the treatment groups (data not shown).

Example 16: Efficacy of ADC1 Compared to ADC SAR DM4 in a Gastric PDX Mouse Model (GAPF313)

Anti-tumor efficacy in vivo was evaluated in the human patient-derived gastric xenograft model GAPF313 (Shanghai LideBiotech CO., LTD). Tumor fragments were transplanted subcutaneously into the right flank of six to eight weeks old immunodeficient female mice (NU-Foxn1nu, Charles River). When tumors reached a mean volume of about 180 $mm^3$, 6 mice/group were treated 3 times every second week starting from day 0 intravenously with vehicle (saline solution), ADC1 (4 mg/kg or 7 mg/kg Q2W×3) or ADC SAR DM4 (4.7 mg/kg Q2W×3). Tumor length (L) and width (W1) were measured with calipers and tumor volumes were calculated using the formula L×(W^2)/2.

Figure 35:
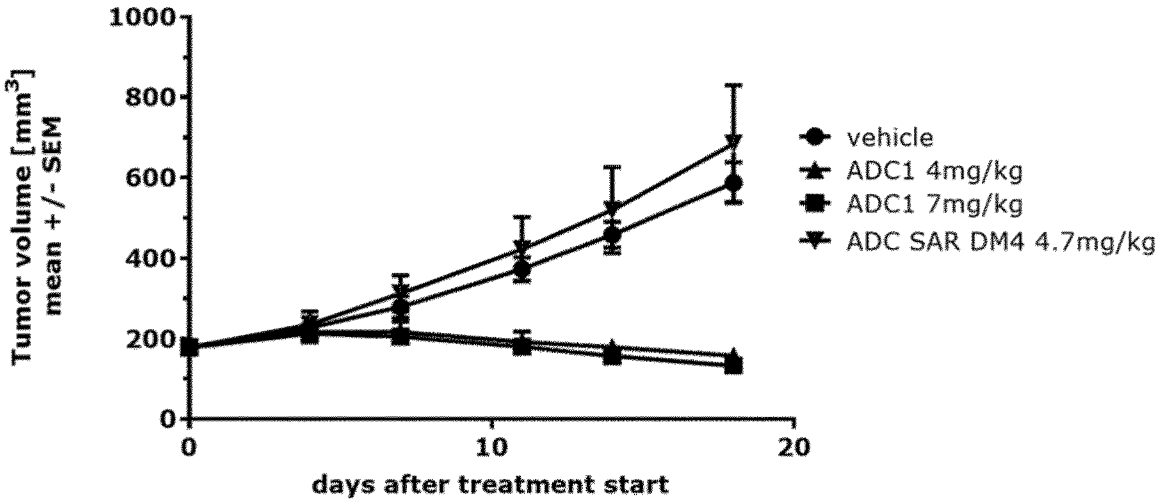
FIG. 35: Efficacy of ADC1 compared to ADC SAR DM4 in a gastric PDX model, GAPF313 (interim analysis of an ongoing experiment)

Interim data analysis of the ongoing experiment demonstrates a clear anti-tumor efficacy of ADC1 in this model and no effect of ADC SAR DM4 (FIG. 35). All treatments were well tolerated (data not shown).

Example 17: Safety Profile of ADC1—a Pilot Toxicity Study in Cynomolgus Monkeys To investigate the safety profile, ADC1 was administered by 30-min i.v. infusion to cynomolgus monkeys, three times with a 3-week interval (on day 1, 22 and 43), at dosages of 0, 3, 10, and 30 mg/kg, and animals were sacrificed on day 50 for gross and histopathological examination. As a result, it was found that ADC1 has a comparatively favorable safety profile in that ADC1 lacks toxicity in certain organs which are affected by toxic side effects of known ADCs.

The invention claimed is:

1. An immunoconjugate comprising an antibody covalently linked via a linker to exatecan, the immunoconjugate having a formula (IV):

(IV)

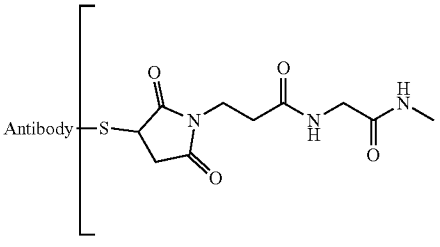

-continued

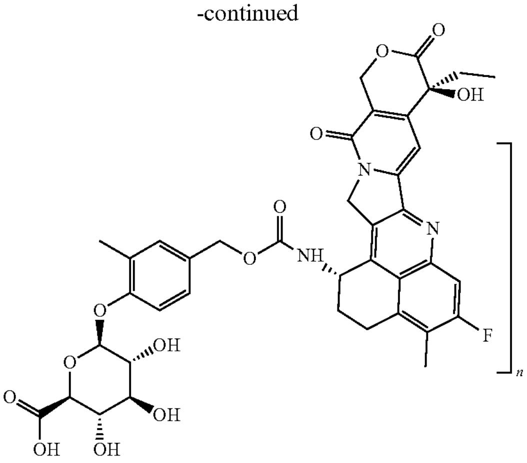

, wherein:

the antibody binds to human CEACAM5 protein and comprises:

a CDR1-H consisting of the amino acid sequence of SEQ ID NO: 3, a CDR2-H consisting of the amino acid sequence of SEQ ID NO: 4, a CDR3-H consisting of the amino acid sequence of SEQ ID NO: 5, a CDR1-L consisting of the amino acid sequence of SEQ ID NO: 6, a CDR2-L consisting of the amino acid sequence of SEQ ID NO: 7, and a CDR3-L consisting of the amino acid sequence of SEQ ID NO: 8;

S is a sulfur atom of the antibody, and n is between 1 and 10.

2. The immunoconjugate according to claim 1, wherein n is between 7 and 8.

3. The immunoconjugate according to claim 1, wherein n is between 7.5 and 8.0.

4. A pharmaceutical composition, comprising; the immunoconjugate according to claim 1, and a pharmaceutically acceptable carrier, diluent, and/or excipient.

5. The immunoconjugate according to claim 1, wherein the antibody comprises a heavy chain variable region (VH) comprising the amino acid sequence of SEQ ID NO: 9 and a light chain variable region (VL) comprising the amino acid sequence of SEQ ID NO: 10.

6. The immunoconjugate according to claim 5, wherein n is between 7 and 8.

7. The immunoconjugate according to claim 5, wherein n is between 7.5 and 8.0.

8. A pharmaceutical composition, comprising: the immunoconjugate according to claim 5, and a pharmaceutically acceptable carrier, diluent, and/or excipient.

9. The immunoconjugate according to claim 1, wherein the antibody comprises a heavy chain constant region (CH) comprising the amino acid sequence of SEQ ID NO: 11 and a light chain constant region (CL) comprising the amino acid sequence of SEQ ID NO: 12.

10. The immunoconjugate according to claim 9, wherein n is between 7 and 8.

11. The immunoconjugate according to claim 9, wherein n is between 7.5 and 8.0.

12. A pharmaceutical composition, comprising; the immunoconjugate according to claim 9, and a pharmaceutically acceptable carrier, diluent, and/or excipient.

13. The immunoconjugate according to claim 1, wherein the antibody comprises a heavy chain (HC) comprising the amino acid sequence of SEQ ID NO: 13 and a light chain (LC) comprising the amino acid sequence of SEQ ID NO: 14.

14. The immunoconjugate according to claim 13, wherein n is between 7 and 8.

15. The immunoconjugate according to claim 13, wherein n is between 7.5 and 8.0.

16. A pharmaceutical composition, comprising; the immunoconjugate according to claim 13, and a pharmaceutically acceptable carrier, diluent, and/or excipient.

* * * * *

SEQUENCE LISTING

```
<160> NUMBER OF SEQ ID NOS: 30

<210> SEQ ID NO 1
<211> LENGTH: 702
<212> TYPE: PRT
<213> ORGANISM: Homo sapiens
<220> FEATURE:
<221> NAME/KEY: MISC_FEATURE
<223> OTHER INFORMATION: Human CEACAM5 protein sequence according to
      GenBank accession number AAA51967.1

<400> SEQUENCE: 1

Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
```

-continued

```
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685
```

```
Val Gly Ile Met Ile Gly Val Leu Val Gly Val Ala Leu Ile
    690                 695                 700


<210> SEQ ID NO 2
<211> LENGTH: 705
<212> TYPE: PRT
<213> ORGANISM: Macaca fascicularis
<220> FEATURE:
<221> NAME/KEY: MISC_FEATURE
<223> OTHER INFORMATION: Macaca fascicularis CEACAM5 protein sequence
      (NCBI Reference Sequence XP_005589491.1)

<400> SEQUENCE: 2

Met Gly Ser Pro Ser Ala Pro Leu His Arg Trp Cys Ile Pro Trp Gln
1               5                   10                  15

Thr Leu Leu Leu Thr Ala Ser Leu Leu Thr Phe Trp Asn Pro Pro Thr
            20                  25                  30

Thr Ala Gln Leu Thr Ile Glu Ser Arg Pro Phe Asn Val Ala Glu Gly
        35                  40                  45

Lys Glu Val Leu Leu Leu Ala His Asn Val Ser Gln Asn Leu Phe Gly
    50                  55                  60

Tyr Ile Trp Tyr Lys Gly Glu Arg Val Asp Ala Ser Arg Arg Ile Gly
65                  70                  75                  80

Ser Cys Val Ile Arg Thr Gln Gln Ile Thr Pro Gly Pro Ala His Ser
                85                  90                  95

Gly Arg Glu Thr Ile Asp Phe Asn Ala Ser Leu Leu Ile His Asn Val
            100                 105                 110

Thr Gln Ser Asp Thr Gly Ser Tyr Thr Ile Gln Val Ile Lys Glu Asp
        115                 120                 125

Leu Val Asn Glu Glu Ala Thr Gly Gln Phe Arg Val Tyr Pro Glu Leu
    130                 135                 140

Pro Lys Pro Tyr Ile Ser Ser Asn Asn Ser Asn Pro Val Glu Asp Lys
145                 150                 155                 160

Asp Ala Val Ala Leu Thr Cys Glu Pro Glu Thr Gln Asp Thr Thr Tyr
                165                 170                 175

Leu Trp Trp Val Asn Asn Gln Ser Leu Pro Val Ser Pro Arg Leu Glu
            180                 185                 190

Leu Ser Ser Asp Asn Arg Thr Leu Thr Val Phe Asn Ile Pro Arg Asn
        195                 200                 205

Asp Thr Thr Ser Tyr Lys Cys Glu Thr Gln Asn Pro Val Ser Val Arg
    210                 215                 220

Arg Ser Asp Pro Val Thr Leu Asn Val Leu Tyr Gly Pro Asp Ala Pro
225                 230                 235                 240

Thr Ile Ser Pro Leu Asn Thr Pro Tyr Arg Ala Gly Glu Asn Leu Asn
                245                 250                 255

Leu Ser Cys His Ala Ala Ser Asn Pro Thr Ala Gln Tyr Phe Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Ala Ile Thr Val Tyr Ala
305                 310                 315                 320

Glu Leu Pro Lys Pro Tyr Ile Thr Ser Asn Asn Ser Asn Pro Ile Glu
                325                 330                 335
```

Asp Lys Asp Ala Val Thr Leu Thr Cys Glu Pro Glu Thr Gln Asp Thr
340 345 350

Thr Tyr Leu Trp Trp Val Asn Asn Gln Ser Leu Ser Val Ser Ser Arg
355 360 365

Leu Glu Leu Ser Asn Asp Asn Arg Thr Leu Thr Val Phe Asn Ile Pro
370 375 380

Arg Asn Asp Thr Thr Phe Tyr Glu Cys Glu Thr Gln Asn Pro Val Ser
385 390 395 400

Val Arg Arg Ser Asp Pro Val Thr Leu Asn Val Leu Tyr Gly Pro Asp
405 410 415

Ala Pro Thr Ile Ser Pro Leu Asn Thr Pro Tyr Arg Ala Gly Glu Asn
420 425 430

Leu Asn Leu Ser Cys His Ala Ala Ser Asn Pro Ala Ala Gln Tyr Ser
435 440 445

Trp Phe Val Asn Gly Thr Phe Gln Gln Ser Thr Gln Glu Leu Phe Ile
450 455 460

Pro Asn Ile Thr Val Asn Asn Ser Gly Ser Tyr Met Cys Gln Ala His
465 470 475 480

Asn Ser Ala Thr Gly Leu Asn Arg Thr Thr Val Thr Ala Ile Thr Val
485 490 495

Tyr Val Glu Leu Pro Lys Pro Tyr Ile Ser Ser Asn Asn Ser Asn Pro
500 505 510

Ile Glu Asp Lys Asp Ala Val Thr Leu Thr Cys Glu Pro Val Ala Glu
515 520 525

Asn Thr Thr Tyr Leu Trp Trp Val Asn Asn Gln Ser Leu Ser Val Ser
530 535 540

Pro Arg Leu Gln Leu Ser Asn Gly Asn Arg Ile Leu Thr Leu Leu Ser
545 550 555 560

Val Thr Arg Asn Asp Thr Gly Pro Tyr Glu Cys Gly Ile Gln Asn Ser
565 570 575

Glu Ser Ala Lys Arg Ser Asp Pro Val Thr Leu Asn Val Thr Tyr Gly
580 585 590

Pro Asp Thr Pro Ile Ile Ser Pro Pro Asp Leu Ser Tyr Arg Ser Gly
595 600 605

Ala Asn Leu Asn Leu Ser Cys His Ser Asp Ser Asn Pro Ser Pro Gln
610 615 620

Tyr Ser Trp Leu Ile Asn Gly Thr Leu Arg Gln His Thr Gln Val Leu
625 630 635 640

Phe Ile Ser Lys Ile Thr Ser Asn Asn Asn Gly Ala Tyr Ala Cys Phe
645 650 655

Val Ser Asn Leu Ala Thr Gly Arg Asn Asn Ser Ile Val Lys Asn Ile
660 665 670

Ser Val Ser Ser Gly Asp Ser Ala Pro Gly Ser Ser Gly Leu Ser Ala
675 680 685

Arg Ala Thr Val Gly Ile Ile Ile Gly Met Leu Val Gly Val Ala Leu
690 695 700

Met
705

<210> SEQ ID NO 3
<211> LENGTH: 10
<212> TYPE: PRT
<213> ORGANISM: Artificial Sequence
<220> FEATURE:
<223> OTHER INFORMATION: CDR1-H of mAb1

<400> SEQUENCE: 3

Asp Gly Ser Val Ser Arg Gly Gly Tyr Tyr
1 5 10

<210> SEQ ID NO 4
<211> LENGTH: 7
<212> TYPE: PRT
<213> ORGANISM: Artificial Sequence
<220> FEATURE:
<223> OTHER INFORMATION: CDR2-H of mAb1

<400> SEQUENCE: 4

Ile Tyr Tyr Ser Gly Ser Thr
1 5

<210> SEQ ID NO 5
<211> LENGTH: 11
<212> TYPE: PRT
<213> ORGANISM: Artificial Sequence
<220> FEATURE:
<223> OTHER INFORMATION: CDR3-H of mAb1

<400> SEQUENCE: 5

Ala Arg Gly Ile Ala Val Ala Pro Phe Asp Tyr
1 5 10

<210> SEQ ID NO 6
<211> LENGTH: 6
<212> TYPE: PRT
<213> ORGANISM: Artificial Sequence
<220> FEATURE:
<223> OTHER INFORMATION: CDR1-L of mAb1

<400> SEQUENCE: 6

Gln Ser Val Arg Ser Asn
1 5

<210> SEQ ID NO 7
<211> LENGTH: 3
<212> TYPE: PRT
<213> ORGANISM: Artificial Sequence
<220> FEATURE:
<223> OTHER INFORMATION: CDR2-L of mAb1

<400> SEQUENCE: 7

Ala Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: CDR3-L of mAb1

<400> SEQUENCE: 8

Gln Gln Tyr Thr Asn Trp Pro Phe Thr
1 5

<210> SEQ ID NO 9
<211> LENGTH: 119
<212> TYPE: PRT
<213> ORGANISM: Artificial Sequence
<220> FEATURE:
<223> OTHER INFORMATION: VH of mAb1

<400> SEQUENCE: 9

```
Glu Val Gln Leu Gln Glu Ser Gly Pro Gly Leu Val Lys Pro Ser Gln
1               5                   10                  15

Thr Leu Ser Leu Thr Cys Thr Val Ser Asp Gly Ser Val Ser Arg Gly
            20                  25                  30

Gly Tyr Tyr Leu Thr Trp Ile Arg Gln His Pro Gly Lys Gly Leu Glu
        35                  40                  45

Trp Ile Gly Tyr Ile Tyr Tyr Ser Gly Ser Thr Tyr Phe Asn Pro Ser
    50                  55                  60

Leu Arg Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ile Ala Val Ala Pro Phe Asp Tyr Trp Gly Gln Gly
            100                 105                 110

Thr Leu Val Thr Val Ser Ser
        115
```

<210> SEQ ID NO 10
<211> LENGTH: 107
<212> TYPE: PRT
<213> ORGANISM: Artificial Sequence
<220> FEATURE:
<223> OTHER INFORMATION: VL of mAb1

<400> SEQUENCE: 10

```
Glu Ile Val Leu Thr Gln Ser Pro Ala Thr Leu Ser Val Ser Pro Gly
1               5                   10                  15

Glu Arg Ala Thr Leu Ser Cys Arg Thr Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Thr Asn Trp Pro Phe
                85                  90                  95

Thr Phe Gly Pro Gly Thr Lys Val Asp Ile Lys
            100                 105
```

<210> SEQ ID NO 11
<211> LENGTH: 328
<212> TYPE: PRT
<213> ORGANISM: Artificial Sequence
<220> FEATURE:
<223> OTHER INFORMATION: CH of mAb1

<400> SEQUENCE: 11

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

-continued

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325


<210> SEQ ID NO 12
<211> LENGTH: 107
<212> TYPE: PRT
<213> ORGANISM: Artificial Sequence
<220> FEATURE:
<223> OTHER INFORMATION: CL of mAb1

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95
```

```
Pro Val Thr Lys Ser Phe Asn Arg Gly Glu Cys
            100                 105


<210> SEQ ID NO 13
<211> LENGTH: 447
<212> TYPE: PRT
<213> ORGANISM: Artificial Sequence
<220> FEATURE:
<223> OTHER INFORMATION: HC of mAb1

<400> SEQUENCE: 13

Glu Val Gln Leu Gln Glu Ser Gly Pro Gly Leu Val Lys Pro Ser Gln
1               5                   10                  15

Thr Leu Ser Leu Thr Cys Thr Val Ser Asp Gly Ser Val Ser Arg Gly
            20                  25                  30

Gly Tyr Tyr Leu Thr Trp Ile Arg Gln His Pro Gly Lys Gly Leu Glu
        35                  40                  45

Trp Ile Gly Tyr Ile Tyr Tyr Ser Gly Ser Thr Tyr Phe Asn Pro Ser
    50                  55                  60

Leu Arg Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ile Ala Val Ala Pro Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 14
<211> LENGTH: 214
<212> TYPE: PRT
<213> ORGANISM: Artificial Sequence
<220> FEATURE:
<223> OTHER INFORMATION: LC of mAb1

<400> SEQUENCE: 14

Glu Ile Val Leu Thr Gln Ser Pro Ala Thr Leu Ser Val Ser Pro Gly
1               5                   10                  15

Glu Arg Ala Thr Leu Ser Cys Arg Thr Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Thr Asn Trp Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 15
<211> LENGTH: 1404
<212> TYPE: DNA
<213> ORGANISM: Artificial Sequence
<220> FEATURE:
<223> OTHER INFORMATION: DNA sequence encoding HC of mAb1

<400> SEQUENCE: 15
```

```
atggagaccg acaccctgct gctgtgggtg ctgctgctgt gggtgcccgg gtcgaccggt      60
gaggtgcagc tgcaggagtc gggcccagga ctggtgaagc cttcacagac cctgtccctc     120
acctgcactg tctctgatgg ctccgtcagc aggggtggtt actacttgac ctggatccgc     180
cagcacccag ggaagggcct ggagtggatt gggtacatct attacagtgg gagcacctac     240
ttcaacccgt ccctcaggag tcgggttacc atgtcagtag acacgtctaa gaaccagttc     300
tccctgaagc tgagctctgt gactgccgcg gacacggccg tgtattactg tgcgagaggg     360
atagcagtgg ctccctttga ctactggggc cagggaaccc tggtcaccgt ctcttcagct     420
agcaccaagg gccccagcgt gttccccctg gcccccagca gcaagtccac aagcggagga     480
acagccgccc tgggctgcct ggtgaaggac tacttccccg agcccgtgac cgtgtcctgg     540
aacagcggag ccctgacctc cggcgtgcac accttccccg ccgtgctgca gagcagcggc     600
ctgtacagcc tgagcagcgt ggtgacagtg ccaagcagca gcctgggaac ccagacctac     660
atctgcaacg tgaaccacaa gcccagcaac accaaggtgg acaagagagt ggagcccaag     720
agctgcgaca agacccatac ctgtccaccc tgcccagccc ccccagtggc cggaccctcc     780
gtgttcctgt tcccccccaa gcccaaggac accctgatga tcagcaggac ccccgaggtg     840
acctgcgtgg tggtggacgt gagccacgag gacccagagg tgaagttcaa ttggtatgtg     900
gacggcgtgg aggtgcacaa cgccaagacc aagcccagag aggaacagta caacagcacc     960
tacagggtgg tgtccgtgct gaccgtgctg caccaggact ggctgaacgg caaggaatac    1020
aagtgcaagg tctccaacaa ggccctgccc tccagcatcg agaaaaccat cagcaaggcc    1080
aagggccagc cacgggagcc ccaggtgtac acactgcccc catctcggga agaaatgacc    1140
aagaaccagg tgtccctgac ctgtctggtg aagggctttt accccagcga catcgccgtg    1200
gagtgggaga gcaacggcca gcccgagaac aactacaaga ccaccccccc tgtgctggac    1260
agcgacggca gcttcttcct gtacagcaag ctgaccgtgg acaagtccag gtggcagcag    1320
ggcaacgtgt tcagctgcag cgtgatgcac gaggccctgc acaaccacta cacacagaag    1380
agcctgagcc tgtcccccgg ctga                                          1404
```

<210> SEQ ID NO 16
<211> LENGTH: 708
<212> TYPE: DNA
<213> ORGANISM: Artificial Sequence
<220> FEATURE:
<223> OTHER INFORMATION: DNA sequence encoding LC of mAb1

<400> SEQUENCE: 16

```
atgagggccc tgctggctag actgctgctg tgcgtgctgg tcgtgtccga cagcaagggc      60
gaaatcgtac tcacgcagtc tccagccacc ctgtctgtgt ctccagggga aagagccacc     120
ctctcctgca ggaccagtca gagtgttcgc agcaacttag cctggtacca gcagaagcct     180
ggccaggctc ccaggctcct catctatgct gcatccacca gggccactgg tatcccagcc     240
aggttcagtg gcagtgggtc tgggacagag ttcactctca ccatcagcag cctgcagtct     300
gaagattttg cagtttatta ctgtcagcag tatactaact ggccattcac tttcggccct     360
gggaccaaag tggacatcaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
```

ctgagcaaag cagactacga gaaacacaaa gtctacgcct gcgaagtcac ccatcagggc 660
ctgagctcgc ccgtcacaaa gagcttcaac aggggagagt gttgatag 708

<210> SEQ ID NO 17
<211> LENGTH: 449
<212> TYPE: PRT
<213> ORGANISM: Artificial Sequence
<220> FEATURE:
<223> OTHER INFORMATION: HC of antibody hu8G4

<400> SEQUENCE: 17

Glu Val Gln Leu Val Glu Ser Gly Pro Gly Leu Val Lys Pro Ser Gln
1 5 10 15

Thr Leu Ser Leu Thr Cys Thr Val Ser Asp Gly Ser Val Ser Arg Gly
20 25 30

Gly Tyr Tyr Leu Thr Trp Ile Arg Gln His Pro Gly Lys Gly Leu Glu
35 40 45

Trp Ile Gly Tyr Ile Tyr Tyr Ser Gly Ser Thr Tyr Phe Asn Pro Ser
50 55 60

Leu Arg Ser Arg Leu Thr Met Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Gly Ile Ala Val Ala Pro Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Arg Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

```
Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 18
<211> LENGTH: 214
<212> TYPE: PRT
<213> ORGANISM: Artificial Sequence
<220> FEATURE:
<223> OTHER INFORMATION: LC of antibody hu8G4

<400> SEQUENCE: 18

Glu Thr Thr Leu Thr Gln Ser Pro Ala Thr Leu Ser Val Ser Pro Gly
1               5                   10                  15

Glu Arg Ala Thr Leu Ser Cys Arg Thr Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Phe Cys Gln Gln Tyr Thr Asn Trp Pro Phe
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 19
<211> LENGTH: 449
<212> TYPE: PRT
<213> ORGANISM: Artificial Sequence
<220> FEATURE:
```

-continued

<223> OTHER INFORMATION: HC of optimized antibody Variant 1

<400> SEQUENCE: 19

```
Glu Val Gln Leu Gln Glu Ser Gly Pro Gly Leu Val Lys Pro Ser Gln
1               5                   10                  15

Thr Leu Ser Leu Thr Cys Thr Val Ser Asp Gly Ser Val Ser Arg Gly
            20                  25                  30

Gly Tyr Tyr Leu Thr Trp Ile Arg Gln His Pro Gly Lys Gly Leu Glu
        35                  40                  45

Trp Ile Gly Tyr Ile Tyr Tyr Ser Gly Ser Thr Tyr Phe Asn Pro Ser
    50                  55                  60

Leu Arg Ser Arg Leu Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ile Ala Val Ala Pro Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 20
<211> LENGTH: 214
<212> TYPE: PRT
<213> ORGANISM: Artificial Sequence
<220> FEATURE:
<223> OTHER INFORMATION: LC of optimized antibody Variant 1

<400> SEQUENCE: 20

```
Glu Thr Thr Leu Thr Gln Ser Pro Ala Thr Leu Ser Val Ser Pro Gly
1               5                   10                  15

Glu Arg Ala Thr Leu Ser Cys Arg Thr Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Phe Cys Gln Gln Tyr Thr Asn Trp Pro Phe
                85                  90                  95

Thr Phe Gly Pro Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 21
<211> LENGTH: 214
<212> TYPE: PRT
<213> ORGANISM: Artificial Sequence
<220> FEATURE:
<223> OTHER INFORMATION: LC of optimized antibody Variant 2

<400> SEQUENCE: 21

```
Glu Ile Val Leu Thr Gln Ser Pro Ala Thr Leu Ser Val Ser Pro Gly
1               5                   10                  15

Glu Arg Ala Thr Leu Ser Cys Arg Thr Ser Gln Ser Val Arg Ser Asn
            20                  25                  30
```

```
Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Thr Asn Trp Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 22
<211> LENGTH: 214
<212> TYPE: PRT
<213> ORGANISM: Artificial Sequence
<220> FEATURE:
<223> OTHER INFORMATION: LC of optimized antibody Variant 4

<400> SEQUENCE: 22

Glu Ile Val Met Thr Gln Ser Pro Ala Thr Leu Ser Val Ser Pro Gly
1               5                   10                  15

Glu Arg Ala Thr Leu Ser Cys Arg Thr Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Thr Asn Trp Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 23
<211> LENGTH: 214
<212> TYPE: PRT
<213> ORGANISM: Artificial Sequence
<220> FEATURE:
<223> OTHER INFORMATION: LC of optimized antibody Variant 5

<400> SEQUENCE: 23

Glu Ile Val Met Thr Gln Ser Pro Ala Thr Leu Ser Val Ser Pro Gly
1               5                   10                  15

Glu Arg Ala Thr Leu Ser Cys Arg Thr Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Thr Asn Trp Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 24
<211> LENGTH: 449
<212> TYPE: PRT
<213> ORGANISM: Artificial Sequence
<220> FEATURE:
<223> OTHER INFORMATION: HC of optimized antibody Variant 6

<400> SEQUENCE: 24

Glu Val Gln Leu Gln Glu Ser Gly Pro Gly Leu Val Lys Pro Ser Gln
1               5                   10                  15

Thr Leu Ser Leu Thr Cys Thr Val Ser Asp Gly Ser Val Ser Arg Gly
            20                  25                  30

Gly Tyr Tyr Leu Thr Trp Ile Arg Gln His Pro Gly Lys Gly Leu Glu
        35                  40                  45
```

-continued

```
Trp Ile Gly Tyr Ile Tyr Tyr Ser Gly Ser Thr Tyr Phe Asn Pro Ser
    50                  55                  60

Leu Arg Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ile Ala Val Ala Pro Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

-continued

<210> SEQ ID NO 25
<211> LENGTH: 450
<212> TYPE: PRT
<213> ORGANISM: Artificial Sequence
<220> FEATURE:
<223> OTHER INFORMATION: HC of huMab2-3 (allotype)

<400> SEQUENCE: 25

```
Glu Val Gln Leu Gln Glu Ser Gly Pro Gly Leu Val Lys Pro Gly Gly
1               5                   10                  15

Ser Leu Ser Leu Ser Cys Ala Ala Ser Gly Phe Val Phe Ser Ser Tyr
            20                  25                  30

Asp Met Ser Trp Val Arg Gln Thr Pro Glu Arg Gly Leu Glu Trp Val
        35                  40                  45

Ala Tyr Ile Ser Ser Gly Gly Gly Ile Thr Tyr Ala Pro Ser Thr Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Thr Ser Glu Asp Thr Ala Val Tyr Tyr Cys
                85                  90                  95

Ala Ala His Tyr Phe Gly Ser Ser Gly Pro Phe Ala Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
```

-continued 370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 26
<211> LENGTH: 214
<212> TYPE: PRT
<213> ORGANISM: Artificial Sequence
<220> FEATURE:
<223> OTHER INFORMATION: LC of huMab2-3

<400> SEQUENCE: 26

Asp Ile Gln Met Thr Gln Ser Pro Ala Ser Leu Ser Ala Ser Val Gly
1 5 10 15

Asp Arg Val Thr Ile Thr Cys Arg Ala Ser Glu Asn Ile Phe Ser Tyr
20 25 30

Leu Ala Trp Tyr Gln Gln Lys Pro Gly Lys Ser Pro Lys Leu Leu Val
35 40 45

Tyr Asn Thr Arg Thr Leu Ala Glu Gly Val Pro Ser Arg Phe Ser Gly
50 55 60

Ser Gly Ser Gly Thr Asp Phe Ser Leu Thr Ile Ser Ser Leu Gln Pro
65 70 75 80

Glu Asp Phe Ala Thr Tyr Tyr Cys Gln His His Tyr Gly Thr Pro Phe
85 90 95

Thr Phe Gly Ser Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 27
<211> LENGTH: 449
<212> TYPE: PRT
<213> ORGANISM: Artificial Sequence
<220> FEATURE:
<223> OTHER INFORMATION: HC of hmn-14

<400> SEQUENCE: 27

-continued

```
Glu Val Gln Leu Val Glu Ser Gly Gly Gly Val Val Gln Pro Gly Arg
1               5                   10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Phe Thr Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
            420                 425                 430

Ala Leu His Asn His Tyr Thr Gln Lys Ser Leu Ser Leu Ser Pro Gly
        435                 440                 445

Lys


<210> SEQ ID NO 28
<211> LENGTH: 213
<212> TYPE: PRT
<213> ORGANISM: Artificial Sequence
<220> FEATURE:
<223> OTHER INFORMATION: LC of hmn-14

<400> SEQUENCE: 28

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ser
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Leu Tyr Arg Ser
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 29
<211> LENGTH: 441
<212> TYPE: PRT
<213> ORGANISM: Artificial Sequence
<220> FEATURE:
<223> OTHER INFORMATION: HC of rb8G4

<400> SEQUENCE: 29

Glu Val Gln Leu Gln Glu Ser Gly Pro Gly Leu Val Lys Pro Ser Gln
1               5                   10                  15

Thr Leu Ser Leu Thr Cys Thr Val Ser Asp Gly Ser Val Ser Arg Gly
            20                  25                  30

Gly Tyr Tyr Leu Thr Trp Ile Arg Gln His Pro Gly Lys Gly Leu Glu
        35                  40                  45

Trp Ile Gly Tyr Ile Tyr Tyr Ser Gly Ser Thr Tyr Phe Asn Pro Ser
```

-continued

```
    50                  55                  60

Leu Arg Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ile Ala Val Ala Pro Phe Asp Tyr Trp Gly Gln Gly
            100                 105                 110

Thr Leu Val Thr Val Ser Ser Gln Pro Lys Ala Pro Ser Val Phe Pro
        115                 120                 125

Leu Ala Pro Cys Cys Gly Asp Thr Pro Ser Ser Thr Val Thr Leu Gly
    130                 135                 140

Cys Leu Val Lys Gly Tyr Leu Pro Glu Pro Val Thr Val Thr Trp Asn
145                 150                 155                 160

Ser Gly Thr Leu Thr Asn Gly Val Arg Thr Phe Pro Ser Val Arg Gln
                165                 170                 175

Ser Ser Gly Leu Tyr Ser Leu Ser Ser Val Val Ser Val Thr Ser Ser
            180                 185                 190

Ser Gln Pro Val Thr Cys Asn Val Ala His Pro Ala Thr Asn Thr Lys
        195                 200                 205

Val Asp Lys Thr Val Ala Pro Ser Thr Cys Ser Lys Pro Thr Cys Pro
    210                 215                 220

Pro Pro Glu Leu Leu Gly Gly Pro Ser Val Phe Ile Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Glu Asp Asp Pro Glu Val Gln Phe Thr Trp Tyr
            260                 265                 270

Ile Asn Asn Glu Gln Val Arg Thr Ala Arg Pro Pro Leu Arg Glu Gln
        275                 280                 285

Gln Phe Asn Ser Thr Ile Arg Val Val Ser Thr Leu Pro Ile Ala His
    290                 295                 300

Glu Asp Trp Leu Arg Gly Lys Glu Phe Lys Cys Lys Val His Asn Lys
305                 310                 315                 320

Ala Leu Pro Ala Pro Ile Glu Lys Thr Ile Ser Lys Ala Arg Gly Gln
                325                 330                 335

Pro Leu Glu Pro Lys Val Tyr Thr Met Gly Pro Pro Arg Glu Glu Leu
            340                 345                 350

Ser Ser Arg Ser Val Ser Leu Thr Cys Met Ile Asn Gly Phe Tyr Pro
        355                 360                 365

Ser Asp Ile Ser Val Glu Trp Glu Lys Asn Gly Lys Ala Glu Asp Asn
    370                 375                 380

Tyr Lys Thr Thr Pro Ala Val Leu Asp Ser Asp Gly Ser Tyr Phe Leu
385                 390                 395                 400

Tyr Ser Lys Leu Ser Val Pro Thr Ser Glu Trp Gln Arg Gly Asp Val
                405                 410                 415

Phe Thr Cys Ser Val Met His Glu Ala Leu His Asn His Tyr Thr Gln
            420                 425                 430
```

-continued

```
Lys Ser Ile Ser Arg Ser Pro Gly Lys
        435                 440


<210> SEQ ID NO 30
<211> LENGTH: 213
<212> TYPE: PRT
<213> ORGANISM: Artificial Sequence
<220> FEATURE:
<223> OTHER INFORMATION: LC of rb8G4

<400> SEQUENCE: 30

Glu Ile Val Leu Thr Gln Ser Pro Ala Thr Leu Ser Val Ser Pro Gly
1               5                   10                  15

Glu Arg Ala Thr Leu Ser Cys Arg Thr Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Thr Asn Trp Pro Phe
                85                  90                  95

Thr Phe Gly Pro Gly Thr Lys Val Asp Ile Lys Arg Asp Pro Val Ala
            100                 105                 110

Pro Ser Val Leu Leu Phe Pro Pro Ser Lys Glu Glu Leu Thr Thr Gly
        115                 120                 125

Thr Ala Thr Ile Val Cys Val Ala Asn Lys Phe Tyr Pro Ser Asp Ile
    130                 135                 140

Thr Val Thr Trp Lys Val Asp Gly Thr Thr Gln Gln Ser Gly Ile Glu
145                 150                 155                 160

Asn Ser Lys Thr Pro Gln Ser Pro Glu Asp Asn Thr Tyr Ser Leu Ser
                165                 170                 175

Ser Thr Leu Ser Leu Thr Ser Ala Gln Tyr Asn Ser His Ser Val Tyr
            180                 185                 190

Thr Cys Glu Val Val Gln Gly Ser Ala Ser Pro Ile Val Gln Ser Phe
        195                 200                 205

Asn Arg Gly Asp Cys
    210
```